US011491215B2

United States Patent
Fischer et al.

(10) Patent No.: US 11,491,215 B2
(45) Date of Patent: Nov. 8, 2022

(54) **ANTIGENIC COMBINATIONS AGAINST *FRANCISELLA* BACTERIA AND RELATED NANOLIPOPROTEIN PARTICLES, COMPOSITIONS, METHODS AND SYSTEMS**

(71) Applicants: LAWRENCE LIVERMORE NATIONAL SECURITY, LLC, Livermore, CA (US); STC.UNM, Albuquerque, NM (US)

(72) Inventors: Nicholas Fischer, Livermore, CA (US); Amy Rasley, Livermore, CA (US); Terry Wu, Albuquerque, NM (US); Julie Lovchik, Albuquerque, NM (US)

(73) Assignees: LAWRENCE LIVERMORE NATIONAL SECURITY, LLC, Livermore, CA (US); REGENTS OF THE UNIVERSITY OF NEW MEXICO, Albuquerque, NM (US)

(*) Notice: Subject to any disclaimer, the term of this patent is extended or adjusted under 35 U.S.C. 154(b) by 99 days.

(21) Appl. No.: 16/543,463

(22) Filed: Aug. 16, 2019

(65) Prior Publication Data
US 2020/0108133 A1    Apr. 9, 2020

Related U.S. Application Data

(63) Continuation-in-part of application No. 16/422,263, filed on May 24, 2019, now abandoned.

(60) Provisional application No. 62/676,222, filed on May 24, 2018.

(51) Int. Cl.
| | | |
|---|---|---|
| *A61K 39/02* | (2006.01) | |
| *A61K 39/39* | (2006.01) | |
| *B82Y 5/00* | (2011.01) | |
| *A61K 39/00* | (2006.01) | |

(52) U.S. Cl.
CPC .......... *A61K 39/0208* (2013.01); *A61K 39/39* (2013.01); *A61K 2039/543* (2013.01); *A61K 2039/55555* (2013.01); *A61K 2039/55572* (2013.01); *A61K 2039/6087* (2013.01); *B82Y 5/00* (2013.01)

(58) Field of Classification Search
None
See application file for complete search history.

(56) References Cited

U.S. PATENT DOCUMENTS

| | | |
|---|---|---|
| 8,481,024 B2 | 7/2013 | Horwitz et al. |
| 8,883,729 B2 | 11/2014 | Hoeprich et al. |
| 8,889,623 B2 | 11/2014 | Hoeprich et al. |
| 2009/0068254 A1* | 3/2009 | Bacon ............. A61K 9/127 424/450 |

FOREIGN PATENT DOCUMENTS

| | | | | |
|---|---|---|---|---|
| GB | 1800417.6 | * | 1/2018 | ........... A61K 9/0019 |
| WO | WO-2008127296 A2 | * | 10/2008 | ......... A61K 39/0208 |
| WO | WO-2014114926 A1 | * | 7/2014 | ......... A61K 39/0208 |
| WO | WO-2019138210 A1 | * | 7/2019 | ........... A61K 9/0019 |

OTHER PUBLICATIONS

Uniprot Accession No. Q5NEC5 Feb. 1, 2005 (Year: 2005).*
Altschul, S.F., et al., "Gapped BLAST and PSI-BLAST a new generation of protein database search programs," *Nucleic Acids Res* vol. 25(17): p. 3389-402, (1997). 14 Pages.
Apicella, M.A., et al., "Identification, characterization and immunogenicity of a O-antigen capsular polysaccharide of Francisella tularensis," *PLoS One* vol. 5(7): p. ef11060, (2010). 18 pages.
Ashtekar, AR, et al., "A mucosal subunit vaccine protects against lethal respiratory infection with Francisella tularensis LVS," *PLoS One* vol. 7(11): p. e50460, (Nov. 2012). 14 Pages.
Barker, J.H., et al., "Evidence Suggesting That Francisella tularensis O-Antigen Capsule Contains a Lipid A-Like Molecule That is Structurally Distinct from the More Abundant Free Lipid A," *PLoS One*11 (6): e0157842,(Jun. 2016). 15 Pages.
Barker, J.H., et al., "Metabolic labeling to characterize the overall composition of Francisella lipid A and Lipopolysaccharide grown in broth and in human phagocytes," *Innate Immun.* vol. 20(1): p. 88-103, (2014). 24 Pages.
Chalabaev, S., et al., "3-Deoxy-D-manno-octulosonic acid (Kdo) hydrolaseidentified in Francisella tularensis, Helicobacter pylori, and Legionellapneumophila," *Journal of Biological Chemistry* vol. 285(45): p. 34330-34336. (Nov. 2010). 8 Pages.
Cole, L.E., et al., "Antigen-specific B-1a antibodies induces by Francisella tularensis LPS provide long-term protection against F. tularensis LVS challenge," *PNAS* vol. 106(11): 4343-48, (Mar. 2009). 6 Pages.
Conlan, J.W., et al., "Mice intradermally-inoculated with the intact lipopolysaccharide, but not the lipid A or O-chain, from Francisella tularensis LVS rapidly acquire varying degrees of enhanced resistance against systemic or aerogenic challenge with virulent strains of the pathogen," *Microbial Pathogenesis* 34(2003) :39-45, (2003). 7 Pages.
Davidson, E., et al., "A high-throughput shotgun mutagenesis approach to mapping B-cell antibody epitopes,". Immunology vol. 143(1): p. 13-20, (2014). 8 Pages.

(Continued)

*Primary Examiner* — Oluwatosin A Ogunbiyi
(74) *Attorney, Agent, or Firm* — Steinfl + Bruno LLP

(57) ABSTRACT

Provided herein are antigenic combinations and related compositions, methods and systems for immunizing a host from an infection caused by *Francisella* bacterium. The antigenic combination comprises an antigenic polysaccharide component from a *Francisella* bacterium capable of triggering a humoral immune response in an individual, a protein antigen component from the *Francisella* bacterium capable of triggering a cellular immune response in the individual, and an adjuvant, the antigenic *Francisella* polysaccharide component, the *Francisella* protein antigen component and the adjuvant are in a suitable amount to immunize an individual against the *Francisella* bacterium.

42 Claims, 79 Drawing Sheets
Specification includes a Sequence Listing.

(56) References Cited

OTHER PUBLICATIONS

De Castro, C., et al., "Microbe-associated molecular patterns in innate immunity: Extraction and chemical analysis of gram-negative bacterial lipopolysaccharides," *Methods Enzymol* vol. 480: p. 89-115, (2010). 27 Pages.
Dreisbach, V.C., et al., "Purified lipopolysaccharide from Francisella tularensis live vaccine strain (LVS) induces protective immunity against LVS infection that requires B cells and gamma interferon," *Infect Immun*. vol. 68(4): p. 1988-96, (2000). 9 Pages.
Foley, J.E., et al., "Tularemia". *Vet Microbial* vol. 140(3-4): p. 332-8. (2010). 7 Pages.
Hajjar, AM., et al., "Lack of in vitro and in vivo recognition of Francisella tularensis subspecies lipopolysaccharide by Toll-like receptors," *Infect Immun* vol. 74(12): p. 6730-8, (2006). 9 Pages.
Huber, B., et al., Description of *Francisella hispaniensis* sp. nov., isolated from human blood, reclassification of Francisella novicida (Larson et al. 1955) Olsufiev et al. 1959 as *Francisella tularensis* subsp. *novicida* comb. nov. and emended description of the genus *Francisella*. Int J Syst Evol Microbial vol. 60: p. 1887-96, (2010). 10 Pages.
Johnson, L.S., et al., "Hidden Markov model speed heuristic and iterative HMM search procedure," *BMC Bioinformatics* 11: p. 431. (2010). 8 Pages.
Koren, E., et al., Clinical validation of the 'in silico' prediction of immunogenicity of a human recombinant therapeutic protein. *Clinical Immunology* vol. 124(1): p. 26-32, (2007). 7 Pages.
Li Pira, G., et al., "High throughput T epitope mapping and vaccine development," *Journal of Biomedicine and Biotechnology* 2010: Article ID 325720, p. 1-12, (2010). 12 Pages.
Lu, Z., et al., "Antibodies to both terminal and internal B-cells epitopes of Francisella tularensis O-Polysaccharide produced by patients with Tularemia," *Clinical Vacc. Imm*. 21(2): pp. 227-233, (Feb. 2014). 7 Pages.
Lu, Z., et al., "Functional and Structural Characterization of Francisella tularensis O-Antigen Antibodies at the Low End of Antigen Reactivity," *Monoclonal Antibodies in Immunodiagnosis and Immunotherapy* 33(4): 235-45, (2014). 11 Pages.
Lu, Z., et al., "Protective B-cell epitopes of Francisella tularensis O-polysaccharide in a mouse model of respiratory tularaemia," *Immunology* vol. 136(3): p. 352-360, (2012).
McCormick, A.A, et al., "Intranasal administration of a two-dose adjuvanted multiantigen TMV-subunit conjugate vaccine fully protects mice against Francisella tularensis LVS challenge," *PLoS One* vol. 13(4): p. e0194614, (Apr. 2018). 21 Pages.
Mikalsen, J., et al., "*Francisella asiatica* sp. nov. isolated from farmed tilapia (*Oreochromis* sp.) and elevation of *Francisella philomiragia* subsp. *Noatunensis* to species rank as *Francisella noatunensis* comb. nov., sp. Nov.," Int J Syst Evol Micro biol, (Sep. 25, 2009). Abstract Only.
Nair, A.B., et al., "A simple practice guide for dose conversion between animals and human," *J Basic Clin Pharm* ol. 7(2): p. 27-31, (2016). 5 pages.
Okan, N.A., et al., "The atypical lipopolysaccharide of Francisella," *Carbohydr Res*. 378: 79-83. (Aug. 2013). 11 Pages.
Ottem, K.F., et al., "Elevation of *Francisella philomiragia* subsp. *noatunensis* Mikalsen et al. (2007) to *Francisella noatunensis* comb. nov. [syn.Francisella piscicida Ottem et al. (2008) syn. nov.] and characterization of *Francisella noatunensis* subsp. *orientalis* subsp. nov., two important fish pathogens." *J Appl Microbial* vol. 106(4): p. 1231-43, (2009). 13 pages.
Pearson, W.R., et al., Improved tools for biological sequence comparison. *Proc Natl Acad Sci USA* vol. 85(8): p. 2444-8. (1988). 5 Pages.
Pearson, W.R., "Searching protein sequence libraries: comparison of the sensitivity and selectivity of the Smith-Waterman and FASTA algorithms," Genomics vol. 11(3): p. 635-50, (1991). 16 Pages.
Post, D.M.B., et al., "Characterization of Inner and Outer Membrane Proteins from Francisella tularensis Strains LVS and Schu S4 and Identification of Potential Subunit Vaccine Candidates," *MBio* vol. 8(5), (Oct. 2017). 11 Pages.
Prior, J.L., et al., "Characterization of the O antigen gene cluster and structural analysis of the O antigen of *Francisella tularensis* subsp. Tularensis," *J Med Microbial* vol. 52: p. 845-51, (2003). 7 Pages.
Pupo, E., et al., "Complexity and solutions to the isolation problem of Gram negative lipopolysaccharides' bacteria molecular species," *Biotecnologia Aplicada* vol. 26(1): pp. 9-15, (2009). 7 Pages.
Qu, P.H., et al., "*Francisella guangzhouensis* sp. nov., isolated from air-conditioning Systems," *Int J Syst Evol Microbial* vol. 63(Pt 10): p. 3628-35, (2013). 8 Pages.
Rezania, S., et al., "Extraction, Purification and Characterization of Lipopolysaccharide from *Escherichia coli* and *Salmonella typhi,*" *Avicenna J Med Biotechnol* vol. 3(1): p. 3-9, (2011). 7 Pages.
Ridley, B.L., et al., "The type and yield of lipopolysaccharide from symbiotically deficient rhizobium lipopolysaccharide mutants vary depending on the extraction method," Glycobiology vol. 10(10): p. 1013-23, (2000). 11 Pages.
Roche, M.I., et al., "Characterization of monoclonal antibodies to terminal and internal 0-antigen epitopes of Francisella tularensis lipopolysaccharide," Hybridoma (Larchmt) vol. 30(1): p. 19-28, (2011). 10 Pages.
Rodriguez., S.A., et al., "Targeted Inactivation of Francisella tularensis Genes by Group II Introns," *Appl. Environmental MicroBio*. 74(9); pp. 2619-2626, (May 2008). 8 pages.
Rynkiewicz, M.J., et al., "Structural analysis of a protective epitope of the Francisella tularensis 0-polysaccharide," *Biochemistry* vol. 51 (28): p. 5684-5694, (2012). 24 pages.
Schilling, B., et al., "Characterization of lipid A acylation patterns in Francisella tularensis, Francisella novicida, and Francisella philomiragia using multiple-stage mass spectrometry and matrix-assisted laser desorption/ionization on an intermediate vacuum source linear ion trap," Anal Chem vol. 79(3): p. 1034-42, (2007). 9 Pages.
Smith, T.F., et al., Identification of common molecular subsequences. *J Mol Biol*. vol. 147(1): p. 195-7, (1981). 4 Pages.
Stead, C.M., et al., "Removal of the outer Kdo from Helicobacter pylori lipopolysaccharide and its impact on the bacterial surface," *Molecular microbiology* vol. 78(4): p. 837-852, (Nov. 2010). 25 Pages.
Sun, P., et al., "New protein fold revealed by a 1.65 A resolution crystal structure of Francisella tularensis pathogenicity island protein IgIC," Protein Sci. vol. 16(11): p. 2560-3, (2007). 4 Pages.
Thomas, R.M., et al., "The immunologically distinct O antigensfrom *Francisella tularensis* subspecies *tularensis* and Francisella novicida areboth virulence determinants and protective antigens," Infect Immun vol. 75(1): p. 371-8, (Jan. 2007). 8 Pages.
Watanabe, S., et al., "Liposomal lipopolysaccharide initiates TRIF-dependent signaling pathway independent of CD14," PLoS One, vol. 8(4): p. e60078, (Apr. 2013). 7 Pages.
Whelan A.O., et al., "Protection induced by a Francisella tularensis subunit vaccine delivered by glucan particles," *PLoS One* 13(10): e0200213, (Oct. 2018). 30 Pages.
Zhao, J., et al., "A two-component Kdo hydrolase in the inner membrane of Francisella novicida," *Molecular microbiology* vol. 78(4): p. 820-836, (2010). 17 Pages.
Conlan, J.W., et al. "Mice vaccinated with the O-antigen of Francisella tularensis LVS lipopolysaccharide conjugated to bovine serum albumin develop varying degrees of protective immunity against systemic or aerosol challenge with virulent type A and type B strains of the pathogen", Vaccine, 20 (2002), pp. 3465-3471.
Fulop, M. et al. "Role of antibody to lipopolysaccharide in protection against low- and high-virulence strains of Francisella tularensis", Vaccine, 19 (2001), pp. 4465-4472.
Fulop, M. et al. "Role of lipopolysaccharide and a major outer membrane protein from Francisella tularensis in the induction of immunity against tularemia", Vaccine, vol. 13,No. 13(1995), pp. 1220-1225.

* cited by examiner

FIG. 5A
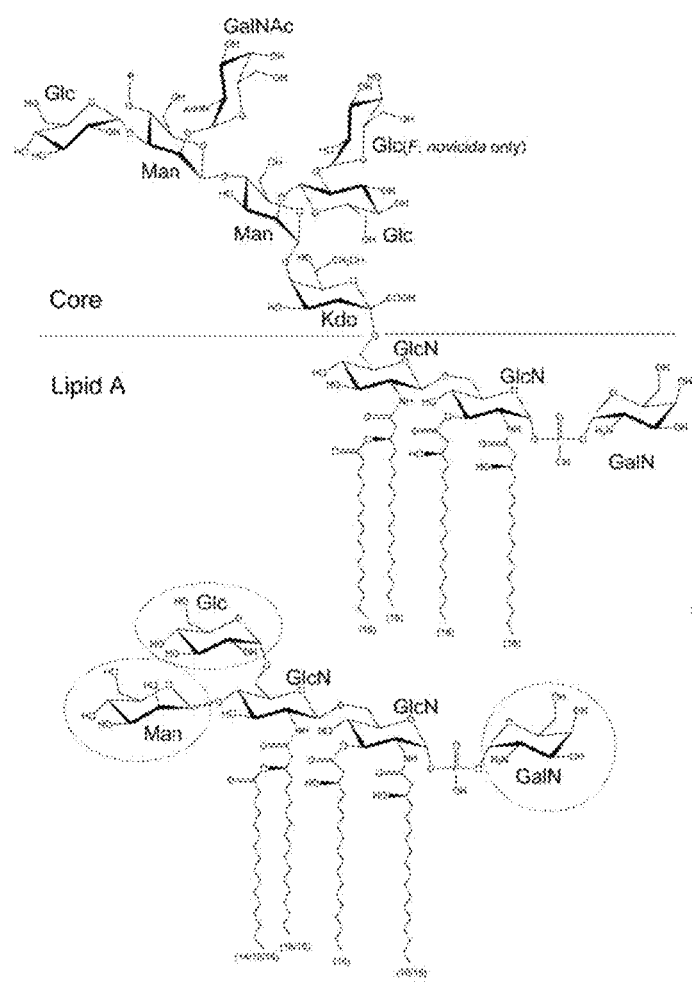
FIG. 5B
FIG. 5C
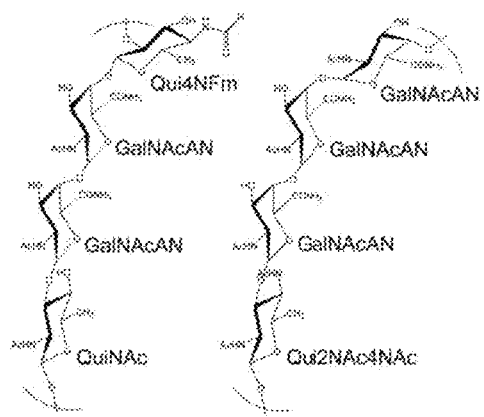
FIG. 5D
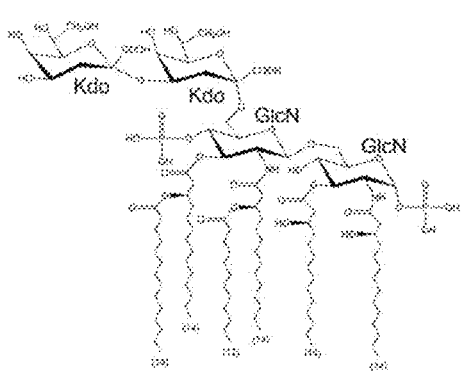
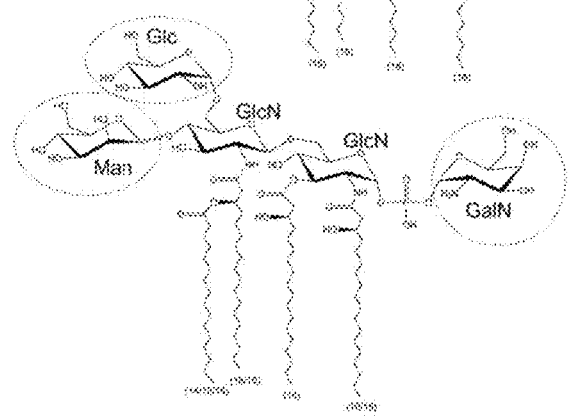
FIG. 5E

*F. tularensis* LVS lipid A

FIG. 6

| Search Parameters | |
|---|---|
| Program | blastp |
| Word size | 3 |
| Expect value | 10 |
| Hitlist size | 500 |
| Gapcosts | 11,1 |
| Matrix | BLOSUM62 |
| Filter string | F |
| Genetic Code | 1 |
| Window Size | 40 |
| Threshold | 11 |
| Composition-based state | 2 |

| Database | |
|---|---|
| Posted date | Apr 3, 2019 2:24 AM |
| Number of letters | 62,356,884 |
| Number of sequences | 73,403 |
| Entrez query | Includes: Francisellaceae (taxid:34064) |
| | Excludes: uncultured/environmental sample sequences |

FIG. 26

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_103205 | WP_003022149.1 | 100 | 211 | 0 | 0 | 1 | 211 | 1 | 211 | 9.95E-155 | 427 | 100 |
| Query_103205 | WP_014367985.1 | 100 | 209 | 0 | 0 | 3 | 211 | 1 | 209 | 3.57E-153 | 423 | 100 |
| Query_103205 | WP_003017834.1 | 99.052 | 211 | 2 | 0 | 1 | 211 | 1 | 211 | 3.60E-153 | 423 | 99.53 |
| Query_103205 | CAA70085.1 | 99.043 | 209 | 2 | 0 | 3 | 211 | 1 | 209 | 1.46E-151 | 419 | 99.52 |
| Query_103205 | WP_080555373.1 | 97.156 | 211 | 6 | 0 | 1 | 211 | 1 | 211 | 1.26E-150 | 417 | 99.53 |
| Query_103205 | WP_014548675.1 | 97.129 | 209 | 6 | 0 | 3 | 211 | 1 | 209 | 4.68E-149 | 412 | 99.52 |
| Query_103205 | WP_088821456.1 | 95.735 | 211 | 9 | 0 | 1 | 211 | 1 | 211 | 3.04E-147 | 408 | 98.1 |
| Query_103205 | WP_035736493.1 | 95.694 | 209 | 9 | 0 | 3 | 211 | 1 | 209 | 6.32E-146 | 405 | 98.09 |
| Query_103205 | 2QWU_A | 96.19 | 210 | 8 | 0 | 2 | 211 | 2 | 211 | 7.58E-146 | 405 | 96.19 |
| Query_103205 | WP_003034531.1 | 90.521 | 211 | 20 | 0 | 1 | 211 | 1 | 211 | 1.47E-140 | 391 | 96.21 |
| Query_103205 | WP_084387526.1 | 90.047 | 211 | 21 | 0 | 1 | 211 | 1 | 211 | 1.70E-140 | 391 | 96.21 |
| Query_103205 | EET21129.1 | 90.995 | 211 | 19 | 0 | 1 | 211 | 1 | 211 | 2.07E-139 | 388 | 94.31 |
| Query_103205 | AJI45477.1 | 90.431 | 209 | 20 | 0 | 3 | 211 | 1 | 209 | 3.56E-139 | 388 | 96.17 |
| Query_103205 | OIN84828.1 | 89.952 | 209 | 21 | 0 | 3 | 211 | 1 | 209 | 4.63E-139 | 387 | 96.17 |
| Query_103205 | WP_094888840.1 | 89.573 | 211 | 22 | 0 | 1 | 211 | 1 | 211 | 6.55E-138 | 385 | 94.31 |
| Query_103205 | WP_035722451.1 | 90.909 | 209 | 19 | 0 | 3 | 211 | 1 | 209 | 7.68E-138 | 384 | 94.26 |
| Query_103205 | WP_042517844.1 | 90.909 | 209 | 19 | 0 | 3 | 211 | 1 | 209 | 8.67E-138 | 384 | 94.74 |
| Query_103205 | WP_114729686.1 | 89.1 | 211 | 23 | 0 | 1 | 211 | 1 | 211 | 1.51E-137 | 384 | 94.79 |
| Query_103205 | WP_912280721.1 | 90.431 | 209 | 20 | 0 | 3 | 211 | 1 | 209 | 4.96E-137 | 382 | 93.78 |
| Query_103205 | WP_114702023.1 | 88.626 | 211 | 24 | 0 | 1 | 211 | 1 | 211 | 9.21E-137 | 382 | 94.31 |
| Query_103205 | WP_071628792.1 | 89.474 | 209 | 22 | 0 | 3 | 211 | 1 | 209 | 1.27E-136 | 381 | 95.22 |
| Query_103205 | WP_014714932.1 | 89.474 | 209 | 22 | 0 | 3 | 211 | 1 | 209 | 2.49E-136 | 380 | 94.26 |
| Query_103205 | WP_913922767.1 | 89.474 | 209 | 22 | 0 | 3 | 211 | 1 | 209 | 2.35E-135 | 378 | 94.74 |
| Query_103205 | ACA58076.1 | 87.981 | 208 | 25 | 0 | 3 | 210 | 1 | 208 | 2.38E-134 | 375 | 93.75 |
| Query_103205 | WP_064460842.1 | 84.541 | 207 | 32 | 0 | 3 | 209 | 1 | 207 | 1.04E-128 | 361 | 93.24 |
| Query_103205 | WP_119331267.1 | 82.464 | 211 | 37 | 0 | 1 | 211 | 1 | 211 | 3.83E-117 | 332 | 90.05 |
| Query_103205 | ACB59232.1 | 83.158 | 190 | 32 | 0 | 6 | 195 | 1 | 190 | 2.33E-115 | 327 | 92.11 |
| Query_103205 | WP_071663793.1 | 81.818 | 209 | 38 | 0 | 3 | 211 | 1 | 209 | 2.63E-115 | 327 | 89.95 |
| Query_103205 | WP_040009617.1 | 66.184 | 207 | 70 | 0 | 5 | 211 | 4 | 210 | 8.25E-95 | 275 | 83.09 |
| Query_103205 | WP_112869164.1 | 58.173 | 208 | 86 | 1 | 3 | 209 | 1 | 208 | 3.77E-89 | 261 | 77.88 |
| Query_103205 | WP_072712866.1 | 33.654 | 208 | 129 | 5 | 7 | 207 | 4 | 209 | 1.45E-30 | 112 | 56.73 |

FIG. 27A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_29468 | WP_003021930.1 | 100 | 642 | 0 | 0 | 1 | 642 | 1 | 642 | 0 | 1294 | 100 |
| Query_29468 | WP_003025465.1 | 99.688 | 642 | 2 | 0 | 1 | 642 | 1 | 642 | 0 | 1292 | 100 |
| Query_29468 | WP_025329380.1 | 99.533 | 642 | 3 | 0 | 1 | 642 | 1 | 642 | 0 | 1289 | 99.84 |
| Query_29468 | WP_004337259.1 | 99.688 | 642 | 2 | 0 | 1 | 642 | 1 | 642 | 0 | 1288 | 99.84 |
| Query_29468 | WP_003016262.1 | 99.533 | 642 | 3 | 0 | 1 | 642 | 1 | 642 | 0 | 1288 | 99.84 |
| Query_29468 | WP_104926592.1 | 99.377 | 642 | 4 | 0 | 1 | 642 | 1 | 642 | 0 | 1287 | 99.84 |
| Query_29468 | WP_071514203.1 | 99.221 | 642 | 5 | 0 | 1 | 642 | 1 | 642 | 0 | 1286 | 99.84 |
| Query_29468 | WP_003040064.1 | 99.377 | 642 | 4 | 0 | 1 | 642 | 1 | 642 | 0 | 1286 | 99.69 |
| Query_29468 | WP_032729579.1 | 99.376 | 641 | 4 | 0 | 1 | 641 | 1 | 641 | 0 | 1286 | 99.84 |
| Query_29468 | WP_061317835.1 | 99.377 | 642 | 4 | 0 | 1 | 642 | 1 | 642 | 0 | 1285 | 99.69 |
| Query_29468 | P48205.1 | 99.221 | 642 | 5 | 0 | 1 | 642 | 1 | 642 | 0 | 1285 | 99.69 |
| Query_29468 | WP_071304574.1 | 99.221 | 642 | 5 | 0 | 1 | 642 | 1 | 642 | 0 | 1285 | 99.69 |
| Query_29468 | WP_012429572.1 | 99.221 | 642 | 5 | 0 | 1 | 642 | 1 | 642 | 0 | 1284 | 99.84 |
| Query_29468 | WP_071660127.1 | 99.221 | 642 | 5 | 0 | 1 | 642 | 1 | 642 | 0 | 1283 | 99.53 |
| Query_29468 | WP_004339671.1 | 99.22 | 641 | 5 | 0 | 1 | 641 | 1 | 641 | 0 | 1282 | 99.53 |
| Query_29468 | WP_014548646.1 | 98.442 | 642 | 10 | 0 | 1 | 642 | 1 | 642 | 0 | 1276 | 99.38 |
| Query_29468 | WP_066046462.1 | 98.287 | 642 | 11 | 0 | 1 | 642 | 1 | 642 | 0 | 1274 | 99.22 |
| Query_29468 | ORM38778.1 | 96.88 | 641 | 20 | 0 | 1 | 641 | 1 | 641 | 0 | 1258 | 98.91 |
| Query_29468 | WP_071628822.1 | 96.568 | 641 | 22 | 0 | 1 | 641 | 1 | 641 | 0 | 1256 | 98.6 |
| Query_29468 | OEZ33366.1 | 96.573 | 642 | 22 | 0 | 1 | 642 | 1 | 642 | 0 | 1253 | 98.75 |
| Query_29468 | WP_064461309.1 | 96.885 | 642 | 16 | 1 | 1 | 642 | 1 | 638 | 0 | 1252 | 98.44 |
| Query_29468 | WP_035736443.1 | 95.794 | 642 | 27 | 0 | 1 | 642 | 1 | 642 | 0 | 1207 | 98.6 |
| Query_29468 | WP_133942439.1 | 92.056 | 642 | 51 | 0 | 1 | 642 | 1 | 642 | 0 | 1202 | 96.57 |
| Query_29468 | WP_035719931.1 | 91.9 | 642 | 52 | 0 | 1 | 642 | 1 | 642 | 0 | 1199 | 96.42 |
| Query_29468 | WP_040006431.1 | 91.745 | 642 | 53 | 0 | 1 | 642 | 1 | 642 | 0 | 1184 | 96.88 |
| Query_29468 | WP_039124325.1 | 92 | 625 | 50 | 0 | 1 | 625 | 1 | 625 | 0 | 1169 | 95.52 |
| Query_29468 | WP_042517891.1 | 96.106 | 642 | 25 | 0 | 1 | 642 | 1 | 642 | 0 | 1165 | 98.75 |
| Query_29468 | WP_004287426.1 | 95.95 | 642 | 26 | 0 | 1 | 642 | 1 | 642 | 0 | 1165 | 98.91 |
| Query_29468 | WP_012280751.1 | 95.95 | 642 | 26 | 0 | 1 | 642 | 1 | 642 | 0 | 1164 | 98.91 |
| Query_29468 | WP_119330811.1 | 93.223 | 605 | 41 | 0 | 1 | 605 | 1 | 605 | 0 | 1163 | 97.85 |
| Query_29468 | WP_088821437.1 | 96.5 | 600 | 21 | 0 | 1 | 600 | 1 | 600 | 0 | 1162 | 98.83 |
| Query_29468 | WP_071664484.1 | 93.058 | 605 | 42 | 0 | 1 | 605 | 1 | 605 | 0 | 1159 | 97.52 |
| Query_29468 | WP_013922807.1 | 94.548 | 642 | 35 | 0 | 1 | 642 | 1 | 642 | 0 | 1153 | 97.66 |
| Query_29468 | WP_044526543.1 | 94.548 | 642 | 35 | 0 | 1 | 642 | 1 | 642 | 0 | 1151 | 98.6 |
| Query_29468 | WP_014714552.1 | 94.081 | 642 | 38 | 0 | 1 | 642 | 1 | 642 | 0 | 1147 | 98.44 |
| Query_29468 | WP_088772058.1 | 90.513 | 643 | 60 | 1 | 1 | 642 | 1 | 643 | 0 | 1147 | 94.71 |
| Query_29468 | WP_112869814.1 | 90.187 | 642 | 63 | 0 | 1 | 642 | 1 | 642 | 0 | 1138 | 95.48 |
| Query_29468 | WP_072711799.1 | 92.835 | 642 | 46 | 0 | 1 | 642 | 1 | 642 | 0 | 1137 | 97.2 |
| Query_29468 | ADG86429.1 | 71.184 | 642 | 181 | 4 | 1 | 642 | 1 | 638 | 0 | 908 | 83.33 |
| Query_29468 | ADG86428.1 | 71.028 | 642 | 181 | 4 | 1 | 641 | 1 | 638 | 0 | 900 | 85.83 |
| Query_29468 | PZU05381.1 | 67.683 | 656 | 194 | 7 | 1 | 642 | 1 | 652 | 0 | 889 | 81.86 |
| Query_29468 | AWX41139.1 | 97.611 | 293 | 7 | 0 | 38 | 330 | 1 | 293 | 0 | 585 | 98.98 |
| Query_29468 | AWX41141.1 | 95.222 | 293 | 14 | 0 | 38 | 330 | 1 | 293 | 0 | 574 | 98.98 |

FIG. 28A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_39701 | WP_003020782.1 | 100 | 417 | 0 | 0 | 1 | 417 | 1 | 417 | 0 | 846 | 100 |
| Query_39701 | WP_003014506.1 | 99.76 | 417 | 1 | 0 | 1 | 417 | 1 | 417 | 0 | 845 | 100 |
| Query_39701 | WP_003026584.1 | 99.52 | 417 | 2 | 0 | 1 | 417 | 1 | 417 | 0 | 844 | 100 |
| Query_39701 | WP_014549353.1 | 99.52 | 417 | 2 | 0 | 1 | 417 | 1 | 417 | 0 | 843 | 100 |
| Query_39701 | WP_003018363.1 | 99.281 | 417 | 3 | 0 | 1 | 417 | 1 | 417 | 0 | 842 | 100 |
| Query_39701 | WP_071304009.1 | 99.281 | 417 | 3 | 0 | 1 | 417 | 1 | 417 | 0 | 842 | 100 |
| Query_39701 | WP_003035501.1 | 99.281 | 417 | 3 | 0 | 1 | 417 | 1 | 417 | 0 | 841 | 99.76 |
| Query_39701 | WP_003038361.1 | 99.281 | 417 | 3 | 0 | 1 | 417 | 1 | 417 | 0 | 841 | 99.76 |
| Query_39701 | WP_003033016.1 | 99.041 | 417 | 4 | 0 | 1 | 417 | 1 | 417 | 0 | 840 | 99.52 |
| Query_39701 | WP_071660085.1 | 99.041 | 417 | 4 | 0 | 1 | 417 | 1 | 417 | 0 | 838 | 99.76 |
| Query_39701 | WP_104929157.1 | 98.801 | 417 | 5 | 0 | 1 | 417 | 1 | 417 | 0 | 837 | 99.28 |
| Query_39701 | EDZ90079.1 | 99.02 | 408 | 4 | 0 | 10 | 417 | 1 | 408 | 0 | 820 | 99.51 |
| Query_39701 | WP_085124407.1 | 99.748 | 397 | 1 | 0 | 1 | 397 | 1 | 397 | 0 | 808 | 100 |
| Query_39701 | WP_066465739.1 | 94.484 | 417 | 23 | 0 | 1 | 417 | 1 | 417 | 0 | 803 | 97.12 |
| Query_39701 | WP_014547642.1 | 94.245 | 417 | 24 | 0 | 1 | 417 | 1 | 417 | 0 | 801 | 96.88 |
| Query_39701 | OEZ33591.1 | 87.56 | 418 | 51 | 1 | 1 | 417 | 1 | 418 | 0 | 759 | 96.89 |
| Query_39701 | WP_064461395.1 | 87.56 | 418 | 51 | 1 | 1 | 417 | 1 | 418 | 0 | 757 | 96.17 |
| Query_39701 | ORM39009.1 | 87.56 | 418 | 51 | 1 | 1 | 417 | 1 | 418 | 0 | 754 | 96.17 |
| Query_39701 | WP_071629645.1 | 87.901 | 405 | 48 | 1 | 14 | 417 | 14 | 418 | 0 | 740 | 97.78 |
| Query_39701 | WP_010031851.1 | 99.725 | 363 | 1 | 0 | 1 | 363 | 1 | 363 | 0 | 733 | 100 |
| Query_39701 | WP_042524452.1 | 76.316 | 418 | 98 | 1 | 1 | 417 | 1 | 418 | 0 | 665 | 88.52 |
| Query_39701 | WP_012279961.1 | 76.555 | 418 | 97 | 1 | 1 | 417 | 1 | 418 | 0 | 665 | 88.52 |
| Query_39701 | WP_088820857.1 | 76.316 | 418 | 98 | 1 | 1 | 417 | 1 | 418 | 0 | 663 | 88.28 |
| Query_39701 | WP_035735050.1 | 76.316 | 418 | 98 | 1 | 1 | 417 | 1 | 418 | 0 | 663 | 88.28 |
| Query_39701 | WP_004286503.1 | 76.077 | 418 | 99 | 1 | 1 | 417 | 1 | 418 | 0 | 663 | 88.28 |
| Query_39701 | WP_042515882.1 | 76.077 | 418 | 99 | 1 | 1 | 417 | 1 | 418 | 0 | 661 | 88.28 |
| Query_39701 | WP_044525619.1 | 76.077 | 418 | 99 | 1 | 1 | 417 | 1 | 418 | 0 | 659 | 88.28 |
| Query_39701 | WP_013922151.1 | 74.762 | 420 | 101 | 3 | 1 | 417 | 1 | 418 | 0 | 648 | 88.1 |
| Query_39701 | WP_014714420.1 | 74.641 | 418 | 105 | 1 | 1 | 417 | 1 | 418 | 0 | 646 | 87.8 |
| Query_39701 | WP_046009048.1 | 68.692 | 428 | 123 | 3 | 1 | 417 | 1 | 428 | 0 | 624 | 86.92 |
| Query_39701 | WP_072711384.1 | 67.453 | 424 | 131 | 2 | 1 | 417 | 1 | 424 | 0 | 605 | 85.14 |
| Query_39701 | WP_088773160.1 | 65.094 | 424 | 141 | 2 | 1 | 417 | 1 | 424 | 0 | 590 | 84.67 |
| Query_39701 | WP_133941060.1 | 66.746 | 418 | 134 | 3 | 1 | 417 | 1 | 414 | 0 | 588 | 84.21 |
| Query_39701 | WP_035721332.1 | 67.225 | 418 | 132 | 3 | 1 | 417 | 1 | 414 | 0 | 587 | 83.97 |
| Query_39701 | KEI34757.1 | 69.898 | 392 | 116 | 2 | 27 | 417 | 2 | 392 | 0 | 580 | 86.48 |
| Query_39701 | WP_039122941.1 | 65.311 | 418 | 140 | 3 | 1 | 417 | 1 | 414 | 0 | 576 | 84.69 |
| Query_39701 | WP_112869377.1 | 63.549 | 417 | 146 | 2 | 1 | 417 | 1 | 411 | 0 | 563 | 84.17 |
| Query_39701 | WP_071663134.1 | 51.699 | 412 | 190 | 5 | 5 | 415 | 9 | 412 | 2.17E-150 | 433 | 71.84 |
| Query_39701 | WP_119329848.1 | 51.942 | 412 | 189 | 6 | 5 | 415 | 9 | 412 | 1.90E-149 | 430 | 72.09 |
| Query_39701 | KHS51617.1 | 99.512 | 205 | 1 | 0 | 1 | 205 | 1 | 205 | 6.30E-147 | 416 | 100 |
| Query_39701 | ORU24913.1 | 99.476 | 191 | 1 | 0 | 1 | 191 | 1 | 191 | 8.69E-135 | 384 | 100 |
| Query_39701 | AFU48858.1 | 100 | 152 | 0 | 0 | 57 | 208 | 1 | 152 | 4.72E-105 | 307 | 100 |
| Query_39701 | AFU48860.1 | 100 | 144 | 0 | 0 | 65 | 208 | 1 | 144 | 1.71E-98 | 290 | 100 |
| Query_39701 | ORU24547.1 | 100 | 135 | 0 | 0 | 283 | 417 | 1 | 135 | 5.77E-93 | 276 | 100 |
| Query_39701 | KHS55373.1 | 100 | 132 | 0 | 0 | 286 | 417 | 1 | 132 | 2.06E-90 | 270 | 100 |
| Query_39701 | AFU48859.1 | 100 | 131 | 0 | 0 | 57 | 187 | 1 | 131 | 9.77E-88 | 263 | 100 |
| Query_39701 | ORU21639.1 | 100 | 102 | 0 | 0 | 187 | 288 | 1 | 102 | 1.79E-67 | 209 | 100 |
| Query_39701 | AFU48861.1 | 100 | 96 | 0 | 0 | 88 | 183 | 1 | 96 | 5.96E-61 | 192 | 100 |

FIG. 29A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_313085 | WP_003019797.1 | 100 | 489 | 0 | 0 | 1 | 489 | 1 | 489 | 0 | 991 | 100 |
| Query_313085 | WP_032731406.1 | 99.796 | 489 | 1 | 0 | 1 | 489 | 1 | 489 | 0 | 989 | 99.8 |
| Query_313085 | WP_011457535.1 | 99.796 | 489 | 1 | 0 | 1 | 489 | 1 | 489 | 0 | 989 | 99.8 |
| Query_313085 | WP_003019657.1 | 99.591 | 489 | 2 | 0 | 1 | 489 | 1 | 489 | 0 | 987 | 99.8 |
| Query_313085 | WP_012429097.1 | 99.591 | 489 | 2 | 0 | 1 | 489 | 1 | 489 | 0 | 986 | 99.59 |
| Query_313085 | WP_003037689.1 | 99.387 | 489 | 3 | 0 | 1 | 489 | 1 | 489 | 0 | 985 | 99.39 |
| Query_313085 | WP_104928415.1 | 99.182 | 489 | 4 | 0 | 1 | 489 | 1 | 489 | 0 | 983 | 99.18 |
| Query_313085 | WP_003035121.1 | 98.978 | 489 | 5 | 0 | 1 | 489 | 1 | 489 | 0 | 980 | 98.98 |
| Query_313085 | WP_014550261.1 | 98.978 | 489 | 5 | 0 | 1 | 489 | 1 | 489 | 0 | 980 | 98.98 |
| Query_313085 | WP_004339939.1 | 98.773 | 489 | 6 | 0 | 1 | 489 | 1 | 489 | 0 | 978 | 98.77 |
| Query_313085 | WP_071513956.1 | 98.364 | 489 | 8 | 0 | 1 | 489 | 1 | 489 | 0 | 975 | 98.77 |
| Query_313085 | WP_003041240.1 | 98.569 | 489 | 7 | 0 | 1 | 489 | 1 | 489 | 0 | 974 | 98.57 |
| Query_313085 | WP_066045255.1 | 94.274 | 489 | 28 | 0 | 1 | 489 | 1 | 489 | 0 | 939 | 96.93 |
| Query_313085 | WP_014548973.1 | 93.865 | 489 | 30 | 0 | 1 | 489 | 1 | 489 | 0 | 938 | 96.32 |
| Query_313085 | WP_071629792.1 | 91.02 | 490 | 43 | 1 | 1 | 489 | 1 | 490 | 0 | 904 | 94.08 |
| Query_313085 | WP_064461694.1 | 88.776 | 490 | 49 | 2 | 1 | 489 | 1 | 485 | 0 | 873 | 92.65 |
| Query_313085 | WP_013922347.1 | 85.947 | 491 | 66 | 3 | 1 | 489 | 1 | 490 | 0 | 855 | 91.85 |
| Query_313085 | WP_012280375.1 | 85.714 | 490 | 65 | 3 | 1 | 489 | 1 | 486 | 0 | 849 | 91.63 |
| Query_313085 | WP_035737040.1 | 85.714 | 490 | 65 | 3 | 1 | 489 | 1 | 486 | 0 | 849 | 91.63 |
| Query_313085 | WP_088821704.1 | 85.51 | 490 | 66 | 3 | 1 | 489 | 1 | 486 | 0 | 848 | 91.63 |
| Query_313085 | WP_004286997.1 | 85.51 | 490 | 66 | 3 | 1 | 489 | 1 | 486 | 0 | 847 | 91.43 |
| Query_313085 | WP_042516984.1 | 85.306 | 490 | 67 | 3 | 1 | 489 | 1 | 486 | 0 | 847 | 91.63 |
| Query_313085 | WP_044526928.1 | 85.306 | 490 | 66 | 4 | 1 | 489 | 1 | 485 | 0 | 842 | 91.43 |
| Query_313085 | WP_014714633.1 | 84.082 | 490 | 72 | 4 | 1 | 489 | 1 | 485 | 0 | 832 | 90.82 |
| Query_313085 | WP_040009268.1 | 83.027 | 489 | 83 | 0 | 1 | 489 | 1 | 489 | 0 | 819 | 89.57 |
| Query_313085 | WP_072713326.1 | 82.353 | 493 | 83 | 2 | 1 | 489 | 1 | 493 | 0 | 814 | 88.64 |
| Query_313085 | WP_088773255.1 | 80.282 | 497 | 87 | 4 | 1 | 489 | 1 | 494 | 0 | 801 | 87.53 |
| Query_313085 | WP_039123168.1 | 79.31 | 493 | 94 | 4 | 1 | 489 | 1 | 489 | 0 | 793 | 87.02 |
| Query_313085 | WP_035720486.1 | 79.837 | 491 | 94 | 3 | 1 | 489 | 1 | 488 | 0 | 789 | 87.78 |
| Query_313085 | WP_119329635.1 | 79.022 | 491 | 93 | 4 | 1 | 489 | 1 | 483 | 0 | 786 | 87.37 |
| Query_313085 | WP_071663366.1 | 78.615 | 491 | 95 | 4 | 1 | 489 | 1 | 483 | 0 | 781 | 87.17 |
| Query_313085 | WP_133940871.1 | 79.065 | 492 | 100 | 3 | 1 | 489 | 1 | 492 | 0 | 780 | 87.4 |
| Query_313085 | WP_112870698.1 | 77.8 | 491 | 103 | 5 | 1 | 489 | 1 | 487 | 0 | 767 | 86.97 |
| Query_313085 | ORU23621.1 | 100 | 351 | 0 | 0 | 139 | 489 | 1 | 351 | 0 | 714 | 100 |
| Query_313085 | OEZ33039.1 | 90.541 | 370 | 34 | 1 | 121 | 489 | 1 | 370 | 0 | 686 | 95.14 |
| Query_313085 | ORM38404.1 | 90.96 | 354 | 31 | 1 | 137 | 489 | 1 | 354 | 0 | 655 | 94.35 |
| Query_313085 | PZU05201.1 | 50.122 | 409 | 175 | 5 | 104 | 489 | 3 | 405 | 1.10E-136 | 460 | 68.22 |
| Query_313085 | WP_014714760.1 | 31.703 | 511 | 295 | 13 | 22 | 487 | 23 | 524 | 6.75E-63 | 214 | 49.9 |
| Query_313085 | WP_088772031.1 | 31.061 | 528 | 312 | 14 | 1 | 487 | 106 | 622 | 1.40E-62 | 215 | 51.52 |
| Query_313085 | WP_066046550.1 | 31.569 | 510 | 288 | 14 | 26 | 487 | 127 | 623 | 1.47E-62 | 215 | 51.18 |
| Query_313085 | WP_039124051.1 | 29.367 | 521 | 304 | 11 | 22 | 487 | 23 | 534 | 4.16E-62 | 212 | 49.9 |
| Query_313085 | WP_014548838.1 | 31.041 | 509 | 292 | 12 | 26 | 487 | 127 | 623 | 4.72E-62 | 214 | 50.29 |
| Query_313085 | WP_071663733.1 | 31.299 | 508 | 295 | 11 | 26 | 487 | 133 | 632 | 4.96E-61 | 211 | 50.79 |
| Query_313085 | WP_130195327.1 | 30.196 | 510 | 299 | 12 | 26 | 487 | 27 | 527 | 5.01E-61 | 209 | 49.41 |
| Query_313085 | WP_012429229.1 | 30.196 | 510 | 299 | 12 | 26 | 487 | 27 | 527 | 7.37E-61 | 208 | 49.41 |
| Query_313085 | OEZ33168.1 | 31.846 | 493 | 293 | 14 | 26 | 487 | 27 | 507 | 9.17E-61 | 207 | 51.52 |
| Query_313085 | WP_061317611.1 | 29.845 | 516 | 297 | 12 | 26 | 487 | 27 | 531 | 1.38E-60 | 207 | 49.42 |
| Query_313085 | WP_010031779.1 | 29.651 | 516 | 298 | 12 | 26 | 487 | 27 | 531 | 1.82E-60 | 207 | 49.42 |
| Query_313085 | WP_003018356.1 | 29.651 | 516 | 298 | 12 | 26 | 487 | 27 | 531 | 2.24E-60 | 207 | 49.42 |
| Query_313085 | WP_004287209.1 | 31.507 | 511 | 288 | 14 | 26 | 487 | 126 | 623 | 2.25E-60 | 209 | 50.1 |
| Query_313085 | WP_133942526.1 | 30.286 | 525 | 299 | 14 | 22 | 487 | 23 | 539 | 2.43E-60 | 207 | 49.71 |
| Query_313085 | WP_085180322.1 | 29.651 | 516 | 298 | 12 | 26 | 487 | 27 | 531 | 2.51E-60 | 207 | 49.42 |
| Query_313085 | WP_011648578.1 | 29.651 | 516 | 298 | 12 | 26 | 487 | 27 | 531 | 2.51E-60 | 207 | 49.42 |
| Query_313085 | WP_088821606.1 | 31.496 | 508 | 292 | 14 | 26 | 487 | 126 | 623 | 3.19E-60 | 209 | 50.39 |
| Query_313085 | WP_012280566.1 | 30.966 | 507 | 296 | 12 | 26 | 487 | 126 | 623 | 3.26E-60 | 209 | 49.9 |
| Query_313085 | WP_042517550.1 | 31.496 | 508 | 292 | 14 | 26 | 487 | 126 | 623 | 3.57E-60 | 208 | 50.39 |
| Query_313085 | WP_119330869.1 | 31.299 | 508 | 295 | 11 | 26 | 487 | 133 | 632 | 4.43E-60 | 208 | 50.79 |
| Query_313085 | WP_042523893.1 | 30.891 | 505 | 298 | 11 | 26 | 487 | 126 | 622 | 4.88E-60 | 208 | 49.9 |
| Query_313085 | WP_035736788.1 | 31.755 | 507 | 291 | 15 | 26 | 487 | 126 | 622 | 4.98E-60 | 208 | 51.28 |
| Query_313085 | WP_072713148.1 | 31.068 | 515 | 289 | 14 | 26 | 487 | 129 | 630 | 5.00E-60 | 208 | 50.49 |
| Query_313085 | WP_003025969.1 | 30.934 | 514 | 290 | 14 | 26 | 487 | 131 | 631 | 5.41E-60 | 208 | 50 |
| Query_313085 | WP_004339154.1 | 30.724 | 511 | 295 | 14 | 26 | 487 | 131 | 631 | 1.14E-59 | 207 | 50.1 |

FIG. 30A

| | | | | | | | | | | | | |
|---|---|---|---|---|---|---|---|---|---|---|---|---|
| Query_313085 | WP_064460731.1 | 30.223 | 493 | 301 | 12 | 26 | 487 | 27 | 507 | 1.19E-59 | 204 | 51.52 |
| Query_313085 | WP_003040481.1 | 30.214 | 513 | 295 | 12 | 26 | 487 | 131 | 631 | 1.59E-59 | 207 | 49.12 |
| Query_313085 | WP_104928487.1 | 30.214 | 513 | 295 | 12 | 26 | 487 | 131 | 631 | 1.91E-59 | 207 | 49.12 |
| Query_313085 | WP_071660486.1 | 30.214 | 513 | 295 | 12 | 26 | 487 | 131 | 631 | 1.93E-59 | 207 | 49.12 |
| Query_313085 | WP_112869527.1 | 29.249 | 506 | 306 | 11 | 26 | 487 | 126 | 623 | 2.11E-59 | 206 | 51.78 |
| Query_313085 | WP_003037461.1 | 30.739 | 514 | 291 | 14 | 26 | 487 | 131 | 631 | 2.12E-59 | 206 | 49.81 |
| Query_313085 | WP_014550161.1 | 30.739 | 514 | 291 | 14 | 26 | 487 | 131 | 631 | 2.18E-59 | 206 | 49.81 |
| Query_313085 | WP_035721111.1 | 29.658 | 526 | 301 | 13 | 22 | 487 | 23 | 539 | 2.52E-59 | 204 | 49.62 |
| Query_313085 | WP_071304684.1 | 30.739 | 514 | 291 | 14 | 26 | 487 | 131 | 631 | 2.63E-59 | 206 | 49.81 |
| Query_313085 | WP_071514054.1 | 30.739 | 514 | 291 | 14 | 26 | 487 | 131 | 631 | 2.68E-59 | 206 | 49.81 |
| Query_313085 | WP_032729629.1 | 29.961 | 514 | 295 | 13 | 26 | 487 | 131 | 631 | 2.88E-59 | 206 | 50 |
| Query_313085 | WP_040010308.1 | 30.178 | 507 | 298 | 12 | 26 | 487 | 130 | 625 | 5.23E-59 | 205 | 51.08 |
| Query_313085 | WP_003014487.1 | 29.457 | 516 | 299 | 12 | 26 | 487 | 27 | 531 | 5.73E-59 | 203 | 49.22 |
| Query_313085 | WP_044526779.1 | 31.673 | 502 | 294 | 13 | 26 | 487 | 126 | 618 | 2.43E-58 | 203 | 51.2 |
| Query_313085 | WP_003022341.1 | 30.545 | 514 | 292 | 14 | 26 | 487 | 131 | 631 | 4.77E-58 | 203 | 49.61 |
| Query_313085 | WP_071628636.1 | 29.862 | 509 | 300 | 11 | 26 | 487 | 131 | 629 | 1.11E-57 | 202 | 48.53 |
| Query_313085 | ORU24918.1 | 29.079 | 478 | 282 | 10 | 57 | 487 | 3 | 470 | 3.62E-54 | 189 | 48.54 |
| Query_313085 | ORU24951.1 | 100 | 81 | 0 | 0 | 37 | 117 | 1 | 81 | 1.12E-47 | 159 | 100 |
| Query_313085 | AEI35711.1 | 32.692 | 312 | 181 | 8 | 198 | 487 | 58 | 362 | 7.33E-47 | 167 | 55.45 |
| Query_313085 | EET19808.1 | 30.719 | 459 | 253 | 14 | 26 | 432 | 131 | 576 | 8.63E-47 | 171 | 49.46 |

FIG. 30A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_158387 | WP_004337461.1 | 100 | 393 | 0 | 0 | 1 | 393 | 1 | 393 | 0 | 795 | 100 |
| Query_158387 | EET18958.1 | 100 | 392 | 0 | 0 | 2 | 393 | 1 | 392 | 0 | 793 | 100 |
| Query_158387 | WP_012119008.1 | 99.491 | 393 | 2 | 0 | 1 | 393 | 1 | 393 | 0 | 792 | 99.75 |
| Query_158387 | WP_011648727.1 | 99.237 | 393 | 3 | 0 | 1 | 393 | 1 | 393 | 0 | 791 | 99.75 |
| Query_158387 | WP_082265790.1 | 99.237 | 393 | 3 | 0 | 1 | 393 | 1 | 393 | 0 | 791 | 99.75 |
| Query_158387 | WP_003016530.1 | 99.237 | 393 | 3 | 0 | 1 | 393 | 1 | 393 | 0 | 791 | 99.75 |
| Query_158387 | AFX70969.1 | 99.49 | 392 | 2 | 0 | 2 | 393 | 1 | 392 | 0 | 790 | 99.74 |
| Query_158387 | WP_011886549.1 | 99.237 | 393 | 3 | 0 | 1 | 393 | 1 | 393 | 0 | 789 | 99.49 |
| Query_158387 | CAJ79767.1 | 99.235 | 392 | 3 | 0 | 2 | 393 | 1 | 392 | 0 | 788 | 99.74 |
| Query_158387 | AHH46672.1 | 99.235 | 392 | 3 | 0 | 2 | 393 | 1 | 392 | 0 | 788 | 99.74 |
| Query_158387 | WP_084387664.1 | 98.982 | 393 | 4 | 0 | 1 | 393 | 1 | 393 | 0 | 788 | 99.24 |
| Query_158387 | EKM85906.1 | 99.235 | 392 | 3 | 0 | 2 | 393 | 1 | 392 | 0 | 787 | 99.49 |
| Query_158387 | OIN83032.1 | 98.98 | 392 | 4 | 0 | 2 | 393 | 1 | 392 | 0 | 786 | 99.23 |
| Query_158387 | WP_082264147.1 | 98.728 | 393 | 5 | 0 | 1 | 393 | 1 | 393 | 0 | 785 | 98.98 |
| Query_158387 | WP_003033601.1 | 98.728 | 393 | 5 | 0 | 1 | 393 | 1 | 393 | 0 | 784 | 99.24 |
| Query_158387 | ACD31118.1 | 98.724 | 392 | 5 | 0 | 2 | 393 | 1 | 392 | 0 | 783 | 98.98 |
| Query_158387 | WP_003036235.1 | 98.473 | 393 | 6 | 0 | 1 | 393 | 1 | 393 | 0 | 782 | 98.98 |
| Query_158387 | ABK89647.1 | 98.724 | 392 | 5 | 0 | 2 | 393 | 1 | 392 | 0 | 781 | 99.23 |
| Query_158387 | AEB27709.1 | 98.469 | 392 | 6 | 0 | 2 | 393 | 1 | 392 | 0 | 780 | 98.98 |
| Query_158387 | WP_066046377.1 | 97.704 | 392 | 9 | 0 | 2 | 393 | 1 | 392 | 0 | 776 | 98.98 |
| Query_158387 | WP_080555338.1 | 96.438 | 393 | 14 | 0 | 1 | 393 | 1 | 393 | 0 | 770 | 98.47 |
| Query_158387 | AEE26426.1 | 96.429 | 392 | 14 | 0 | 2 | 393 | 1 | 392 | 0 | 767 | 98.47 |
| Query_158387 | WP_003019246.1 | 99.467 | 375 | 2 | 0 | 19 | 393 | 1 | 375 | 0 | 757 | 99.73 |
| Query_158387 | WP_114702149.1 | 92.839 | 391 | 28 | 0 | 1 | 391 | 1 | 391 | 0 | 744 | 96.42 |
| Query_158387 | WP_071629378.1 | 92.821 | 390 | 28 | 0 | 2 | 391 | 1 | 390 | 0 | 741 | 96.41 |
| Query_158387 | ORM39213.1 | 88.718 | 390 | 44 | 0 | 2 | 391 | 1 | 390 | 0 | 711 | 94.62 |
| Query_158387 | WP_064461089.1 | 88.432 | 389 | 45 | 0 | 2 | 390 | 1 | 389 | 0 | 707 | 93.57 |
| Query_158387 | OEZ33784.1 | 87.468 | 391 | 48 | 1 | 2 | 391 | 1 | 391 | 0 | 694 | 92.84 |
| Query_158387 | WP_013923374.1 | 84.359 | 390 | 59 | 1 | 2 | 391 | 1 | 388 | 0 | 664 | 92.31 |
| Query_158387 | AAB60857.1 | 98.802 | 334 | 4 | 0 | 1 | 334 | 1 | 334 | 0 | 663 | 99.1 |
| Query_158387 | EET21740.1 | 83.12 | 391 | 64 | 1 | 1 | 391 | 1 | 389 | 0 | 662 | 92.58 |
| Query_158387 | WP_035722631.1 | 83.077 | 390 | 64 | 1 | 2 | 391 | 1 | 388 | 0 | 659 | 92.56 |
| Query_158387 | WP_012279669.1 | 83.077 | 390 | 64 | 1 | 2 | 391 | 1 | 388 | 0 | 659 | 92.31 |
| Query_158387 | WP_042518746.1 | 82.821 | 390 | 65 | 1 | 2 | 391 | 1 | 388 | 0 | 658 | 92.56 |
| Query_158387 | WP_035735392.1 | 82.821 | 390 | 65 | 1 | 2 | 391 | 1 | 388 | 0 | 657 | 92.31 |
| Query_158387 | WP_088821066.1 | 82.564 | 390 | 66 | 1 | 2 | 391 | 1 | 388 | 0 | 656 | 92.31 |
| Query_158387 | WP_042523020.1 | 82.564 | 390 | 66 | 1 | 2 | 391 | 1 | 388 | 0 | 656 | 92.31 |
| Query_158387 | WP_044525931.1 | 82.821 | 390 | 65 | 1 | 2 | 391 | 1 | 388 | 0 | 655 | 92.05 |
| Query_158387 | WP_014715233.1 | 81.026 | 390 | 72 | 1 | 2 | 391 | 1 | 388 | 0 | 641 | 90.77 |
| Query_158387 | WP_088772132.1 | 76.709 | 395 | 88 | 1 | 1 | 391 | 1 | 395 | 0 | 617 | 88.61 |
| Query_158387 | WP_072711912.1 | 76.203 | 395 | 88 | 3 | 2 | 391 | 1 | 394 | 0 | 604 | 87.34 |
| Query_158387 | 1921195A | 91.369 | 336 | 23 | 3 | 2 | 334 | 1 | 333 | 0 | 602 | 93.15 |
| Query_158387 | WP_040010534.1 | 74.937 | 395 | 94 | 2 | 2 | 391 | 1 | 395 | 0 | 599 | 87.59 |
| Query_158387 | WP_112870437.1 | 70.455 | 396 | 108 | 5 | 2 | 392 | 1 | 392 | 0 | 557 | 83.33 |
| Query_158387 | WP_119329985.1 | 71.212 | 396 | 85 | 3 | 1 | 391 | 1 | 372 | 0 | 541 | 80.56 |
| Query_158387 | WP_133940393.1 | 68.922 | 399 | 108 | 7 | 2 | 390 | 1 | 393 | 0 | 535 | 80.7 |
| Query_158387 | ABI18328.1 | 83.125 | 320 | 52 | 1 | 2 | 321 | 1 | 318 | 0 | 535 | 92.5 |
| Query_158387 | WP_035718634.1 | 68.672 | 399 | 109 | 7 | 2 | 390 | 1 | 393 | 0 | 532 | 80.95 |
| Query_158387 | ABN58779.1 | 82.911 | 316 | 52 | 1 | 2 | 317 | 1 | 314 | 0 | 527 | 92.09 |
| Query_158387 | WP_039124408.1 | 66.915 | 402 | 112 | 7 | 2 | 390 | 1 | 394 | 0 | 521 | 78.36 |
| Query_158387 | ACH73175.1 | 83.571 | 280 | 44 | 1 | 2 | 281 | 1 | 278 | 8.17E-167 | 468 | 91.79 |
| Query_158387 | AAD12748.1 | 99.119 | 227 | 2 | 0 | 1 | 227 | 1 | 227 | 5.90E-160 | 449 | 99.12 |
| Query_158387 | AAT94352.1 | 100 | 217 | 0 | 0 | 1 | 217 | 1 | 217 | 1.37E-154 | 435 | 100 |
| Query_158387 | WP_071664645.1 | 63.027 | 403 | 111 | 7 | 2 | 391 | 1 | 378 | 8.33E-151 | 432 | 73.45 |
| Query_158387 | AAD12748.1 | 83.26 | 227 | 36 | 1 | 1 | 227 | 1 | 225 | 4.15E-135 | 385 | 91.19 |
| Query_158387 | ACU30069.1 | 71.698 | 265 | 65 | 4 | 73 | 327 | 1 | 265 | 5.23E-128 | 369 | 80 |
| Query_158387 | ABC57955.1 | 82.412 | 199 | 33 | 1 | 1 | 199 | 1 | 197 | 6.37E-115 | 333 | 90.95 |
| Query_158387 | CAJ98792.1 | 99.359 | 156 | 1 | 0 | 1 | 156 | 1 | 156 | 4.67E-106 | 309 | 100 |
| Query_158387 | CAJ98795.1 | 98.718 | 156 | 2 | 0 | 1 | 156 | 1 | 156 | 6.12E-105 | 306 | 99.36 |
| Query_158387 | CAJ98803.1 | 98.077 | 156 | 3 | 0 | 1 | 156 | 1 | 156 | 4.41E-104 | 304 | 98.72 |
| Query_158387 | CAJ98793.1 | 98.077 | 156 | 3 | 0 | 1 | 156 | 1 | 156 | 5.25E-104 | 304 | 98.72 |
| Query_158387 | AYC07520.1 | 99.296 | 142 | 1 | 0 | 2 | 143 | 1 | 142 | 3.88E-95 | 281 | 99.3 |

FIG. 31A

| | | | | | | | | | | | | |
|---|---|---|---|---|---|---|---|---|---|---|---|---|
| Query_158387 | AYC07521.1 | 98.592 | 142 | 2 | 0 | 2 | 143 | 1 | 142 | 2.03E-94 | 279 | 98.59 |
| Query_158387 | WP_133940395.1 | 61.983 | 242 | 79 | 6 | 2 | 236 | 1 | 236 | 2.19E-89 | 270 | 74.38 |
| Query_158387 | WP_051686737.1 | 61.983 | 242 | 79 | 6 | 2 | 236 | 1 | 236 | 4.44E-89 | 269 | 74.38 |
| Query_158387 | CAJ98862.1 | 82.051 | 156 | 26 | 1 | 1 | 156 | 1 | 154 | 8.39E-87 | 260 | 92.31 |
| Query_158387 | ADM15007.1 | 99.16 | 119 | 1 | 0 | 1 | 119 | 1 | 119 | 1.75E-77 | 235 | 99.16 |
| Query_158387 | ADM15009.1 | 99.138 | 116 | 1 | 0 | 1 | 116 | 1 | 116 | 2.80E-75 | 229 | 99.14 |
| Query_158387 | AAT94354.1 | 100 | 108 | 0 | 0 | 1 | 108 | 1 | 108 | 1.36E-69 | 214 | 100 |
| Query_158387 | KFJ67792.1 | 42.723 | 213 | 110 | 5 | 8 | 210 | 5 | 215 | 4.66E-48 | 163 | 56.34 |
| Query_158387 | APA83890.1 | 42.254 | 213 | 111 | 5 | 8 | 210 | 5 | 215 | 2.18E-47 | 161 | 55.87 |
| Query_158387 | APC96012.1 | 42.254 | 213 | 111 | 5 | 8 | 210 | 5 | 215 | 2.53E-47 | 161 | 55.87 |
| Query_158387 | ABK90570.1 | 42.254 | 213 | 111 | 5 | 8 | 210 | 5 | 215 | 2.58E-47 | 161 | 55.87 |
| Query_158387 | AJI73303.1 | 41.784 | 213 | 112 | 5 | 8 | 210 | 5 | 215 | 6.24E-47 | 160 | 55.4 |
| Query_158387 | AEE88139.1 | 41.784 | 213 | 112 | 5 | 8 | 210 | 5 | 215 | 8.06E-47 | 160 | 55.4 |
| Query_158387 | ACX32331.1 | 97.436 | 78 | 2 | 0 | 78 | 155 | 1 | 78 | 8.75E-47 | 155 | 100 |
| Query_158387 | OIN84218.1 | 41.784 | 213 | 112 | 5 | 8 | 210 | 5 | 215 | 1.27E-46 | 159 | 55.4 |
| Query_158387 | APC96337.1 | 47.904 | 167 | 65 | 5 | 61 | 211 | 1 | 161 | 3.60E-44 | 151 | 62.87 |
| Query_158387 | WP_119330837.1 | 47.305 | 167 | 66 | 5 | 61 | 211 | 1 | 161 | 1.95E-43 | 149 | 62.28 |
| Query_158387 | ACD31474.1 | 41.589 | 214 | 110 | 7 | 8 | 210 | 5 | 214 | 3.00E-43 | 150 | 55.14 |
| Query_158387 | AEE27088.1 | 46.25 | 160 | 76 | 4 | 61 | 210 | 1 | 160 | 1.42E-40 | 141 | 60 |
| Query_158387 | EDN38454.1 | 45 | 160 | 78 | 4 | 61 | 210 | 1 | 160 | 2.12E-39 | 138 | 59.38 |
| Query_158387 | ABO46063.1 | 44.099 | 161 | 77 | 6 | 61 | 210 | 1 | 159 | 3.21E-35 | 127 | 58.39 |
| Query_158387 | WP_071664761.1 | 50.794 | 126 | 53 | 3 | 95 | 211 | 15 | 140 | 3.26E-34 | 124 | 64.29 |
| Query_158387 | CAJ80315.1 | 44.737 | 152 | 72 | 5 | 69 | 210 | 2 | 151 | 9.10E-33 | 120 | 57.24 |
| Query_158387 | WP_052298578.1 | 48.8 | 125 | 55 | 3 | 95 | 210 | 15 | 139 | 4.47E-32 | 118 | 60.8 |
| Query_158387 | WP_071514896.1 | 48 | 125 | 56 | 3 | 95 | 210 | 15 | 139 | 2.01E-31 | 117 | 60.8 |
| Query_158387 | WP_032728742.1 | 48 | 125 | 56 | 3 | 95 | 210 | 15 | 139 | 2.69E-31 | 116 | 60.8 |
| Query_158387 | WP_032730059.1 | 48 | 125 | 56 | 3 | 95 | 210 | 15 | 139 | 2.98E-31 | 116 | 60.8 |
| Query_158387 | WP_104929213.1 | 48 | 125 | 56 | 3 | 95 | 210 | 15 | 139 | 3.79E-31 | 116 | 60.8 |
| Query_158387 | WP_072713585.1 | 47.458 | 118 | 52 | 2 | 103 | 210 | 25 | 142 | 1.04E-30 | 115 | 63.56 |
| Query_158387 | WP_032732592.1 | 47.2 | 125 | 57 | 3 | 95 | 210 | 15 | 139 | 1.05E-30 | 115 | 60 |
| Query_158387 | WP_043024640.1 | 47.2 | 125 | 57 | 3 | 95 | 210 | 15 | 139 | 1.24E-30 | 114 | 60 |
| Query_158387 | WP_024533564.1 | 47.2 | 125 | 55 | 4 | 95 | 210 | 15 | 137 | 3.91E-29 | 110 | 60 |
| Query_158387 | WP_025329575.1 | 46.4 | 125 | 56 | 4 | 95 | 210 | 15 | 137 | 5.46E-28 | 107 | 59.2 |
| Query_158387 | KFJ36319.1 | 46.825 | 126 | 55 | 5 | 95 | 210 | 5 | 128 | 1.03E-27 | 106 | 59.52 |
| Query_158387 | WP_010032862.1 | 47.2 | 125 | 54 | 5 | 95 | 210 | 15 | 136 | 2.42E-27 | 105 | 60 |
| Query_158387 | WP_003022716.1 | 46.825 | 126 | 55 | 5 | 95 | 210 | 15 | 138 | 2.64E-27 | 105 | 59.52 |
| Query_158387 | WP_032685393.1 | 46.032 | 126 | 56 | 5 | 95 | 210 | 15 | 138 | 1.16E-26 | 104 | 58.73 |

FIG. 31A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_11837 | WP_003020907.1 | 100 | 149 | 0 | 0 | 1 | 149 | 1 | 149 | 2.32E-107 | 302 | 100 |
| Query_11837 | WP_003033116.1 | 99.329 | 149 | 1 | 0 | 1 | 149 | 1 | 149 | 1.42E-106 | 300 | 100 |
| Query_11837 | WP_012429270.1 | 98.658 | 149 | 2 | 0 | 1 | 149 | 1 | 149 | 4.65E-106 | 299 | 100 |
| Query_11837 | WP_003014685.1 | 98.658 | 149 | 2 | 0 | 1 | 149 | 1 | 149 | 8.51E-106 | 298 | 99.33 |
| Query_11837 | WP_014549396.1 | 98.658 | 149 | 2 | 0 | 1 | 149 | 1 | 149 | 9.81E-106 | 298 | 99.33 |
| Query_11837 | WP_061315686.1 | 97.987 | 149 | 3 | 0 | 1 | 149 | 1 | 149 | 6.07E-105 | 296 | 98.66 |
| Query_11837 | WP_042899678.1 | 99.315 | 146 | 1 | 0 | 4 | 149 | 1 | 146 | 1.44E-104 | 295 | 100 |
| Query_11837 | ORU21605.1 | 97.931 | 145 | 3 | 0 | 5 | 149 | 1 | 145 | 2.61E-102 | 289 | 99.31 |
| Query_11837 | WP_071629587.1 | 87.5 | 152 | 16 | 1 | 1 | 149 | 1 | 152 | 1.03E-95 | 273 | 94.74 |
| Query_11837 | WP_003035609.1 | 91.275 | 149 | 2 | 1 | 1 | 149 | 1 | 138 | 1.30E-94 | 270 | 91.95 |
| Query_11837 | WP_066045667.1 | 88.591 | 149 | 16 | 1 | 1 | 149 | 1 | 148 | 8.89E-93 | 265 | 91.95 |
| Query_11837 | WP_014547709.1 | 91.275 | 149 | 12 | 1 | 1 | 149 | 1 | 148 | 1.54E-90 | 259 | 93.29 |
| Query_11837 | AWM99607.1 | 98.413 | 126 | 2 | 0 | 1 | 126 | 1 | 126 | 6.85E-88 | 252 | 100 |
| Query_11837 | ORM39049.1 | 84.211 | 152 | 14 | 2 | 1 | 149 | 1 | 145 | 3.44E-87 | 251 | 89.47 |
| Query_11837 | AWM99603.1 | 97.619 | 126 | 3 | 0 | 1 | 126 | 1 | 126 | 6.08E-87 | 250 | 98.41 |
| Query_11837 | AAR37397.1 | 85.034 | 147 | 12 | 2 | 1 | 144 | 1 | 140 | 3.59E-85 | 246 | 89.8 |
| Query_11837 | AAR37400.1 | 85.034 | 147 | 12 | 2 | 1 | 144 | 1 | 140 | 8.82E-85 | 245 | 89.8 |
| Query_11837 | AAR37408.1 | 84.354 | 147 | 13 | 2 | 1 | 144 | 1 | 140 | 1.48E-84 | 244 | 89.12 |
| Query_11837 | AAR37407.1 | 85.034 | 147 | 12 | 2 | 1 | 144 | 1 | 140 | 2.05E-84 | 244 | 89.12 |
| Query_11837 | AAR37405.1 | 84.354 | 147 | 13 | 2 | 1 | 144 | 1 | 140 | 2.12E-84 | 244 | 89.8 |
| Query_11837 | OEZ33626.1 | 80.537 | 149 | 25 | 1 | 1 | 149 | 1 | 145 | 9.05E-84 | 243 | 88.59 |
| Query_11837 | AAR37403.1 | 83.673 | 147 | 14 | 2 | 1 | 144 | 1 | 140 | 1.12E-83 | 242 | 88.44 |
| Query_11837 | AAR37404.1 | 83.673 | 147 | 14 | 2 | 1 | 144 | 1 | 140 | 1.12E-83 | 242 | 88.44 |
| Query_11837 | AAR37412.1 | 84.354 | 147 | 13 | 2 | 1 | 144 | 1 | 140 | 1.21E-83 | 242 | 89.12 |
| Query_11837 | AAR37406.1 | 84.247 | 146 | 13 | 2 | 1 | 143 | 1 | 139 | 1.23E-83 | 242 | 89.73 |
| Query_11837 | AAR37402.1 | 83.673 | 147 | 14 | 2 | 1 | 144 | 1 | 140 | 5.22E-83 | 240 | 89.12 |
| Query_11837 | AAR37410.1 | 82.993 | 147 | 15 | 2 | 1 | 144 | 1 | 140 | 5.51E-82 | 238 | 87.76 |
| Query_11837 | AAR37398.1 | 84.173 | 139 | 12 | 2 | 1 | 136 | 1 | 132 | 1.16E-78 | 229 | 89.21 |
| Query_11837 | AAO43577.1 | 100 | 110 | 0 | 0 | 25 | 134 | 1 | 110 | 8.02E-78 | 226 | 100 |
| Query_11837 | AEE80937.1 | 81.56 | 141 | 16 | 2 | 1 | 138 | 1 | 134 | 3.72E-77 | 225 | 86.52 |
| Query_11837 | AAP37462.1 | 99.091 | 110 | 1 | 0 | 25 | 134 | 1 | 110 | 4.69E-77 | 224 | 99.09 |
| Query_11837 | ABO87309.1 | 99.091 | 110 | 1 | 0 | 25 | 134 | 1 | 110 | 5.71E-77 | 224 | 99.09 |
| Query_11837 | AEE80939.1 | 80.142 | 141 | 18 | 2 | 1 | 138 | 1 | 134 | 7.10E-76 | 222 | 86.52 |
| Query_11837 | ADQ28102.1 | 81.295 | 139 | 16 | 2 | 1 | 136 | 1 | 132 | 1.45E-75 | 221 | 88.49 |
| Query_11837 | WP_044525678.1 | 73.154 | 149 | 36 | 1 | 1 | 149 | 1 | 145 | 5.59E-75 | 220 | 81.88 |
| Query_11837 | CBK46795.1 | 100 | 106 | 0 | 0 | 21 | 126 | 1 | 106 | 5.81E-74 | 216 | 100 |
| Query_11837 | AAR37399.1 | 83.459 | 133 | 12 | 2 | 1 | 130 | 1 | 126 | 7.02E-74 | 217 | 88.72 |
| Query_11837 | ADQ28101.1 | 79.856 | 139 | 18 | 2 | 1 | 136 | 1 | 132 | 9.13E-74 | 217 | 87.05 |
| Query_11837 | CBK46783.1 | 99.057 | 106 | 1 | 0 | 21 | 126 | 1 | 106 | 3.44E-73 | 214 | 99.06 |
| Query_11837 | WP_014714496.1 | 73.333 | 150 | 34 | 3 | 1 | 149 | 1 | 145 | 5.40E-73 | 215 | 82.67 |
| Query_11837 | WP_064461353.1 | 80.263 | 152 | 20 | 2 | 1 | 149 | 1 | 145 | 8.28E-73 | 215 | 87.5 |
| Query_11837 | WP_013922217.1 | 70.199 | 151 | 38 | 2 | 1 | 149 | 1 | 146 | 2.05E-71 | 211 | 78.81 |
| Query_11837 | WP_040008893.1 | 66.447 | 152 | 48 | 1 | 1 | 149 | 1 | 152 | 2.27E-71 | 211 | 80.26 |
| Query_11837 | WP_012279901.1 | 73.333 | 150 | 35 | 2 | 1 | 149 | 1 | 146 | 2.56E-71 | 211 | 81.33 |
| Query_11837 | ACC76811.1 | 83.594 | 128 | 11 | 2 | 1 | 125 | 1 | 121 | 9.99E-70 | 206 | 87.5 |
| Query_11837 | ADK35102.1 | 84.252 | 127 | 10 | 2 | 1 | 124 | 1 | 120 | 1.79E-69 | 206 | 86.19 |
| Query_11837 | ADM14998.1 | 96.058 | 103 | 2 | 0 | 1 | 103 | 1 | 103 | 2.78E-69 | 204 | 99.03 |
| Query_11837 | ADM14997.1 | 97.087 | 103 | 3 | 0 | 1 | 103 | 1 | 103 | 1.45E-68 | 202 | 98.06 |
| Query_11837 | ACC76810.1 | 83.333 | 126 | 11 | 2 | 1 | 123 | 1 | 119 | 2.20E-68 | 202 | 87.3 |
| Query_11837 | ADM15001.1 | 97.115 | 104 | 2 | 1 | 1 | 103 | 1 | 104 | 1.18E-67 | 200 | 98.08 |
| Query_11837 | ADK35103.1 | 81.102 | 127 | 14 | 2 | 1 | 124 | 1 | 120 | 1.23E-67 | 201 | 87.4 |
| Query_11837 | ABH18327.1 | 70.833 | 144 | 37 | 2 | 1 | 143 | 1 | 140 | 4.86E-67 | 200 | 79.17 |
| Query_11837 | ADG21973.1 | 98 | 100 | 2 | 0 | 1 | 100 | 9 | 108 | 2.15E-66 | 197 | 99 |
| Query_11837 | ABO87311.1 | 89.091 | 110 | 1 | 1 | 25 | 134 | 1 | 99 | 4.63E-66 | 196 | 89.09 |
| Query_11837 | EET20174.1 | 71.223 | 139 | 35 | 2 | 12 | 149 | 1 | 135 | 1.37E-63 | 191 | 79.86 |
| Query_11837 | WP_088773100.1 | 59.603 | 151 | 56 | 1 | 1 | 149 | 1 | 148 | 2.89E-62 | 188 | 78.15 |
| Query_11837 | AMD39429.1 | 97.895 | 95 | 2 | 0 | 1 | 95 | 1 | 95 | 2.19E-61 | 184 | 98.95 |
| Query_11837 | ABN58778.1 | 71.756 | 131 | 32 | 2 | 14 | 143 | 1 | 127 | 3.08E-59 | 180 | 79.39 |
| Query_11837 | WP_072711461.1 | 59.355 | 155 | 57 | 2 | 1 | 149 | 1 | 155 | 3.10E-59 | 181 | 75.48 |
| Query_11837 | WP_112869313.1 | 56.494 | 154 | 59 | 3 | 1 | 149 | 1 | 151 | 2.23E-58 | 179 | 73.38 |
| Query_11837 | ABH10688.1 | 71.318 | 129 | 32 | 2 | 14 | 141 | 1 | 125 | 6.91E-58 | 176 | 79.07 |
| Query_11837 | ADK35101.1 | 81.89 | 127 | 13 | 2 | 1 | 124 | 1 | 120 | 5.88E-57 | 174 | 85.83 |

FIG. 32A

| | | | | | | | | | | | |
|---|---|---|---|---|---|---|---|---|---|---|---|
| Query_11837 | WP_035720081.1 | 57.718 | 149 | 55 | 2 | 1 | 149 | 1 | 141 | 3.04E-56 | 173 | 70.47 |
| Query_11837 | WP_133942189.1 | 57.792 | 154 | 49 | 3 | 1 | 149 | 1 | 143 | 1.31E-55 | 171 | 68.83 |
| Query_11837 | CBK46779.1 | 82.075 | 106 | 16 | 2 | 21 | 126 | 1 | 102 | 2.42E-55 | 169 | 89.62 |
| Query_11837 | WP_039125643.1 | 56.376 | 149 | 61 | 1 | 1 | 149 | 1 | 145 | 5.03E-55 | 170 | 71.14 |
| Query_11837 | CBK46773.1 | 79.817 | 109 | 12 | 2 | 21 | 126 | 1 | 102 | 6.21E-55 | 168 | 86.24 |
| Query_11837 | AAR37411.1 | 75.455 | 110 | 23 | 1 | 1 | 110 | 1 | 106 | 6.48E-53 | 163 | 83.64 |
| Query_11837 | CAJ98810.1 | 87.368 | 95 | 0 | 1 | 1 | 95 | 1 | 83 | 4.49E-51 | 157 | 87.37 |
| Query_11837 | ACF39176.1 | 84 | 100 | 15 | 1 | 1 | 100 | 1 | 99 | 1.41E-50 | 157 | 88 |
| Query_11837 | CAJ98812.1 | 86.316 | 95 | 1 | 1 | 1 | 95 | 1 | 83 | 2.93E-50 | 155 | 87.37 |
| Query_11837 | CAJ98808.1 | 85.263 | 95 | 2 | 1 | 1 | 95 | 1 | 83 | 1.50E-49 | 154 | 86.32 |
| Query_11837 | CAJ98815.1 | 85.263 | 95 | 2 | 1 | 1 | 95 | 1 | 83 | 1.82E-49 | 154 | 86.32 |
| Query_11837 | ACM92001.1 | 98.718 | 78 | 1 | 0 | 15 | 92 | 1 | 78 | 2.58E-49 | 153 | 98.72 |
| Query_11837 | WP_071663082.1 | 52.98 | 151 | 61 | 3 | 1 | 149 | 1 | 143 | 4.17E-49 | 155 | 68.87 |
| Query_11837 | WP_119329891.1 | 52.98 | 151 | 61 | 3 | 1 | 149 | 1 | 143 | 4.86E-49 | 154 | 69.54 |
| Query_11837 | AYU70536.1 | 98.701 | 77 | 1 | 0 | 16 | 92 | 2 | 78 | 1.12E-48 | 151 | 98.7 |
| Query_11837 | ACA83745.1 | 84.783 | 92 | 13 | 1 | 1 | 92 | 1 | 91 | 9.59E-48 | 149 | 88.04 |
| Query_11837 | AFN27214.1 | 79 | 100 | 11 | 2 | 1 | 97 | 1 | 93 | 3.21E-47 | 148 | 85 |
| Query_11837 | AFT63214.1 | 98.667 | 75 | 1 | 0 | 17 | 91 | 1 | 75 | 1.08E-46 | 146 | 98.67 |
| Query_11837 | CAJ98816.1 | 81.053 | 95 | 6 | 1 | 1 | 95 | 1 | 83 | 2.54E-46 | 145 | 83.16 |
| Query_11837 | AAO85265.1 | 86.316 | 95 | 12 | 1 | 1 | 95 | 1 | 94 | 3.98E-46 | 145 | 89.47 |
| Query_11837 | AFT63208.1 | 98.63 | 73 | 1 | 0 | 16 | 88 | 1 | 73 | 4.80E-45 | 142 | 98.63 |
| Query_11837 | AFT63207.1 | 98.63 | 73 | 1 | 0 | 15 | 87 | 1 | 73 | 8.77E-45 | 141 | 98.63 |
| Query_11837 | BAF51613.1 | 100 | 70 | 0 | 0 | 24 | 93 | 1 | 70 | 2.66E-44 | 140 | 100 |
| Query_11837 | AFT63211.1 | 98.611 | 72 | 1 | 0 | 17 | 88 | 1 | 72 | 3.28E-44 | 140 | 98.61 |
| Query_11837 | AHY22324.1 | 98.592 | 71 | 1 | 0 | 19 | 89 | 1 | 71 | 4.99E-44 | 139 | 98.59 |
| Query_11837 | BAF51615.1 | 98.571 | 70 | 1 | 0 | 24 | 93 | 1 | 70 | 1.42E-43 | 138 | 98.57 |
| Query_11837 | BAF51614.1 | 97.143 | 70 | 2 | 0 | 24 | 93 | 1 | 70 | 1.72E-42 | 135 | 97.14 |
| Query_11837 | AFO52510.1 | 83.529 | 85 | 13 | 1 | 1 | 85 | 1 | 84 | 2.92E-41 | 133 | 87.06 |
| Query_11837 | ADE35086.1 | 98.507 | 67 | 1 | 0 | 16 | 82 | 1 | 67 | 4.20E-40 | 129 | 98.51 |
| Query_11837 | CAJ98814.1 | 73.684 | 95 | 13 | 1 | 1 | 95 | 1 | 83 | 1.47E-39 | 129 | 78.95 |
| Query_11837 | CAJ98813.1 | 73.684 | 95 | 13 | 1 | 1 | 95 | 1 | 83 | 3.13E-39 | 128 | 77.89 |
| Query_11837 | AAO85266.1 | 69.792 | 96 | 23 | 3 | 1 | 95 | 1 | 91 | 7.79E-35 | 117 | 77.08 |
| Query_11837 | AII31797.1 | 76.623 | 77 | 8 | 2 | 19 | 92 | 1 | 70 | 2.42E-32 | 110 | 81.82 |
| Query_11837 | ADR80696.1 | 71.795 | 78 | 18 | 1 | 15 | 92 | 1 | 74 | 1.08E-30 | 106 | 79.49 |
| Query_11837 | AHY22327.1 | 75.676 | 74 | 8 | 2 | 19 | 89 | 1 | 67 | 6.01E-30 | 103 | 81.08 |
| Query_11837 | AII31796.1 | 84.507 | 71 | 10 | 1 | 19 | 89 | 1 | 70 | 1.48E-29 | 103 | 85.92 |
| Query_11837 | ACD39780.1 | 77.465 | 71 | 12 | 2 | 19 | 89 | 1 | 67 | 5.52E-29 | 101 | 84.51 |
| Query_11837 | ACD39779.1 | 76.056 | 71 | 13 | 2 | 19 | 89 | 1 | 67 | 3.06E-28 | 99.8 | 83.1 |
| Query_11837 | WP_040010702.1 | 38.854 | 157 | 85 | 4 | 1 | 149 | 1 | 154 | 4.31E-24 | 91.7 | 53.5 |
| Query_11837 | WP_041268144.1 | 37.762 | 143 | 79 | 4 | 1 | 136 | 1 | 140 | 2.25E-23 | 90.1 | 55.24 |
| Query_11837 | ABZ86626.1 | 37.762 | 143 | 79 | 4 | 1 | 136 | 6 | 145 | 2.29E-23 | 90.1 | 55.24 |
| Query_11837 | WP_004286417.1 | 36.709 | 158 | 88 | 5 | 1 | 149 | 1 | 155 | 5.57E-23 | 89 | 53.16 |
| Query_11837 | WP_035735113.1 | 36.076 | 158 | 89 | 5 | 1 | 149 | 1 | 155 | 8.84E-23 | 88.6 | 53.16 |
| Query_11837 | WP_044527099.1 | 37.063 | 143 | 80 | 4 | 1 | 136 | 1 | 140 | 2.38E-22 | 87.4 | 55.94 |
| Query_11837 | AFO52511.1 | 60 | 85 | 29 | 2 | 2 | 85 | 3 | 83 | 3.35E-22 | 84.7 | 69.41 |
| Query_11837 | WP_041257449.1 | 37.063 | 143 | 80 | 4 | 1 | 136 | 1 | 140 | 5.51E-22 | 86.3 | 55.24 |
| Query_11837 | AFJ42951.1 | 37.063 | 143 | 80 | 4 | 1 | 136 | 6 | 145 | 5.78E-22 | 86.7 | 55.24 |
| Query_11837 | WP_072711464.1 | 35.758 | 165 | 86 | 4 | 1 | 149 | 1 | 161 | 1.01E-21 | 85.9 | 49.09 |
| Query_11837 | ALA48985.1 | 97.222 | 36 | 1 | 0 | 74 | 109 | 1 | 36 | 1.27E-21 | 82 | 97.22 |
| Query_11837 | WP_013922220.1 | 37.063 | 143 | 80 | 4 | 1 | 136 | 1 | 140 | 2.80E-21 | 84.7 | 53.15 |
| Query_11837 | WP_035720080.1 | 37.324 | 142 | 80 | 3 | 1 | 136 | 1 | 139 | 3.85E-21 | 84.3 | 50.7 |
| Query_11837 | WP_133942190.1 | 37.324 | 142 | 80 | 3 | 1 | 136 | 1 | 139 | 5.31E-21 | 84 | 50.7 |
| Query_11837 | WP_039125641.1 | 35.915 | 142 | 82 | 3 | 1 | 136 | 1 | 139 | 9.96E-20 | 80.5 | 49.3 |
| Query_11837 | WP_071629584.1 | 33.094 | 139 | 90 | 2 | 1 | 136 | 1 | 139 | 4.61E-19 | 79 | 51.8 |
| Query_11837 | WP_066045558.1 | 33.094 | 139 | 90 | 2 | 1 | 136 | 1 | 139 | 7.71E-19 | 78.2 | 52.52 |
| Query_11837 | OEZ33627.1 | 33.813 | 139 | 89 | 2 | 1 | 136 | 1 | 139 | 1.44E-18 | 77.4 | 51.08 |
| Query_11837 | WP_003014689.1 | 33.094 | 139 | 90 | 2 | 1 | 136 | 1 | 139 | 1.56E-18 | 77.4 | 52.52 |
| Query_11837 | WP_012429271.1 | 33.094 | 139 | 90 | 2 | 1 | 136 | 1 | 139 | 1.61E-18 | 77.4 | 52.52 |
| Query_11837 | WP_014547712.1 | 32.374 | 139 | 91 | 2 | 1 | 136 | 1 | 139 | 1.65E-18 | 77.4 | 52.52 |
| Query_11837 | WP_064461351.1 | 33.803 | 142 | 85 | 3 | 1 | 136 | 1 | 139 | 1.70E-18 | 77.4 | 51.41 |

FIG. 32A continued

| | | | | | | | | | | | | |
|---|---|---|---|---|---|---|---|---|---|---|---|---|
| Query_11837 | WP_003030704.1 | 33.094 | 139 | 90 | 2 | 1 | 136 | 1 | 139 | 1.72E-18 | 77.4 | 52.52 |
| Query_11837 | WP_010032568.1 | 33.094 | 139 | 90 | 2 | 1 | 136 | 1 | 139 | 1.72E-18 | 77.4 | 52.52 |
| Query_11837 | WP_003033124.1 | 33.094 | 139 | 90 | 2 | 1 | 136 | 1 | 139 | 1.94E-18 | 77.4 | 51.8 |
| Query_11837 | ORM39050.1 | 33.094 | 139 | 90 | 2 | 1 | 136 | 1 | 139 | 2.53E-18 | 77 | 50.36 |
| Query_11837 | WP_088773098.1 | 34.694 | 147 | 84 | 3 | 1 | 136 | 1 | 146 | 6.06E-18 | 76.3 | 51.02 |
| Query_11837 | WP_071663084.1 | 31.875 | 160 | 96 | 5 | 1 | 149 | 1 | 158 | 1.38E-17 | 75.1 | 46.25 |
| Query_11837 | WP_112869316.1 | 43.529 | 85 | 46 | 1 | 67 | 149 | 70 | 154 | 9.97E-17 | 72.8 | 62.35 |
| Query_11837 | WP_119329889.1 | 31.25 | 160 | 97 | 5 | 1 | 149 | 1 | 158 | 1.51E-16 | 72.4 | 46.25 |
| Query_11837 | ABN56780.1 | 39.08 | 87 | 52 | 1 | 48 | 133 | 16 | 102 | 6.87E-16 | 69.3 | 62.07 |
| Query_11837 | ABI18329.1 | 37.349 | 83 | 51 | 1 | 48 | 129 | 11 | 93 | 2.01E-13 | 62.8 | 61.45 |
| Query_11837 | ACH73176.1 | 42.647 | 68 | 38 | 1 | 48 | 114 | 10 | 77 | 6.00E-13 | 61.2 | 67.65 |
| Query_11837 | ABF21121.1 | 96.774 | 31 | 1 | 0 | 1 | 31 | 1 | 31 | 1.29E-12 | 58.9 | 100 |
| Query_11837 | ABH10689.1 | 37.037 | 81 | 50 | 1 | 48 | 127 | 10 | 90 | 1.30E-12 | 60.5 | 60.49 |
| Query_11837 | ABI18331.1 | 41.176 | 68 | 39 | 1 | 48 | 114 | 36 | 103 | 8.22E-11 | 56.2 | 58.82 |
| Query_11837 | ADK76214.1 | 96 | 25 | 1 | 0 | 1 | 25 | 1 | 25 | 8.63E-08 | 46.2 | 100 |
| Query_11837 | ACD39784.1 | 78.125 | 32 | 0 | 1 | 19 | 50 | 1 | 25 | 1.14E-06 | 43.5 | 78.12 |
| Query_11837 | ACD39781.1 | 68.75 | 32 | 3 | 1 | 19 | 50 | 1 | 25 | 3.23E-04 | 37 | 71.88 |
| Query_11837 | ACD39783.1 | 65.625 | 32 | 4 | 1 | 19 | 50 | 1 | 25 | 5.04E-04 | 36.2 | 71.88 |

FIG. 32A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_29120 | WP_003015055.1 | 100 | 137 | 0 | 0 | 1 | 137 | 1 | 137 | 3.45E-96 | 273 | 100 |
| Query_29120 | WP_003018179.1 | 99.27 | 137 | 1 | 0 | 1 | 137 | 1 | 137 | 5.66E-96 | 273 | 100 |
| Query_29120 | WP_012429332.1 | 99.27 | 137 | 1 | 0 | 1 | 137 | 1 | 137 | 1.57E-95 | 271 | 99.27 |
| Query_29120 | WP_003034620.1 | 98.54 | 137 | 2 | 0 | 1 | 137 | 1 | 137 | 6.05E-95 | 270 | 99.27 |
| Query_29120 | WP_003037248.1 | 97.81 | 137 | 3 | 0 | 1 | 137 | 1 | 137 | 8.99E-95 | 270 | 99.27 |
| Query_29120 | WP_014550084.1 | 97.81 | 137 | 3 | 0 | 1 | 137 | 1 | 137 | 2.66E-94 | 268 | 98.54 |
| Query_29120 | WP_014548727.1 | 90.511 | 137 | 13 | 0 | 1 | 137 | 1 | 137 | 1.03E-87 | 251 | 95.62 |
| Query_29120 | WP_071628742.1 | 89.781 | 137 | 14 | 0 | 1 | 137 | 1 | 137 | 1.00E-84 | 244 | 91.97 |
| Query_29120 | WP_104928544.1 | 96.35 | 137 | 5 | 0 | 1 | 137 | 1 | 137 | 5.79E-84 | 242 | 97.81 |
| Query_29120 | 2MU4_A | 100 | 112 | 0 | 0 | 26 | 137 | 2 | 113 | 8.18E-78 | 226 | 100 |
| Query_29120 | OEZ33091.1 | 87.402 | 127 | 15 | 1 | 11 | 136 | 3 | 129 | 8.38E-76 | 221 | 92.91 |
| Query_29120 | WP_064460807.1 | 81.481 | 135 | 25 | 0 | 1 | 135 | 1 | 135 | 2.62E-75 | 220 | 87.41 |
| Query_29120 | WP_072712974.1 | 48.872 | 133 | 68 | 0 | 1 | 133 | 1 | 133 | 5.62E-43 | 138 | 72.93 |
| Query_29120 | WP_040010419.1 | 50.36 | 139 | 66 | 1 | 1 | 136 | 1 | 139 | 7.16E-42 | 136 | 69.06 |
| Query_29120 | WP_035736560.1 | 43.478 | 138 | 75 | 1 | 1 | 135 | 1 | 138 | 1.60E-37 | 125 | 67.39 |
| Query_29120 | WP_088772594.1 | 45.185 | 135 | 73 | 1 | 1 | 134 | 1 | 135 | 2.07E-37 | 124 | 65.93 |
| Query_29120 | WP_044526643.1 | 42.754 | 138 | 76 | 1 | 1 | 135 | 1 | 138 | 5.68E-36 | 121 | 65.94 |
| Query_29120 | WP_004287328.1 | 42.029 | 138 | 77 | 1 | 1 | 135 | 1 | 138 | 2.08E-35 | 119 | 66.67 |
| Query_29120 | WP_042517774.1 | 43.478 | 138 | 75 | 1 | 1 | 135 | 1 | 138 | 9.15E-35 | 118 | 66.67 |
| Query_29120 | WP_042523746.1 | 42.029 | 138 | 77 | 1 | 1 | 135 | 1 | 138 | 1.10E-34 | 117 | 65.22 |
| Query_29120 | WP_012280669.1 | 43.478 | 138 | 75 | 1 | 1 | 135 | 1 | 138 | 1.18E-34 | 117 | 66.67 |
| Query_29120 | WP_112869635.1 | 44.118 | 136 | 73 | 1 | 1 | 133 | 1 | 136 | 1.45E-30 | 107 | 66.91 |
| Query_29120 | WP_013922705.1 | 40.406 | 138 | 81 | 2 | 1 | 134 | 1 | 138 | 1.40E-28 | 102 | 64.49 |
| Query_29120 | WP_119331126.1 | 43.411 | 129 | 71 | 1 | 6 | 132 | 4 | 132 | 4.47E-28 | 101 | 63.57 |
| Query_29120 | WP_025329053.1 | 40.909 | 132 | 73 | 3 | 1 | 128 | 1 | 131 | 1.31E-26 | 97.1 | 62.12 |
| Query_29120 | WP_003013963.1 | 40.152 | 132 | 74 | 3 | 1 | 128 | 1 | 131 | 1.51E-26 | 97.1 | 62.12 |
| Query_29120 | WP_010032334.1 | 40.152 | 132 | 74 | 3 | 1 | 128 | 1 | 131 | 2.26E-26 | 96.7 | 62.12 |
| Query_29120 | WP_068847524.1 | 40.909 | 132 | 73 | 3 | 1 | 128 | 1 | 131 | 3.00E-26 | 96.3 | 61.36 |
| Query_29120 | WP_011648538.1 | 40.152 | 132 | 74 | 3 | 1 | 128 | 1 | 131 | 5.45E-26 | 95.5 | 62.12 |
| Query_29120 | WP_003022604.1 | 40.152 | 132 | 74 | 3 | 1 | 128 | 1 | 131 | 7.71E-26 | 95.1 | 61.36 |
| Query_29120 | WP_012429033.1 | 39.394 | 132 | 75 | 3 | 1 | 128 | 1 | 131 | 2.66E-25 | 94 | 61.36 |
| Query_29120 | WP_071303874.1 | 39.394 | 132 | 75 | 3 | 1 | 128 | 1 | 131 | 2.69E-25 | 94 | 61.36 |
| Query_29120 | WP_071663447.1 | 44.094 | 127 | 68 | 2 | 8 | 132 | 7 | 132 | 5.80E-25 | 93.2 | 61.42 |
| Query_29120 | WP_003017591.1 | 41.667 | 132 | 71 | 4 | 1 | 128 | 1 | 130 | 7.01E-25 | 92.8 | 61.36 |
| Query_29120 | WP_003040827.1 | 38.636 | 132 | 76 | 3 | 1 | 128 | 1 | 131 | 1.54E-24 | 92 | 60.61 |
| Query_29120 | WP_003038073.1 | 40.87 | 115 | 66 | 1 | 16 | 128 | 17 | 131 | 2.20E-24 | 91.7 | 62.61 |
| Query_29120 | WP_003032658.1 | 40.87 | 115 | 66 | 1 | 16 | 128 | 17 | 131 | 2.70E-24 | 91.3 | 61.74 |
| Query_29120 | WP_104928312.1 | 38.235 | 136 | 79 | 3 | 1 | 132 | 1 | 135 | 4.70E-24 | 90.5 | 61.03 |
| Query_29120 | WP_012280212.1 | 38.393 | 112 | 69 | 0 | 18 | 129 | 19 | 130 | 5.07E-24 | 90.5 | 63.39 |
| Query_29120 | WP_013921822.1 | 38.393 | 112 | 69 | 0 | 18 | 129 | 19 | 130 | 5.47E-24 | 90.5 | 63.39 |
| Query_29120 | WP_014549153.1 | 40.87 | 115 | 66 | 1 | 16 | 128 | 17 | 131 | 2.63E-23 | 88.6 | 62.61 |
| Query_29120 | WP_072712972.1 | 31.008 | 129 | 89 | 0 | 1 | 129 | 1 | 129 | 1.40E-21 | 84.3 | 58.91 |
| Query_29120 | WP_066045194.1 | 37.5 | 112 | 68 | 1 | 19 | 128 | 20 | 131 | 6.95E-20 | 80.1 | 59.82 |
| Query_29120 | WP_014714152.1 | 34.579 | 107 | 70 | 0 | 23 | 129 | 24 | 130 | 4.26E-19 | 77.8 | 61.68 |
| Query_29120 | WP_044526550.1 | 36.296 | 135 | 77 | 5 | 5 | 133 | 14 | 145 | 8.59E-18 | 75.1 | 61.48 |
| Query_29120 | WP_088772593.1 | 26.984 | 126 | 91 | 1 | 4 | 129 | 1 | 125 | 8.11E-14 | 64.3 | 57.14 |
| Query_29120 | WP_071663446.1 | 35.878 | 131 | 69 | 5 | 8 | 132 | 7 | 128 | 2.97E-13 | 62.8 | 58.02 |
| Query_29120 | WP_119331125.1 | 33.333 | 138 | 77 | 4 | 1 | 132 | 1 | 129 | 7.25E-13 | 62 | 54.35 |
| Query_29120 | WP_072713417.1 | 33.094 | 139 | 81 | 5 | 1 | 133 | 1 | 133 | 2.26E-12 | 60.5 | 51.08 |
| Query_29120 | WP_088771593.1 | 29.496 | 139 | 86 | 3 | 1 | 133 | 1 | 133 | 1.56E-11 | 58.2 | 49.64 |
| Query_29120 | WP_071629866.1 | 33.835 | 133 | 79 | 5 | 1 | 130 | 4 | 130 | 9.02E-11 | 56.2 | 53.38 |
| Query_29120 | WP_003024383.1 | 33.613 | 119 | 72 | 4 | 19 | 136 | 24 | 136 | 5.47E-10 | 54.3 | 53.78 |
| Query_29120 | WP_066046621.1 | 33.613 | 119 | 72 | 4 | 19 | 136 | 24 | 136 | 1.62E-09 | 53.1 | 53.78 |
| Query_29120 | WP_014549076.1 | 33.613 | 119 | 72 | 4 | 19 | 136 | 24 | 136 | 1.67E-09 | 53.1 | 53.78 |
| Query_29120 | WP_003017665.1 | 33.613 | 119 | 72 | 4 | 19 | 136 | 24 | 136 | 1.70E-09 | 53.1 | 53.78 |
| Query_29120 | WP_057113125.1 | 33.613 | 119 | 72 | 4 | 19 | 136 | 24 | 136 | 1.72E-09 | 53.1 | 53.78 |
| Query_29120 | WP_104928361.1 | 33.613 | 119 | 72 | 4 | 19 | 136 | 24 | 136 | 1.76E-09 | 53.1 | 53.78 |
| Query_29120 | WP_071513888.1 | 33.613 | 119 | 72 | 4 | 19 | 136 | 24 | 136 | 1.78E-09 | 53.1 | 53.78 |
| Query_29120 | WP_003037879.1 | 33.613 | 119 | 72 | 4 | 19 | 136 | 24 | 136 | 1.83E-09 | 53.1 | 53.78 |

FIG. 33A

| Query | Subject | % Identity | Length | Mismatch | Gap | Q.start | Q.end | S.start | S.end | E-value | Bit score | % |
|---|---|---|---|---|---|---|---|---|---|---|---|---|
| Query_29120 | WP_003014086.1 | 33.898 | 118 | 71 | 4 | 19 | 135 | 24 | 135 | 1.85E-09 | 52.8 | 53.39 |
| Query_29120 | WP_035720612.1 | 33.981 | 103 | 60 | 2 | 31 | 133 | 37 | 131 | 1.88E-09 | 52.8 | 54.37 |
| Query_29120 | WP_072713415.1 | 32.039 | 103 | 62 | 2 | 31 | 133 | 37 | 131 | 2.20E-09 | 52.8 | 56.31 |
| Query_29120 | WP_088771594.1 | 31.884 | 138 | 82 | 5 | 1 | 132 | 1 | 132 | 2.43E-09 | 52.8 | 50.72 |
| Query_29120 | WP_064461611.1 | 32.353 | 102 | 61 | 2 | 31 | 132 | 37 | 130 | 5.62E-08 | 48.9 | 55.88 |
| Query_29120 | WP_133942480.1 | 28.155 | 103 | 66 | 2 | 31 | 133 | 37 | 131 | 6.62E-08 | 48.9 | 57.28 |
| Query_29120 | WP_039123382.1 | 29.688 | 128 | 77 | 4 | 9 | 132 | 14 | 132 | 1.27E-07 | 48.1 | 50.78 |
| Query_29120 | WP_064461797.1 | 31.858 | 113 | 70 | 4 | 18 | 129 | 23 | 129 | 1.64E-07 | 47.8 | 52.21 |
| Query_29120 | WP_040009682.1 | 32.479 | 117 | 72 | 4 | 18 | 133 | 23 | 133 | 1.74E-07 | 47.8 | 51.28 |
| Query_29120 | WP_066046618.1 | 28.058 | 139 | 84 | 4 | 1 | 132 | 1 | 130 | 2.03E-07 | 47.4 | 51.8 |
| Query_29120 | WP_072713416.1 | 31.481 | 108 | 68 | 2 | 26 | 133 | 32 | 133 | 2.27E-07 | 47.4 | 50 |
| Query_29120 | WP_133942481.1 | 28.986 | 138 | 86 | 4 | 1 | 132 | 1 | 132 | 2.68E-07 | 47.4 | 48.55 |
| Query_29120 | WP_040009684.1 | 32.353 | 102 | 61 | 2 | 31 | 132 | 37 | 130 | 4.83E-07 | 46.6 | 49.02 |
| Query_29120 | ORM38345.1 | 31.25 | 112 | 68 | 3 | 19 | 129 | 35 | 138 | 5.69E-07 | 46.6 | 54.46 |
| Query_29120 | WP_071663935.1 | 29.104 | 134 | 80 | 5 | 7 | 133 | 3 | 128 | 6.82E-07 | 45.8 | 52.99 |
| Query_29120 | WP_044527026.1 | 28.689 | 122 | 75 | 3 | 13 | 132 | 19 | 130 | 6.83E-07 | 45.8 | 51.64 |
| Query_29120 | WP_088771592.1 | 29.31 | 116 | 73 | 3 | 19 | 133 | 24 | 131 | 8.82E-07 | 45.8 | 52.59 |
| Query_29120 | WP_003017667.1 | 29.412 | 102 | 64 | 2 | 31 | 132 | 37 | 130 | 9.43E-07 | 45.8 | 56.86 |
| Query_29120 | WP_014549075.1 | 29.412 | 102 | 64 | 2 | 31 | 132 | 37 | 130 | 9.72E-07 | 45.4 | 56.86 |
| Query_29120 | WP_039123383.1 | 28.155 | 103 | 66 | 2 | 31 | 133 | 37 | 131 | 9.88E-07 | 45.4 | 56.31 |
| Query_29120 | WP_071629865.1 | 25 | 136 | 87 | 3 | 4 | 132 | 3 | 130 | 1.08E-06 | 45.4 | 49.26 |
| Query_29120 | WP_088771595.1 | 31.452 | 124 | 68 | 5 | 12 | 132 | 22 | 131 | 1.22E-06 | 45.4 | 50.81 |
| Query_29120 | OEZ32926.1 | 31 | 100 | 61 | 2 | 31 | 130 | 37 | 128 | 1.58E-06 | 45.1 | 55 |
| Query_29120 | WP_004286894.1 | 29.31 | 116 | 70 | 3 | 19 | 132 | 25 | 130 | 1.70E-06 | 45.1 | 51.72 |
| Query_29120 | WP_041257409.1 | 27.049 | 122 | 77 | 3 | 13 | 132 | 14 | 125 | 1.95E-06 | 44.7 | 50.82 |
| Query_29120 | WP_085076048.1 | 28.431 | 102 | 65 | 2 | 31 | 132 | 2 | 95 | 1.96E-06 | 43.9 | 56.86 |
| Query_29120 | WP_003014087.1 | 28.431 | 102 | 65 | 2 | 31 | 132 | 37 | 130 | 2.60E-06 | 44.3 | 56.86 |
| Query_29120 | WP_003040711.1 | 28.431 | 102 | 65 | 2 | 31 | 132 | 37 | 130 | 3.00E-06 | 44.3 | 56.86 |
| Query_29120 | WP_003022747.1 | 29.412 | 102 | 64 | 2 | 31 | 132 | 37 | 130 | 3.19E-06 | 44.3 | 55.88 |
| Query_29120 | WP_112870817.1 | 29.371 | 143 | 77 | 4 | 1 | 132 | 1 | 130 | 3.42E-06 | 44.3 | 44.76 |
| Query_29120 | WP_014715657.1 | 30.252 | 119 | 76 | 4 | 19 | 136 | 24 | 136 | 4.52E-06 | 43.9 | 51.26 |
| Query_29120 | WP_112870814.1 | 30.392 | 102 | 63 | 2 | 31 | 132 | 37 | 130 | 5.66E-06 | 43.5 | 53.92 |
| Query_29120 | WP_042517058.1 | 27.869 | 122 | 76 | 3 | 13 | 132 | 19 | 130 | 5.81E-06 | 43.5 | 50.82 |
| Query_29120 | WP_112870816.1 | 23.704 | 135 | 89 | 3 | 1 | 129 | 1 | 127 | 7.91E-06 | 43.5 | 47.41 |
| Query_29120 | WP_119331124.1 | 25.18 | 139 | 84 | 4 | 7 | 132 | 3 | 134 | 8.24E-06 | 43.1 | 47.48 |
| Query_29120 | WP_044527027.1 | 29.412 | 119 | 77 | 4 | 19 | 136 | 24 | 136 | 1.03E-05 | 43.1 | 51.26 |
| Query_29120 | WP_013923633.1 | 28.571 | 119 | 78 | 3 | 19 | 136 | 24 | 136 | 1.40E-05 | 42.7 | 50.42 |
| Query_29120 | WP_004286893.1 | 27.731 | 119 | 79 | 3 | 19 | 136 | 24 | 136 | 2.36E-05 | 42 | 48.74 |
| Query_29120 | WP_013923632.1 | 27.586 | 116 | 72 | 3 | 19 | 132 | 25 | 130 | 2.42E-05 | 42 | 50 |
| Query_29120 | WP_035737193.1 | 26.891 | 119 | 80 | 3 | 19 | 136 | 24 | 136 | 3.81E-05 | 41.6 | 48.74 |
| Query_29120 | WP_071663449.1 | 23.239 | 142 | 89 | 4 | 4 | 132 | 1 | 135 | 6.08E-05 | 40.8 | 45.77 |
| Query_29120 | APC97796.1 | 23.741 | 139 | 86 | 4 | 7 | 132 | 3 | 134 | 7.00E-05 | 40.8 | 46.04 |
| Query_29120 | WP_133942482.1 | 28.099 | 121 | 74 | 4 | 13 | 132 | 23 | 131 | 8.08E-05 | 40.4 | 47.11 |
| Query_29120 | WP_112870815.1 | 30.189 | 106 | 60 | 4 | 31 | 131 | 37 | 133 | 1.97E-04 | 39.3 | 53.77 |
| Query_29120 | WP_035720619.1 | 28.682 | 129 | 81 | 5 | 6 | 132 | 13 | 132 | 2.38E-04 | 39.3 | 51.94 |
| Query_29120 | WP_035720611.1 | 25.664 | 113 | 71 | 3 | 13 | 124 | 23 | 123 | 3.32E-04 | 38.9 | 46.02 |
| Query_29120 | WP_119331102.1 | 25.806 | 124 | 81 | 5 | 4 | 125 | 3 | 117 | 5.56E-04 | 38.1 | 50.81 |

FIG. 33A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_232271 | WP_003020882.1 | 100 | 135 | 0 | 0 | 1 | 135 | 1 | 135 | 1.09E-92 | 264 | 100 |
| Query_232271 | WP_003014607.1 | 99.259 | 135 | 1 | 0 | 1 | 135 | 1 | 135 | 3.10E-92 | 263 | 100 |
| Query_232271 | AAX14616.1 | 99.259 | 135 | 1 | 0 | 1 | 135 | 1 | 135 | 5.08E-92 | 262 | 99.26 |
| Query_232271 | ABA60812.1 | 98.519 | 135 | 2 | 0 | 1 | 135 | 1 | 135 | 6.32E-92 | 262 | 100 |
| Query_232271 | WP_003018424.1 | 99.259 | 135 | 1 | 0 | 1 | 135 | 1 | 135 | 9.92E-92 | 261 | 99.26 |
| Query_232271 | WP_011648587.1 | 98.519 | 135 | 2 | 0 | 1 | 135 | 1 | 135 | 3.07E-91 | 260 | 99.26 |
| Query_232271 | ORU24184.1 | 99.219 | 128 | 1 | 0 | 8 | 135 | 1 | 128 | 1.77E-85 | 246 | 100 |
| Query_232271 | WP_003033092.1 | 94.815 | 135 | 7 | 0 | 1 | 135 | 1 | 135 | 2.32E-70 | 207 | 97.04 |
| Query_232271 | WP_071660103.1 | 85.926 | 135 | 19 | 0 | 1 | 135 | 1 | 135 | 6.79E-68 | 201 | 91.11 |
| Query_232271 | WP_071514757.1 | 85.926 | 135 | 19 | 0 | 1 | 135 | 1 | 135 | 1.71E-67 | 200 | 90.37 |
| Query_232271 | ABK78948.1 | 85.926 | 135 | 19 | 0 | 1 | 135 | 1 | 135 | 1.95E-67 | 200 | 90.37 |
| Query_232271 | WP_003035596.1 | 80.597 | 134 | 24 | 1 | 1 | 134 | 1 | 132 | 2.62E-60 | 182 | 87.31 |
| Query_232271 | WP_003041683.1 | 79.699 | 133 | 23 | 2 | 1 | 132 | 1 | 130 | 1.43E-56 | 173 | 85.71 |
| Query_232271 | WP_014547696.1 | 74.815 | 135 | 27 | 2 | 1 | 134 | 1 | 129 | 3.87E-51 | 159 | 77.04 |
| Query_232271 | WP_013922206.1 | 72.18 | 133 | 30 | 2 | 1 | 132 | 1 | 127 | 9.43E-49 | 153 | 76.69 |
| Query_232271 | WP_042524481.1 | 72.18 | 133 | 30 | 2 | 1 | 132 | 1 | 127 | 1.37E-48 | 152 | 77.44 |
| Query_232271 | WP_035719752.1 | 72.932 | 133 | 28 | 2 | 1 | 132 | 1 | 126 | 2.29E-48 | 152 | 80.45 |
| Query_232271 | WP_133942412.1 | 72.18 | 133 | 29 | 2 | 1 | 132 | 1 | 126 | 3.51E-48 | 151 | 80.45 |
| Query_232271 | ORM39040.1 | 69.403 | 134 | 32 | 2 | 1 | 132 | 1 | 127 | 1.35E-45 | 145 | 78.36 |
| Query_232271 | OEZ33615.1 | 70.149 | 134 | 31 | 3 | 1 | 132 | 1 | 127 | 2.18E-45 | 144 | 80.6 |
| Query_232271 | WP_064461363.1 | 70.896 | 134 | 30 | 3 | 1 | 132 | 1 | 127 | 7.75E-45 | 143 | 79.85 |
| Query_232271 | WP_003038443.1 | 68.148 | 135 | 34 | 3 | 1 | 132 | 1 | 129 | 5.01E-42 | 136 | 73.33 |
| Query_232271 | WP_066045592.1 | 65.185 | 135 | 39 | 3 | 1 | 132 | 1 | 130 | 5.48E-41 | 133 | 75.56 |
| Query_232271 | WP_071304047.1 | 65.926 | 135 | 38 | 3 | 1 | 132 | 1 | 130 | 2.34E-40 | 132 | 74.81 |
| Query_232271 | WP_088773113.1 | 62.963 | 135 | 42 | 2 | 1 | 132 | 4 | 133 | 3.28E-39 | 129 | 74.07 |
| Query_232271 | WP_112870292.1 | 64.444 | 135 | 40 | 3 | 1 | 132 | 1 | 130 | 6.56E-39 | 128 | 74.81 |
| Query_232271 | WP_039122881.1 | 62.406 | 133 | 42 | 3 | 3 | 132 | 2 | 129 | 5.19E-36 | 120 | 72.93 |
| Query_232271 | WP_112870031.1 | 50.37 | 135 | 58 | 5 | 1 | 132 | 1 | 129 | 1.99E-32 | 115 | 67.41 |
| Query_232271 | WP_040008928.1 | 63.768 | 138 | 42 | 5 | 1 | 132 | 1 | 136 | 3.80E-32 | 111 | 74.64 |
| Query_232271 | WP_072711442.1 | 48.227 | 141 | 62 | 2 | 1 | 135 | 4 | 139 | 2.50E-30 | 106 | 62.41 |
| Query_232271 | WP_004286431.1 | 56.522 | 138 | 54 | 3 | 1 | 132 | 1 | 138 | 1.71E-29 | 104 | 70.29 |
| Query_232271 | WP_071663086.1 | 58.088 | 136 | 48 | 3 | 1 | 132 | 1 | 131 | 3.03E-28 | 101 | 70.59 |
| Query_232271 | WP_072711443.1 | 52.899 | 138 | 57 | 2 | 1 | 132 | 4 | 139 | 7.49E-28 | 100 | 68.12 |
| Query_232271 | APC97276.1 | 58.209 | 134 | 47 | 3 | 3 | 132 | 2 | 130 | 1.27E-27 | 99.8 | 70.9 |
| Query_232271 | WP_044525666.1 | 54.667 | 150 | 48 | 6 | 1 | 132 | 1 | 148 | 1.49E-27 | 100 | 68.67 |
| Query_232271 | WP_088820886.1 | 55.263 | 152 | 44 | 8 | 1 | 132 | 1 | 148 | 7.11E-26 | 95.9 | 67.76 |
| Query_232271 | WP_012279912.1 | 54.967 | 151 | 48 | 7 | 1 | 133 | 1 | 149 | 8.54E-26 | 95.5 | 67.55 |
| Query_232271 | WP_042516850.1 | 49.682 | 157 | 48 | 5 | 1 | 132 | 1 | 151 | 1.50E-25 | 95.1 | 64.97 |
| Query_232271 | WP_035735097.1 | 48.611 | 144 | 64 | 3 | 1 | 134 | 1 | 144 | 2.48E-25 | 94 | 64.58 |
| Query_232271 | WP_014714485.1 | 52.632 | 152 | 48 | 7 | 1 | 132 | 1 | 148 | 1.30E-24 | 92.4 | 65.79 |
| Query_232271 | WP_083578867.1 | 37.681 | 138 | 75 | 5 | 1 | 134 | 6 | 136 | 2.43E-22 | 86.3 | 57.97 |
| Query_232271 | WP_071629598.1 | 49.66 | 147 | 58 | 5 | 1 | 134 | 1 | 144 | 2.62E-22 | 86.7 | 66.67 |
| Query_232271 | WP_119329887.1 | 46.259 | 147 | 59 | 5 | 1 | 133 | 1 | 141 | 2.01E-21 | 84 | 63.95 |
| Query_232271 | WP_119329886.1 | 36.879 | 141 | 67 | 6 | 2 | 132 | 6 | 134 | 2.18E-20 | 81.3 | 56.74 |
| Query_232271 | WP_004287623.1 | 45.736 | 129 | 62 | 3 | 7 | 132 | 4 | 127 | 2.67E-20 | 84.7 | 65.89 |
| Query_232271 | WP_051907668.1 | 45.038 | 131 | 62 | 3 | 6 | 132 | 8 | 132 | 3.19E-19 | 81.6 | 62.6 |
| Query_232271 | WP_052471582.1 | 44.615 | 130 | 64 | 3 | 6 | 132 | 8 | 132 | 3.46E-19 | 81.6 | 63.08 |
| Query_232271 | WP_042899653.1 | 38.583 | 127 | 69 | 3 | 4 | 121 | 8 | 134 | 1.76E-18 | 77.8 | 51.97 |
| Query_232271 | WP_042903970.1 | 38.583 | 127 | 69 | 3 | 4 | 121 | 5 | 131 | 4.63E-18 | 76.6 | 51.97 |
| Query_232271 | WP_042421994.1 | 38.583 | 127 | 69 | 3 | 4 | 121 | 5 | 131 | 5.27E-18 | 77 | 51.18 |
| Query_232271 | WP_003023580.1 | 38.583 | 127 | 69 | 3 | 4 | 121 | 5 | 131 | 5.29E-18 | 76.6 | 51.18 |
| Query_232271 | WP_133942411.1 | 45.39 | 141 | 67 | 5 | 1 | 132 | 1 | 140 | 5.83E-18 | 75.1 | 60.99 |
| Query_232271 | WP_042600182.1 | 38.583 | 127 | 69 | 3 | 4 | 121 | 5 | 131 | 6.86E-18 | 76.6 | 51.18 |
| Query_232271 | EDO66164.1 | 38.583 | 127 | 69 | 3 | 4 | 121 | 21 | 147 | 7.50E-18 | 76.6 | 51.97 |
| Query_232271 | WP_076731272.1 | 37.795 | 127 | 70 | 3 | 4 | 121 | 5 | 131 | 5.75E-17 | 75.9 | 51.18 |
| Query_232271 | EDZ89927.1 | 38.583 | 127 | 69 | 3 | 4 | 121 | 21 | 147 | 6.10E-17 | 76.3 | 51.18 |
| Query_232271 | EDN35762.1 | 38.583 | 127 | 69 | 3 | 4 | 121 | 21 | 147 | 6.41E-17 | 76.3 | 51.18 |
| Query_232271 | EDX19186.1 | 38.583 | 127 | 69 | 3 | 4 | 121 | 21 | 147 | 6.60E-17 | 76.3 | 51.18 |
| Query_232271 | WP_014549386.1 | 38.583 | 127 | 69 | 3 | 4 | 121 | 5 | 131 | 7.43E-17 | 75.9 | 51.18 |
| Query_232271 | WP_011733603.1 | 38.583 | 127 | 69 | 3 | 4 | 121 | 5 | 131 | 7.80E-17 | 75.9 | 51.18 |
| Query_232271 | WP_032729814.1 | 38.583 | 127 | 69 | 3 | 4 | 121 | 5 | 131 | 8.03E-17 | 75.9 | 51.18 |
| Query_232271 | WP_104929126.1 | 38.583 | 127 | 69 | 3 | 4 | 121 | 5 | 131 | 8.19E-17 | 75.9 | 51.18 |

FIG. 34A

| | | | | | | | | | | | |
|---|---|---|---|---|---|---|---|---|---|---|---|
| Query_232271 | WP_032728437.1 | 38.583 | 127 | 69 | 3 | 4 | 121 | 5 | 131 | 8.27E-17 | 75.9 | 51.16 |
| Query_232271 | WP_039122882.1 | 46.763 | 139 | 64 | 4 | 3 | 132 | 2 | 139 | 1.03E-16 | 72 | 58.99 |
| Query_232271 | WP_071514758.1 | 38.583 | 127 | 69 | 3 | 4 | 121 | 5 | 131 | 1.33E-16 | 75.1 | 51.18 |
| Query_232271 | WP_003035594.1 | 38.583 | 127 | 69 | 3 | 4 | 121 | 5 | 131 | 1.38E-16 | 75.1 | 51.18 |
| Query_232271 | WP_040008929.1 | 34.058 | 138 | 81 | 4 | 4 | 132 | 2 | 138 | 4.79E-16 | 70.1 | 51.45 |
| Query_232271 | WP_035719754.1 | 44.681 | 141 | 68 | 5 | 1 | 132 | 1 | 140 | 7.75E-16 | 69.7 | 60.28 |
| Query_232271 | WP_003033090.1 | 44.286 | 140 | 69 | 4 | 1 | 132 | 1 | 139 | 1.28E-15 | 69.3 | 56.43 |
| Query_232271 | WP_035735095.1 | 38.849 | 139 | 75 | 4 | 3 | 132 | 2 | 139 | 1.66E-15 | 68.9 | 51.08 |
| Query_232271 | WP_112869270.1 | 35.821 | 134 | 68 | 6 | 7 | 132 | 13 | 136 | 1.76E-15 | 71.6 | 53.73 |
| Query_232271 | WP_044247204.1 | 37.008 | 127 | 71 | 3 | 4 | 121 | 5 | 131 | 2.37E-15 | 71.6 | 50.39 |
| Query_232271 | WP_003035595.1 | 44.286 | 140 | 69 | 4 | 1 | 132 | 1 | 139 | 2.46E-15 | 68.6 | 56.43 |
| Query_232271 | WP_066045599.1 | 37.008 | 127 | 71 | 3 | 4 | 121 | 5 | 131 | 2.66E-15 | 71.6 | 50.39 |
| Query_232271 | WP_044525665.1 | 36.111 | 144 | 75 | 5 | 1 | 132 | 1 | 139 | 4.72E-15 | 67.8 | 50.69 |
| Query_232271 | WP_014549387.1 | 45 | 140 | 68 | 4 | 1 | 132 | 1 | 139 | 5.72E-15 | 67.4 | 56.43 |
| Query_232271 | WP_050022779.1 | 44.03 | 134 | 66 | 4 | 3 | 132 | 2 | 130 | 5.87E-15 | 69.7 | 64.18 |
| Query_232271 | WP_013922205.1 | 42.581 | 155 | 48 | 6 | 1 | 132 | 1 | 137 | 1.68E-14 | 66.2 | 52.9 |
| Query_232271 | WP_004286432.1 | 42.958 | 142 | 72 | 4 | 1 | 134 | 1 | 141 | 2.29E-14 | 65.9 | 57.04 |
| Query_232271 | WP_071304046.1 | 43.571 | 140 | 70 | 4 | 1 | 132 | 1 | 139 | 3.78E-14 | 65.5 | 55.71 |
| Query_232271 | WP_042516851.1 | 34.965 | 143 | 75 | 5 | 3 | 132 | 2 | 139 | 6.30E-14 | 64.7 | 51.75 |
| Query_232271 | WP_014547697.1 | 42.857 | 140 | 71 | 3 | 1 | 132 | 1 | 139 | 7.16E-14 | 64.7 | 55 |
| Query_232271 | WP_112869233.1 | 42.609 | 115 | 56 | 4 | 6 | 111 | 4 | 117 | 8.58E-14 | 64.3 | 52.17 |
| Query_232271 | WP_066045596.1 | 43.972 | 141 | 69 | 5 | 1 | 132 | 1 | 140 | 1.38E-13 | 63.9 | 56.03 |
| Query_232271 | WP_003038440.1 | 41.429 | 140 | 73 | 3 | 1 | 132 | 1 | 139 | 2.26E-13 | 63.2 | 54.29 |
| Query_232271 | WP_042524480.1 | 44.286 | 140 | 67 | 5 | 1 | 132 | 1 | 137 | 3.97E-13 | 62.8 | 57.14 |
| Query_232271 | WP_088821220.1 | 28.571 | 126 | 71 | 2 | 7 | 132 | 16 | 122 | 4.43E-13 | 63.5 | 50 |
| Query_232271 | WP_003026532.1 | 41.667 | 156 | 51 | 6 | 1 | 132 | 1 | 140 | 4.70E-13 | 62.4 | 50 |
| Query_232271 | WP_042523304.1 | 28.571 | 126 | 71 | 2 | 7 | 132 | 6 | 112 | 6.03E-13 | 63.2 | 50 |
| Query_232271 | AJI54754.1 | 28.571 | 126 | 71 | 2 | 7 | 132 | 16 | 122 | 6.52E-13 | 63.2 | 50 |
| Query_232271 | WP_012429262.1 | 44.681 | 141 | 68 | 5 | 1 | 132 | 1 | 140 | 7.33E-13 | 62 | 56.74 |
| Query_232271 | AAX14623.1 | 59.184 | 49 | 20 | 0 | 4 | 52 | 5 | 53 | 8.85E-13 | 60.1 | 71.43 |
| Query_232271 | WP_071629599.1 | 42.029 | 138 | 70 | 5 | 7 | 135 | 2 | 138 | 1.60E-12 | 60.8 | 58.7 |
| Query_232271 | WP_072712583.1 | 30 | 130 | 79 | 4 | 6 | 132 | 4 | 124 | 3.67E-12 | 61.6 | 54.62 |
| Query_232271 | AAW78379.1 | 41.026 | 156 | 52 | 6 | 1 | 132 | 1 | 140 | 3.96E-12 | 60.1 | 50 |
| Query_232271 | WP_003020879.1 | 40.506 | 158 | 54 | 6 | 1 | 134 | 1 | 142 | 4.54E-12 | 60.1 | 50.63 |
| Query_232271 | WP_071664714.1 | 60.417 | 48 | 19 | 0 | 4 | 51 | 3 | 50 | 1.87E-11 | 58.2 | 70.83 |
| Query_232271 | WP_071304045.1 | 38.583 | 127 | 69 | 3 | 4 | 121 | 5 | 131 | 3.33E-11 | 60.1 | 51.18 |
| Query_232271 | WP_080774902.1 | 30.435 | 138 | 79 | 4 | 3 | 132 | 6 | 134 | 6.00E-11 | 58.9 | 47.83 |
| Query_232271 | WP_119330133.1 | 77.143 | 35 | 6 | 1 | 1 | 35 | 1 | 33 | 1.07E-10 | 56.2 | 85.71 |
| Query_232271 | WP_112870293.1 | 38.462 | 143 | 62 | 6 | 7 | 132 | 9 | 142 | 1.97E-10 | 55.8 | 48.95 |
| Query_232271 | WP_072712371.1 | 32.877 | 146 | 75 | 5 | 7 | 132 | 31 | 173 | 2.26E-10 | 56.6 | 55.48 |
| Query_232271 | WP_123961575.1 | 40.385 | 156 | 53 | 6 | 1 | 132 | 1 | 140 | 2.75E-10 | 55.5 | 49.36 |
| Query_232271 | WP_080723442.1 | 28.986 | 138 | 81 | 4 | 3 | 132 | 6 | 134 | 4.39E-10 | 56.6 | 47.83 |
| Query_232271 | AFJ42937.1 | 50 | 52 | 26 | 0 | 8 | 59 | 7 | 58 | 4.51E-10 | 52.8 | 69.23 |
| Query_232271 | WP_080775375.1 | 28.261 | 138 | 82 | 4 | 3 | 132 | 6 | 134 | 1.71E-09 | 54.7 | 47.83 |
| Query_232271 | WP_004266433.1 | 38.194 | 144 | 77 | 4 | 1 | 133 | 2 | 144 | 1.74E-09 | 55.1 | 52.78 |
| Query_232271 | WP_012279937.1 | 28.261 | 138 | 82 | 4 | 3 | 132 | 6 | 134 | 1.74E-09 | 54.7 | 47.83 |
| Query_232271 | WP_013922204.1 | 36.154 | 130 | 74 | 3 | 1 | 121 | 2 | 131 | 2.74E-09 | 54.3 | 52.31 |
| Query_232271 | WP_072712761.1 | 47.17 | 53 | 28 | 0 | 4 | 56 | 3 | 55 | 2.82E-09 | 54.3 | 66.04 |
| Query_232271 | ABZ87973.1 | 25.806 | 124 | 73 | 2 | 7 | 130 | 6 | 110 | 2.82E-09 | 52 | 48.39 |
| Query_232271 | WP_041268119.1 | 25.806 | 124 | 73 | 2 | 7 | 130 | 16 | 120 | 2.95E-09 | 52 | 48.39 |
| Query_232271 | OEZ33413.1 | 55.814 | 43 | 19 | 0 | 6 | 48 | 4 | 46 | 2.99E-09 | 52.4 | 74.42 |
| Query_232271 | WP_086820869.1 | 29.286 | 140 | 80 | 5 | 3 | 132 | 4 | 134 | 3.92E-09 | 53.9 | 47.86 |
| Query_232271 | WP_042524479.1 | 35.878 | 131 | 73 | 3 | 1 | 121 | 2 | 131 | 8.23E-09 | 53.1 | 53.44 |
| Query_232271 | WP_112870076.1 | 38.889 | 144 | 64 | 8 | 4 | 129 | 14 | 151 | 1.85E-08 | 52 | 51.39 |
| Query_232271 | AXA34730.1 | 38.889 | 144 | 64 | 8 | 4 | 129 | 5 | 142 | 1.93E-08 | 52 | 51.39 |
| Query_232271 | WP_083578909.1 | 26.061 | 165 | 80 | 7 | 1 | 132 | 1 | 156 | 4.97E-08 | 49.7 | 41.82 |
| Query_232271 | WP_042516852.1 | 31.618 | 136 | 72 | 3 | 1 | 121 | 2 | 131 | 1.07E-07 | 49.7 | 47.06 |
| Query_232271 | WP_072711440.1 | 34.507 | 142 | 82 | 6 | 1 | 132 | 1 | 141 | 1.60E-07 | 47.8 | 56.34 |
| Query_232271 | WP_062399113.1 | 34.868 | 152 | 73 | 7 | 6 | 134 | 5 | 153 | 2.16E-07 | 48.9 | 51.97 |
| Query_232271 | WP_003029368.1 | 24.818 | 137 | 79 | 5 | 7 | 132 | 13 | 136 | 2.51E-07 | 48.1 | 44.53 |

FIG. 34A continued

| Query | Subject | % ID | Len | Mism | Gap | Qstart | Qend | Sstart | Send | E-value | Bit | Cov |
|---|---|---|---|---|---|---|---|---|---|---|---|---|
| Query_232271 | WP_003026557.1 | 24.818 | 137 | 79 | 5 | 7 | 132 | 13 | 136 | 2.54E-07 | 48.1 | 44.53 |
| Query_232271 | WP_014547671.1 | 28.358 | 134 | 78 | 5 | 7 | 132 | 13 | 136 | 3.07E-07 | 48.5 | 45.52 |
| Query_232271 | AEB27329.1 | 24.818 | 137 | 79 | 5 | 7 | 132 | 13 | 136 | 4.06E-07 | 48.1 | 44.53 |
| Query_232271 | EDN35738.1 | 24.818 | 137 | 79 | 5 | 7 | 132 | 13 | 136 | 4.22E-07 | 48.1 | 44.53 |
| Query_232271 | ABK89292.1 | 24.818 | 137 | 79 | 5 | 7 | 132 | 13 | 136 | 4.26E-07 | 48.1 | 44.53 |
| Query_232271 | OIN83080.1 | 24.818 | 137 | 79 | 5 | 7 | 132 | 13 | 136 | 5.22E-07 | 47.8 | 44.53 |
| Query_232271 | WP_025329141.1 | 24.088 | 137 | 80 | 5 | 7 | 132 | 13 | 136 | 1.12E-06 | 46.6 | 43.8 |
| Query_232271 | WP_119330570.1 | 31.343 | 67 | 44 | 1 | 1 | 67 | 1 | 65 | 1.67E-06 | 45.4 | 59.7 |
| Query_232271 | CAJ78832.1 | 97.143 | 35 | 1 | 0 | 1 | 35 | 1 | 35 | 2.80E-06 | 42.4 | 100 |
| Query_232271 | AAX14627.1 | 24.088 | 137 | 80 | 5 | 7 | 132 | 13 | 136 | 2.99E-06 | 45.4 | 42.34 |
| Query_232271 | AAX14624.1 | 23.358 | 137 | 81 | 5 | 7 | 132 | 13 | 136 | 3.47E-06 | 45.1 | 43.07 |
| Query_232271 | WP_010032648.1 | 23.358 | 137 | 81 | 5 | 7 | 132 | 13 | 136 | 3.50E-06 | 45.1 | 43.07 |
| Query_232271 | WP_012279913.1 | 38.849 | 139 | 75 | 4 | 3 | 132 | 2 | 139 | 3.99E-06 | 44.3 | 51.8 |
| Query_232271 | WP_035735093.1 | 31.298 | 131 | 79 | 5 | 1 | 121 | 2 | 131 | 4.89E-06 | 45.1 | 54.96 |
| Query_232271 | AGN89527.1 | 24.427 | 131 | 75 | 5 | 13 | 132 | 5 | 122 | 7.42E-06 | 43.9 | 43.51 |
| Query_232271 | WP_088772263.1 | 31.667 | 60 | 37 | 1 | 5 | 64 | 3 | 58 | 8.75E-06 | 42.7 | 66.67 |
| Query_232271 | ABK78943.1 | 94.286 | 35 | 2 | 0 | 1 | 35 | 1 | 35 | 1.00E-05 | 40.8 | 97.14 |
| Query_232271 | APC97648.1 | 35.714 | 112 | 61 | 3 | 4 | 108 | 3 | 110 | 1.00E-05 | 42.4 | 57.14 |
| Query_232271 | APA82432.1 | 24.427 | 131 | 75 | 5 | 13 | 132 | 5 | 122 | 1.26E-05 | 43.9 | 43.51 |
| Query_232271 | WP_012279914.1 | 30.534 | 131 | 80 | 5 | 1 | 121 | 2 | 131 | 1.27E-05 | 43.9 | 54.2 |
| Query_232271 | WP_088820885.1 | 35.664 | 143 | 74 | 5 | 3 | 132 | 2 | 139 | 1.32E-05 | 42.7 | 51.75 |
| Query_232271 | WP_072712581.1 | 78.378 | 37 | 8 | 0 | 7 | 43 | 4 | 40 | 1.38E-05 | 42.4 | 91.89 |
| Query_232271 | PZU05490.1 | 45 | 40 | 22 | 0 | 3 | 42 | 13 | 52 | 1.57E-05 | 42.7 | 67.5 |
| Query_232271 | WP_071663693.1 | 32.117 | 137 | 75 | 5 | 4 | 132 | 7 | 133 | 1.62E-05 | 43.5 | 49.64 |
| Query_232271 | WP_044525664.1 | 32.331 | 133 | 75 | 4 | 1 | 121 | 2 | 131 | 2.65E-05 | 43.1 | 51.13 |
| Query_232271 | WP_119330907.1 | 32.847 | 137 | 74 | 6 | 4 | 132 | 7 | 133 | 3.27E-05 | 42.7 | 48.91 |
| Query_232271 | WP_035736092.1 | 41.379 | 87 | 35 | 3 | 4 | 90 | 2 | 72 | 6.64E-05 | 40.4 | 55.17 |
| Query_232271 | WP_112869819.1 | 57.143 | 35 | 15 | 0 | 1 | 35 | 1 | 35 | 1.01E-04 | 40.8 | 68.57 |
| Query_232271 | AHB99090.1 | 42.222 | 45 | 26 | 0 | 15 | 59 | 1 | 45 | 1.23E-04 | 38.1 | 64.44 |
| Query_232271 | KFJ42585.1 | 37.838 | 74 | 30 | 3 | 17 | 90 | 1 | 58 | 1.76E-04 | 38.9 | 50 |
| Query_232271 | WP_040010498.1 | 54.286 | 35 | 16 | 0 | 1 | 35 | 1 | 35 | 2.00E-04 | 40 | 71.43 |
| Query_232271 | WP_071628414.1 | 63.043 | 46 | 17 | 0 | 6 | 51 | 4 | 49 | 2.16E-04 | 39.3 | 71.74 |
| Query_232271 | WP_012281147.1 | 70.588 | 34 | 10 | 0 | 8 | 41 | 6 | 39 | 2.29E-04 | 38.9 | 94.12 |
| Query_232271 | WP_014547388.1 | 65.116 | 43 | 15 | 0 | 6 | 48 | 4 | 46 | 2.76E-04 | 38.9 | 74.42 |
| Query_232271 | WP_088771655.1 | 63.83 | 47 | 17 | 0 | 2 | 48 | 4 | 50 | 3.08E-04 | 38.9 | 70.21 |
| Query_232271 | WP_040009729.1 | 74.286 | 35 | 9 | 0 | 6 | 40 | 4 | 38 | 3.24E-04 | 38.9 | 85.71 |
| Query_232271 | AJI56361.1 | 57.692 | 26 | 11 | 0 | 17 | 42 | 1 | 26 | 3.43E-04 | 38.1 | 84.62 |
| Query_232271 | WP_003042898.1 | 65.116 | 43 | 15 | 0 | 6 | 48 | 4 | 46 | 3.48E-04 | 38.9 | 74.42 |
| Query_232271 | WP_003032700.1 | 65.116 | 43 | 15 | 0 | 6 | 48 | 4 | 46 | 3.63E-04 | 38.5 | 74.42 |
| Query_232271 | WP_013921846.1 | 65.116 | 43 | 15 | 0 | 6 | 48 | 7 | 49 | 3.72E-04 | 38.5 | 74.42 |
| Query_232271 | WP_003038120.1 | 65.116 | 43 | 15 | 0 | 6 | 48 | 4 | 46 | 3.81E-04 | 38.5 | 74.42 |
| Query_232271 | KIP30305.1 | 40 | 40 | 24 | 0 | 7 | 46 | 13 | 52 | 4.66E-04 | 37 | 65 |
| Query_232271 | WP_013923266.1 | 48.387 | 62 | 25 | 3 | 7 | 65 | 14 | 71 | 5.12E-04 | 38.1 | 72.58 |
| Query_232271 | WP_040008120.1 | 65 | 40 | 14 | 0 | 4 | 43 | 10 | 49 | 5.26E-04 | 38.1 | 85 |
| Query_232271 | WP_014714165.1 | 62.5 | 40 | 15 | 0 | 1 | 40 | 1 | 40 | 5.67E-04 | 38.1 | 75 |
| Query_232271 | WP_044525365.1 | 62.5 | 40 | 15 | 0 | 1 | 40 | 1 | 40 | 5.73E-04 | 38.1 | 75 |
| Query_232271 | WP_004287871.1 | 66.667 | 42 | 13 | 1 | 7 | 47 | 4 | 45 | 7.16E-04 | 37.7 | 90.48 |
| Query_232271 | WP_012281145.1 | 69.048 | 42 | 12 | 1 | 7 | 47 | 4 | 45 | 7.16E-04 | 37.7 | 90.48 |
| Query_232271 | WP_035736084.1 | 69.048 | 42 | 12 | 1 | 7 | 47 | 4 | 45 | 7.38E-04 | 37.7 | 90.48 |
| Query_232271 | WP_088821150.1 | 57.895 | 38 | 16 | 0 | 4 | 41 | 2 | 39 | 7.48E-04 | 37.7 | 84.21 |
| Query_232271 | WP_044526055.1 | 71.429 | 42 | 11 | 1 | 7 | 47 | 4 | 45 | 7.69E-04 | 37.7 | 92.86 |

FIG. 34A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_180836 | WP_003017553.1 | 100 | 191 | 0 | 0 | 1 | 191 | 1 | 191 | 9.04E-135 | 375 | 100 |
| Query_180836 | WP_003032779.1 | 99.476 | 191 | 1 | 0 | 1 | 191 | 1 | 191 | 3.53E-134 | 374 | 100 |
| Query_180836 | WP_081353669.1 | 99.476 | 191 | 1 | 0 | 1 | 191 | 1 | 191 | 3.53E-134 | 374 | 100 |
| Query_180836 | WP_003038181.1 | 99.476 | 191 | 1 | 0 | 1 | 191 | 1 | 191 | 4.16E-134 | 373 | 100 |
| Query_180836 | WP_011886587.1 | 99.476 | 191 | 1 | 0 | 1 | 191 | 1 | 191 | 1.52E-133 | 372 | 99.48 |
| Query_180836 | WP_080555289.1 | 98.953 | 191 | 2 | 0 | 1 | 191 | 1 | 191 | 2.13E-133 | 372 | 99.48 |
| Query_180836 | WP_003013658.1 | 98.953 | 191 | 2 | 0 | 1 | 191 | 1 | 191 | 3.81E-133 | 371 | 98.95 |
| Query_180836 | WP_003029937.1 | 100 | 179 | 0 | 0 | 13 | 191 | 1 | 179 | 1.44E-124 | 348 | 100 |
| Query_180836 | AEB27059.1 | 99.441 | 179 | 1 | 0 | 13 | 191 | 1 | 179 | 5.88E-124 | 347 | 100 |
| Query_180836 | KFJ68489.1 | 99.441 | 179 | 1 | 0 | 13 | 191 | 1 | 179 | 6.78E-124 | 347 | 100 |
| Query_180836 | EKM84544.1 | 99.441 | 179 | 1 | 0 | 13 | 191 | 1 | 179 | 2.10E-123 | 346 | 99.44 |
| Query_180836 | WP_014547440.1 | 98.883 | 179 | 2 | 0 | 13 | 191 | 1 | 179 | 4.94E-123 | 345 | 99.44 |
| Query_180836 | CAJ78450.1 | 98.883 | 179 | 2 | 0 | 13 | 191 | 1 | 179 | 5.89E-123 | 345 | 98.88 |
| Query_180836 | WP_071628458.1 | 96.089 | 179 | 7 | 0 | 13 | 191 | 1 | 179 | 9.37E-120 | 337 | 98.88 |
| Query_180836 | WP_044526406.1 | 95.531 | 179 | 8 | 0 | 13 | 191 | 1 | 179 | 2.25E-119 | 335 | 98.88 |
| Query_180836 | ORM38863.1 | 94.413 | 179 | 10 | 0 | 13 | 191 | 1 | 179 | 3.35E-118 | 333 | 97.21 |
| Query_180836 | WP_013921898.1 | 94.413 | 179 | 10 | 0 | 13 | 191 | 1 | 179 | 3.35E-118 | 333 | 98.88 |
| Query_180836 | EET20487.1 | 92.818 | 181 | 13 | 0 | 11 | 191 | 2 | 182 | 6.16E-118 | 332 | 98.34 |
| Query_180836 | OEZ33442.1 | 93.855 | 179 | 11 | 0 | 13 | 191 | 1 | 179 | 1.22E-117 | 331 | 97.21 |
| Query_180836 | WP_035722131.1 | 93.296 | 179 | 12 | 0 | 13 | 191 | 1 | 179 | 3.39E-117 | 330 | 98.32 |
| Query_180836 | WP_012280140.1 | 92.737 | 179 | 13 | 0 | 13 | 191 | 1 | 179 | 1.20E-116 | 329 | 97.77 |
| Query_180836 | AFJ42660.1 | 90.608 | 181 | 11 | 1 | 11 | 191 | 2 | 176 | 6.17E-113 | 319 | 95.58 |
| Query_180836 | WP_041257271.1 | 91.061 | 179 | 10 | 1 | 13 | 191 | 1 | 173 | 5.38E-112 | 317 | 95.53 |
| Query_180836 | WP_040010745.1 | 86.034 | 179 | 25 | 0 | 13 | 191 | 1 | 179 | 9.95E-110 | 311 | 95.53 |
| Query_180836 | WP_064461543.1 | 89.944 | 179 | 11 | 1 | 13 | 191 | 1 | 172 | 1.56E-109 | 310 | 92.74 |
| Query_180836 | ORU21661.1 | 98.742 | 159 | 2 | 0 | 33 | 191 | 1 | 159 | 1.56E-107 | 305 | 98.74 |
| Query_180836 | WP_133940932.1 | 86.592 | 179 | 24 | 0 | 13 | 191 | 1 | 179 | 1.58E-107 | 306 | 94.97 |
| Query_180836 | WP_035720448.1 | 85.475 | 179 | 26 | 0 | 13 | 191 | 1 | 179 | 3.11E-106 | 302 | 94.41 |
| Query_180836 | WP_112869247.1 | 83.24 | 179 | 30 | 0 | 13 | 191 | 1 | 179 | 2.24E-104 | 298 | 92.74 |
| Query_180836 | WP_039123246.1 | 83.799 | 179 | 29 | 0 | 13 | 191 | 1 | 179 | 3.04E-103 | 295 | 93.3 |
| Query_180836 | WP_072711142.1 | 80.447 | 179 | 35 | 0 | 13 | 191 | 1 | 179 | 4.66E-101 | 289 | 91.62 |
| Query_180836 | WP_088771696.1 | 78.212 | 179 | 39 | 0 | 13 | 191 | 1 | 179 | 5.60E-98 | 281 | 90.5 |
| Query_180836 | WP_119331179.1 | 75 | 192 | 47 | 1 | 1 | 191 | 1 | 192 | 2.58E-91 | 265 | 86.46 |
| Query_180836 | WP_071663405.1 | 76.536 | 179 | 42 | 0 | 13 | 191 | 1 | 179 | 9.75E-89 | 258 | 89.39 |
| Query_180836 | ORU24511.1 | 100 | 38 | 0 | 0 | 1 | 38 | 1 | 38 | 6.51E-20 | 79 | 100 |

FIG. 35A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_123749 | WP_003022628.1 | 100 | 330 | 0 | 0 | 1 | 330 | 1 | 330 | 0 | 678 | 100 |
| Query_123749 | WP_003014029.1 | 99.697 | 330 | 1 | 0 | 1 | 330 | 1 | 330 | 0 | 674 | 99.7 |
| Query_123749 | WP_085138552.1 | 99.394 | 330 | 2 | 0 | 1 | 330 | 1 | 330 | 0 | 672 | 99.7 |
| Query_123749 | WP_085121366.1 | 99.394 | 330 | 2 | 0 | 1 | 330 | 1 | 330 | 0 | 672 | 99.7 |
| Query_123749 | WP_025329061.1 | 99.394 | 330 | 2 | 0 | 1 | 330 | 1 | 330 | 0 | 672 | 99.39 |
| Query_123749 | WP_081302394.1 | 99.394 | 330 | 2 | 0 | 1 | 330 | 1 | 330 | 0 | 671 | 99.39 |
| Query_123749 | ADA79328.1 | 100 | 326 | 0 | 0 | 5 | 330 | 1 | 326 | 0 | 669 | 100 |
| Query_123749 | WP_082264093.1 | 99.091 | 330 | 2 | 1 | 1 | 330 | 1 | 329 | 0 | 666 | 99.39 |
| Query_123749 | WP_080542754.1 | 97.879 | 330 | 7 | 0 | 1 | 330 | 1 | 330 | 0 | 665 | 98.79 |
| Query_123749 | ABI82121.1 | 99.693 | 326 | 1 | 0 | 5 | 330 | 1 | 326 | 0 | 665 | 99.69 |
| Query_123749 | WP_104928282.1 | 97.576 | 330 | 8 | 0 | 1 | 330 | 1 | 330 | 0 | 664 | 98.79 |
| Query_123749 | ORU86815.1 | 99.387 | 326 | 2 | 0 | 5 | 330 | 1 | 326 | 0 | 664 | 99.69 |
| Query_123749 | ORU49721.1 | 99.387 | 326 | 2 | 0 | 5 | 330 | 1 | 326 | 0 | 664 | 99.69 |
| Query_123749 | AHH46857.1 | 99.387 | 326 | 2 | 0 | 5 | 330 | 1 | 326 | 0 | 663 | 99.39 |
| Query_123749 | WP_081353665.1 | 97.576 | 330 | 8 | 0 | 1 | 330 | 1 | 330 | 0 | 662 | 98.48 |
| Query_123749 | WP_071660016.1 | 98.773 | 326 | 4 | 0 | 5 | 330 | 1 | 326 | 0 | 662 | 99.39 |
| Query_123749 | OCQ60049.1 | 99.387 | 326 | 2 | 0 | 5 | 330 | 1 | 326 | 0 | 662 | 99.39 |
| Query_123749 | WP_003032766.1 | 96.97 | 330 | 10 | 0 | 1 | 330 | 1 | 330 | 0 | 660 | 98.48 |
| Query_123749 | WP_084387490.1 | 96.667 | 330 | 11 | 0 | 1 | 330 | 1 | 330 | 0 | 659 | 98.48 |
| Query_123749 | WP_003042835.1 | 97.853 | 326 | 7 | 0 | 5 | 330 | 1 | 326 | 0 | 659 | 99.39 |
| Query_123749 | WP_080558889.1 | 96.667 | 330 | 11 | 0 | 1 | 330 | 1 | 330 | 0 | 658 | 98.18 |
| Query_123749 | ACD30157.1 | 99.08 | 326 | 2 | 1 | 5 | 330 | 1 | 325 | 0 | 657 | 99.39 |
| Query_123749 | EDN38610.1 | 97.853 | 326 | 7 | 0 | 5 | 330 | 1 | 326 | 0 | 657 | 98.77 |
| Query_123749 | WP_003040990.1 | 97.546 | 326 | 8 | 0 | 5 | 330 | 1 | 326 | 0 | 657 | 99.08 |
| Query_123749 | APA82131.1 | 97.546 | 326 | 8 | 0 | 5 | 330 | 1 | 326 | 0 | 654 | 98.47 |
| Query_123749 | KFJ68355.1 | 96.933 | 326 | 10 | 0 | 5 | 330 | 1 | 326 | 0 | 651 | 98.47 |
| Query_123749 | OIN83362.1 | 96.626 | 326 | 11 | 0 | 5 | 330 | 1 | 326 | 0 | 650 | 98.47 |
| Query_123749 | AEB27049.1 | 96.626 | 326 | 11 | 0 | 5 | 330 | 1 | 326 | 0 | 650 | 98.16 |
| Query_123749 | WP_003027490.1 | 95.152 | 330 | 0 | 1 | 1 | 330 | 1 | 314 | 0 | 635 | 95.15 |
| Query_123749 | KFJ64957.1 | 95.092 | 326 | 0 | 1 | 5 | 330 | 1 | 310 | 0 | 626 | 95.09 |
| Query_123749 | WP_080555287.1 | 87.988 | 333 | 37 | 2 | 1 | 330 | 1 | 333 | 0 | 602 | 93.09 |
| Query_123749 | WP_082810685.1 | 87.087 | 333 | 40 | 2 | 1 | 330 | 1 | 333 | 0 | 597 | 92.79 |
| Query_123749 | AEB27950.1 | 87.842 | 329 | 37 | 2 | 5 | 330 | 1 | 329 | 0 | 593 | 93.01 |
| Query_123749 | KYW87150.1 | 86.93 | 329 | 40 | 2 | 5 | 330 | 1 | 329 | 0 | 588 | 92.71 |
| Query_123749 | WP_064461549.1 | 82.675 | 329 | 54 | 1 | 5 | 330 | 1 | 329 | 0 | 554 | 91.19 |
| Query_123749 | APC90815.1 | 88.302 | 265 | 31 | 0 | 27 | 291 | 1 | 265 | 2.66E-176 | 490 | 93.96 |
| Query_123749 | WP_013921888.1 | 69.108 | 314 | 72 | 3 | 22 | 329 | 17 | 311 | 3.24E-156 | 440 | 80.57 |
| Query_123749 | WP_004286747.1 | 67.385 | 325 | 94 | 3 | 5 | 329 | 1 | 313 | 1.44E-154 | 436 | 81.23 |
| Query_123749 | WP_042517264.1 | 67.077 | 325 | 95 | 3 | 5 | 329 | 1 | 313 | 1.75E-154 | 436 | 81.23 |
| Query_123749 | WP_040009815.1 | 66.564 | 326 | 89 | 4 | 5 | 329 | 1 | 307 | 2.15E-154 | 435 | 80.06 |
| Query_123749 | WP_012280150.1 | 67.385 | 325 | 94 | 3 | 5 | 329 | 1 | 313 | 4.34E-154 | 435 | 80.92 |
| Query_123749 | WP_042524303.1 | 67.077 | 325 | 95 | 3 | 5 | 329 | 1 | 313 | 8.07E-153 | 431 | 80.62 |
| Query_123749 | WP_044525397.1 | 68.831 | 308 | 85 | 2 | 22 | 329 | 17 | 313 | 9.00E-153 | 431 | 82.79 |
| Query_123749 | WP_035737412.1 | 67.857 | 308 | 88 | 2 | 22 | 329 | 17 | 313 | 1.18E-152 | 431 | 81.49 |
| Query_123749 | API85931.1 | 68.382 | 272 | 83 | 2 | 5 | 274 | 1 | 271 | 6.43E-142 | 405 | 86.03 |
| Query_123749 | AFJ42649.1 | 64.784 | 301 | 95 | 2 | 22 | 322 | 17 | 306 | 2.40E-140 | 400 | 80.07 |
| Query_123749 | WP_112869366.1 | 60.323 | 310 | 120 | 2 | 5 | 312 | 1 | 309 | 5.49E-137 | 391 | 79.03 |
| Query_123749 | TDT73524.1 | 64.394 | 264 | 89 | 3 | 5 | 264 | 3 | 265 | 8.78E-122 | 352 | 82.58 |
| Query_123749 | WP_035720460.1 | 58.156 | 282 | 97 | 3 | 25 | 285 | 22 | 303 | 5.34E-119 | 345 | 76.24 |
| Query_123749 | WP_039123215.1 | 57.045 | 291 | 101 | 7 | 25 | 302 | 20 | 299 | 4.02E-117 | 340 | 78.01 |
| Query_123749 | WP_071663397.1 | 48.828 | 256 | 126 | 4 | 5 | 257 | 1 | 254 | 2.64E-84 | 255 | 71.88 |
| Query_123749 | WP_119331189.1 | 49.789 | 237 | 115 | 3 | 24 | 257 | 19 | 254 | 3.31E-82 | 251 | 73 |
| Query_123749 | WP_012280171.1 | 45.581 | 215 | 113 | 2 | 22 | 236 | 17 | 227 | 1.25E-64 | 204 | 68.37 |
| Query_123749 | WP_013921867.1 | 45.116 | 215 | 114 | 2 | 22 | 236 | 17 | 227 | 2.45E-63 | 201 | 67.44 |
| Query_123749 | API87262.1 | 34.802 | 227 | 141 | 4 | 15 | 236 | 10 | 234 | 4.77E-41 | 144 | 60.35 |
| Query_123749 | WP_088772877.1 | 34.199 | 231 | 147 | 4 | 15 | 243 | 10 | 237 | 2.09E-37 | 134 | 56.28 |
| Query_123749 | WP_004288167.1 | 34.211 | 228 | 140 | 5 | 15 | 241 | 10 | 228 | 2.81E-37 | 134 | 57.89 |
| Query_123749 | WP_044525789.1 | 34.211 | 228 | 140 | 5 | 15 | 241 | 10 | 228 | 1.16E-36 | 132 | 57.46 |
| Query_123749 | WP_041263828.1 | 31.304 | 230 | 148 | 5 | 13 | 241 | 8 | 228 | 3.06E-34 | 125 | 56.96 |
| Query_123749 | WP_084645217.1 | 34.135 | 208 | 130 | 4 | 34 | 236 | 1 | 206 | 1.37E-33 | 123 | 59.62 |
| Query_123749 | WP_088772880.1 | 34.591 | 159 | 98 | 5 | 55 | 211 | 7 | 161 | 1.66E-19 | 85.1 | 56.6 |
| Query_123749 | WP_072713014.1 | 39.796 | 98 | 56 | 2 | 9 | 104 | 4 | 100 | 1.64E-18 | 80.5 | 65.31 |
| Query_123749 | AEI36710.1 | 29.05 | 179 | 118 | 4 | 64 | 241 | 7 | 177 | 5.32E-18 | 80.9 | 53.07 |
| Query_123749 | WP_072713012.1 | 33.654 | 104 | 68 | 1 | 135 | 238 | 1 | 103 | 4.00E-11 | 59.7 | 55.77 |

FIG. 36A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_344588 | WP_003018151.1 | 100 | 161 | 0 | 0 | 1 | 161 | 1 | 161 | 3.46E-115 | 323 | 100 |
| Query_344588 | WP_082265773.1 | 99.379 | 161 | 1 | 0 | 1 | 161 | 1 | 161 | 9.91E-115 | 322 | 100 |
| Query_344588 | WP_003015015.1 | 98.137 | 161 | 3 | 0 | 1 | 161 | 1 | 161 | 7.24E-113 | 317 | 99.38 |
| Query_344588 | ABO46367.1 | 100 | 157 | 0 | 0 | 5 | 161 | 1 | 157 | 1.36E-112 | 316 | 100 |
| Query_344588 | AFX70317.1 | 98.089 | 157 | 3 | 0 | 5 | 161 | 1 | 157 | 2.31E-110 | 311 | 99.36 |
| Query_344588 | WP_080555426.1 | 91.875 | 160 | 13 | 0 | 1 | 160 | 1 | 160 | 2.39E-106 | 301 | 97.5 |
| Query_344588 | AAT77116.1 | 100 | 146 | 0 | 0 | 16 | 161 | 1 | 146 | 1.31E-103 | 293 | 100 |
| Query_344588 | AHH46118.1 | 99.315 | 146 | 1 | 0 | 16 | 161 | 1 | 146 | 4.16E-103 | 292 | 100 |
| Query_344588 | CAJ79057.1 | 98.63 | 146 | 2 | 0 | 16 | 161 | 1 | 146 | 1.27E-102 | 291 | 100 |
| Query_344588 | WP_014548754.1 | 97.241 | 145 | 4 | 0 | 16 | 160 | 1 | 145 | 6.07E-100 | 284 | 97.93 |
| Query_344588 | WP_071628721.1 | 95.89 | 146 | 6 | 0 | 16 | 161 | 1 | 146 | 1.86E-99 | 283 | 97.26 |
| Query_344588 | WP_064460800.1 | 95.172 | 145 | 7 | 0 | 16 | 160 | 1 | 145 | 3.37E-98 | 280 | 97.24 |
| Query_344588 | OIN83099.1 | 97.98 | 99 | 2 | 0 | 63 | 161 | 1 | 99 | 1.28E-65 | 196 | 97.98 |
| Query_344588 | OIN84354.1 | 100 | 61 | 0 | 0 | 1 | 61 | 1 | 61 | 5.74E-37 | 122 | 100 |

FIG. 37A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_310745 | WP_003022747.1 | 100 | 130 | 0 | 0 | 1 | 130 | 1 | 130 | 9.64E-90 | 256 | 100 |
| Query_310745 | WP_003017667.1 | 99.231 | 130 | 1 | 0 | 1 | 130 | 1 | 130 | 6.44E-89 | 254 | 99.23 |
| Query_310745 | WP_003014087.1 | 98.462 | 130 | 2 | 0 | 1 | 130 | 1 | 130 | 1.62E-88 | 253 | 99.23 |
| Query_310745 | WP_003040711.1 | 97.692 | 130 | 3 | 0 | 1 | 130 | 1 | 130 | 1.30E-87 | 251 | 99.23 |
| Query_310745 | WP_014549075.1 | 96.923 | 130 | 4 | 0 | 1 | 130 | 1 | 130 | 6.19E-87 | 249 | 98.46 |
| Query_310745 | WP_066046618.1 | 96.154 | 130 | 5 | 0 | 1 | 130 | 1 | 130 | 3.54E-86 | 247 | 97.69 |
| Query_310745 | ORM38345.1 | 89.764 | 127 | 13 | 0 | 1 | 127 | 12 | 138 | 9.56E-80 | 231 | 95.28 |
| Query_310745 | WP_071629865.1 | 90 | 130 | 13 | 0 | 1 | 130 | 1 | 130 | 6.77E-71 | 209 | 93.85 |
| Query_310745 | WP_064461611.1 | 89.231 | 130 | 14 | 0 | 1 | 130 | 1 | 130 | 9.52E-71 | 208 | 94.62 |
| Query_310745 | OEZ32926.1 | 89.764 | 127 | 13 | 0 | 1 | 127 | 1 | 127 | 2.16E-70 | 207 | 94.49 |
| Query_310745 | WP_085076048.1 | 97.895 | 95 | 2 | 0 | 36 | 130 | 1 | 95 | 3.03E-62 | 186 | 98.95 |
| Query_310745 | WP_042517058.1 | 66.154 | 130 | 44 | 0 | 1 | 130 | 1 | 130 | 2.84E-59 | 179 | 79.23 |
| Query_310745 | WP_044527026.1 | 65.385 | 130 | 45 | 0 | 1 | 130 | 1 | 130 | 3.24E-58 | 176 | 78.46 |
| Query_310745 | WP_039123383.1 | 64.615 | 130 | 44 | 2 | 1 | 129 | 1 | 129 | 9.05E-57 | 173 | 80 |
| Query_310745 | WP_088771592.1 | 66.154 | 130 | 44 | 0 | 1 | 130 | 1 | 130 | 6.70E-55 | 168 | 80.77 |
| Query_310745 | WP_112870814.1 | 60.769 | 130 | 51 | 0 | 1 | 130 | 1 | 130 | 9.57E-53 | 163 | 80 |
| Query_310745 | WP_133942480.1 | 65.385 | 130 | 45 | 0 | 1 | 130 | 1 | 130 | 6.35E-51 | 158 | 79.23 |
| Query_310745 | WP_072713415.1 | 67.692 | 130 | 42 | 0 | 1 | 130 | 1 | 130 | 3.62E-50 | 156 | 82.31 |
| Query_310745 | WP_041257409.1 | 61.6 | 125 | 48 | 0 | 6 | 130 | 1 | 125 | 4.91E-50 | 155 | 75.2 |
| Query_310745 | WP_013923632.1 | 66.154 | 130 | 44 | 0 | 1 | 130 | 1 | 130 | 6.89E-49 | 153 | 79.23 |
| Query_310745 | WP_071513888.1 | 61.417 | 127 | 46 | 2 | 3 | 127 | 4 | 129 | 1.06E-48 | 152 | 77.95 |
| Query_310745 | WP_004286894.1 | 66.154 | 130 | 44 | 0 | 1 | 130 | 1 | 130 | 1.30E-48 | 152 | 79.23 |
| Query_310745 | WP_072713417.1 | 58.462 | 130 | 51 | 2 | 3 | 130 | 4 | 132 | 1.42E-48 | 152 | 77.69 |
| Query_310745 | WP_040009684.1 | 70.769 | 130 | 38 | 0 | 1 | 130 | 1 | 130 | 1.69E-48 | 152 | 83.85 |
| Query_310745 | WP_104928361.1 | 60.63 | 127 | 47 | 2 | 3 | 127 | 4 | 129 | 5.57E-48 | 151 | 77.17 |
| Query_310745 | WP_057113125.1 | 60.63 | 127 | 47 | 2 | 3 | 127 | 4 | 129 | 7.33E-48 | 150 | 77.17 |
| Query_310745 | WP_003014086.1 | 60.63 | 127 | 47 | 2 | 3 | 127 | 4 | 129 | 7.33E-48 | 150 | 77.17 |
| Query_310745 | WP_003017665.1 | 60.63 | 127 | 47 | 2 | 3 | 127 | 4 | 129 | 7.82E-48 | 150 | 77.17 |
| Query_310745 | WP_003037879.1 | 59.843 | 127 | 48 | 2 | 3 | 127 | 4 | 129 | 3.99E-47 | 149 | 76.38 |
| Query_310745 | WP_003024383.1 | 59.843 | 127 | 48 | 2 | 3 | 127 | 4 | 129 | 6.68E-47 | 148 | 76.38 |
| Query_310745 | WP_044527027.1 | 58.462 | 130 | 51 | 2 | 3 | 130 | 4 | 132 | 1.85E-46 | 147 | 75.38 |
| Query_310745 | WP_066046621.1 | 59.843 | 127 | 48 | 2 | 3 | 127 | 4 | 129 | 1.87E-46 | 147 | 75.59 |
| Query_310745 | WP_014715657.1 | 56.923 | 130 | 53 | 2 | 3 | 130 | 4 | 132 | 5.22E-46 | 146 | 74.62 |
| Query_310745 | WP_014549076.1 | 59.055 | 127 | 49 | 2 | 3 | 127 | 4 | 129 | 8.92E-46 | 145 | 74.8 |
| Query_310745 | WP_035720612.1 | 64.341 | 129 | 46 | 0 | 1 | 129 | 1 | 129 | 3.14E-45 | 144 | 80.62 |
| Query_310745 | WP_004286893.1 | 57.692 | 130 | 52 | 2 | 3 | 130 | 4 | 132 | 3.43E-45 | 144 | 73.85 |
| Query_310745 | WP_039123382.1 | 56.154 | 130 | 54 | 2 | 3 | 130 | 4 | 132 | 3.57E-45 | 144 | 71.54 |
| Query_310745 | WP_071629866.1 | 58.268 | 127 | 50 | 2 | 3 | 127 | 4 | 129 | 1.05E-44 | 142 | 74.02 |
| Query_310745 | WP_035737193.1 | 57.692 | 130 | 52 | 2 | 3 | 130 | 4 | 132 | 1.05E-44 | 142 | 73.08 |
| Query_310745 | WP_133942481.1 | 53.435 | 131 | 58 | 2 | 2 | 130 | 3 | 132 | 2.00E-43 | 139 | 70.23 |
| Query_310745 | WP_071663448.1 | 54.615 | 130 | 57 | 1 | 1 | 130 | 1 | 128 | 2.11E-42 | 137 | 70 |
| Query_310745 | WP_040009682.1 | 55.385 | 130 | 55 | 2 | 3 | 130 | 4 | 132 | 2.56E-42 | 136 | 71.54 |
| Query_310745 | WP_088771594.1 | 53.846 | 130 | 57 | 2 | 3 | 130 | 4 | 132 | 8.89E-42 | 135 | 73.85 |
| Query_310745 | WP_119331125.1 | 53.077 | 130 | 59 | 1 | 1 | 130 | 2 | 129 | 1.08E-41 | 135 | 70.77 |
| Query_310745 | WP_064461797.1 | 53.906 | 128 | 56 | 2 | 3 | 128 | 4 | 130 | 1.11E-41 | 135 | 71.88 |
| Query_310745 | WP_071663935.1 | 51.969 | 127 | 60 | 1 | 3 | 129 | 1 | 126 | 1.58E-41 | 134 | 70.87 |
| Query_310745 | WP_112870815.1 | 59.829 | 117 | 42 | 2 | 17 | 129 | 18 | 133 | 1.61E-41 | 134 | 73.5 |
| Query_310745 | WP_072713416.1 | 55.285 | 123 | 52 | 2 | 10 | 130 | 11 | 132 | 6.91E-41 | 133 | 73.17 |
| Query_310745 | WP_035720619.1 | 56.034 | 116 | 48 | 2 | 17 | 130 | 18 | 132 | 1.64E-40 | 132 | 73.28 |
| Query_310745 | WP_013923633.1 | 51.538 | 130 | 60 | 2 | 3 | 130 | 4 | 132 | 3.81E-40 | 131 | 70 |
| Query_310745 | WP_088771593.1 | 50.769 | 130 | 61 | 2 | 3 | 130 | 4 | 132 | 2.78E-39 | 129 | 69.23 |
| Query_310745 | AFJ44131.1 | 59.77 | 87 | 35 | 0 | 44 | 130 | 1 | 87 | 1.72E-30 | 105 | 74.71 |
| Query_310745 | WP_112870816.1 | 40.458 | 131 | 76 | 2 | 1 | 130 | 1 | 130 | 4.32E-26 | 100 | 63.36 |
| Query_310745 | WP_133942482.1 | 37.815 | 119 | 68 | 3 | 16 | 130 | 15 | 131 | 1.06E-17 | 73.9 | 58.82 |
| Query_310745 | WP_112870817.1 | 34.483 | 116 | 70 | 3 | 19 | 130 | 17 | 130 | 7.75E-16 | 69.3 | 59.48 |
| Query_310745 | WP_040009680.1 | 30.827 | 133 | 83 | 4 | 2 | 130 | 4 | 131 | 1.70E-15 | 68.6 | 57.89 |
| Query_310745 | WP_035720611.1 | 35.043 | 117 | 70 | 3 | 18 | 130 | 17 | 131 | 1.70E-15 | 68.6 | 58.12 |
| Query_310745 | WP_112869689.1 | 32.308 | 130 | 82 | 2 | 3 | 130 | 1 | 126 | 2.21E-15 | 68.2 | 56.15 |
| Query_310745 | WP_071629867.1 | 30.534 | 131 | 85 | 3 | 4 | 130 | 3 | 131 | 2.50E-15 | 67.8 | 57.25 |
| Query_310745 | WP_088771595.1 | 31.897 | 116 | 73 | 3 | 19 | 130 | 18 | 131 | 2.87E-15 | 67.8 | 57.76 |
| Query_310745 | WP_119331126.1 | 30.435 | 138 | 82 | 4 | 1 | 130 | 1 | 132 | 3.84E-15 | 67.8 | 56.52 |
| Query_310745 | WP_013923179.1 | 31.538 | 130 | 83 | 3 | 3 | 130 | 2 | 127 | 1.04E-14 | 66.2 | 56.92 |
| Query_310745 | WP_119331124.1 | 34.328 | 134 | 82 | 2 | 3 | 130 | 1 | 134 | 3.22E-14 | 65.1 | 50 |
| Query_310745 | WP_042523347.1 | 33.846 | 130 | 80 | 3 | 3 | 130 | 1 | 126 | 5.41E-14 | 64.3 | 56.15 |

FIG. 38A

| | | | | | | | | | | | |
|---|---|---|---|---|---|---|---|---|---|---|---|
| Query_310745 | WP_044526228.1 | 32.308 | 130 | 82 | 3 | 3 | 130 | 1 | 126 | 1.27E-13 | 63.5 | 56.15 |
| Query_310745 | EET21452.1 | 32.576 | 132 | 83 | 3 | 1 | 130 | 2 | 129 | 1.42E-13 | 63.5 | 55.3 |
| Query_310745 | WP_071663449.1 | 33.582 | 134 | 83 | 2 | 3 | 130 | 2 | 135 | 1.81E-13 | 63.2 | 50 |
| Query_310745 | APC97796.1 | 33.582 | 134 | 83 | 2 | 3 | 130 | 1 | 134 | 1.87E-13 | 63.2 | 50 |
| Query_310745 | WP_035735696.1 | 33.077 | 130 | 81 | 3 | 3 | 130 | 1 | 126 | 2.10E-13 | 62.8 | 55.38 |
| Query_310745 | WP_042518318.1 | 33.077 | 130 | 81 | 3 | 3 | 130 | 1 | 126 | 2.75E-13 | 62.8 | 55.38 |
| Query_310745 | WP_088821246.1 | 33.077 | 130 | 81 | 3 | 3 | 130 | 1 | 126 | 2.90E-13 | 62.4 | 55.38 |
| Query_310745 | WP_041265065.1 | 32.308 | 130 | 82 | 3 | 3 | 130 | 1 | 126 | 3.83E-13 | 62.4 | 55.38 |
| Query_310745 | WP_041257334.1 | 31.538 | 130 | 83 | 3 | 3 | 130 | 1 | 126 | 7.74E-13 | 61.6 | 55.38 |
| Query_310745 | WP_003022749.1 | 28.571 | 133 | 86 | 4 | 2 | 130 | 4 | 131 | 9.18E-13 | 61.2 | 56.39 |
| Query_310745 | WP_035722569.1 | 32.308 | 130 | 82 | 3 | 3 | 130 | 1 | 126 | 9.48E-13 | 61.2 | 55.38 |
| Query_310745 | WP_003029954.1 | 28.571 | 133 | 86 | 4 | 2 | 130 | 4 | 131 | 9.79E-13 | 61.2 | 56.39 |
| Query_310745 | WP_012280996.1 | 33.077 | 130 | 81 | 3 | 3 | 130 | 1 | 126 | 1.35E-12 | 60.8 | 54.62 |
| Query_310745 | WP_072712422.1 | 31.061 | 132 | 78 | 3 | 3 | 130 | 1 | 123 | 1.63E-12 | 60.5 | 52.27 |
| Query_310745 | WP_071513887.1 | 28.571 | 133 | 86 | 4 | 2 | 130 | 4 | 131 | 2.02E-12 | 60.5 | 56.39 |
| Query_310745 | WP_003032563.1 | 28.571 | 133 | 86 | 4 | 2 | 130 | 4 | 131 | 2.53E-12 | 60.1 | 55.64 |
| Query_310745 | WP_003037882.1 | 28.571 | 133 | 86 | 4 | 2 | 130 | 4 | 131 | 2.93E-12 | 60.1 | 55.64 |
| Query_310745 | WP_071660573.1 | 28.571 | 133 | 86 | 4 | 2 | 130 | 4 | 131 | 3.16E-12 | 60.1 | 55.64 |
| Query_310745 | WP_071663447.1 | 31.884 | 138 | 80 | 5 | 1 | 130 | 1 | 132 | 6.01E-12 | 59.3 | 52.9 |
| Query_310745 | WP_088772534.1 | 29.231 | 130 | 83 | 3 | 3 | 130 | 1 | 123 | 6.74E-12 | 58.9 | 53.08 |
| Query_310745 | AHB98450.1 | 33.898 | 118 | 72 | 3 | 15 | 130 | 4 | 117 | 1.26E-11 | 58.2 | 55.08 |
| Query_310745 | WP_066046623.1 | 28.358 | 134 | 90 | 3 | 1 | 130 | 1 | 132 | 2.49E-11 | 57.8 | 53.73 |
| Query_310745 | WP_014549077.1 | 29.31 | 116 | 76 | 3 | 19 | 130 | 19 | 132 | 9.46E-11 | 56.2 | 54.31 |
| Query_310745 | WP_112869317.1 | 30.37 | 135 | 85 | 3 | 2 | 130 | 3 | 134 | 4.55E-10 | 54.3 | 51.85 |
| Query_310745 | WP_072713418.1 | 35.366 | 82 | 46 | 3 | 2 | 79 | 4 | 82 | 5.06E-10 | 53.1 | 59.76 |
| Query_310745 | AFJ43429.1 | 31.579 | 114 | 72 | 3 | 19 | 130 | 1 | 110 | 1.58E-09 | 52.4 | 54.39 |
| Query_310745 | WP_064461610.1 | 28.448 | 116 | 77 | 3 | 19 | 130 | 18 | 131 | 2.10E-08 | 52.4 | 53.45 |
| Query_310745 | WP_040007667.1 | 27.826 | 115 | 71 | 3 | 20 | 130 | 19 | 125 | 1.19E-08 | 50.4 | 50.43 |
| Query_310745 | WP_039123489.1 | 29.008 | 131 | 87 | 2 | 3 | 127 | 1 | 131 | 6.13E-08 | 48.9 | 49.62 |
| Query_310745 | WP_014548727.1 | 30.435 | 138 | 82 | 4 | 1 | 130 | 1 | 132 | 6.24E-08 | 48.9 | 52.17 |
| Query_310745 | WP_044525473.1 | 31.25 | 144 | 81 | 5 | 1 | 130 | 1 | 140 | 8.50E-08 | 48.5 | 51.39 |
| Query_310745 | CAJ78544.1 | 38.462 | 65 | 33 | 3 | 2 | 62 | 4 | 65 | 1.56E-07 | 46.6 | 66.15 |
| Query_310745 | WP_071663484.1 | 29.032 | 93 | 65 | 1 | 38 | 130 | 33 | 124 | 1.84E-07 | 47.4 | 52.69 |
| Query_310745 | WP_071628742.1 | 30.435 | 138 | 82 | 4 | 1 | 130 | 1 | 132 | 2.03E-07 | 47.4 | 50.72 |
| Query_310745 | WP_133940846.1 | 28.421 | 95 | 67 | 1 | 37 | 130 | 40 | 134 | 1.43E-06 | 45.1 | 52.63 |
| Query_310745 | WP_088820736.1 | 31.25 | 112 | 67 | 3 | 28 | 130 | 31 | 141 | 1.52E-06 | 45.1 | 50 |
| Query_310745 | OEZ33510.1 | 27.027 | 111 | 72 | 2 | 29 | 130 | 32 | 142 | 1.98E-06 | 44.7 | 50.45 |
| Query_310745 | WP_119331102.1 | 27.957 | 93 | 66 | 1 | 38 | 130 | 33 | 124 | 2.34E-06 | 44.3 | 50.54 |
| Query_310745 | OEZ33091.1 | 28.947 | 114 | 68 | 3 | 23 | 123 | 4 | 117 | 2.76E-06 | 44.3 | 51.75 |
| Query_310745 | WP_014547525.1 | 24.648 | 142 | 93 | 3 | 3 | 130 | 1 | 142 | 3.31E-06 | 44.3 | 46.48 |
| Query_310745 | WP_042524179.1 | 27.966 | 118 | 79 | 2 | 17 | 130 | 16 | 131 | 3.61E-06 | 43.9 | 54.24 |
| Query_310745 | WP_104928544.1 | 29.508 | 122 | 71 | 3 | 23 | 130 | 12 | 132 | 4.13E-06 | 43.9 | 51.64 |
| Query_310745 | WP_088821759.1 | 27.966 | 118 | 79 | 2 | 17 | 130 | 16 | 131 | 5.93E-06 | 43.5 | 53.39 |
| Query_310745 | WP_012280071.1 | 30.556 | 144 | 83 | 5 | 1 | 130 | 1 | 141 | 6.05E-06 | 43.5 | 47.92 |
| Query_310745 | WP_004286659.1 | 30.556 | 144 | 83 | 5 | 1 | 130 | 1 | 141 | 6.11E-06 | 43.5 | 47.92 |
| Query_310745 | WP_040010419.1 | 26.812 | 138 | 85 | 5 | 3 | 130 | 4 | 135 | 6.57E-06 | 43.5 | 50 |
| Query_310745 | WP_014715658.1 | 28.814 | 118 | 78 | 2 | 17 | 130 | 16 | 131 | 6.78E-06 | 43.1 | 53.39 |
| Query_310745 | WP_064461486.1 | 25.893 | 112 | 74 | 2 | 28 | 130 | 31 | 142 | 6.86E-06 | 43.5 | 50.89 |
| Query_310745 | WP_012280290.1 | 27.966 | 118 | 79 | 2 | 17 | 130 | 3 | 118 | 6.88E-06 | 43.1 | 53.39 |
| Query_310745 | WP_064460807.1 | 28.689 | 122 | 72 | 4 | 23 | 130 | 12 | 132 | 8.01E-06 | 43.1 | 51.64 |
| Query_310745 | WP_066046345.1 | 26.389 | 144 | 90 | 4 | 1 | 130 | 1 | 142 | 8.25E-06 | 43.1 | 47.22 |
| Query_310745 | WP_035737195.1 | 27.966 | 118 | 79 | 2 | 17 | 130 | 16 | 131 | 8.68E-06 | 42.7 | 53.39 |
| Query_310745 | WP_003018179.1 | 29.496 | 139 | 82 | 4 | 1 | 130 | 1 | 132 | 9.91E-06 | 42.7 | 50.36 |
| Query_310745 | WP_044527028.1 | 27.966 | 118 | 79 | 2 | 17 | 130 | 16 | 131 | 9.93E-06 | 42.7 | 52.54 |
| Query_310745 | WP_003037248.1 | 29.496 | 139 | 82 | 4 | 1 | 130 | 1 | 132 | 1.02E-05 | 42.7 | 50.36 |
| Query_310745 | WP_012429839.1 | 26.126 | 111 | 73 | 2 | 29 | 130 | 32 | 142 | 1.12E-05 | 42.7 | 49.55 |
| Query_310745 | WP_041263869.1 | 27.928 | 111 | 70 | 4 | 29 | 130 | 32 | 141 | 1.14E-05 | 42.7 | 52.25 |
| Query_310745 | AEI35117.1 | 27.928 | 111 | 70 | 4 | 29 | 130 | 22 | 131 | 1.40E-05 | 42.4 | 52.25 |
| Query_310745 | ORM38344.1 | 41.667 | 48 | 24 | 2 | 19 | 62 | 18 | 65 | 1.46E-05 | 41.2 | 64.58 |
| Query_310745 | WP_003034620.1 | 28.777 | 139 | 83 | 4 | 1 | 130 | 1 | 132 | 1.69E-05 | 42.4 | 50.36 |
| Query_310745 | WP_004286892.1 | 27.966 | 118 | 79 | 2 | 17 | 130 | 16 | 131 | 1.75E-05 | 42 | 52.54 |
| Query_310745 | WP_013923634.1 | 26.087 | 92 | 66 | 1 | 39 | 130 | 42 | 131 | 1.80E-05 | 42 | 53.26 |
| Query_310745 | WP_003015055.1 | 28.777 | 139 | 83 | 4 | 1 | 130 | 1 | 132 | 1.82E-05 | 42 | 50.36 |

FIG. 38A continued

| | | | | | | | | | | | | |
|---|---|---|---|---|---|---|---|---|---|---|---|---|
| Query_310745 | WP_012429332.1 | 28.777 | 139 | 83 | 4 | 1 | 130 | 1 | 132 | 1.82E-05 | 42 | 50.36 |
| Query_310745 | WP_035736560.1 | 28.431 | 102 | 65 | 2 | 37 | 130 | 34 | 135 | 2.04E-05 | 42 | 51.96 |
| Query_310745 | WP_035720462.1 | 28.421 | 95 | 67 | 1 | 37 | 130 | 39 | 133 | 2.04E-05 | 42 | 51.58 |
| Query_310745 | WP_014550064.1 | 28.448 | 116 | 72 | 3 | 24 | 130 | 19 | 132 | 2.25E-05 | 42 | 52.59 |
| Query_310745 | WP_014714288.1 | 33.708 | 89 | 50 | 2 | 49 | 129 | 52 | 139 | 2.26E-05 | 42 | 55.06 |
| Query_310745 | WP_042517061.1 | 27.966 | 118 | 79 | 2 | 17 | 130 | 16 | 131 | 2.36E-05 | 41.6 | 52.54 |
| Query_310745 | WP_003021668.1 | 26.126 | 111 | 73 | 2 | 29 | 130 | 32 | 142 | 4.06E-05 | 41.2 | 49.55 |
| Query_310745 | WP_071628545.1 | 25.694 | 144 | 91 | 4 | 1 | 130 | 1 | 142 | 4.10E-05 | 41.2 | 47.22 |
| Query_310745 | WP_014549273.1 | 26.126 | 111 | 73 | 2 | 29 | 130 | 32 | 142 | 4.68E-05 | 41.2 | 48.65 |
| Query_310745 | WP_003041523.1 | 26.126 | 111 | 73 | 2 | 29 | 130 | 32 | 142 | 4.73E-05 | 41.2 | 48.65 |
| Query_310745 | WP_003035282.1 | 26.126 | 111 | 73 | 2 | 29 | 130 | 32 | 142 | 4.93E-05 | 41.2 | 48.65 |
| Query_310745 | WP_003014244.1 | 26.126 | 111 | 73 | 2 | 29 | 130 | 32 | 142 | 5.74E-05 | 40.8 | 48.65 |
| Query_310745 | WP_071514869.1 | 25.225 | 111 | 74 | 2 | 29 | 130 | 32 | 142 | 1.26E-04 | 40 | 48.65 |
| Query_310745 | 2MU4_A | 28.155 | 103 | 64 | 2 | 37 | 130 | 7 | 108 | 1.66E-04 | 39.3 | 53.4 |
| Query_310745 | ORM38923.1 | 25.225 | 111 | 74 | 2 | 29 | 130 | 32 | 142 | 2.42E-04 | 39.3 | 48.65 |
| Query_310745 | WP_025329094.1 | 25.225 | 111 | 74 | 2 | 29 | 130 | 32 | 142 | 2.68E-04 | 38.9 | 47.75 |
| Query_310745 | WP_072712974.1 | 26.496 | 117 | 73 | 4 | 24 | 130 | 19 | 132 | 5.68E-04 | 38.1 | 52.99 |
| Query_310745 | WP_040010014.1 | 25 | 144 | 92 | 4 | 1 | 130 | 1 | 142 | 5.72E-04 | 38.1 | 45.83 |
| Query_310745 | WP_044526643.1 | 26.471 | 102 | 67 | 2 | 37 | 130 | 34 | 135 | 6.37E-04 | 38.1 | 50.98 |

FIG. 38A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_224066 | CAG45447.1 | 100 | 199 | 0 | 0 | 1 | 199 | 1 | 199 | 8.14E-144 | 399 | 100 |
| Query_224066 | KFJ45213.1 | 100 | 198 | 0 | 0 | 2 | 199 | 1 | 198 | 8.04E-143 | 396 | 100 |
| Query_224066 | OCQ62312.1 | 98.995 | 199 | 2 | 0 | 1 | 199 | 1 | 199 | 2.47E-142 | 395 | 99.5 |
| Query_224066 | EKM88246.1 | 99.497 | 199 | 1 | 0 | 1 | 199 | 86 | 284 | 2.59E-142 | 398 | 100 |
| Query_224066 | KHS55050.1 | 98.995 | 199 | 2 | 0 | 1 | 199 | 86 | 284 | 1.10E-141 | 396 | 99.5 |
| Query_224066 | KIP30507.1 | 98.99 | 198 | 2 | 0 | 2 | 199 | 1 | 198 | 2.58E-141 | 392 | 99.49 |
| Query_224066 | WP_101686179.1 | 98.995 | 199 | 2 | 0 | 1 | 199 | 373 | 571 | 3.53E-137 | 395 | 99.5 |
| Query_224066 | WP_010031938.1 | 98.995 | 199 | 2 | 0 | 1 | 199 | 373 | 571 | 3.89E-137 | 395 | 99.5 |
| Query_224066 | WP_101703942.1 | 98.995 | 199 | 2 | 0 | 1 | 199 | 373 | 571 | 4.16E-137 | 395 | 99.5 |
| Query_224066 | WP_011648737.1 | 98.995 | 199 | 2 | 0 | 1 | 199 | 376 | 574 | 5.24E-137 | 395 | 99.5 |
| Query_224066 | WP_003016679.1 | 98.995 | 199 | 2 | 0 | 1 | 199 | 376 | 574 | 5.42E-137 | 395 | 99.5 |
| Query_224066 | WP_003025539.1 | 98.995 | 199 | 2 | 0 | 1 | 199 | 398 | 596 | 5.60E-137 | 395 | 99.5 |
| Query_224066 | WP_032731369.1 | 98.492 | 199 | 3 | 0 | 1 | 199 | 398 | 596 | 2.38E-136 | 394 | 99.5 |
| Query_224066 | WP_025329442.1 | 98.492 | 199 | 3 | 0 | 1 | 199 | 398 | 596 | 3.44E-136 | 394 | 99.5 |
| Query_224066 | WP_071304531.1 | 97.99 | 199 | 4 | 0 | 1 | 199 | 398 | 596 | 5.49E-136 | 393 | 98.99 |
| Query_224066 | WP_004339565.1 | 97.99 | 199 | 4 | 0 | 1 | 199 | 398 | 596 | 3.23E-135 | 391 | 98.99 |
| Query_224066 | WP_003036972.1 | 97.99 | 199 | 4 | 0 | 1 | 199 | 398 | 596 | 3.48E-135 | 391 | 98.99 |
| Query_224066 | WP_014549976.1 | 97.99 | 199 | 4 | 0 | 1 | 199 | 398 | 596 | 3.97E-135 | 391 | 98.99 |
| Query_224066 | WP_003039892.1 | 97.99 | 199 | 4 | 0 | 1 | 199 | 398 | 596 | 4.14E-135 | 391 | 98.99 |
| Query_224066 | WP_003034334.1 | 96.482 | 199 | 7 | 0 | 1 | 199 | 398 | 596 | 9.36E-134 | 387 | 98.49 |
| Query_224066 | WP_014548529.1 | 96.482 | 199 | 7 | 0 | 1 | 199 | 398 | 596 | 3.13E-133 | 386 | 98.49 |
| Query_224066 | WP_104928646.1 | 96.482 | 199 | 7 | 0 | 1 | 199 | 398 | 596 | 4.68E-132 | 383 | 97.99 |
| Query_224066 | WP_066044755.1 | 95.98 | 199 | 8 | 0 | 1 | 199 | 398 | 596 | 5.56E-132 | 383 | 97.99 |
| Query_224066 | AJI66889.1 | 98.78 | 164 | 2 | 0 | 1 | 164 | 373 | 536 | 9.64E-110 | 325 | 99.39 |
| Query_224066 | WP_044526461.1 | 73.869 | 199 | 50 | 1 | 1 | 199 | 399 | 595 | 4.11E-101 | 304 | 88.44 |
| Query_224066 | WP_012279663.1 | 72.864 | 199 | 52 | 1 | 1 | 199 | 399 | 595 | 4.36E-100 | 301 | 88.44 |
| Query_224066 | WP_042523027.1 | 72.362 | 199 | 53 | 1 | 1 | 199 | 399 | 595 | 8.87E-100 | 300 | 88.44 |
| Query_224066 | WP_035736288.1 | 72.362 | 199 | 53 | 1 | 1 | 199 | 399 | 595 | 9.17E-100 | 300 | 88.44 |
| Query_224066 | WP_041257403.1 | 69.347 | 199 | 59 | 1 | 1 | 199 | 86 | 282 | 1.28E-99 | 290 | 86.93 |
| Query_224066 | WP_004287998.1 | 72.362 | 199 | 53 | 1 | 1 | 199 | 399 | 595 | 1.54E-99 | 300 | 88.44 |
| Query_224066 | WP_042518020.1 | 72.362 | 199 | 53 | 1 | 1 | 199 | 399 | 595 | 3.03E-99 | 299 | 87.94 |
| Query_224066 | WP_088821369.1 | 71.357 | 199 | 55 | 1 | 1 | 199 | 399 | 595 | 4.58E-98 | 296 | 87.44 |
| Query_224066 | WP_013922895.1 | 69.849 | 199 | 58 | 1 | 1 | 199 | 399 | 595 | 6.22E-96 | 291 | 84.42 |
| Query_224066 | AJI75458.1 | 68.571 | 140 | 42 | 1 | 60 | 199 | 1 | 138 | 3.61E-66 | 200 | 85.71 |
| Query_224066 | WP_112870315.1 | 52.261 | 199 | 92 | 1 | 1 | 199 | 401 | 596 | 3.33E-64 | 208 | 68.34 |
| Query_224066 | WP_040008214.1 | 50.495 | 202 | 90 | 4 | 1 | 199 | 407 | 601 | 2.46E-56 | 187 | 65.84 |
| Query_224066 | WP_088772169.1 | 34.601 | 263 | 107 | 6 | 2 | 199 | 1 | 263 | 6.80E-38 | 132 | 49.81 |
| Query_224066 | WP_072712702.1 | 60.87 | 92 | 36 | 0 | 1 | 92 | 393 | 484 | 9.70E-32 | 121 | 78.26 |
| Query_224066 | WP_072711301.1 | 56.842 | 95 | 41 | 0 | 1 | 95 | 408 | 502 | 5.63E-30 | 116 | 73.68 |
| Query_224066 | WP_072711303.1 | 56.842 | 95 | 41 | 0 | 1 | 95 | 432 | 526 | 9.72E-30 | 115 | 73.68 |
| Query_224066 | WP_013922051.1 | 55.789 | 95 | 42 | 0 | 1 | 95 | 420 | 514 | 1.28E-28 | 112 | 71.58 |
| Query_224066 | WP_071663583.1 | 38.679 | 106 | 63 | 1 | 1 | 106 | 391 | 494 | 4.91E-17 | 79 | 61.32 |
| Query_224066 | WP_071663583.1 | 40.625 | 96 | 57 | 0 | 1 | 96 | 500 | 595 | 1.10E-13 | 69.3 | 59.38 |

FIG. 39A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_162689 | WP_003021156.1 | 100 | 270 | 0 | 0 | 1 | 270 | 1 | 270 | 0 | 551 | 100 |
| Query_162689 | WP_003026094.1 | 99.63 | 270 | 1 | 0 | 1 | 270 | 1 | 270 | 0 | 549 | 99.63 |
| Query_162689 | WP_003015948.1 | 99.259 | 270 | 2 | 0 | 1 | 270 | 1 | 270 | 0 | 548 | 99.63 |
| Query_162689 | WP_057113059.1 | 99.259 | 270 | 2 | 0 | 1 | 270 | 1 | 270 | 0 | 547 | 99.26 |
| Query_162689 | WP_003018977.1 | 98.889 | 270 | 3 | 0 | 1 | 270 | 1 | 270 | 0 | 545 | 98.89 |
| Query_162689 | WP_012429490.1 | 98.889 | 270 | 3 | 0 | 1 | 270 | 1 | 270 | 0 | 544 | 98.89 |
| Query_162689 | WP_003033853.1 | 94.7 | 283 | 2 | 1 | 1 | 270 | 1 | 283 | 0 | 539 | 94.7 |
| Query_162689 | WP_003036552.1 | 94.346 | 283 | 3 | 1 | 1 | 270 | 1 | 283 | 0 | 538 | 94.7 |
| Query_162689 | WP_071514423.1 | 94.346 | 283 | 3 | 1 | 1 | 270 | 1 | 283 | 0 | 537 | 94.35 |
| Query_162689 | WP_003042481.1 | 94.346 | 283 | 3 | 1 | 1 | 270 | 1 | 283 | 0 | 537 | 94.35 |
| Query_162689 | WP_014549789.1 | 94.346 | 283 | 3 | 1 | 1 | 270 | 1 | 283 | 0 | 537 | 94.35 |
| Query_162689 | WP_104928797.1 | 93.993 | 283 | 4 | 1 | 1 | 270 | 1 | 283 | 0 | 535 | 94.35 |
| Query_162689 | WP_014548163.1 | 87.413 | 286 | 20 | 1 | 1 | 270 | 1 | 286 | 0 | 505 | 90.56 |
| Query_162689 | WP_066045345.1 | 86.364 | 286 | 23 | 1 | 1 | 270 | 1 | 286 | 1.03E-180 | 498 | 89.51 |
| Query_162689 | WP_071629059.1 | 84.375 | 288 | 27 | 3 | 1 | 270 | 1 | 288 | 9.22E-177 | 488 | 89.93 |
| Query_162689 | OEZ33837.1 | 83.681 | 288 | 29 | 3 | 1 | 270 | 1 | 288 | 1.31E-174 | 483 | 88.89 |
| Query_162689 | ORM39266.1 | 81.25 | 288 | 36 | 3 | 1 | 270 | 1 | 288 | 2.04E-168 | 467 | 86.81 |
| Query_162689 | WP_042523356.1 | 76.667 | 270 | 62 | 1 | 1 | 270 | 1 | 269 | 4.10E-156 | 436 | 88.15 |
| Query_162689 | WP_042518308.1 | 76.667 | 270 | 62 | 1 | 1 | 270 | 1 | 269 | 5.33E-156 | 435 | 88.52 |
| Query_162689 | WP_035735680.1 | 76.296 | 270 | 63 | 1 | 1 | 270 | 1 | 269 | 1.45E-155 | 434 | 88.89 |
| Query_162689 | WP_088821250.1 | 76.296 | 270 | 63 | 1 | 1 | 270 | 1 | 269 | 3.75E-155 | 433 | 88.52 |
| Query_162689 | WP_012280990.1 | 77.007 | 274 | 52 | 3 | 1 | 270 | 1 | 267 | 1.57E-154 | 431 | 86.86 |
| Query_162689 | WP_064461022.1 | 80.072 | 276 | 49 | 5 | 1 | 270 | 1 | 276 | 5.26E-154 | 431 | 87.32 |
| Query_162689 | WP_004287703.1 | 75.926 | 270 | 64 | 1 | 1 | 270 | 1 | 269 | 1.80E-153 | 429 | 87.78 |
| Query_162689 | WP_030005616.1 | 77.656 | 273 | 57 | 2 | 1 | 270 | 1 | 272 | 2.02E-153 | 429 | 86.81 |
| Query_162689 | WP_014714970.1 | 77.574 | 272 | 57 | 2 | 2 | 270 | 4 | 274 | 1.74E-152 | 426 | 86.76 |
| Query_162689 | WP_044526237.1 | 76.557 | 273 | 60 | 2 | 1 | 270 | 1 | 272 | 2.38E-152 | 426 | 87.18 |
| Query_162689 | WP_013923188.1 | 70.671 | 283 | 69 | 2 | 1 | 270 | 1 | 282 | 6.11E-148 | 415 | 83.39 |
| Query_162689 | WP_040007642.1 | 62.116 | 293 | 88 | 1 | 1 | 270 | 1 | 293 | 5.43E-134 | 380 | 77.82 |
| Query_162689 | WP_039125012.1 | 63.799 | 279 | 91 | 3 | 1 | 270 | 1 | 278 | 4.84E-125 | 357 | 77.78 |
| Query_162689 | WP_035718720.1 | 64.158 | 279 | 91 | 4 | 1 | 270 | 1 | 279 | 2.67E-116 | 335 | 78.49 |
| Query_162689 | WP_133940319.1 | 63.441 | 279 | 93 | 4 | 1 | 270 | 1 | 279 | 1.41E-115 | 333 | 78.14 |
| Query_162689 | WP_112870213.1 | 58.065 | 279 | 108 | 2 | 1 | 270 | 1 | 279 | 4.67E-113 | 327 | 74.91 |
| Query_162689 | WP_072712436.1 | 55.351 | 271 | 92 | 3 | 1 | 270 | 1 | 243 | 2.32E-103 | 301 | 71.22 |
| Query_162689 | WP_088772543.1 | 53.137 | 271 | 98 | 3 | 1 | 270 | 1 | 243 | 1.30E-100 | 294 | 70.48 |
| Query_162689 | WP_071664542.1 | 60.731 | 219 | 86 | 0 | 52 | 270 | 22 | 240 | 2.73E-94 | 278 | 73.97 |
| Query_162689 | WP_119330077.1 | 59.259 | 216 | 88 | 0 | 55 | 270 | 24 | 239 | 9.51E-91 | 269 | 73.61 |
| Query_162689 | WP_035737223.1 | 37.091 | 275 | 142 | 6 | 3 | 266 | 1 | 255 | 1.37E-49 | 164 | 53.09 |
| Query_162689 | EET20620.1 | 36.462 | 277 | 145 | 6 | 1 | 266 | 8 | 264 | 2.15E-49 | 164 | 53.43 |
| Query_162689 | WP_044527041.1 | 37.091 | 275 | 142 | 6 | 3 | 266 | 1 | 255 | 2.84E-49 | 164 | 52.36 |
| Query_162689 | WP_035722165.1 | 36.727 | 275 | 143 | 6 | 3 | 266 | 1 | 255 | 9.90E-49 | 162 | 52.73 |
| Query_162689 | WP_088821769.1 | 36.727 | 275 | 143 | 6 | 3 | 266 | 1 | 255 | 1.15E-48 | 162 | 52.73 |
| Query_162689 | WP_012280276.1 | 36.727 | 275 | 143 | 6 | 3 | 266 | 1 | 255 | 6.23E-48 | 160 | 52.36 |
| Query_162689 | WP_014715675.1 | 36 | 275 | 145 | 6 | 3 | 266 | 1 | 255 | 3.96E-47 | 158 | 52.36 |
| Query_162689 | WP_112869596.1 | 30.168 | 179 | 98 | 6 | 1 | 168 | 1 | 163 | 1.06E-14 | 73.6 | 50.84 |
| Query_162689 | WP_051686745.1 | 31.746 | 126 | 73 | 3 | 1 | 122 | 1 | 117 | 4.03E-13 | 68.6 | 57.94 |
| Query_162689 | WP_039125803.1 | 31.746 | 126 | 72 | 3 | 1 | 122 | 1 | 116 | 5.44E-13 | 68.2 | 57.14 |
| Query_162689 | WP_012429668.1 | 30.814 | 172 | 94 | 6 | 1 | 167 | 1 | 152 | 1.24E-12 | 67.8 | 49.42 |
| Query_162689 | WP_003021256.1 | 30.814 | 172 | 94 | 6 | 1 | 167 | 1 | 152 | 1.38E-12 | 67.4 | 49.42 |
| Query_162689 | WP_003026674.1 | 30.814 | 172 | 94 | 6 | 1 | 167 | 1 | 152 | 2.06E-12 | 67 | 48.84 |
| Query_162689 | WP_072712510.1 | 47.692 | 65 | 30 | 1 | 62 | 122 | 59 | 123 | 2.44E-12 | 66.6 | 69.23 |
| Query_162689 | WP_003019051.1 | 30.233 | 172 | 95 | 6 | 1 | 167 | 1 | 152 | 4.00E-12 | 66.2 | 48.84 |
| Query_162689 | WP_025329358.1 | 30.233 | 172 | 95 | 6 | 1 | 167 | 1 | 152 | 4.15E-12 | 66.2 | 48.84 |
| Query_162689 | WP_133940629.1 | 30.952 | 126 | 74 | 3 | 1 | 122 | 1 | 117 | 4.17E-12 | 65.9 | 56.35 |
| Query_162689 | WP_003042217.1 | 30.233 | 172 | 95 | 5 | 1 | 167 | 1 | 152 | 5.05E-12 | 65.9 | 48.26 |
| Query_162689 | WP_015083939.1 | 30.814 | 172 | 94 | 7 | 1 | 167 | 1 | 152 | 1.22E-11 | 64.7 | 49.42 |
| Query_162689 | WP_003015633.1 | 29.651 | 172 | 96 | 6 | 1 | 167 | 1 | 152 | 1.39E-11 | 64.7 | 48.84 |
| Query_162689 | WP_042520366.1 | 29.651 | 172 | 96 | 6 | 1 | 167 | 1 | 152 | 1.48E-11 | 64.3 | 48.26 |
| Query_162689 | WP_014549654.1 | 29.651 | 172 | 96 | 5 | 1 | 167 | 1 | 152 | 1.90E-11 | 64.3 | 47.67 |
| Query_162689 | WP_071660301.1 | 29.651 | 172 | 96 | 5 | 1 | 167 | 1 | 152 | 2.66E-11 | 63.5 | 47.67 |
| Query_162689 | WP_032729950.1 | 29.651 | 172 | 96 | 5 | 1 | 167 | 1 | 152 | 2.66E-11 | 63.5 | 47.67 |
| Query_162689 | WP_104928905.1 | 29.651 | 172 | 96 | 5 | 1 | 167 | 1 | 152 | 2.69E-11 | 63.5 | 47.67 |

FIG. 40A

| | | | | | | | | | | | | |
|---|---|---|---|---|---|---|---|---|---|---|---|---|
| Query_162689 | WP_071304241.1 | 29.651 | 172 | 96 | 5 | 1 | 167 | 1 | 152 | 2.71E-11 | 63.5 | 47.67 |
| Query_162689 | WP_003036264.1 | 29.651 | 172 | 96 | 5 | 1 | 167 | 1 | 152 | 2.71E-11 | 63.5 | 47.67 |
| Query_162689 | WP_014714996.1 | 28.571 | 175 | 95 | 6 | 1 | 170 | 1 | 150 | 1.04E-10 | 62 | 49.71 |
| Query_162689 | WP_088772301.1 | 40.741 | 81 | 44 | 1 | 46 | 122 | 42 | 122 | 2.23E-10 | 60.8 | 58.02 |
| Query_162689 | WP_013923216.1 | 34.234 | 111 | 52 | 4 | 63 | 168 | 61 | 155 | 2.24E-10 | 60.8 | 54.95 |
| Query_162689 | WP_012280965.1 | 28.161 | 174 | 95 | 6 | 1 | 170 | 1 | 148 | 3.26E-10 | 60.5 | 49.43 |
| Query_162689 | WP_051011713.1 | 31.013 | 158 | 84 | 6 | 15 | 167 | 1 | 138 | 3.36E-10 | 60.5 | 48.1 |
| Query_162689 | WP_042518272.1 | 29.282 | 181 | 84 | 8 | 1 | 170 | 1 | 148 | 3.68E-10 | 60.5 | 48.62 |
| Query_162689 | WP_066046302.1 | 43.59 | 78 | 40 | 1 | 46 | 119 | 42 | 119 | 1.43E-09 | 58.5 | 55.13 |
| Query_162689 | WP_044526261.1 | 29.143 | 175 | 94 | 6 | 1 | 170 | 1 | 150 | 1.76E-09 | 58.2 | 50.86 |
| Query_162689 | WP_014548404.1 | 47.143 | 70 | 31 | 2 | 54 | 119 | 52 | 119 | 5.50E-09 | 56.6 | 58.57 |
| Query_162689 | WP_071629187.1 | 48.387 | 62 | 28 | 1 | 62 | 119 | 58 | 119 | 1.21E-08 | 55.8 | 61.29 |
| Query_162689 | WP_035735625.1 | 33.036 | 112 | 49 | 4 | 63 | 170 | 59 | 148 | 5.24E-08 | 53.9 | 51.79 |
| Query_162689 | WP_042523389.1 | 33.036 | 112 | 49 | 4 | 63 | 170 | 59 | 148 | 5.35E-08 | 53.9 | 51.79 |
| Query_162689 | WP_035722563.1 | 33.036 | 112 | 49 | 4 | 63 | 170 | 59 | 148 | 5.45E-08 | 53.9 | 51.79 |
| Query_162689 | WP_088821270.1 | 33.036 | 112 | 49 | 4 | 63 | 170 | 59 | 148 | 5.78E-08 | 53.9 | 51.79 |
| Query_162689 | EET21415.1 | 33.036 | 112 | 49 | 4 | 63 | 170 | 41 | 130 | 7.59E-08 | 53.1 | 51.79 |
| Query_162689 | WP_119330642.1 | 35.385 | 65 | 38 | 1 | 62 | 122 | 50 | 114 | 4.48E-06 | 48.1 | 60 |
| Query_162689 | WP_064460988.1 | 41.935 | 62 | 32 | 1 | 62 | 119 | 61 | 122 | 8.04E-06 | 47 | 56.45 |
| Query_162689 | ORM39325.1 | 41.935 | 62 | 32 | 1 | 62 | 119 | 55 | 116 | 1.09E-05 | 46.6 | 56.45 |
| Query_162689 | WP_071664307.1 | 32.308 | 65 | 40 | 1 | 62 | 122 | 51 | 115 | 5.70E-05 | 44.7 | 58.46 |
| Query_162689 | OEZ33914.1 | 39.062 | 64 | 33 | 2 | 62 | 119 | 58 | 121 | 1.11E-04 | 43.5 | 57.81 |
| Query_162689 | AFX70748.1 | 32.955 | 88 | 42 | 3 | 81 | 167 | 14 | 85 | 1.57E-04 | 43.1 | 47.73 |
| Query_162689 | WP_040008017.1 | 33.846 | 65 | 39 | 1 | 62 | 122 | 51 | 115 | 4.16E-04 | 42 | 56.92 |

FIG. 40A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_182084 | WP_003020193.1 | 100 | 456 | 0 | 0 | 1 | 456 | 1 | 456 | 0 | 941 | 100 |
| Query_182084 | WP_003027004.1 | 99.781 | 456 | 1 | 0 | 1 | 456 | 1 | 456 | 0 | 939 | 100 |
| Query_182084 | WP_042528233.1 | 99.561 | 456 | 2 | 0 | 1 | 456 | 1 | 456 | 0 | 938 | 100 |
| Query_182084 | WP_003014787.1 | 99.561 | 456 | 2 | 0 | 1 | 456 | 1 | 456 | 0 | 938 | 100 |
| Query_182084 | WP_012429326.1 | 99.561 | 456 | 2 | 0 | 1 | 456 | 1 | 456 | 0 | 938 | 100 |
| Query_182084 | WP_003018054.1 | 99.561 | 456 | 2 | 0 | 1 | 456 | 1 | 456 | 0 | 936 | 99.78 |
| Query_182084 | WP_061317650.1 | 99.342 | 456 | 3 | 0 | 1 | 456 | 1 | 456 | 0 | 936 | 100 |
| Query_182084 | WP_003033283.1 | 98.904 | 456 | 5 | 0 | 1 | 456 | 1 | 456 | 0 | 932 | 99.78 |
| Query_182084 | WP_014549470.1 | 98.465 | 456 | 7 | 0 | 1 | 456 | 1 | 456 | 0 | 929 | 99.56 |
| Query_182084 | WP_071514690.1 | 98.246 | 456 | 8 | 0 | 1 | 456 | 1 | 456 | 0 | 928 | 99.34 |
| Query_182084 | WP_104929059.1 | 98.246 | 456 | 8 | 0 | 1 | 456 | 1 | 456 | 0 | 928 | 99.12 |
| Query_182084 | WP_003041852.1 | 98.465 | 456 | 7 | 0 | 1 | 456 | 1 | 456 | 0 | 927 | 98.9 |
| Query_182084 | WP_071660386.1 | 98.026 | 456 | 9 | 0 | 1 | 456 | 1 | 456 | 0 | 925 | 98.9 |
| Query_182084 | WP_003038556.1 | 98.026 | 456 | 9 | 0 | 1 | 456 | 1 | 456 | 0 | 925 | 99.12 |
| Query_182084 | WP_003035742.1 | 98.026 | 456 | 9 | 0 | 1 | 456 | 1 | 456 | 0 | 925 | 99.12 |
| Query_182084 | WP_071304115.1 | 98.246 | 456 | 8 | 0 | 1 | 456 | 1 | 456 | 0 | 924 | 99.12 |
| Query_182084 | WP_012279807.1 | 96.93 | 456 | 14 | 0 | 1 | 456 | 1 | 456 | 0 | 917 | 98.9 |
| Query_182084 | WP_066044853.1 | 94.956 | 456 | 23 | 0 | 1 | 456 | 1 | 456 | 0 | 886 | 98.46 |
| Query_182084 | WP_004288208.1 | 94.298 | 456 | 26 | 0 | 1 | 456 | 1 | 456 | 0 | 883 | 97.59 |
| Query_182084 | WP_035735222.1 | 94.298 | 456 | 26 | 0 | 1 | 456 | 1 | 456 | 0 | 882 | 97.59 |
| Query_182084 | WP_014547811.1 | 94.079 | 456 | 27 | 0 | 1 | 456 | 1 | 456 | 0 | 882 | 98.25 |
| Query_182084 | WP_088820961.1 | 94.298 | 456 | 26 | 0 | 1 | 456 | 1 | 456 | 0 | 882 | 97.81 |
| Query_182084 | WP_042522804.1 | 94.518 | 456 | 25 | 0 | 1 | 456 | 1 | 456 | 0 | 880 | 97.37 |
| Query_182084 | WP_042518973.1 | 93.64 | 456 | 29 | 0 | 1 | 456 | 1 | 456 | 0 | 878 | 97.15 |
| Query_182084 | WP_014715076.1 | 92.982 | 456 | 32 | 0 | 1 | 456 | 1 | 456 | 0 | 870 | 97.59 |
| Query_182084 | WP_044525771.1 | 93.421 | 456 | 30 | 0 | 1 | 456 | 1 | 456 | 0 | 870 | 97.37 |
| Query_182084 | WP_013923556.1 | 91.228 | 456 | 40 | 0 | 1 | 456 | 1 | 456 | 0 | 852 | 96.27 |
| Query_182084 | OEZ33687.1 | 87.445 | 454 | 57 | 0 | 1 | 454 | 1 | 454 | 0 | 813 | 93.39 |
| Query_182084 | ORM39113.1 | 87.004 | 454 | 59 | 0 | 1 | 454 | 1 | 454 | 0 | 810 | 93.17 |
| Query_182084 | WP_071629500.1 | 86.623 | 456 | 61 | 0 | 1 | 456 | 1 | 456 | 0 | 808 | 94.08 |
| Query_182084 | WP_064460889.1 | 86.184 | 456 | 63 | 0 | 1 | 456 | 1 | 456 | 0 | 801 | 92.32 |
| Query_182084 | APC91998.1 | 86.199 | 442 | 61 | 0 | 15 | 456 | 1 | 442 | 0 | 777 | 93.89 |
| Query_182084 | WP_040008733.1 | 83.772 | 456 | 73 | 1 | 1 | 456 | 1 | 455 | 0 | 775 | 92.11 |
| Query_182084 | WP_072713050.1 | 82.599 | 454 | 78 | 1 | 1 | 454 | 1 | 453 | 0 | 772 | 91.41 |
| Query_182084 | WP_088772900.1 | 79.075 | 454 | 94 | 1 | 1 | 454 | 1 | 453 | 0 | 751 | 89.65 |
| Query_182084 | WP_133941588.1 | 77.093 | 454 | 103 | 1 | 1 | 454 | 1 | 453 | 0 | 729 | 88.33 |
| Query_182084 | WP_039125057.1 | 76.211 | 454 | 108 | 0 | 1 | 454 | 1 | 454 | 0 | 723 | 87.67 |
| Query_182084 | WP_035719859.1 | 75.551 | 454 | 110 | 1 | 1 | 454 | 1 | 453 | 0 | 712 | 87.89 |
| Query_182084 | ORU24791.1 | 99.42 | 345 | 2 | 0 | 112 | 456 | 1 | 345 | 0 | 707 | 100 |
| Query_182084 | TDT72146.1 | 76.364 | 440 | 103 | 1 | 15 | 454 | 1 | 439 | 0 | 697 | 87.95 |
| Query_182084 | WP_112870232.1 | 73.246 | 456 | 119 | 2 | 1 | 456 | 1 | 453 | 0 | 690 | 85.31 |
| Query_182084 | KEI35444.1 | 74.773 | 440 | 110 | 1 | 15 | 454 | 1 | 439 | 0 | 681 | 87.5 |
| Query_182084 | WP_119330303.1 | 71.806 | 454 | 125 | 2 | 1 | 453 | 1 | 452 | 0 | 672 | 84.8 |
| Query_182084 | WP_071663939.1 | 71.586 | 454 | 126 | 2 | 1 | 453 | 1 | 452 | 0 | 672 | 85.02 |
| Query_182084 | ORU23780.1 | 100 | 117 | 0 | 0 | 1 | 117 | 1 | 117 | 2.13E-81 | 247 | 100 |
| Query_182084 | PZU05441.1 | 25.06 | 419 | 243 | 11 | 5 | 387 | 8 | 391 | 3.10E-40 | 150 | 48.69 |
| Query_182084 | WP_133940775.1 | 26.049 | 410 | 247 | 13 | 1 | 387 | 1 | 385 | 3.03E-33 | 130 | 46.1 |
| Query_182084 | WP_119329714.1 | 26.617 | 402 | 265 | 12 | 1 | 387 | 1 | 387 | 3.72E-32 | 128 | 48.26 |
| Query_182084 | WP_071663275.1 | 26.276 | 392 | 248 | 11 | 1 | 373 | 1 | 370 | 8.99E-32 | 127 | 47.96 |
| Query_182084 | WP_039123227.1 | 26.57 | 414 | 248 | 12 | 1 | 387 | 1 | 385 | 4.14E-31 | 125 | 46.14 |
| Query_182084 | WP_035720398.1 | 27.561 | 410 | 249 | 13 | 1 | 387 | 1 | 385 | 4.14E-31 | 125 | 45.85 |
| Query_182084 | WP_014714173.1 | 25.373 | 469 | 303 | 13 | 1 | 445 | 1 | 446 | 1.23E-30 | 123 | 45.42 |
| Query_182084 | WP_030003305.1 | 25.373 | 469 | 303 | 13 | 1 | 445 | 1 | 446 | 1.44E-30 | 123 | 45.42 |
| Query_182084 | WP_044525373.1 | 26.05 | 476 | 291 | 16 | 1 | 445 | 1 | 446 | 1.60E-30 | 123 | 45.59 |
| Query_182084 | WP_104928297.1 | 25.786 | 477 | 298 | 15 | 1 | 449 | 1 | 449 | 1.92E-30 | 123 | 43.61 |
| Query_182084 | ORM38842.1 | 26.157 | 432 | 270 | 13 | 1 | 410 | 1 | 405 | 4.49E-30 | 122 | 44.44 |
| Query_182084 | WP_004286778.1 | 25.8 | 469 | 301 | 14 | 1 | 445 | 1 | 446 | 4.63E-30 | 122 | 46.06 |
| Query_182084 | WP_003032716.1 | 25.577 | 477 | 299 | 15 | 1 | 449 | 1 | 449 | 4.67E-30 | 122 | 43.61 |
| Query_182084 | WP_035737365.1 | 25.586 | 469 | 302 | 14 | 1 | 445 | 1 | 446 | 7.91E-30 | 121 | 46.27 |
| Query_182084 | WP_004337014.1 | 25.786 | 477 | 298 | 15 | 1 | 449 | 1 | 449 | 8.20E-30 | 121 | 43.4 |
| Query_182084 | WP_042517221.1 | 25.586 | 469 | 302 | 14 | 1 | 445 | 1 | 446 | 8.38E-30 | 121 | 46.27 |
| Query_182084 | WP_003028489.1 | 25.786 | 477 | 298 | 15 | 1 | 449 | 1 | 449 | 1.32E-29 | 120 | 43.19 |

FIG. 41A

| | | | | | | | | | | | |
|---|---|---|---|---|---|---|---|---|---|---|---|
| Query_182084 | WP_064461571.1 | 26.852 | 432 | 267 | 13 | 1 | 410 | 1 | 405 | 1.44E-29 | 120 | 43.96 |
| Query_182084 | WP_042524274.1 | 24.733 | 469 | 306 | 14 | 1 | 445 | 1 | 446 | 1.56E-29 | 120 | 46.27 |
| Query_182084 | KEI35069.1 | 27.295 | 403 | 245 | 13 | 8 | 387 | 3 | 380 | 1.73E-29 | 120 | 45.66 |
| Query_182084 | WP_012429865.1 | 25.786 | 477 | 298 | 15 | 1 | 449 | 1 | 449 | 1.82E-29 | 120 | 43.19 |
| Query_182084 | WP_057113146.1 | 25.786 | 477 | 298 | 15 | 1 | 449 | 1 | 449 | 2.17E-29 | 120 | 43.19 |
| Query_182084 | WP_003014165.1 | 25.577 | 477 | 299 | 15 | 1 | 449 | 1 | 449 | 2.61E-29 | 120 | 43.19 |
| Query_182084 | WP_012280184.1 | 25.16 | 469 | 304 | 14 | 1 | 445 | 1 | 446 | 3.20E-29 | 119 | 45.63 |
| Query_182084 | WP_014549174.1 | 25.577 | 477 | 299 | 15 | 1 | 449 | 1 | 449 | 3.81E-29 | 119 | 43.4 |
| Query_182084 | WP_071513794.1 | 25.577 | 477 | 299 | 15 | 1 | 449 | 1 | 449 | 5.77E-29 | 119 | 43.19 |
| Query_182084 | WP_071303893.1 | 25.577 | 477 | 299 | 15 | 1 | 449 | 1 | 449 | 7.28E-29 | 118 | 43.19 |
| Query_182084 | WP_003040924.1 | 25.367 | 477 | 300 | 15 | 1 | 449 | 1 | 449 | 7.80E-29 | 118 | 43.19 |
| Query_182084 | WP_003038131.1 | 25.577 | 477 | 299 | 15 | 1 | 449 | 1 | 449 | 1.01E-28 | 118 | 43.19 |
| Query_182084 | WP_112869088.1 | 25.428 | 409 | 259 | 13 | 1 | 387 | 1 | 385 | 1.33E-28 | 117 | 45.23 |
| Query_182084 | WP_071628421.1 | 25.223 | 448 | 268 | 15 | 1 | 417 | 1 | 412 | 1.42E-28 | 117 | 44.2 |
| Query_182084 | WP_003021772.1 | 25.577 | 477 | 299 | 15 | 1 | 449 | 1 | 449 | 1.61E-28 | 117 | 42.98 |
| Query_182084 | OEZ33418.1 | 26.107 | 429 | 274 | 14 | 1 | 410 | 1 | 405 | 3.08E-28 | 117 | 44.52 |
| Query_182084 | WP_085115145.1 | 26.582 | 395 | 245 | 11 | 1 | 373 | 1 | 372 | 5.88E-28 | 114 | 43.29 |
| Query_182084 | WP_066045144.1 | 24.884 | 430 | 274 | 14 | 1 | 408 | 1 | 403 | 2.90E-27 | 114 | 45.12 |
| Query_182084 | WP_014547396.1 | 24.312 | 436 | 287 | 13 | 1 | 417 | 1 | 412 | 3.58E-27 | 114 | 44.95 |
| Query_182084 | WP_088771668.1 | 25.616 | 406 | 264 | 10 | 1 | 387 | 1 | 387 | 8.81E-27 | 112 | 44.83 |
| Query_182084 | WP_040009741.1 | 25.654 | 382 | 256 | 11 | 1 | 368 | 1 | 368 | 1.26E-25 | 109 | 47.64 |
| Query_182084 | WP_072711099.1 | 25.369 | 406 | 263 | 12 | 1 | 387 | 1 | 385 | 2.97E-25 | 108 | 46.96 |
| Query_182084 | WP_013921854.1 | 25.316 | 474 | 297 | 15 | 1 | 445 | 1 | 446 | 6.47E-24 | 104 | 44.51 |
| Query_182084 | ORU24642.1 | 25.895 | 363 | 221 | 12 | 112 | 449 | 1 | 340 | 2.79E-21 | 95.1 | 42.7 |
| Query_182084 | PZU05048.1 | 52.564 | 78 | 35 | 1 | 77 | 152 | 1 | 78 | 1.10E-20 | 86.7 | 69.23 |
| Query_182084 | PZU05047.1 | 29.814 | 161 | 112 | 1 | 196 | 356 | 7 | 166 | 3.30E-18 | 83.2 | 52.8 |
| Query_182084 | WP_088772912.1 | 25.725 | 276 | 173 | 10 | 96 | 348 | 93 | 359 | 2.39E-11 | 66.2 | 46.01 |
| Query_182084 | WP_066044840.1 | 25.435 | 460 | 285 | 22 | 17 | 442 | 4 | 439 | 5.61E-09 | 58.5 | 40.65 |
| Query_182084 | WP_014715063.1 | 23.958 | 288 | 185 | 11 | 84 | 348 | 83 | 359 | 1.20E-08 | 57.8 | 45.83 |
| Query_182084 | PZU05439.1 | 24.254 | 268 | 174 | 10 | 96 | 357 | 99 | 343 | 2.81E-08 | 56.6 | 43.28 |
| Query_182084 | WP_014547797.1 | 24.86 | 358 | 229 | 14 | 107 | 442 | 100 | 439 | 6.61E-08 | 55.5 | 40.78 |
| Query_182084 | WP_014547795.1 | 25.338 | 296 | 170 | 14 | 84 | 348 | 83 | 358 | 7.62E-08 | 55.1 | 46.28 |
| Query_182084 | WP_035735206.1 | 23.958 | 288 | 185 | 11 | 84 | 348 | 94 | 370 | 1.21E-07 | 54.7 | 45.14 |
| Query_182084 | WP_071663926.1 | 25 | 280 | 169 | 13 | 95 | 346 | 93 | 359 | 2.30E-07 | 53.5 | 45.71 |
| Query_182084 | WP_088820952.1 | 24.466 | 421 | 250 | 21 | 61 | 454 | 70 | 449 | 2.36E-07 | 53.5 | 42.28 |
| Query_182084 | WP_112870479.1 | 24.643 | 280 | 171 | 13 | 95 | 347 | 104 | 370 | 3.21E-07 | 53.1 | 45.36 |
| Query_182084 | WP_066044837.1 | 24.306 | 288 | 183 | 14 | 84 | 348 | 83 | 358 | 3.51E-07 | 53.1 | 48.26 |
| Query_182084 | WP_035735209.1 | 24.76 | 416 | 255 | 23 | 61 | 454 | 70 | 449 | 3.69E-07 | 53.1 | 43.27 |
| Query_182084 | WP_044525759.1 | 25 | 372 | 233 | 18 | 107 | 454 | 100 | 449 | 4.14E-07 | 52.8 | 43.01 |
| Query_182084 | WP_085075864.1 | 24.825 | 286 | 180 | 14 | 84 | 346 | 83 | 356 | 5.54E-07 | 52.4 | 47.55 |
| Query_182084 | WP_104929073.1 | 24.739 | 287 | 179 | 13 | 84 | 346 | 83 | 356 | 6.01E-07 | 52.4 | 46.69 |
| Query_182084 | WP_003023189.1 | 24.825 | 286 | 180 | 14 | 84 | 346 | 83 | 356 | 6.28E-07 | 52.4 | 47.55 |
| Query_182084 | EDN33988.1 | 24.825 | 286 | 180 | 14 | 84 | 346 | 88 | 361 | 6.67E-07 | 52.4 | 47.55 |
| Query_182084 | WP_003018035.1 | 24.825 | 286 | 180 | 14 | 84 | 346 | 83 | 356 | 7.57E-07 | 52 | 47.55 |
| Query_182084 | WP_003033245.1 | 24.739 | 287 | 179 | 13 | 84 | 346 | 83 | 356 | 7.69E-07 | 52 | 46.69 |
| Query_182084 | WP_101677626.1 | 24.825 | 286 | 180 | 14 | 84 | 346 | 83 | 356 | 7.88E-07 | 52 | 47.55 |
| Query_182084 | WP_003038534.1 | 24.825 | 286 | 180 | 14 | 84 | 346 | 83 | 356 | 8.03E-07 | 52 | 47.2 |
| Query_182084 | ABI82474.1 | 24.825 | 286 | 180 | 14 | 84 | 346 | 88 | 361 | 8.10E-07 | 52 | 47.55 |
| Query_182084 | WP_071304105.1 | 24.825 | 286 | 180 | 14 | 84 | 346 | 83 | 356 | 8.24E-07 | 52 | 47.2 |
| Query_182084 | WP_119330290.1 | 24.101 | 278 | 174 | 11 | 95 | 346 | 93 | 359 | 1.28E-06 | 51.2 | 43.88 |
| Query_182084 | WP_088820950.1 | 22.648 | 287 | 190 | 12 | 84 | 348 | 83 | 359 | 1.37E-06 | 51.2 | 45.64 |
| Query_182084 | WP_004288218.1 | 24.865 | 370 | 236 | 19 | 107 | 454 | 100 | 449 | 1.58E-06 | 50.8 | 42.97 |
| Query_182084 | WP_012279816.1 | 24.865 | 370 | 236 | 19 | 107 | 454 | 100 | 449 | 1.63E-06 | 50.8 | 42.7 |
| Query_182084 | WP_042518991.1 | 24.221 | 289 | 183 | 12 | 84 | 348 | 94 | 370 | 1.83E-06 | 50.8 | 45.33 |
| Query_182084 | EDN37318.1 | 24.126 | 286 | 182 | 13 | 84 | 346 | 88 | 361 | 2.63E-06 | 50.4 | 46.85 |
| Query_182084 | WP_044525757.1 | 22.222 | 288 | 190 | 11 | 84 | 348 | 83 | 359 | 2.95E-06 | 50.1 | 45.14 |
| Query_182084 | WP_003041831.1 | 24.126 | 286 | 182 | 13 | 84 | 346 | 83 | 356 | 3.12E-06 | 50.1 | 46.85 |
| Query_182084 | WP_032732367.1 | 24.126 | 286 | 182 | 13 | 84 | 346 | 83 | 356 | 3.34E-06 | 50.1 | 46.85 |
| Query_182084 | AEB27456.1 | 24.126 | 286 | 182 | 13 | 84 | 346 | 83 | 356 | 3.37E-06 | 50.1 | 46.85 |
| Query_182084 | WP_042518989.1 | 24.595 | 370 | 237 | 19 | 107 | 454 | 100 | 449 | 3.48E-06 | 50.1 | 43.24 |

FIG. 41A continued

| Query | Subject | % ID | Len1 | Len2 | Mis | S1 | E1 | S2 | E2 | E-value | Bit | Score |
|---|---|---|---|---|---|---|---|---|---|---|---|---|
| Query_182084 | WP_042528231.1 | 24.476 | 286 | 181 | 14 | 84 | 346 | 83 | 356 | 4.95E-06 | 49.3 | 47.2 |
| Query_182084 | WP_071514703.1 | 24.126 | 286 | 182 | 13 | 84 | 346 | 83 | 356 | 5.55E-06 | 49.3 | 46.85 |
| Query_182084 | WP_133940558.1 | 22.93 | 314 | 181 | 10 | 92 | 351 | 118 | 424 | 5.70E-06 | 49.3 | 41.08 |
| Query_182084 | WP_003041834.1 | 21.814 | 408 | 262 | 18 | 83 | 454 | 63 | 449 | 7.73E-06 | 48.9 | 42.89 |
| Query_182084 | WP_057113244.1 | 22.071 | 367 | 250 | 15 | 107 | 454 | 100 | 449 | 8.08E-06 | 48.9 | 44.14 |
| Query_182084 | WP_042522787.1 | 24.595 | 370 | 237 | 19 | 107 | 454 | 100 | 449 | 9.45E-06 | 48.5 | 43.24 |
| Query_182084 | WP_012279819.1 | 23.203 | 306 | 185 | 11 | 84 | 348 | 94 | 390 | 1.01E-05 | 48.5 | 43.14 |
| Query_182084 | WP_004288221.1 | 22.801 | 307 | 185 | 12 | 84 | 348 | 94 | 390 | 1.09E-05 | 48.5 | 43.65 |
| Query_182084 | WP_064460885.1 | 22.135 | 384 | 246 | 15 | 94 | 442 | 74 | 439 | 1.16E-05 | 48.1 | 41.15 |
| Query_182084 | WP_072713068.1 | 22.872 | 188 | 135 | 5 | 171 | 353 | 226 | 408 | 1.27E-05 | 48.1 | 48.4 |
| Query_182084 | WP_013923566.1 | 21.549 | 297 | 181 | 11 | 95 | 348 | 103 | 390 | 1.32E-05 | 48.1 | 42.42 |
| Query_182084 | WP_072713065.1 | 23.504 | 234 | 164 | 6 | 107 | 331 | 100 | 327 | 1.52E-05 | 47.8 | 41.45 |
| Query_182084 | WP_035718783.1 | 22.364 | 313 | 194 | 11 | 95 | 367 | 90 | 393 | 1.52E-05 | 47.8 | 41.85 |
| Query_182084 | WP_004336885.1 | 22.071 | 367 | 250 | 15 | 107 | 454 | 100 | 449 | 1.63E-05 | 47.8 | 44.14 |
| Query_182084 | WP_013923547.1 | 21.642 | 268 | 172 | 11 | 95 | 359 | 86 | 318 | 1.69E-05 | 47.8 | 43.66 |
| Query_182084 | WP_040008749.1 | 22.997 | 287 | 178 | 11 | 96 | 346 | 112 | 391 | 1.87E-05 | 47.8 | 44.6 |
| Query_182084 | WP_013923563.1 | 24.279 | 416 | 257 | 23 | 61 | 454 | 70 | 449 | 2.45E-05 | 47.4 | 43.03 |
| Query_182084 | WP_071660391.1 | 21.585 | 366 | 253 | 15 | 107 | 454 | 100 | 449 | 2.82E-05 | 47 | 43.72 |
| Query_182084 | WP_003018039.1 | 21.798 | 367 | 251 | 15 | 107 | 454 | 100 | 449 | 3.02E-05 | 47 | 44.14 |
| Query_182084 | WP_012279798.1 | 22.626 | 358 | 219 | 17 | 95 | 443 | 86 | 394 | 3.32E-05 | 46.6 | 41.34 |
| Query_182084 | WP_088772910.1 | 23.504 | 234 | 164 | 6 | 107 | 331 | 100 | 327 | 3.70E-05 | 46.6 | 42.31 |
| Query_182084 | WP_025329182.1 | 21.798 | 367 | 251 | 15 | 107 | 454 | 100 | 449 | 3.90E-05 | 46.6 | 44.14 |
| Query_182084 | WP_051686768.1 | 24.352 | 193 | 133 | 6 | 107 | 291 | 100 | 287 | 4.55E-05 | 46.2 | 43.52 |
| Query_182084 | WP_004288199.1 | 23.677 | 359 | 214 | 17 | 95 | 443 | 86 | 394 | 5.28E-05 | 46.2 | 41.23 |
| Query_182084 | WP_044525779.1 | 22.626 | 358 | 219 | 17 | 95 | 443 | 86 | 394 | 5.43E-05 | 46.2 | 41.62 |
| Query_182084 | WP_003038537.1 | 20.69 | 377 | 243 | 16 | 107 | 454 | 100 | 449 | 6.09E-05 | 45.8 | 42.71 |
| Query_182084 | WP_088820967.1 | 22.626 | 358 | 219 | 17 | 95 | 443 | 86 | 394 | 6.99E-05 | 45.8 | 41.34 |
| Query_182084 | WP_012429319.1 | 21.798 | 367 | 251 | 15 | 107 | 454 | 100 | 449 | 7.00E-05 | 45.8 | 44.14 |
| Query_182084 | WP_071629509.1 | 22.112 | 303 | 182 | 12 | 95 | 351 | 127 | 421 | 7.46E-05 | 45.8 | 41.58 |
| Query_182084 | WP_035735231.1 | 22.346 | 358 | 220 | 17 | 95 | 443 | 86 | 394 | 7.50E-05 | 45.4 | 41.62 |
| Query_182084 | WP_042522819.1 | 22.626 | 358 | 219 | 17 | 95 | 443 | 86 | 394 | 7.98E-05 | 45.4 | 41.34 |
| Query_182084 | ORM39110.1 | 21.33 | 361 | 238 | 14 | 107 | 442 | 100 | 439 | 8.05E-05 | 45.4 | 41.83 |
| Query_182084 | WP_112870391.1 | 23.176 | 233 | 166 | 7 | 107 | 331 | 100 | 327 | 8.11E-05 | 45.4 | 42.49 |
| Query_182084 | WP_104929071.1 | 21.833 | 371 | 246 | 16 | 107 | 454 | 100 | 449 | 8.41E-05 | 45.4 | 43.13 |
| Query_182084 | WP_071514701.1 | 23.013 | 239 | 159 | 8 | 107 | 331 | 100 | 327 | 1.50E-04 | 44.7 | 42.68 |
| Query_182084 | WP_071304122.1 | 21.245 | 273 | 167 | 11 | 95 | 359 | 86 | 318 | 1.53E-04 | 44.7 | 42.49 |
| Query_182084 | WP_014715064.1 | 23.45 | 371 | 240 | 15 | 107 | 454 | 100 | 449 | 1.54E-04 | 44.7 | 39.62 |
| Query_182084 | WP_003020166.1 | 21.526 | 367 | 252 | 15 | 107 | 454 | 100 | 449 | 1.63E-04 | 44.7 | 43.87 |
| Query_182084 | WP_003041870.1 | 21.245 | 273 | 167 | 11 | 95 | 359 | 86 | 318 | 1.67E-04 | 44.7 | 42.49 |
| Query_182084 | WP_003027034.1 | 21.526 | 367 | 252 | 15 | 107 | 454 | 100 | 449 | 1.81E-04 | 44.3 | 43.87 |
| Query_182084 | WP_071514683.1 | 20.879 | 273 | 168 | 11 | 95 | 359 | 86 | 318 | 2.01E-04 | 44.3 | 42.12 |
| Query_182084 | WP_003035764.1 | 20.879 | 273 | 168 | 11 | 95 | 359 | 86 | 318 | 2.10E-04 | 44.3 | 42.12 |
| Query_182084 | WP_003033305.1 | 21.245 | 273 | 167 | 11 | 95 | 359 | 86 | 318 | 2.14E-04 | 44.3 | 42.12 |
| Query_182084 | WP_071304106.1 | 20.274 | 365 | 237 | 15 | 107 | 442 | 100 | 439 | 2.14E-04 | 44.3 | 42.19 |
| Query_182084 | WP_071660379.1 | 21.245 | 273 | 167 | 11 | 95 | 359 | 86 | 318 | 2.19E-04 | 44.3 | 42.12 |
| Query_182084 | WP_064460884.1 | 25.532 | 188 | 126 | 6 | 171 | 351 | 208 | 388 | 2.40E-04 | 44.3 | 48.94 |
| Query_182084 | ORU21543.1 | 28.333 | 120 | 78 | 3 | 1 | 117 | 1 | 115 | 2.73E-04 | 41.2 | 47.5 |
| Query_182084 | WP_030003386.1 | 22.626 | 358 | 219 | 17 | 95 | 443 | 86 | 394 | 3.15E-04 | 43.5 | 41.34 |
| Query_182084 | WP_003033250.1 | 21.552 | 348 | 216 | 12 | 17 | 331 | 4 | 327 | 3.37E-04 | 43.5 | 39.37 |
| Query_182084 | WP_014549461.1 | 21.633 | 245 | 155 | 8 | 107 | 331 | 100 | 327 | 3.58E-04 | 43.5 | 41.22 |
| Query_182084 | WP_042518960.1 | 22.067 | 358 | 221 | 16 | 95 | 443 | 86 | 394 | 4.32E-04 | 43.1 | 40.5 |
| Query_182084 | WP_012429784.1 | 21.429 | 266 | 174 | 10 | 95 | 359 | 86 | 317 | 4.73E-04 | 43.1 | 43.23 |
| Query_182084 | WP_003020220.1 | 21.429 | 266 | 174 | 10 | 95 | 359 | 86 | 317 | 4.98E-04 | 43.1 | 43.61 |
| Query_182084 | WP_014548556.1 | 20.074 | 269 | 181 | 10 | 92 | 359 | 83 | 318 | 5.74E-04 | 42.7 | 42.75 |
| Query_182084 | WP_003017010.1 | 21.429 | 266 | 174 | 10 | 95 | 359 | 86 | 317 | 5.99E-04 | 42.7 | 43.23 |
| Query_182084 | WP_071629489.1 | 19.291 | 254 | 172 | 7 | 106 | 359 | 98 | 318 | 6.54E-04 | 42.7 | 42.91 |
| Query_182084 | WP_088772892.1 | 23.81 | 315 | 191 | 16 | 26 | 331 | 18 | 292 | 6.61E-04 | 42.7 | 43.17 |
| Query_182084 | WP_003019464.1 | 21.429 | 266 | 174 | 10 | 95 | 359 | 86 | 317 | 6.77E-04 | 42.7 | 43.23 |
| Query_182084 | PZU05437.1 | 19.485 | 272 | 186 | 11 | 107 | 356 | 101 | 361 | 7.95E-04 | 42.4 | 44.12 |
| Query_182084 | WP_052399150.1 | 21.93 | 228 | 143 | 9 | 106 | 331 | 98 | 292 | 8.67E-04 | 42.4 | 42.54 |

FIG. 41A continued

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_191882 | 3MSU_A | 100 | 424 | 0 | 0 | 1 | 424 | 4 | 427 | 0 | 889 | 100 |
| Query_191882 | WP_003017322.1 | 100 | 424 | 0 | 0 | 1 | 424 | 1 | 424 | 0 | 889 | 100 |
| Query_191882 | EDN38382.1 | 99.764 | 424 | 1 | 0 | 1 | 424 | 1 | 424 | 0 | 885 | 99.76 |
| Query_191882 | ABO46133.1 | 99.762 | 421 | 1 | 0 | 4 | 424 | 1 | 421 | 0 | 881 | 100 |
| Query_191882 | EDN36925.1 | 99.057 | 424 | 4 | 0 | 1 | 424 | 1 | 424 | 0 | 860 | 99.53 |
| Query_191882 | WP_003028605.1 | 100 | 419 | 0 | 0 | 6 | 424 | 1 | 419 | 0 | 878 | 100 |
| Query_191882 | WP_003024620.1 | 99.761 | 419 | 1 | 0 | 6 | 424 | 1 | 419 | 0 | 877 | 100 |
| Query_191882 | WP_003041254.1 | 99.761 | 419 | 1 | 0 | 6 | 424 | 1 | 419 | 0 | 876 | 99.76 |
| Query_191882 | WP_012429093.1 | 99.523 | 419 | 2 | 0 | 6 | 424 | 1 | 419 | 0 | 875 | 99.76 |
| Query_191882 | WP_032729662.1 | 99.284 | 419 | 3 | 0 | 6 | 424 | 1 | 419 | 0 | 872 | 99.52 |
| Query_191882 | WP_071513952.1 | 99.045 | 419 | 4 | 0 | 6 | 424 | 1 | 419 | 0 | 870 | 99.52 |
| Query_191882 | KHS55394.1 | 100 | 407 | 0 | 0 | 18 | 424 | 1 | 407 | 0 | 854 | 100 |
| Query_191882 | WP_014548978.1 | 96.659 | 419 | 14 | 0 | 6 | 424 | 1 | 419 | 0 | 854 | 98.57 |
| Query_191882 | WP_066045251.1 | 96.42 | 419 | 15 | 0 | 6 | 424 | 1 | 419 | 0 | 853 | 98.33 |
| Query_191882 | OEZ32979.1 | 94.511 | 419 | 23 | 0 | 6 | 424 | 1 | 419 | 0 | 833 | 97.61 |
| Query_191882 | WP_064461801.1 | 94.033 | 419 | 25 | 0 | 6 | 424 | 1 | 419 | 0 | 828 | 96.9 |
| Query_191882 | WP_071629797.1 | 94.988 | 419 | 21 | 0 | 6 | 424 | 1 | 419 | 0 | 824 | 98.57 |
| Query_191882 | WP_004286991.1 | 91.647 | 419 | 35 | 0 | 6 | 424 | 1 | 419 | 0 | 818 | 95.94 |
| Query_191882 | WP_040009282.1 | 90.692 | 419 | 39 | 0 | 6 | 424 | 1 | 419 | 0 | 813 | 96.66 |
| Query_191882 | WP_012280370.1 | 90.931 | 419 | 38 | 0 | 6 | 424 | 1 | 419 | 0 | 813 | 95.47 |
| Query_191882 | WP_044526934.1 | 90.692 | 419 | 39 | 0 | 6 | 424 | 1 | 419 | 0 | 811 | 95.23 |
| Query_191882 | WP_072713332.1 | 90.931 | 419 | 38 | 0 | 6 | 424 | 1 | 419 | 0 | 808 | 96.66 |
| Query_191882 | ORM38351.1 | 94.272 | 419 | 24 | 0 | 6 | 424 | 1 | 419 | 0 | 806 | 97.14 |
| Query_191882 | WP_014714627.1 | 89.737 | 419 | 43 | 0 | 6 | 424 | 1 | 419 | 0 | 803 | 94.99 |
| Query_191882 | ORU21712.1 | 100 | 384 | 0 | 0 | 6 | 389 | 1 | 384 | 0 | 800 | 100 |
| Query_191882 | WP_013922341.1 | 89.26 | 419 | 45 | 0 | 6 | 424 | 1 | 419 | 0 | 800 | 95.23 |
| Query_191882 | WP_039123183.1 | 87.351 | 419 | 53 | 0 | 6 | 424 | 1 | 419 | 0 | 790 | 95.7 |
| Query_191882 | WP_088773261.1 | 86.396 | 419 | 57 | 0 | 6 | 424 | 1 | 419 | 0 | 778 | 94.51 |
| Query_191882 | WP_035720499.1 | 89.021 | 419 | 46 | 0 | 6 | 424 | 1 | 419 | 0 | 777 | 96.9 |
| Query_191882 | WP_133940883.1 | 88.783 | 419 | 47 | 0 | 6 | 424 | 1 | 419 | 0 | 775 | 96.42 |
| Query_191882 | WP_112870703.1 | 82.816 | 419 | 72 | 0 | 6 | 424 | 1 | 419 | 0 | 738 | 93.56 |
| Query_191882 | WP_119329629.1 | 80.43 | 419 | 82 | 0 | 6 | 424 | 1 | 419 | 0 | 706 | 90.45 |
| Query_191882 | WP_071663372.1 | 80.43 | 419 | 82 | 0 | 6 | 424 | 1 | 419 | 0 | 702 | 91.41 |
| Query_191882 | PZU05019.1 | 50.591 | 423 | 201 | 4 | 6 | 424 | 1 | 419 | 4.80E-157 | 450 | 68.79 |
| Query_191882 | ABS59348.1 | 98.286 | 175 | 3 | 0 | 236 | 410 | 1 | 175 | 2.23E-124 | 358 | 98.86 |
| Query_191882 | ORU24173.1 | 100 | 41 | 0 | 0 | 384 | 424 | 1 | 41 | 3.11E-24 | 95.1 | 100 |

FIG. 42A

| QUERY | ACCESSION | % IDENTITY | ALIGNMENT LENGTH | MISMATCHES | GAP OPENS | Q. START | Q. END | START | END | E-VALUE | BIT SCORE | % POSITIVES |
|---|---|---|---|---|---|---|---|---|---|---|---|---|
| Query_65921 | WP_003021668.1 | 100 | 144 | 0 | 0 | 1 | 144 | 1 | 144 | 6.06E-99 | 281 | 100 |
| Query_65921 | WP_003014244.1 | 99.306 | 144 | 1 | 0 | 1 | 144 | 1 | 144 | 5.68E-98 | 278 | 99.31 |
| Query_65921 | WP_003041523.1 | 98.611 | 144 | 2 | 0 | 1 | 144 | 1 | 144 | 7.90E-98 | 278 | 99.31 |
| Query_65921 | WP_025329094.1 | 98.611 | 144 | 2 | 0 | 1 | 144 | 1 | 144 | 2.98E-97 | 276 | 98.61 |
| Query_65921 | WP_014549273.1 | 97.917 | 144 | 3 | 0 | 1 | 144 | 1 | 144 | 4.52E-97 | 276 | 98.61 |
| Query_65921 | WP_003035282.1 | 97.917 | 144 | 3 | 0 | 1 | 144 | 1 | 144 | 4.52E-97 | 276 | 98.61 |
| Query_65921 | WP_071514869.1 | 97.222 | 144 | 4 | 0 | 1 | 144 | 1 | 144 | 1.26E-96 | 275 | 98.61 |
| Query_65921 | WP_012429839.1 | 97.917 | 144 | 3 | 0 | 1 | 144 | 1 | 144 | 2.51E-96 | 274 | 97.92 |
| Query_65921 | WP_014547525.1 | 95.833 | 144 | 6 | 0 | 1 | 144 | 1 | 144 | 2.13E-95 | 271 | 98.61 |
| Query_65921 | WP_066046345.1 | 95.139 | 144 | 7 | 0 | 1 | 144 | 1 | 144 | 4.69E-95 | 271 | 98.61 |
| Query_65921 | WP_064461486.1 | 88.889 | 144 | 16 | 0 | 1 | 144 | 1 | 144 | 2.80E-88 | 254 | 93.75 |
| Query_65921 | WP_071628545.1 | 88.583 | 144 | 15 | 0 | 1 | 144 | 1 | 144 | 2.21E-86 | 249 | 94.44 |
| Query_65921 | ORM38923.1 | 88.889 | 144 | 16 | 0 | 1 | 144 | 1 | 144 | 5.14E-85 | 245 | 91.67 |
| Query_65921 | OEZ33510.1 | 87.5 | 144 | 18 | 0 | 1 | 144 | 1 | 144 | 6.40E-85 | 245 | 90.97 |
| Query_65921 | WP_072711228.1 | 68.75 | 144 | 45 | 0 | 1 | 144 | 1 | 144 | 6.29E-65 | 194 | 85.42 |
| Query_65921 | WP_040010014.1 | 66.667 | 144 | 48 | 0 | 1 | 144 | 1 | 144 | 2.29E-64 | 193 | 81.25 |
| Query_65921 | WP_088773173.1 | 66.667 | 144 | 48 | 0 | 1 | 144 | 1 | 144 | 5.48E-62 | 187 | 83.33 |
| Query_65921 | WP_088820736.1 | 62.5 | 144 | 53 | 1 | 1 | 144 | 1 | 143 | 5.18E-55 | 169 | 75.69 |
| Query_65921 | WP_044525473.1 | 63.194 | 144 | 51 | 2 | 1 | 144 | 1 | 142 | 1.30E-53 | 166 | 76.39 |
| Query_65921 | WP_012280071.1 | 60.417 | 144 | 56 | 1 | 1 | 144 | 1 | 143 | 2.75E-53 | 165 | 75 |
| Query_65921 | WP_004286659.1 | 60.417 | 144 | 56 | 1 | 1 | 144 | 1 | 143 | 3.21E-53 | 165 | 75 |
| Query_65921 | WP_035720462.1 | 61.538 | 143 | 46 | 2 | 1 | 143 | 1 | 134 | 4.87E-51 | 159 | 74.13 |
| Query_65921 | WP_014714288.1 | 61.111 | 144 | 54 | 2 | 1 | 144 | 1 | 142 | 1.01E-50 | 159 | 74.31 |
| Query_65921 | WP_041263869.1 | 58.333 | 144 | 59 | 1 | 1 | 144 | 1 | 143 | 9.78E-49 | 154 | 76.39 |
| Query_65921 | AEI35117.1 | 60.15 | 133 | 52 | 1 | 12 | 144 | 2 | 133 | 6.59E-46 | 146 | 78.2 |
| Query_65921 | WP_039123489.1 | 50 | 144 | 64 | 1 | 1 | 144 | 1 | 136 | 5.57E-40 | 131 | 66.67 |
| Query_65921 | WP_133940846.1 | 51.049 | 143 | 62 | 1 | 1 | 143 | 1 | 135 | 2.28E-39 | 130 | 66.43 |
| Query_65921 | WP_112869317.1 | 45.139 | 144 | 71 | 1 | 1 | 144 | 1 | 136 | 5.95E-38 | 126 | 68.75 |
| Query_65921 | WP_112870816.1 | 30.986 | 142 | 83 | 3 | 1 | 142 | 4 | 130 | 6.42E-10 | 54.7 | 47.18 |
| Query_65921 | WP_133942482.1 | 28.873 | 142 | 89 | 3 | 1 | 142 | 2 | 131 | 1.80E-08 | 50.4 | 47.89 |
| Query_65921 | WP_035720611.1 | 30.597 | 134 | 81 | 3 | 1 | 134 | 2 | 123 | 3.74E-08 | 49.7 | 47.76 |
| Query_65921 | WP_072713415.1 | 33.333 | 105 | 61 | 2 | 38 | 142 | 35 | 130 | 3.79E-08 | 49.7 | 48.57 |
| Query_65921 | WP_040009680.1 | 29.787 | 141 | 87 | 3 | 2 | 142 | 3 | 131 | 4.86E-08 | 49.3 | 48.23 |
| Query_65921 | WP_088771595.1 | 30.496 | 141 | 86 | 3 | 2 | 142 | 3 | 131 | 5.22E-08 | 49.3 | 46.1 |
| Query_65921 | WP_112870817.1 | 29.577 | 142 | 88 | 4 | 1 | 142 | 1 | 130 | 1.98E-07 | 47.8 | 46.48 |
| Query_65921 | WP_112870814.1 | 28.873 | 142 | 87 | 3 | 1 | 142 | 3 | 130 | 2.07E-07 | 47.8 | 45.77 |
| Query_65921 | WP_088771592.1 | 30.275 | 109 | 67 | 2 | 34 | 142 | 31 | 130 | 5.76E-07 | 46.6 | 46.79 |
| Query_65921 | WP_072713416.1 | 28.788 | 132 | 81 | 4 | 15 | 142 | 10 | 132 | 9.46E-07 | 45.8 | 46.97 |
| Query_65921 | WP_042517058.1 | 31.724 | 145 | 81 | 5 | 1 | 142 | 1 | 130 | 1.19E-06 | 45.4 | 47.59 |
| Query_65921 | WP_044527026.1 | 32.414 | 145 | 80 | 5 | 1 | 142 | 1 | 130 | 1.34E-06 | 45.4 | 46.9 |
| Query_65921 | WP_088771593.1 | 27.891 | 147 | 83 | 5 | 1 | 142 | 4 | 132 | 7.71E-06 | 43.5 | 44.9 |
| Query_65921 | WP_040009679.1 | 29.524 | 105 | 65 | 2 | 38 | 142 | 35 | 130 | 9.18E-06 | 43.1 | 47.62 |
| Query_65921 | WP_064461611.1 | 30.337 | 89 | 54 | 1 | 54 | 142 | 50 | 130 | 1.17E-05 | 42.7 | 51.69 |
| Query_65921 | WP_085076048.1 | 28.889 | 90 | 56 | 1 | 53 | 142 | 14 | 95 | 4.33E-05 | 40.8 | 51.11 |
| Query_65921 | WP_071663448.1 | 27.523 | 109 | 70 | 2 | 34 | 142 | 29 | 128 | 4.81E-05 | 41.2 | 49.54 |
| Query_65921 | WP_003022749.1 | 30.07 | 143 | 84 | 5 | 2 | 142 | 3 | 131 | 6.09E-05 | 40.8 | 50.35 |
| Query_65921 | WP_003022747.1 | 28.889 | 90 | 56 | 1 | 53 | 142 | 49 | 130 | 6.30E-05 | 40.8 | 51.11 |
| Query_65921 | WP_071513887.1 | 28.369 | 141 | 89 | 3 | 2 | 142 | 3 | 131 | 6.54E-05 | 40.8 | 48.23 |
| Query_65921 | WP_003017667.1 | 28.889 | 90 | 56 | 1 | 53 | 142 | 49 | 130 | 7.11E-05 | 40.8 | 51.11 |
| Query_65921 | WP_003014087.1 | 28.889 | 90 | 56 | 1 | 53 | 142 | 49 | 130 | 7.64E-05 | 40.8 | 51.11 |
| Query_65921 | WP_004286894.1 | 31.25 | 112 | 66 | 3 | 32 | 142 | 29 | 130 | 8.46E-05 | 40.4 | 47.32 |
| Query_65921 | WP_003037882.1 | 28.369 | 141 | 89 | 3 | 2 | 142 | 3 | 131 | 8.52E-05 | 40.4 | 47.52 |
| Query_65921 | WP_119331124.1 | 27.273 | 143 | 94 | 3 | 1 | 142 | 1 | 134 | 8.91E-05 | 40.4 | 46.85 |
| Query_65921 | WP_071663935.1 | 30.496 | 141 | 83 | 3 | 1 | 141 | 1 | 126 | 9.58E-05 | 40.4 | 41.84 |
| Query_65921 | WP_071660573.1 | 28.369 | 141 | 89 | 3 | 2 | 142 | 3 | 131 | 9.82E-05 | 40.4 | 47.52 |
| Query_65921 | APC97796.1 | 26.573 | 143 | 95 | 3 | 1 | 142 | 1 | 134 | 1.04E-04 | 40.4 | 46.15 |
| Query_65921 | WP_071663449.1 | 26.573 | 143 | 95 | 3 | 1 | 142 | 2 | 135 | 1.10E-04 | 40.4 | 46.15 |
| Query_65921 | WP_035720612.1 | 28.846 | 104 | 65 | 2 | 38 | 141 | 35 | 129 | 1.15E-04 | 40 | 48.08 |
| Query_65921 | WP_119331125.1 | 28.333 | 120 | 75 | 3 | 25 | 142 | 19 | 129 | 1.34E-04 | 40 | 49.17 |
| Query_65921 | WP_041257409.1 | 30 | 140 | 80 | 5 | 6 | 142 | 1 | 125 | 1.36E-04 | 40 | 46.43 |

FIG. 43A

| | | | | | | | | | | | | |
|---|---|---|---|---|---|---|---|---|---|---|---|---|
| Query_65921 | WP_003032563.1 | 28.369 | 141 | 89 | 3 | 2 | 142 | 3 | 131 | 1.82E-04 | 39.7 | 47.52 |
| Query_65921 | WP_072713418.1 | 34.524 | 84 | 53 | 2 | 2 | 85 | 3 | 84 | 2.12E-04 | 38.9 | 53.57 |
| Query_65921 | WP_014549075.1 | 27.778 | 90 | 57 | 1 | 53 | 142 | 49 | 130 | 2.19E-04 | 39.3 | 51.11 |
| Query_65921 | WP_066046618.1 | 27.778 | 90 | 57 | 1 | 53 | 142 | 49 | 130 | 2.24E-04 | 39.3 | 51.11 |
| Query_65921 | WP_013923632.1 | 29.204 | 113 | 69 | 3 | 31 | 142 | 28 | 130 | 2.61E-04 | 39.3 | 46.9 |
| Query_65921 | WP_035720619.1 | 27.941 | 136 | 71 | 4 | 14 | 142 | 17 | 132 | 2.93E-04 | 39.3 | 46.32 |
| Query_65921 | WP_003029954.1 | 29.371 | 143 | 85 | 5 | 2 | 142 | 3 | 131 | 3.02E-04 | 38.9 | 49.65 |
| Query_65921 | ORM38345.1 | 27.007 | 137 | 84 | 4 | 5 | 139 | 16 | 138 | 3.25E-04 | 39.3 | 45.99 |
| Query_65921 | WP_014549077.1 | 28.873 | 142 | 87 | 4 | 2 | 142 | 4 | 132 | 3.56E-04 | 38.9 | 47.89 |
| Query_65921 | WP_071663484.1 | 30.097 | 103 | 62 | 3 | 41 | 143 | 33 | 125 | 4.51E-04 | 38.5 | 50.49 |
| Query_65921 | WP_071629867.1 | 26.95 | 141 | 91 | 4 | 2 | 142 | 3 | 131 | 4.61E-04 | 38.5 | 51.06 |
| Query_65921 | OEZ32926.1 | 29.07 | 86 | 53 | 1 | 54 | 139 | 50 | 127 | 5.66E-04 | 38.5 | 50 |
| Query_65921 | WP_071629865.1 | 26.667 | 90 | 58 | 1 | 53 | 142 | 49 | 130 | 7.22E-04 | 38.1 | 51.11 |
| Query_65921 | WP_064461610.1 | 28.873 | 142 | 87 | 4 | 2 | 142 | 3 | 131 | 8.02E-04 | 37.7 | 47.89 |
| Query_65921 | WP_003040711.1 | 26.667 | 90 | 58 | 1 | 53 | 142 | 49 | 130 | 8.23E-04 | 37.7 | 51.11 |
| Query_65921 | WP_133942480.1 | 29.213 | 89 | 55 | 1 | 54 | 142 | 50 | 130 | 8.50E-04 | 37.7 | 48.31 |

FIG. 43A continued

SEQUENCE LISTING

<160> NUMBER OF SEQ ID NOS: 88

<210> SEQ ID NO 1
<211> LENGTH: 636
<212> TYPE: DNA
<213> ORGANISM: Francisella tularensis subsp. Tularensis SCHU S4
<220> FEATURE:
<221> NAME/KEY: CDS
<222> LOCATION: (1)..(636)

<400> SEQUENCE: 1

| atg att atg agt gag atg ata aca aga caa cag gta aca agt ggc gag | 48 |
| Met Ile Met Ser Glu Met Ile Thr Arg Gln Gln Val Thr Ser Gly Glu | |
| 1               5                   10                  15       | |

| acc att cat gtg aga act gat cct act gca tgt ata gga tct cat cct | 96 |
| Thr Ile His Val Arg Thr Asp Pro Thr Ala Cys Ile Gly Ser His Pro | |
|         20                  25                  30              | |

| aat tgt aga tta ttt att gat tct tta act ata gct ggg gag aaa ctt | 144 |
| Asn Cys Arg Leu Phe Ile Asp Ser Leu Thr Ile Ala Gly Glu Lys Leu | |
|     35                  40                  45                  | |

| gat aaa aat atc gtt gct ata gat ggt gga gag gat gtc acg aaa gct | 192 |
| Asp Lys Asn Ile Val Ala Ile Asp Gly Gly Glu Asp Val Thr Lys Ala | |
| 50                  55                  60                      | |

| gat tcg gct aca gct gct gct agt gta ata cgt tta tct ata acg cca | 240 |
| Asp Ser Ala Thr Ala Ala Ala Ser Val Ile Arg Leu Ser Ile Thr Pro | |
| 65                  70                  75                  80  | |

| ggc tct ata aat cca aca ata agt att act ctt ggt gtt cta att aaa | 288 |
| Gly Ser Ile Asn Pro Thr Ile Ser Ile Thr Leu Gly Val Leu Ile Lys | |
|             85                  90                  95          | |

| tca aat gtt aga act aaa att gaa gag aaa gtt tcg agt ata tta caa | 336 |
| Ser Asn Val Arg Thr Lys Ile Glu Glu Lys Val Ser Ser Ile Leu Gln | |
|         100                 105                 110             | |

| gca agt gct aca gat atg aaa att aag tta ggt aat tct aat aaa aaa | 384 |
| Ala Ser Ala Thr Asp Met Lys Ile Lys Leu Gly Asn Ser Asn Lys Lys | |
|     115                 120                 125                 | |

| caa gag tat aaa act gat gaa gca tgg ggt att atg ata gat cta tct | 432 |
| Gln Glu Tyr Lys Thr Asp Glu Ala Trp Gly Ile Met Ile Asp Leu Ser | |
| 130                 135                 140                     | |

| aat tta gag tta tat cca ata agt gct aag gct ttt agt att agt ata | 480 |
| Asn Leu Glu Leu Tyr Pro Ile Ser Ala Lys Ala Phe Ser Ile Ser Ile | |
| 145                 150                 155                 160 | |

| gag cca aca gaa ctt atg ggt gtt tca aaa gat gga atg aga tat cat | 528 |
| Glu Pro Thr Glu Leu Met Gly Val Ser Lys Asp Gly Met Arg Tyr His | |
|             165                 170                 175         | |

| att ata tct ata gat ggt ctt aca aca tct caa gga agt ttg cca gta | 576 |
| Ile Ile Ser Ile Asp Gly Leu Thr Thr Ser Gln Gly Ser Leu Pro Val | |
|         180                 185                 190             | |

| tgt tgc gca gct agc aca gat aaa gga gtt gct aaa ata gga tat att | 624 |
| Cys Cys Ala Ala Ser Thr Asp Lys Gly Val Ala Lys Ile Gly Tyr Ile | |
|     195                 200                 205                 | |

| gca gct gca tag | 636 |
| Ala Ala Ala     | |
|     210         | |

<210> SEQ ID NO 2
<211> LENGTH: 211
<212> TYPE: PRT
<213> ORGANISM: Francisella tularensis subsp. Tularensis SCHU S4

<400> SEQUENCE: 2

Met Ile Met Ser Glu Met Ile Thr Arg Gln Gln Val Thr Ser Gly Glu
1               5                   10                  15

```
Thr Ile His Val Arg Thr Asp Pro Thr Ala Cys Ile Gly Ser His Pro
         20                  25                  30

Asn Cys Arg Leu Phe Ile Asp Ser Leu Thr Ile Ala Gly Glu Lys Leu
         35                  40                  45

Asp Lys Asn Ile Val Ala Ile Asp Gly Gly Glu Asp Val Thr Lys Ala
 50                  55                  60

Asp Ser Ala Thr Ala Ala Ser Val Ile Arg Leu Ser Ile Thr Pro
 65                  70                  75                  80

Gly Ser Ile Asn Pro Thr Ile Ser Ile Thr Leu Gly Val Leu Ile Lys
                 85                  90                  95

Ser Asn Val Arg Thr Lys Ile Glu Glu Lys Val Ser Ser Ile Leu Gln
             100                 105                 110

Ala Ser Ala Thr Asp Met Lys Ile Lys Leu Gly Asn Ser Asn Lys Lys
             115                 120                 125

Gln Glu Tyr Lys Thr Asp Glu Ala Trp Gly Ile Met Ile Asp Leu Ser
130                 135                 140

Asn Leu Glu Leu Tyr Pro Ile Ser Ala Lys Ala Phe Ser Ile Ser Ile
145                 150                 155                 160

Glu Pro Thr Glu Leu Met Gly Val Ser Lys Asp Gly Met Arg Tyr His
                 165                 170                 175

Ile Ile Ser Ile Asp Gly Leu Thr Thr Ser Gln Gly Ser Leu Pro Val
             180                 185                 190

Cys Cys Ala Ala Ser Thr Asp Lys Gly Val Ala Lys Ile Gly Tyr Ile
             195                 200                 205

Ala Ala Ala
     210

<210> SEQ ID NO 3
<211> LENGTH: 1929
<212> TYPE: DNA
<213> ORGANISM: Francisella tularensis subsp. Tularensis SCHU S4
<220> FEATURE:
<221> NAME/KEY: CDS
<222> LOCATION: (1)..(1929)

<400> SEQUENCE: 3 atg gga aaa ata ata ggt ata gat tta ggt act act aac tct tgt ctt      48
Met Gly Lys Ile Ile Gly Ile Asp Leu Gly Thr Thr Asn Ser Cys Leu
1               5                  10                  15 gct att atg gat ggc aag act gct aaa gtt att gag aat gct gaa gga      96
Ala Ile Met Asp Gly Lys Thr Ala Lys Val Ile Glu Asn Ala Glu Gly
             20                  25                  30 cat aga aca aca cct tca gtt gtg gca tat act gat agc ggt gaa ata     144
His Arg Thr Thr Pro Ser Val Val Ala Tyr Thr Asp Ser Gly Glu Ile
         35                  40                  45 tta gta ggt caa gct gct aaa aga caa gct gta act aac cct gat aat     192
Leu Val Gly Gln Ala Ala Lys Arg Gln Ala Val Thr Asn Pro Asp Asn
 50                  55                  60 aca ttc ttt gct atc aag aga ctt ata ggt cgt aag tac gat gat aaa     240
Thr Phe Phe Ala Ile Lys Arg Leu Ile Gly Arg Lys Tyr Asp Asp Lys
65                  70                  75                  80 gct gta caa gaa gat att aaa aag aaa gta cct tat gcg gta att aaa     288
Ala Val Gln Glu Asp Ile Lys Lys Lys Val Pro Tyr Ala Val Ile Lys
                 85                  90                  95 gct gat aat ggt gat gct tgg gtt gct act aaa gaa ggc aaa aaa atg     336
Ala Asp Asn Gly Asp Ala Trp Val Ala Thr Lys Glu Gly Lys Lys Met
             100                 105                 110
```

| | |
|---|---|
| gct cca cca caa gtt tct gca gaa gtt cta aga aaa atg aaa aaa aca<br>Ala Pro Pro Gln Val Ser Ala Glu Val Leu Arg Lys Met Lys Lys Thr<br>    115                          120                       125 | 384 |
| gca gaa gac tat cta ggt gaa cca gtt aca gaa gct gta att aca gtg<br>Ala Glu Asp Tyr Leu Gly Glu Pro Val Thr Glu Ala Val Ile Thr Val<br>130                       135                     140 | 432 |
| cca gca tac ttt aac gat agt caa aga caa gct aca aaa gat gct ggt<br>Pro Ala Tyr Phe Asn Asp Ser Gln Arg Gln Ala Thr Lys Asp Ala Gly<br>145                       150                     155                   160 | 480 |
| aaa ata gca ggt ctt gaa gtt aaa aga att atc aac gag cct aca gcg<br>Lys Ile Ala Gly Leu Glu Val Lys Arg Ile Ile Asn Glu Pro Thr Ala<br>                165                     170                     175 | 528 |
| gca gcg ctg gca tat ggt gta gac tct aag aaa ggt gag caa act gta<br>Ala Ala Leu Ala Tyr Gly Val Asp Ser Lys Lys Gly Glu Gln Thr Val<br>                180                     185                     190 | 576 |
| gcg gtg tat gac cta ggt ggt gga aca ttc gat atc tca att att gag<br>Ala Val Tyr Asp Leu Gly Gly Gly Thr Phe Asp Ile Ser Ile Ile Glu<br>        195                     200                     205 | 624 |
| att gct gat gtt gat ggc gat aac caa atc gaa gta tta tca acc aat<br>Ile Ala Asp Val Asp Gly Asp Asn Gln Ile Glu Val Leu Ser Thr Asn<br>210                       215                     220 | 672 |
| ggt gat act ttc tta ggt ggt gaa gac ttc gac ttg gct tta atg aac<br>Gly Asp Thr Phe Leu Gly Gly Glu Asp Phe Asp Leu Ala Leu Met Asn<br>225                       230                     235                   240 | 720 |
| tat cta att gac gag ttc aaa aaa gag caa ggt ata gat ctt cac aat<br>Tyr Leu Ile Asp Glu Phe Lys Lys Glu Gln Gly Ile Asp Leu His Asn<br>                       245                     250                   255 | 768 |
| gat aag ctt gct tta caa aga gtt aga gag gct gct gag aaa gct aaa<br>Asp Lys Leu Ala Leu Gln Arg Val Arg Glu Ala Ala Glu Lys Ala Lys<br>                260                     265                     270 | 816 |
| gta gaa tta tct tca gca caa caa act gat gtt aac cta cct tac atc<br>Val Glu Leu Ser Ser Ala Gln Gln Thr Asp Val Asn Leu Pro Tyr Ile<br>                     275                     280                   285 | 864 |
| aca gca gat gct act gga cct aag cac tta aat atc aaa gta act aga<br>Thr Ala Asp Ala Thr Gly Pro Lys His Leu Asn Ile Lys Val Thr Arg<br>290                       295                     300 | 912 |
| gct aag ttt gag tct tta gtt tct gat ctt gta atg aga tca ctt gag<br>Ala Lys Phe Glu Ser Leu Val Ser Asp Leu Val Met Arg Ser Leu Glu<br>305                       310                     315                   320 | 960 |
| cct tgt aag aaa gct ctt gaa gat gct ggt tta agt aag tct gat att<br>Pro Cys Lys Lys Ala Leu Glu Asp Ala Gly Leu Ser Lys Ser Asp Ile<br>                       325                     330                   335 | 1008 |
| aca gaa gta tta cta gtg ggt gga caa act cgt atg cct cta gta caa<br>Thr Glu Val Leu Leu Val Gly Gly Gln Thr Arg Met Pro Leu Val Gln<br>                340                     345                     350 | 1056 |
| gag aaa gta aaa gag ttt ttt ggt aaa gag cca cgt aaa gat gtg aac<br>Glu Lys Val Lys Glu Phe Phe Gly Lys Glu Pro Arg Lys Asp Val Asn<br>        355                     360                     365 | 1104 |
| cct gat gaa gct gtt gca gtt ggt gcg gct att caa ggt ggt gta tta<br>Pro Asp Glu Ala Val Ala Val Gly Ala Ala Ile Gln Gly Gly Val Leu<br>370                       375                     380 | 1152 |
| gca ggt gat gtt aaa gat att ctt tta ttg gat gta aca ccg ctt tct<br>Ala Gly Asp Val Lys Asp Ile Leu Leu Leu Asp Val Thr Pro Leu Ser<br>385                       390                     395                   400 | 1200 |
| cta ggt att gag act atg gga ggt gtt atg act aag ctt atc gag aga<br>Leu Gly Ile Glu Thr Met Gly Gly Val Met Thr Lys Leu Ile Glu Arg<br>                       405                     410                   415 | 1248 |
| aat act acg att cct act aag aag tcg caa gta ttc tca aca gct gaa<br>Asn Thr Thr Ile Pro Thr Lys Lys Ser Gln Val Phe Ser Thr Ala Glu<br>                420                     425                     430 | 1296 |

```
gat aac cag cct gcg gta act att cat gta ctt caa ggt gag cgt gaa    1344
Asp Asn Gln Pro Ala Val Thr Ile His Val Leu Gln Gly Glu Arg Glu
            435                 440                 445 atg gct tct gca aac aaa tct tta ggt aga ttt gat ctg gca gat att    1392
Met Ala Ser Ala Asn Lys Ser Leu Gly Arg Phe Asp Leu Ala Asp Ile
        450                 455                 460 cca cca gcg cca cgt ggt atg cca caa att gag gtt act ttt gat ata    1440
Pro Pro Ala Pro Arg Gly Met Pro Gln Ile Glu Val Thr Phe Asp Ile
465                 470                 475                 480 gat gct aac ggt ata tta aat gtg tct gct aaa gat aaa gct act ggt    1488
Asp Ala Asn Gly Ile Leu Asn Val Ser Ala Lys Asp Lys Ala Thr Gly
                485                 490                 495 aaa gag caa aat att gtg att aag tct tca agt ggt tta tct gaa gag    1536
Lys Glu Gln Asn Ile Val Ile Lys Ser Ser Ser Gly Leu Ser Glu Glu
            500                 505                 510 gat atc gaa aaa atg gta caa gac gct gaa gct aat gca gaa gca gat    1584
Asp Ile Glu Lys Met Val Gln Asp Ala Glu Ala Asn Ala Glu Ala Asp
        515                 520                 525 aaa aag ttc cat gat tta gtt act gct aga aat act gct gat aac tta    1632
Lys Lys Phe His Asp Leu Val Thr Ala Arg Asn Thr Ala Asp Asn Leu
530                 535                 540 att cat agc tca aga aaa gca att caa gaa ctg ggt gac aaa gta aca    1680
Ile His Ser Ser Arg Lys Ala Ile Gln Glu Leu Gly Asp Lys Val Thr
545                 550                 555                 560 gca gca gaa aaa gaa aaa atc gaa gaa gct tgt aaa gag ctt gaa gca    1728
Ala Ala Glu Lys Glu Lys Ile Glu Glu Ala Cys Lys Glu Leu Glu Ala
                565                 570                 575 gca act aaa ggt gat gat aag caa gcg att gaa tct aaa act aag gct    1776
Ala Thr Lys Gly Asp Asp Lys Gln Ala Ile Glu Ser Lys Thr Lys Ala
            580                 585                 590 cta gaa gaa gca ttt gcg cca ata gct caa aaa gct tat gct gag caa    1824
Leu Glu Glu Ala Phe Ala Pro Ile Ala Gln Lys Ala Tyr Ala Glu Gln
        595                 600                 605 gct caa gct gct gtt gcc caa ggt ggt gct aaa gct gaa gaa cct aag    1872
Ala Gln Ala Ala Val Ala Gln Gly Gly Ala Lys Ala Glu Glu Pro Lys
610                 615                 620 aaa gaa gaa gat gtt gtt gat gct gac ttt gag gat gtt gaa gac gac    1920
Lys Glu Glu Asp Val Val Asp Ala Asp Phe Glu Asp Val Glu Asp Asp
625                 630                 635                 640 aaa aaa taa                                                        1929
Lys Lys

<210> SEQ ID NO 4
<211> LENGTH: 642
<212> TYPE: PRT
<213> ORGANISM: Francisella tularensis subsp. Tularensis SCHU S4

<400> SEQUENCE: 4

Met Gly Lys Ile Ile Gly Ile Asp Leu Gly Thr Thr Asn Ser Cys Leu
1               5                   10                  15

Ala Ile Met Asp Gly Lys Thr Ala Lys Val Ile Glu Asn Ala Glu Gly
            20                  25                  30

His Arg Thr Thr Pro Ser Val Val Ala Tyr Thr Asp Ser Gly Glu Ile
        35                  40                  45

Leu Val Gly Gln Ala Ala Lys Arg Gln Ala Val Thr Asn Pro Asp Asn
    50                  55                  60

Thr Phe Phe Ala Ile Lys Arg Leu Ile Gly Arg Lys Tyr Asp Asp Lys
65                  70                  75                  80
```

```
Ala Val Gln Glu Asp Ile Lys Lys Val Pro Tyr Ala Val Ile Lys
                85                  90                  95

Ala Asp Asn Gly Asp Ala Trp Val Ala Thr Lys Glu Gly Lys Lys Met
            100                 105                 110

Ala Pro Pro Gln Val Ser Ala Glu Val Leu Arg Lys Met Lys Lys Thr
            115                 120                 125

Ala Glu Asp Tyr Leu Gly Glu Pro Val Thr Glu Ala Ile Thr Val
            130                 135                 140

Pro Ala Tyr Phe Asn Asp Ser Gln Arg Gln Ala Thr Lys Asp Ala Gly
145                 150                 155                 160

Lys Ile Ala Gly Leu Glu Val Lys Arg Ile Ile Asn Glu Pro Thr Ala
                165                 170                 175

Ala Ala Leu Ala Tyr Gly Val Asp Ser Lys Lys Gly Glu Gln Thr Val
            180                 185                 190

Ala Val Tyr Asp Leu Gly Gly Gly Thr Phe Asp Ile Ser Ile Ile Glu
            195                 200                 205

Ile Ala Asp Val Asp Gly Asp Asn Gln Ile Glu Val Leu Ser Thr Asn
    210                 215                 220

Gly Asp Thr Phe Leu Gly Gly Glu Asp Phe Asp Leu Ala Leu Met Asn
225                 230                 235                 240

Tyr Leu Ile Asp Glu Phe Lys Lys Glu Gln Gly Ile Asp Leu His Asn
                245                 250                 255

Asp Lys Leu Ala Leu Gln Arg Val Arg Glu Ala Ala Glu Lys Ala Lys
            260                 265                 270

Val Glu Leu Ser Ser Ala Gln Gln Thr Asp Val Asn Leu Pro Tyr Ile
            275                 280                 285

Thr Ala Asp Ala Thr Gly Pro Lys His Leu Asn Ile Lys Val Thr Arg
    290                 295                 300

Ala Lys Phe Glu Ser Leu Val Ser Asp Leu Val Met Arg Ser Leu Glu
305                 310                 315                 320

Pro Cys Lys Lys Ala Leu Glu Asp Ala Gly Leu Ser Lys Ser Asp Ile
            325                 330                 335

Thr Glu Val Leu Leu Val Gly Gly Gln Thr Arg Met Pro Leu Val Gln
            340                 345                 350

Glu Lys Val Lys Glu Phe Phe Gly Lys Glu Pro Arg Lys Asp Val Asn
            355                 360                 365

Pro Asp Glu Ala Val Ala Val Gly Ala Ala Ile Gln Gly Gly Val Leu
370                 375                 380

Ala Gly Asp Val Lys Asp Ile Leu Leu Leu Asp Val Thr Pro Leu Ser
385                 390                 395                 400

Leu Gly Ile Glu Thr Met Gly Gly Val Met Thr Lys Leu Ile Glu Arg
                405                 410                 415

Asn Thr Thr Ile Pro Thr Lys Lys Ser Gln Val Phe Ser Thr Ala Glu
            420                 425                 430

Asp Asn Gln Pro Ala Val Thr Ile His Val Leu Gln Gly Glu Arg Glu
            435                 440                 445

Met Ala Ser Ala Asn Lys Ser Leu Gly Arg Phe Asp Leu Ala Asp Ile
450                 455                 460

Pro Pro Ala Pro Arg Gly Met Pro Gln Ile Glu Val Thr Phe Asp Ile
465                 470                 475                 480

Asp Ala Asn Gly Ile Leu Asn Val Ser Ala Lys Asp Lys Ala Thr Gly
                485                 490                 495

Lys Glu Gln Asn Ile Val Ile Lys Ser Ser Ser Gly Leu Ser Glu Glu
```

```
                 500                 505                 510
Asp Ile Glu Lys Met Val Gln Asp Ala Glu Ala Asn Ala Glu Ala Asp
            515                 520                 525

Lys Lys Phe His Asp Leu Val Thr Ala Arg Asn Thr Ala Asp Asn Leu
        530                 535                 540

Ile His Ser Ser Arg Lys Ala Ile Gln Glu Leu Gly Asp Lys Val Thr
545                 550                 555                 560

Ala Ala Glu Lys Glu Lys Ile Glu Glu Ala Cys Lys Glu Leu Glu Ala
                565                 570                 575

Ala Thr Lys Gly Asp Asp Lys Gln Ala Ile Glu Ser Lys Thr Lys Ala
            580                 585                 590

Leu Glu Glu Ala Phe Ala Pro Ile Ala Gln Lys Ala Tyr Ala Glu Gln
        595                 600                 605

Ala Gln Ala Ala Val Ala Gln Gly Gly Ala Lys Ala Glu Glu Pro Lys
    610                 615                 620

Lys Glu Glu Asp Val Val Asp Ala Asp Phe Glu Asp Val Glu Asp Asp
625                 630                 635                 640

Lys Lys

<210> SEQ ID NO 5
<211> LENGTH: 1254
<212> TYPE: DNA
<213> ORGANISM: Francisella tularensis subsp. Tularensis SCHU S4
<220> FEATURE:
<221> NAME/KEY: CDS
<222> LOCATION: (1)..(1254)

<400> SEQUENCE: 5 atg aaa aaa tta ctg aaa cta tgc tta atg aca tca tta att aca aca      48
Met Lys Lys Leu Leu Lys Leu Cys Leu Met Thr Ser Leu Ile Thr Thr
1               5                   10                  15 ctc tca gcc tgc caa aca cta gat gat aaa gat aaa gat agt ggt cca      96
Leu Ser Ala Cys Gln Thr Leu Asp Asp Lys Asp Lys Asp Ser Gly Pro
            20                  25                  30 cta aca ttt cca aca tta gaa cct tgt act gcc gag cta ctt caa tca     144
Leu Thr Phe Pro Thr Leu Glu Pro Cys Thr Ala Glu Leu Leu Gln Ser
        35                  40                  45 aat caa tct ttt ata tgt gta aaa gaa caa aca gga cct gat cta atc     192
Asn Gln Ser Phe Ile Cys Val Lys Glu Gln Thr Gly Pro Asp Leu Ile
    50                  55                  60 gaa aca aat ata aaa ttt gat gct gat agc tat aca tta aac act cag     240
Glu Thr Asn Ile Lys Phe Asp Ala Asp Ser Tyr Thr Leu Asn Thr Gln
65                  70                  75                  80 gct aaa gaa gtt tta gat aag ctt ttt gct tat ttg aaa cta act gat     288
Ala Lys Glu Val Leu Asp Lys Leu Phe Ala Tyr Leu Lys Leu Thr Asp
                85                  90                  95 act aca aat ttc aca att aaa ggt tat gct gga aaa gtt gaa tca aaa     336
Thr Thr Asn Phe Thr Ile Lys Gly Tyr Ala Gly Lys Val Glu Ser Lys
            100                 105                 110 att ctc aca gat cag aaa atc cta acc gac tat aat att aga cta tca     384
Ile Leu Thr Asp Gln Lys Ile Leu Thr Asp Tyr Asn Ile Arg Leu Ser
        115                 120                 125 aaa aac cgt gct agt agt gtc gaa gaa tac ctt gta aac aaa ggt ctt     432
Lys Asn Arg Ala Ser Ser Val Glu Glu Tyr Leu Val Asn Lys Gly Leu
    130                 135                 140 ggc tct agt gat gga att act att aaa gcc tta ggt tat caa gat cct     480
Gly Ser Ser Asp Gly Ile Thr Ile Lys Ala Leu Gly Tyr Gln Asp Pro
145                 150                 155                 160
```

| | | | | | | | | | | | | | | | | |
|---|---|---|---|---|---|---|---|---|---|---|---|---|---|---|---|---|
| atc | gcc | cct | aat | gac | tca | acc | tca | agt | aga | gct | ata | aat | cag | cgc | gtt | 528 |
| Ile | Ala | Pro | Asn | Asp | Ser | Thr | Ser | Ser | Arg | Ala | Ile | Asn | Gln | Arg | Val | |
| | | | | 165 | | | | 170 | | | | | 175 | | | |
| gaa | att | act | cta | aaa | agt | aga | ctt | ata | gag | caa | att | gat | aat | att | gaa | 576 |
| Glu | Ile | Thr | Leu | Lys | Ser | Arg | Leu | Ile | Glu | Gln | Ile | Asp | Asn | Ile | Glu | |
| | | | 180 | | | | | 185 | | | | | 190 | | | |
| aat | aac | tta | gag | cat | gtc | aga | cca | gct | gaa | tat | aca | aaa | ttc | ttc | tca | 624 |
| Asn | Asn | Leu | Glu | His | Val | Arg | Pro | Ala | Glu | Tyr | Thr | Lys | Phe | Phe | Ser | |
| | | 195 | | | | | 200 | | | | | 205 | | | | |
| aat | gta | tat | tta | ctt | aat | gat | aat | cag | ata | gac | aat | att | tca | aga | ata | 672 |
| Asn | Val | Tyr | Leu | Leu | Asn | Asp | Asn | Gln | Ile | Asp | Asn | Ile | Ser | Arg | Ile | |
| | 210 | | | | | 215 | | | | | 220 | | | | | |
| tac | aat | tct | aga | gag | aaa | cgc | cca | ata | ctc | gga | att | aac | ttt | aaa | atc | 720 |
| Tyr | Asn | Ser | Arg | Glu | Lys | Arg | Pro | Ile | Leu | Gly | Ile | Asn | Phe | Lys | Ile | |
| 225 | | | | 230 | | | | | 235 | | | | | 240 | | |
| ttt | gct | aac | aaa | gaa | tat | aca | gca | gcc | aag | gat | aac | agt | aac | ttc | ata | 768 |
| Phe | Ala | Asn | Lys | Glu | Tyr | Thr | Ala | Ala | Lys | Asp | Asn | Ser | Asn | Phe | Ile | |
| | | | 245 | | | | | 250 | | | | | 255 | | | |
| ata | ata | tcc | gaa | cca | aaa | cca | ata | tct | tca | ttt | aat | gat | gat | aaa | aaa | 816 |
| Ile | Ile | Ser | Glu | Pro | Lys | Pro | Ile | Ser | Ser | Phe | Asn | Asp | Asp | Lys | Lys | |
| | | 260 | | | | | 265 | | | | | 270 | | | | |
| gtc | tat | aga | cta | ggc | tca | gca | aaa | tat | gat | tat | acc | ttt | aaa | ggt | ata | 864 |
| Val | Tyr | Arg | Leu | Gly | Ser | Ala | Lys | Tyr | Asp | Tyr | Thr | Phe | Lys | Gly | Ile | |
| | 275 | | | | | 280 | | | | | 285 | | | | | |
| aca | gca | ttg | acg | ata | act | aat | tta | agt | cgt | gaa | gct | agt | gta | ggc | aat | 912 |
| Thr | Ala | Leu | Thr | Ile | Thr | Asn | Leu | Ser | Arg | Glu | Ala | Ser | Val | Gly | Asn | |
| | 290 | | | | | 295 | | | | | 300 | | | | | |
| tat | gta | ata | cct | aat | gat | att | gtt | tca | caa | caa | ctg | cca | gaa | caa | act | 960 |
| Tyr | Val | Ile | Pro | Asn | Asp | Ile | Val | Ser | Gln | Gln | Leu | Pro | Glu | Gln | Thr | |
| 305 | | | | 310 | | | | | 315 | | | | | 320 | | |
| ttt | aaa | atg | aaa | agt | aaa | ata | aca | gct | aat | gta | ctt | gaa | gat | gta | atg | 1008 |
| Phe | Lys | Met | Lys | Ser | Lys | Ile | Thr | Ala | Asn | Val | Leu | Glu | Asp | Val | Met | |
| | | | 325 | | | | | 330 | | | | | 335 | | | |
| aat | act | aat | aca | ttc | tca | tct | tcg | tat | aat | agt | att | cta | ttg | aac | aaa | 1056 |
| Asn | Thr | Asn | Thr | Phe | Ser | Ser | Ser | Tyr | Asn | Ser | Ile | Leu | Leu | Asn | Lys | |
| | | | 340 | | | | | 345 | | | | | 350 | | | |
| ggc | gct | gct | gat | ggc | ttg | aaa | gta | ggc | gct | caa | gtt | att | tta | tat | gaa | 1104 |
| Gly | Ala | Ala | Asp | Gly | Leu | Lys | Val | Gly | Ala | Gln | Val | Ile | Leu | Tyr | Glu | |
| | | 355 | | | | | 360 | | | | | 365 | | | | |
| cca | gaa | acc | aga | gta | gat | ggt | ttt | cca | gtc | cca | cct | aaa | tat | att | ggt | 1152 |
| Pro | Glu | Thr | Arg | Val | Asp | Gly | Phe | Pro | Val | Pro | Pro | Lys | Tyr | Ile | Gly | |
| | 370 | | | | | 375 | | | | | 380 | | | | | |
| tat | ggt | ttt | atc | tat | aga | gaa | tct | caa | cac | tac | tct | ata | gcc | cta | att | 1200 |
| Tyr | Gly | Phe | Ile | Tyr | Arg | Glu | Ser | Gln | His | Tyr | Ser | Ile | Ala | Leu | Ile | |
| 385 | | | | 390 | | | | | 395 | | | | | 400 | | |
| gtc | aat | tca | cta | caa | gaa | att | aca | aat | aat | tca | atg | gca | acg | act | att | 1248 |
| Val | Asn | Ser | Leu | Gln | Glu | Ile | Thr | Asn | Asn | Ser | Met | Ala | Thr | Thr | Ile | |
| | | | 405 | | | | | 410 | | | | | 415 | | | |
| tta | taa | | | | | | | | | | | | | | | 1254 |
| Leu | | | | | | | | | | | | | | | | |

<210> SEQ ID NO 6
<211> LENGTH: 417
<212> TYPE: PRT
<213> ORGANISM: Francisella tularensis subsp. Tularensis SCHU S4

<400> SEQUENCE: 6

Met Lys Lys Leu Leu Lys Leu Cys Leu Met Thr Ser Leu Ile Thr Thr
1               5                   10                  15

Leu Ser Ala Cys Gln Thr Leu Asp Asp Lys Asp Lys Asp Ser Gly Pro

```
            20                  25                  30
Leu Thr Phe Pro Thr Leu Glu Pro Cys Thr Ala Glu Leu Leu Gln Ser
            35                  40                  45

Asn Gln Ser Phe Ile Cys Val Lys Glu Gln Thr Gly Pro Asp Leu Ile
        50                  55                  60

Glu Thr Asn Ile Lys Phe Asp Ala Asp Ser Tyr Thr Leu Asn Thr Gln
65                  70                  75                  80

Ala Lys Glu Val Leu Asp Lys Leu Phe Ala Tyr Leu Lys Leu Thr Asp
                85                  90                  95

Thr Thr Asn Phe Thr Ile Lys Gly Tyr Ala Gly Lys Val Glu Ser Lys
            100                 105                 110

Ile Leu Thr Asp Gln Lys Ile Leu Thr Asp Tyr Asn Ile Arg Leu Ser
            115                 120                 125

Lys Asn Arg Ala Ser Ser Val Glu Glu Tyr Leu Val Asn Lys Gly Leu
        130                 135                 140

Gly Ser Ser Asp Gly Ile Thr Ile Lys Ala Leu Gly Tyr Gln Asp Pro
145                 150                 155                 160

Ile Ala Pro Asn Asp Ser Thr Ser Arg Ala Ile Asn Gln Arg Val
                165                 170                 175

Glu Ile Thr Leu Lys Ser Arg Leu Ile Glu Gln Ile Asp Asn Ile Glu
            180                 185                 190

Asn Asn Leu Glu His Val Arg Pro Ala Glu Tyr Thr Lys Phe Phe Ser
            195                 200                 205

Asn Val Tyr Leu Leu Asn Asp Asn Gln Ile Asp Asn Ile Ser Arg Ile
        210                 215                 220

Tyr Asn Ser Arg Glu Lys Arg Pro Ile Leu Gly Ile Asn Phe Lys Ile
225                 230                 235                 240

Phe Ala Asn Lys Glu Tyr Thr Ala Ala Lys Asp Asn Ser Asn Phe Ile
                245                 250                 255

Ile Ile Ser Glu Pro Lys Pro Ile Ser Ser Phe Asn Asp Asp Lys Lys
            260                 265                 270

Val Tyr Arg Leu Gly Ser Ala Lys Tyr Asp Tyr Thr Phe Lys Gly Ile
        275                 280                 285

Thr Ala Leu Thr Ile Thr Asn Leu Ser Arg Glu Ala Ser Val Gly Asn
        290                 295                 300

Tyr Val Ile Pro Asn Asp Ile Val Ser Gln Gln Leu Pro Glu Gln Thr
305                 310                 315                 320

Phe Lys Met Lys Ser Lys Ile Thr Ala Asn Val Leu Glu Asp Val Met
                325                 330                 335

Asn Thr Asn Thr Phe Ser Ser Ser Tyr Asn Ser Ile Leu Leu Asn Lys
            340                 345                 350

Gly Ala Ala Asp Gly Leu Lys Val Gly Ala Gln Val Ile Leu Tyr Glu
        355                 360                 365

Pro Glu Thr Arg Val Asp Gly Phe Pro Val Pro Lys Tyr Ile Gly
        370                 375                 380

Tyr Gly Phe Ile Tyr Arg Glu Ser Gln His Tyr Ser Ile Ala Leu Ile
385                 390                 395                 400

Val Asn Ser Leu Gln Glu Ile Thr Asn Asn Ser Met Ala Thr Thr Ile
                405                 410                 415

Leu

<210> SEQ ID NO 7
<211> LENGTH: 1470
```

```
<212> TYPE: DNA
<213> ORGANISM: Francisella tularensis subsp. Tularensis SCHU S4
<220> FEATURE:
<221> NAME/KEY: CDS
<222> LOCATION: (1)..(1470)

<400> SEQUENCE: 7 atg gtt gaa tta aaa gta cct atg ttc cca gag tct gta gca gat ggc       48
Met Val Glu Leu Lys Val Pro Met Phe Pro Glu Ser Val Ala Asp Gly
1               5                   10                  15 aca tta gct caa tgg aat aaa aac gaa ggt gac ttt gta aat gag ggc       96
Thr Leu Ala Gln Trp Asn Lys Asn Glu Gly Asp Phe Val Asn Glu Gly
            20                  25                  30 gat atc ttg gca gag att gag act gat aaa gtt gtt cta gaa gta cct      144
Asp Ile Leu Ala Glu Ile Glu Thr Asp Lys Val Val Leu Glu Val Pro
        35                  40                  45 gca aca tct agt ggt gtt tta aaa ggg ata aaa aaa cat gct ggt gat      192
Ala Thr Ser Ser Gly Val Leu Lys Gly Ile Lys Lys His Ala Gly Asp
    50                  55                  60 aca gtg ctt tca gaa gag tca tta gcg atc att gat act gct gtt tct      240
Thr Val Leu Ser Glu Glu Ser Leu Ala Ile Ile Asp Thr Ala Val Ser
65                  70                  75                  80 aca tct gaa cct aac caa caa act act aat caa gga aat gct tca gaa      288
Thr Ser Glu Pro Asn Gln Gln Thr Thr Asn Gln Gly Asn Ala Ser Glu
                85                  90                  95 gca act gct act ggg caa gaa att gat att aag gcg cct gta ttt cca      336
Ala Thr Ala Thr Gly Gln Glu Ile Asp Ile Lys Ala Pro Val Phe Pro
            100                 105                 110 gag tct gta gca gat ggc acg atc tca gag tgg cat aag aaa gag ggt      384
Glu Ser Val Ala Asp Gly Thr Ile Ser Glu Trp His Lys Lys Glu Gly
        115                 120                 125 gag gct gtt tct gag ggt gat atc tta gca gag att gag act gat aag      432
Glu Ala Val Ser Glu Gly Asp Ile Leu Ala Glu Ile Glu Thr Asp Lys
    130                 135                 140 gtt gtt cta gag gtt ccg gca aca tca aat ggt gtt ttg aca aaa ata      480
Val Val Leu Glu Val Pro Ala Thr Ser Asn Gly Val Leu Thr Lys Ile
145                 150                 155                 160 tta aaa aca gca gga gag act gta cta tct gca gag ctt atc gct aag      528
Leu Lys Thr Ala Gly Glu Thr Val Leu Ser Ala Glu Leu Ile Ala Lys
                165                 170                 175 att aca gca gga ggc gca act gct act acg aaa tca gaa gct tcg gtg      576
Ile Thr Ala Gly Gly Ala Thr Ala Thr Thr Lys Ser Glu Ala Ser Val
            180                 185                 190 gga gtt tct caa gca aat aat gat ccg cat cta gta cct tca gca cgt      624
Gly Val Ser Gln Ala Asn Asn Asp Pro His Leu Val Pro Ser Ala Arg
        195                 200                 205 aaa gct ttt aat gca agc ggc ttg gat act gct gct aat atc gaa ggt      672
Lys Ala Phe Asn Ala Ser Gly Leu Asp Thr Ala Ala Asn Ile Glu Gly
    210                 215                 220 aca ggt aaa aaa ggg cgt ata act tct gaa gat gtc aaa aaa gca gtt      720
Thr Gly Lys Lys Gly Arg Ile Thr Ser Glu Asp Val Lys Lys Ala Val
225                 230                 235                 240 gca tca gta aat aaa cct caa caa cag aca gtt gtt ata aat caa ggt      768
Ala Ser Val Asn Lys Pro Gln Gln Gln Thr Val Val Ile Asn Gln Gly
                245                 250                 255 gct aga tat gaa aaa aga gtc aag atg act cgt ctg cgt cag act ata      816
Ala Arg Tyr Glu Lys Arg Val Lys Met Thr Arg Leu Arg Gln Thr Ile
            260                 265                 270 gca aat agg tta gtt gag gtt caa cat act aat gca atc tta act act      864
Ala Asn Arg Leu Val Glu Val Gln His Thr Asn Ala Ile Leu Thr Thr
        275                 280                 285
```

```
ttc aat gaa gta gat atg agt gca gtt atg gag ctt aga aac aaa tat    912
Phe Asn Glu Val Asp Met Ser Ala Val Met Glu Leu Arg Asn Lys Tyr
    290                 295                 300 aaa gat atg ttt gtc aaa gaa cat gat act aag ctt ggc ttt atg tct    960
Lys Asp Met Phe Val Lys Glu His Asp Thr Lys Leu Gly Phe Met Ser
305                 310                 315                 320 ttc ttt atc aaa gca gca aca gaa gca ctt aag aaa ttc cca gat gta   1008
Phe Phe Ile Lys Ala Ala Thr Glu Ala Leu Lys Lys Phe Pro Asp Val
            325                 330                 335 aat gcc tct att gat ggt gat gag att gtt tac cat aat tat ttt gat   1056
Asn Ala Ser Ile Asp Gly Asp Glu Ile Val Tyr His Asn Tyr Phe Asp
            340                 345                 350 att ggt att gct gta ggt act gat agg ggt cta gtg gta cct gta cta   1104
Ile Gly Ile Ala Val Gly Thr Asp Arg Gly Leu Val Val Pro Val Leu
            355                 360                 365 aga gat aca gat act aaa tct cta gct gaa tta gaa gcc gat gtt tta   1152
Arg Asp Thr Asp Thr Lys Ser Leu Ala Glu Leu Glu Ala Asp Val Leu
    370                 375                 380 gac aaa gcg att aaa ggt cgt gat ggt aaa tta agc ctt gaa gat atg   1200
Asp Lys Ala Ile Lys Gly Arg Asp Gly Lys Leu Ser Leu Glu Asp Met
385                 390                 395                 400 caa ggt ggt aca ttt acg att aca aat ggc gga act tat ggt tcg atg   1248
Gln Gly Gly Thr Phe Thr Ile Thr Asn Gly Gly Thr Tyr Gly Ser Met
            405                 410                 415 tta tct acg cct att att aat tca ccg caa agt gct att tta ggt atg   1296
Leu Ser Thr Pro Ile Ile Asn Ser Pro Gln Ser Ala Ile Leu Gly Met
            420                 425                 430 cat aat att gtt gag cgt cct gta gtt gtt aag ggt gag att aag att   1344
His Asn Ile Val Glu Arg Pro Val Val Val Lys Gly Glu Ile Lys Ile
            435                 440                 445 cgt cca att atg tat tta gcg tta tct tac gac cat aga atc att gat   1392
Arg Pro Ile Met Tyr Leu Ala Leu Ser Tyr Asp His Arg Ile Ile Asp
    450                 455                 460 ggc ggt aca tct gta aga ttc ttg aag atg atc aaa gag cta att gaa   1440
Gly Gly Thr Ser Val Arg Phe Leu Lys Met Ile Lys Glu Leu Ile Glu
465                 470                 475                 480 gat cca aat aga att ctt cta caa gta tag                           1470
Asp Pro Asn Arg Ile Leu Leu Gln Val
            485
```

<210> SEQ ID NO 8
<211> LENGTH: 489
<212> TYPE: PRT
<213> ORGANISM: Francisella tularensis subsp. Tularensis SCHU S4

<400> SEQUENCE: 8

```
Met Val Glu Leu Lys Val Pro Met Phe Pro Glu Ser Val Ala Asp Gly
1               5                   10                  15

Thr Leu Ala Gln Trp Asn Lys Asn Glu Gly Asp Phe Val Asn Glu Gly
            20                  25                  30

Asp Ile Leu Ala Glu Ile Glu Thr Asp Lys Val Val Leu Glu Val Pro
        35                  40                  45

Ala Thr Ser Ser Gly Val Leu Lys Gly Ile Lys Lys His Ala Gly Asp
    50                  55                  60

Thr Val Leu Ser Glu Glu Ser Leu Ala Ile Ile Asp Thr Ala Val Ser
65                  70                  75                  80

Thr Ser Glu Pro Asn Gln Gln Thr Thr Asn Gln Gly Asn Ala Ser Glu
                85                  90                  95
```

```
Ala Thr Ala Thr Gly Gln Glu Ile Asp Ile Lys Ala Pro Val Phe Pro
            100                 105                 110

Glu Ser Val Ala Asp Gly Thr Ile Ser Glu Trp His Lys Lys Glu Gly
        115                 120                 125

Glu Ala Val Ser Glu Gly Asp Ile Leu Ala Glu Ile Glu Thr Asp Lys
    130                 135                 140

Val Val Leu Glu Val Pro Ala Thr Ser Asn Gly Val Leu Thr Lys Ile
145                 150                 155                 160

Leu Lys Thr Ala Gly Glu Thr Val Leu Ser Ala Glu Leu Ile Ala Lys
                165                 170                 175

Ile Thr Ala Gly Gly Ala Thr Ala Thr Thr Lys Ser Glu Ala Ser Val
            180                 185                 190

Gly Val Ser Gln Ala Asn Asn Asp Pro His Leu Val Pro Ser Ala Arg
        195                 200                 205

Lys Ala Phe Asn Ala Ser Gly Leu Asp Thr Ala Ala Asn Ile Glu Gly
    210                 215                 220

Thr Gly Lys Lys Gly Arg Ile Thr Ser Glu Asp Val Lys Lys Ala Val
225                 230                 235                 240

Ala Ser Val Asn Lys Pro Gln Gln Gln Thr Val Val Ile Asn Gln Gly
                245                 250                 255

Ala Arg Tyr Glu Lys Arg Val Lys Met Thr Arg Leu Arg Gln Thr Ile
            260                 265                 270

Ala Asn Arg Leu Val Glu Val Gln His Thr Asn Ala Ile Leu Thr Thr
        275                 280                 285

Phe Asn Glu Val Asp Met Ser Ala Val Met Glu Leu Arg Asn Lys Tyr
    290                 295                 300

Lys Asp Met Phe Val Lys Glu His Asp Thr Lys Leu Gly Phe Met Ser
305                 310                 315                 320

Phe Phe Ile Lys Ala Ala Thr Glu Ala Leu Lys Lys Phe Pro Asp Val
                325                 330                 335

Asn Ala Ser Ile Asp Gly Asp Glu Ile Val Tyr His Asn Tyr Phe Asp
            340                 345                 350

Ile Gly Ile Ala Val Gly Thr Asp Arg Gly Leu Val Val Pro Val Leu
        355                 360                 365

Arg Asp Thr Asp Thr Lys Ser Leu Ala Glu Leu Glu Ala Asp Val Leu
    370                 375                 380

Asp Lys Ala Ile Lys Gly Arg Asp Gly Lys Leu Ser Leu Glu Asp Met
385                 390                 395                 400

Gln Gly Gly Thr Phe Thr Ile Thr Asn Gly Gly Thr Tyr Gly Ser Met
                405                 410                 415

Leu Ser Thr Pro Ile Ile Asn Ser Pro Gln Ser Ala Ile Leu Gly Met
            420                 425                 430

His Asn Ile Val Glu Arg Pro Val Val Lys Gly Glu Ile Lys Ile
        435                 440                 445

Arg Pro Ile Met Tyr Leu Ala Leu Ser Tyr Asp His Arg Ile Ile Asp
    450                 455                 460

Gly Gly Thr Ser Val Arg Phe Leu Lys Met Ile Lys Glu Leu Ile Glu
465                 470                 475                 480

Asp Pro Asn Arg Ile Leu Leu Gln Val
                485

<210> SEQ ID NO 9
<211> LENGTH: 450
<212> TYPE: DNA
```

<213> ORGANISM: Francisella tularensis subsp. Tularensis SCHU S4
<220> FEATURE:
<221> NAME/KEY: CDS
<222> LOCATION: (1)..(450)

<400> SEQUENCE: 9

| | | | | | | | | | | | | | | | | |
|---|---|---|---|---|---|---|---|---|---|---|---|---|---|---|---|---|
| atg | aaa | aaa | ata | att | gag | ctt | agt | ctt | tta | tct | tta | tca | atc | gca | ggt | 48 |
| Met | Lys | Lys | Ile | Ile | Glu | Leu | Ser | Leu | Leu | Ser | Leu | Ser | Ile | Ala | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tta | gcg | agc | tgt | tct | act | cta | ggg | tta | ggt | ggc | tct | gat | gat | gca | aaa | 96 |
| Leu | Ala | Ser | Cys | Ser | Thr | Leu | Gly | Leu | Gly | Gly | Ser | Asp | Asp | Ala | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| gct | tca | gct | aaa | gat | act | gct | gct | gct | cag | aca | gct | act | act | gag | caa | 144 |
| Ala | Ser | Ala | Lys | Asp | Thr | Ala | Ala | Ala | Gln | Thr | Ala | Thr | Thr | Glu | Gln | |
| | 35 | | | | | 40 | | | | | 45 | | | | | |

| | | | | | | | | | | | | | | | | |
|---|---|---|---|---|---|---|---|---|---|---|---|---|---|---|---|---|
| gct | gct | gct | gta | tct | aag | cca | act | gca | aaa | gta | agt | tta | aat | aaa | ctt | 192 |
| Ala | Ala | Ala | Val | Ser | Lys | Pro | Thr | Ala | Lys | Val | Ser | Leu | Asn | Lys | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| ggt | cag | gat | aaa | ata | aaa | gca | act | gta | tat | aca | aca | tac | aat | aat | aac | 240 |
| Gly | Gln | Asp | Lys | Ile | Lys | Ala | Thr | Val | Tyr | Thr | Thr | Tyr | Asn | Asn | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cca | caa | gga | agt | gta | aga | tta | caa | tgg | cag | gct | cca | gaa | ggt | tct | aag | 288 |
| Pro | Gln | Gly | Ser | Val | Arg | Leu | Gln | Trp | Gln | Ala | Pro | Glu | Gly | Ser | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| tgc | cat | gat | aca | agc | ttc | cca | att | act | aag | tat | gct | gag | aag | aac | gat | 336 |
| Cys | His | Asp | Thr | Ser | Phe | Pro | Ile | Thr | Lys | Tyr | Ala | Glu | Lys | Asn | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | act | tgg | gca | act | gta | aca | gtt | aag | caa | ggt | aat | aac | ttc | tgt | agc | 384 |
| Lys | Thr | Trp | Ala | Thr | Val | Thr | Val | Lys | Gln | Gly | Asn | Asn | Phe | Cys | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| ggt | aag | tgg | aca | gct | aat | gta | gtt | tat | gac | aaa | gaa | gta | atc | gct | tct | 432 |
| Gly | Lys | Trp | Thr | Ala | Asn | Val | Val | Tyr | Asp | Lys | Glu | Val | Ile | Ala | Ser | |
| | 130 | | | | | 135 | | | | | 140 | | | | | |

| | | | | | |
|---|---|---|---|---|---|
| gat | tca | ata | aat | att | taa | 450 |
| Asp | Ser | Ile | Asn | Ile | | |
| 145 | | | | | | |

<210> SEQ ID NO 10
<211> LENGTH: 149
<212> TYPE: PRT
<213> ORGANISM: Francisella tularensis subsp. Tularensis SCHU S4

<400> SEQUENCE: 10

Met Lys Lys Ile Ile Glu Leu Ser Leu Leu Ser Leu Ser Ile Ala Gly
1               5                   10                  15

Leu Ala Ser Cys Ser Thr Leu Gly Leu Gly Gly Ser Asp Asp Ala Lys
            20                  25                  30

Ala Ser Ala Lys Asp Thr Ala Ala Ala Gln Thr Ala Thr Thr Glu Gln
        35                  40                  45

Ala Ala Ala Val Ser Lys Pro Thr Ala Lys Val Ser Leu Asn Lys Leu
    50                  55                  60

Gly Gln Asp Lys Ile Lys Ala Thr Val Tyr Thr Thr Tyr Asn Asn Asn
65                  70                  75                  80

Pro Gln Gly Ser Val Arg Leu Gln Trp Gln Ala Pro Glu Gly Ser Lys
                85                  90                  95

Cys His Asp Thr Ser Phe Pro Ile Thr Lys Tyr Ala Glu Lys Asn Asp
            100                 105                 110

Lys Thr Trp Ala Thr Val Thr Val Lys Gln Gly Asn Asn Phe Cys Ser
        115                 120                 125

```
Gly Lys Trp Thr Ala Asn Val Val Tyr Asp Lys Glu Val Ile Ala Ser
        130                 135                 140

Asp Ser Ile Asn Ile
145

<210> SEQ ID NO 11
<211> LENGTH: 1182
<212> TYPE: DNA
<213> ORGANISM: Francisella tularensis subsp. Tularensis SCHU S4
<220> FEATURE:
<221> NAME/KEY: CDS
<222> LOCATION: (1)..(1182)

<400> SEQUENCE: 11 ttg atg aga tta aaa agt att gtt ata gct aca act gta tta tta ggt      48
Leu Met Arg Leu Lys Ser Ile Val Ile Ala Thr Thr Val Leu Leu Gly
1               5                   10                  15 tca gct aca gca tct atc gct gca ggt tca gat aat atc gat aca tta      96
Ser Ala Thr Ala Ser Ile Ala Ala Gly Ser Asp Asn Ile Asp Thr Leu
            20                  25                  30 gca aac act aat tca gct act aca caa agc agt ggt ttt gca gct aat     144
Ala Asn Thr Asn Ser Ala Thr Thr Gln Ser Ser Gly Phe Ala Ala Asn
        35                  40                  45 aat ttc att gct cct ttt gca aat act tat agc gct ttg act aac aag     192
Asn Phe Ile Ala Pro Phe Ala Asn Thr Tyr Ser Ala Leu Thr Asn Lys
    50                  55                  60 gac aat act tgg ggt cct caa gat aga act ggc cag tgg tac tta ggt     240
Asp Asn Thr Trp Gly Pro Gln Asp Arg Thr Gly Gln Trp Tyr Leu Gly
65                  70                  75                  80 gta gat gct aac ggt cta gct gga act cct aac tct cca tca ggt gct     288
Val Asp Ala Asn Gly Leu Ala Gly Thr Pro Asn Ser Pro Ser Gly Ala
                85                  90                  95 ggt gct aac ttc aca atc ggt tat aac atc aat aaa tac ttc gct gta     336
Gly Ala Asn Phe Thr Ile Gly Tyr Asn Ile Asn Lys Tyr Phe Ala Val
            100                 105                 110 cag tac aac caa tta gtt ggt aga gta ttt gct ggt tta ggt gaa ggt     384
Gln Tyr Asn Gln Leu Val Gly Arg Val Phe Ala Gly Leu Gly Glu Gly
        115                 120                 125 gtt gta aac ttt agt aat aat act atg ttt act cca tat gct gca ggt     432
Val Val Asn Phe Ser Asn Asn Thr Met Phe Thr Pro Tyr Ala Ala Gly
    130                 135                 140 ggt gct ggt tgg gca aat cta gca ggt caa gca aca ggt gct tgg gat     480
Gly Ala Gly Trp Ala Asn Leu Ala Gly Gln Ala Thr Gly Ala Trp Asp
145                 150                 155                 160 gtg ggt ggt ggt ctt aag ttt gaa cta tct aga aat gtt caa gca agt     528
Val Gly Gly Gly Leu Lys Phe Glu Leu Ser Arg Asn Val Gln Ala Ser
                165                 170                 175 gtt gac tac aga tat atc caa aca atg gca cct agt aat att tct ggt     576
Val Asp Tyr Arg Tyr Ile Gln Thr Met Ala Pro Ser Asn Ile Ser Gly
            180                 185                 190 gct aat ggc aga gcg ggt act aac atg att ggt gct ggt tta aca tgg     624
Ala Asn Gly Arg Ala Gly Thr Asn Met Ile Gly Ala Gly Leu Thr Trp
        195                 200                 205 ttc ttt ggt ggc aaa gat act act aat aat gac act ggt aat att cag     672
Phe Phe Gly Gly Lys Asp Thr Thr Asn Asn Asp Thr Gly Asn Ile Gln
    210                 215                 220 gat aat ggt gcg act aca gct gct caa act gtt gct atg cca act att     720
Asp Asn Gly Ala Thr Thr Ala Ala Gln Thr Val Ala Met Pro Thr Ile
225                 230                 235                 240 gat gag tct aag tat gtt tta cct gct ggt att aag caa tgt gaa ggc     768
Asp Glu Ser Lys Tyr Val Leu Pro Ala Gly Ile Lys Gln Cys Glu Gly
```

-continued

```
                    245                 250                 255
aac ttt aat cta act gaa gat ggt gtc gcg tgc tat aca ata aat ggt    816
Asn Phe Asn Leu Thr Glu Asp Gly Val Ala Cys Tyr Thr Ile Asn Gly
        260                 265                 270 gat gat gta aca gtt tac cta gat act aag ttt gct tat gat aaa gct    864
Asp Asp Val Thr Val Tyr Leu Asp Thr Lys Phe Ala Tyr Asp Lys Ala
            275                 280                 285 act tta aat gct aaa ggt aaa aaa gct att gca tct ttt gtt aat ttt    912
Thr Leu Asn Ala Lys Gly Lys Lys Ala Ile Ala Ser Phe Val Asn Phe
        290                 295                 300 atc aag gat agt aac att agc tct gta aca gtt aaa ggt tat gct tct    960
Ile Lys Asp Ser Asn Ile Ser Ser Val Thr Val Lys Gly Tyr Ala Ser
305                 310                 315                 320 caa ggt caa act ggt agc gag ttt gat ata tat aac caa aaa ctt tct   1008
Gln Gly Gln Thr Gly Ser Glu Phe Asp Ile Tyr Asn Gln Lys Leu Ser
                325                 330                 335 gag aag aga gca caa gct gtt gct gat tac atg aag caa tta ggt tta   1056
Glu Lys Arg Ala Gln Ala Val Ala Asp Tyr Met Lys Gln Leu Gly Leu
            340                 345                 350 gat agt gag aaa ata att act aaa ggt ttt ggc tat aat gat act tta   1104
Asp Ser Glu Lys Ile Ile Thr Lys Gly Phe Gly Tyr Asn Asp Thr Leu
        355                 360                 365 ggt ggt att cat aag tct gat ccg cgt aac cag cgt gta gaa gct agc   1152
Gly Gly Ile His Lys Ser Asp Pro Arg Asn Gln Arg Val Glu Ala Ser
370                 375                 380 gta tca gct cca ctt aaa gaa gct aac taa                           1182
Val Ser Ala Pro Leu Lys Glu Ala Asn
385                 390
```

<210> SEQ ID NO 12
<211> LENGTH: 393
<212> TYPE: PRT
<213> ORGANISM: Francisella tularensis subsp. Tularensis SCHU S4

<400> SEQUENCE: 12

```
Leu Met Arg Leu Lys Ser Ile Val Ile Ala Thr Thr Val Leu Leu Gly
1               5                   10                  15

Ser Ala Thr Ala Ser Ile Ala Ala Gly Ser Asp Asn Ile Asp Thr Leu
                20                  25                  30

Ala Asn Thr Asn Ser Ala Thr Thr Gln Ser Ser Gly Phe Ala Ala Asn
            35                  40                  45

Asn Phe Ile Ala Pro Phe Ala Asn Thr Tyr Ser Ala Leu Thr Asn Lys
        50                  55                  60

Asp Asn Thr Trp Gly Pro Gln Asp Arg Thr Gly Gln Trp Tyr Leu Gly
65                  70                  75                  80

Val Asp Ala Asn Gly Leu Ala Gly Thr Pro Asn Ser Pro Ser Gly Ala
                85                  90                  95

Gly Ala Asn Phe Thr Ile Gly Tyr Asn Ile Asn Lys Tyr Phe Ala Val
            100                 105                 110

Gln Tyr Asn Gln Leu Val Gly Arg Val Phe Ala Gly Leu Gly Glu Gly
        115                 120                 125

Val Val Asn Phe Ser Asn Asn Thr Met Phe Thr Pro Tyr Ala Ala Gly
    130                 135                 140

Gly Ala Gly Trp Ala Asn Leu Ala Gly Gln Ala Thr Gly Ala Trp Asp
145                 150                 155                 160

Val Gly Gly Gly Leu Lys Phe Glu Leu Ser Arg Asn Val Gln Ala Ser
                165                 170                 175
```

```
Val Asp Tyr Arg Tyr Ile Gln Thr Met Ala Pro Ser Asn Ile Ser Gly
            180                 185                 190

Ala Asn Gly Arg Ala Gly Thr Asn Met Ile Gly Ala Gly Leu Thr Trp
        195                 200                 205

Phe Phe Gly Gly Lys Asp Thr Thr Asn Asn Asp Thr Gly Asn Ile Gln
    210                 215                 220

Asp Asn Gly Ala Thr Thr Ala Ala Gln Thr Val Ala Met Pro Thr Ile
225                 230                 235                 240

Asp Glu Ser Lys Tyr Val Leu Pro Ala Gly Ile Lys Gln Cys Glu Gly
                245                 250                 255

Asn Phe Asn Leu Thr Glu Asp Gly Val Ala Cys Tyr Thr Ile Asn Gly
            260                 265                 270

Asp Asp Val Thr Val Tyr Leu Asp Thr Lys Phe Ala Tyr Asp Lys Ala
        275                 280                 285

Thr Leu Asn Ala Lys Gly Lys Lys Ala Ile Ala Ser Phe Val Asn Phe
    290                 295                 300

Ile Lys Asp Ser Asn Ile Ser Ser Val Thr Val Lys Gly Tyr Ala Ser
305                 310                 315                 320

Gln Gly Gln Thr Gly Ser Glu Phe Asp Ile Tyr Asn Gln Lys Leu Ser
                325                 330                 335

Glu Lys Arg Ala Gln Ala Val Ala Asp Tyr Met Lys Gln Leu Gly Leu
            340                 345                 350

Asp Ser Glu Lys Ile Ile Thr Lys Gly Phe Gly Tyr Asn Asp Thr Leu
        355                 360                 365

Gly Gly Ile His Lys Ser Asp Pro Arg Asn Arg Val Glu Ala Ser
    370                 375                 380

Val Ser Ala Pro Leu Lys Glu Ala Asn
385                 390

<210> SEQ ID NO 13
<211> LENGTH: 414
<212> TYPE: DNA
<213> ORGANISM: Francisella tularensis subsp. Tularensis SCHU S4
<220> FEATURE:
<221> NAME/KEY: CDS
<222> LOCATION: (1)..(414)

<400> SEQUENCE: 13 atg aaa gga tta aaa gca aaa ata tat ata att ttt ttg gct gca gtg    48
Met Lys Gly Leu Lys Ala Lys Ile Tyr Ile Ile Phe Leu Ala Ala Val
1               5                   10                  15 cta gcg gtt att tca ggc tgt gct act gac aaa gga acc cag tat aaa    96
Leu Ala Val Ile Ser Gly Cys Ala Thr Asp Lys Gly Thr Gln Tyr Lys
            20                  25                  30 gat ggt tat tat ata act acg ctt aac tat aat ttt aat acg gtt tat   144
Asp Gly Tyr Tyr Ile Thr Thr Leu Asn Tyr Asn Phe Asn Thr Val Tyr
        35                  40                  45 aat gct act ctg caa gca ata caa aac gga caa aca ttt gat tat aag   192
Asn Ala Thr Leu Gln Ala Ile Gln Asn Gly Gln Thr Phe Asp Tyr Lys
    50                  55                  60 agt aac cca tat gat ata tca gtt aac aaa aat aat gga act gat gct   240
Ser Asn Pro Tyr Asp Ile Ser Val Asn Lys Asn Asn Gly Thr Asp Ala
65                  70                  75                  80 gag ata gtt tct gct agt gat agc gat tct aca gac tct cta caa gta   288
Glu Ile Val Ser Ala Ser Asp Ser Asp Ser Thr Asp Ser Leu Gln Val
                85                  90                  95 gca atg aag aag tta cct aat aat gct aca agg att tca att aaa tat   336
Ala Met Lys Lys Leu Pro Asn Asn Ala Thr Arg Ile Ser Ile Lys Tyr
```

```
ggt agc caa gga aat tcg att aga tct tca gcg cta ata ggc ata ata     384
Gly Ser Gln Gly Asn Ser Ile Arg Ser Ser Ala Leu Ile Gly Ile Ile
        115                 120                 125 gaa gga aat att cgc tac gct aat aca taa                             414
Glu Gly Asn Ile Arg Tyr Ala Asn Thr
    130                 135

<210> SEQ ID NO 14
<211> LENGTH: 137
<212> TYPE: PRT
<213> ORGANISM: Francisella tularensis subsp. Tularensis SCHU S4

<400> SEQUENCE: 14

Met Lys Gly Leu Lys Ala Lys Ile Tyr Ile Ile Phe Leu Ala Ala Val
1               5                   10                  15

Leu Ala Val Ile Ser Gly Cys Ala Thr Asp Lys Gly Thr Gln Tyr Lys
                20                  25                  30

Asp Gly Tyr Tyr Ile Thr Thr Leu Asn Tyr Asn Phe Asn Thr Val Tyr
            35                  40                  45

Asn Ala Thr Leu Gln Ala Ile Gln Asn Gly Gln Thr Phe Asp Tyr Lys
        50                  55                  60

Ser Asn Pro Tyr Asp Ile Ser Val Asn Lys Asn Asn Gly Thr Asp Ala
65                  70                  75                  80

Glu Ile Val Ser Ala Ser Asp Ser Asp Ser Thr Asp Ser Leu Gln Val
                85                  90                  95

Ala Met Lys Lys Leu Pro Asn Asn Ala Thr Arg Ile Ser Ile Lys Tyr
            100                 105                 110

Gly Ser Gln Gly Asn Ser Ile Arg Ser Ser Ala Leu Ile Gly Ile Ile
        115                 120                 125

Glu Gly Asn Ile Arg Tyr Ala Asn Thr
    130                 135

<210> SEQ ID NO 15
<211> LENGTH: 408
<212> TYPE: DNA
<213> ORGANISM: Francisella tularensis subsp. Tularensis SCHU S4
<220> FEATURE:
<221> NAME/KEY: CDS
<222> LOCATION: (1)..(408)

<400> SEQUENCE: 15 atg aaa aag aaa atg caa aaa ggt ttc tca cta gtt gag tta atg gta    48
Met Lys Lys Lys Met Gln Lys Gly Phe Ser Leu Val Glu Leu Met Val
1               5                   10                  15 gtg atc gcg atc atc gct atc cta gca gct gta gcg atc ccg atg tac    96
Val Ile Ala Ile Ile Ala Ile Leu Ala Ala Val Ala Ile Pro Met Tyr
                20                  25                  30 tct aac tac act aca cgt gct cag tta ggc tct gat cta tct gct cta    144
Ser Asn Tyr Thr Thr Arg Ala Gln Leu Gly Ser Asp Leu Ser Ala Leu
            35                  40                  45 ggt ggt gct aaa gct aca gta gct gaa aga ata gct aac aac aat ggt    192
Gly Gly Ala Lys Ala Thr Val Ala Glu Arg Ile Ala Asn Asn Asn Gly
        50                  55                  60 gat gca tct caa gtt aca att ctt caa gct aat gcc gct gca aat ggt    240
Asp Ala Ser Gln Val Thr Ile Leu Gln Ala Asn Ala Ala Ala Asn Gly
65                  70                  75                  80 ctt cca agt ggt gct tca gtt gct gct ggt act att agt tat cca tca    288
Leu Pro Ser Gly Ala Ser Val Ala Ala Gly Thr Ile Ser Tyr Pro Ser
                85                  90                  95
```

```
aca gta tct ggt gca aca att caa tta gct cct aca gta agt tcc ggt       336
Thr Val Ser Gly Ala Thr Ile Gln Leu Ala Pro Thr Val Ser Ser Gly
            100                 105                 110 gct att act tgg act tgt aat att tca ggt gta tca gca tct caa gta       384
Ala Ile Thr Trp Thr Cys Asn Ile Ser Gly Val Ser Ala Ser Gln Val
            115                 120                 125 cca tct aac tgt aat gct atc taa                                        408
Pro Ser Asn Cys Asn Ala Ile
    130                 135

<210> SEQ ID NO 16
<211> LENGTH: 135
<212> TYPE: PRT
<213> ORGANISM: Francisella tularensis subsp. Tularensis SCHU S4

<400> SEQUENCE: 16

Met Lys Lys Lys Met Gln Lys Gly Phe Ser Leu Val Glu Leu Met Val
1               5                   10                  15

Val Ile Ala Ile Ile Ala Ile Leu Ala Ala Val Ala Ile Pro Met Tyr
            20                  25                  30

Ser Asn Tyr Thr Thr Arg Ala Gln Leu Gly Ser Asp Leu Ser Ala Leu
        35                  40                  45

Gly Gly Ala Lys Ala Thr Val Ala Glu Arg Ile Ala Asn Asn Asn Gly
    50                  55                  60

Asp Ala Ser Gln Val Thr Ile Leu Gln Ala Asn Ala Ala Ala Asn Gly
65                  70                  75                  80

Leu Pro Ser Gly Ala Ser Val Ala Ala Gly Thr Ile Ser Tyr Pro Ser
                85                  90                  95

Thr Val Ser Gly Ala Thr Ile Gln Leu Ala Pro Thr Val Ser Ser Gly
            100                 105                 110

Ala Ile Thr Trp Thr Cys Asn Ile Ser Gly Val Ser Ala Ser Gln Val
            115                 120                 125

Pro Ser Asn Cys Asn Ala Ile
    130                 135

<210> SEQ ID NO 17
<211> LENGTH: 576
<212> TYPE: DNA
<213> ORGANISM: Francisella tularensis subsp. Tularensis SCHU S4
<220> FEATURE:
<221> NAME/KEY: CDS
<222> LOCATION: (1)..(576)

<400> SEQUENCE: 17 atg ttt tat aaa cta aac aag caa gga aga aaa att atg aaa aaa act        48
Met Phe Tyr Lys Leu Asn Lys Gln Gly Arg Lys Ile Met Lys Lys Thr
1               5                   10                  15 ata cta gga gca atg att gct ggt ggt ttg atg gtt tct gca act aca        96
Ile Leu Gly Ala Met Ile Ala Gly Gly Leu Met Val Ser Ala Thr Thr
            20                  25                  30 gct atg gct ggt ggg gta ggt ttt gct aat gtc caa gat att ttt gaa       144
Ala Met Ala Gly Gly Val Gly Phe Ala Asn Val Gln Asp Ile Phe Glu
            35                  40                  45 act tca cct ctt ggt aaa gca aag gta aca gct gat gag aaa aag cta       192
Thr Ser Pro Leu Gly Lys Ala Lys Val Thr Ala Asp Glu Lys Lys Leu
        50                  55                  60 aag cca cag atg gat caa ctt aag caa aac atc act gct tta caa gag       240
Lys Pro Gln Met Asp Gln Leu Lys Gln Asn Ile Thr Ala Leu Gln Glu
65                  70                  75                  80
```

| | | | | | | | | | | | | | |
|---|---|---|---|---|---|---|---|---|---|---|---|---|---|
| aaa | gta | aat | gca | tac | act | caa | gaa | aaa | gat | gat | gtt | caa | aca | gat | gat | 288 |
| Lys | Val | Asn | Ala | Tyr | Thr | Gln | Glu | Lys | Asp | Asp | Val | Gln | Thr | Asp | Asp |
| | | | | 85 | | | | 90 | | | | | 95 | | |

| tct | aaa | ggc | gat | act | aaa | gat | gca | cag | tca | gca | gac | aaa | gta | gaa | aat | 336 |
| Ser | Lys | Gly | Asp | Thr | Lys | Asp | Ala | Gln | Ser | Ala | Asp | Lys | Val | Glu | Asn |
| | | | 100 | | | | | 105 | | | | | 110 | | |

| caa | gat | aag | caa | caa | gct | caa | gca | gat | ctt | gaa | aaa | gca | atg | aaa | gat | 384 |
| Gln | Asp | Lys | Gln | Gln | Ala | Gln | Ala | Asp | Leu | Glu | Lys | Ala | Met | Lys | Asp |
| | | | 115 | | | | | 120 | | | | | 125 | | |

| tac | caa | aac | cta | atg | aat | cag | gtt | caa | aaa | atg | gct | tct | gac | gat | gct | 432 |
| Tyr | Gln | Asn | Leu | Met | Asn | Gln | Val | Gln | Lys | Met | Ala | Ser | Asp | Asp | Ala |
| | | 130 | | | | | 135 | | | | | 140 | | | |

| gat | gcg | ttc | aaa | gat | gct | ttg | act | aag | gct | tct | gct | caa | gtt | gct | aaa | 480 |
| Asp | Ala | Phe | Lys | Asp | Ala | Leu | Thr | Lys | Ala | Ser | Ala | Gln | Val | Ala | Lys |
| 145 | | | | | 150 | | | | | 155 | | | | | 160 |

| gag | aag | caa | ctt | gat | gct | att | tta | cct | gct | gaa | atg | agt | cta | tat | aat | 528 |
| Glu | Lys | Gln | Leu | Asp | Ala | Ile | Leu | Pro | Ala | Glu | Met | Ser | Leu | Tyr | Asn |
| | | | | 165 | | | | | 170 | | | | | 175 | |

| gtt | gat | agt | att | gat | gtt | act | aaa | gat | gtt | ata | gct | aag | atg | caa | taa | 576 |
| Val | Asp | Ser | Ile | Asp | Val | Thr | Lys | Asp | Val | Ile | Ala | Lys | Met | Gln |
| | | | 180 | | | | | 185 | | | | | 190 | | |

```
<210> SEQ ID NO 18
<211> LENGTH: 191
<212> TYPE: PRT
<213> ORGANISM: Francisella tularensis subsp. Tularensis SCHU S4

<400> SEQUENCE: 18
```

Met Phe Tyr Lys Leu Asn Lys Gln Gly Arg Lys Ile Met Lys Lys Thr
1               5                   10                  15

Ile Leu Gly Ala Met Ile Ala Gly Gly Leu Met Val Ser Ala Thr Thr
            20                  25                  30

Ala Met Ala Gly Gly Val Gly Phe Ala Asn Val Gln Asp Ile Phe Glu
        35                  40                  45

Thr Ser Pro Leu Gly Lys Ala Lys Val Thr Ala Asp Glu Lys Lys Leu
    50                  55                  60

Lys Pro Gln Met Asp Gln Leu Lys Gln Asn Ile Thr Ala Leu Gln Glu
65                  70                  75                  80

Lys Val Asn Ala Tyr Thr Gln Glu Lys Asp Asp Val Gln Thr Asp Asp
                85                  90                  95

Ser Lys Gly Asp Thr Lys Asp Ala Gln Ser Ala Asp Lys Val Glu Asn
            100                 105                 110

Gln Asp Lys Gln Gln Ala Gln Ala Asp Leu Glu Lys Ala Met Lys Asp
        115                 120                 125

Tyr Gln Asn Leu Met Asn Gln Val Gln Lys Met Ala Ser Asp Asp Ala
    130                 135                 140

Asp Ala Phe Lys Asp Ala Leu Thr Lys Ala Ser Ala Gln Val Ala Lys
145                 150                 155                 160

Glu Lys Gln Leu Asp Ala Ile Leu Pro Ala Glu Met Ser Leu Tyr Asn
                165                 170                 175

Val Asp Ser Ile Asp Val Thr Lys Asp Val Ile Ala Lys Met Gln
            180                 185                 190

```
<210> SEQ ID NO 19
<211> LENGTH: 993
<212> TYPE: DNA
<213> ORGANISM: Francisella tularensis subsp. Tularensis SCHU S4
<220> FEATURE:
<221> NAME/KEY: CDS
```

<222> LOCATION: (1)..(993)

<400> SEQUENCE: 19

| | | | | | | | | | | | | | | | | |
|---|---|---|---|---|---|---|---|---|---|---|---|---|---|---|---|---|
| atg | gaa | ttt | agt | atg | cgc | aat | ata | ttc | aaa | aaa | aca | tta | tta | ata | tta | 48 |
| Met | Glu | Phe | Ser | Met | Arg | Asn | Ile | Phe | Lys | Lys | Thr | Leu | Leu | Ile | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tta | cta | agc | gta | att | ata | gca | tca | tgt | ggt | atg | cta | tct | aac | gac | cag | 96 |
| Leu | Leu | Ser | Val | Ile | Ile | Ala | Ser | Cys | Gly | Met | Leu | Ser | Asn | Asp | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| ttt | gtt | tat | cta | ggt | cat | ggt | gag | aac | tct | cct | gac | tat | cag | ctc | tat | 144 |
| Phe | Val | Tyr | Leu | Gly | His | Gly | Glu | Asn | Ser | Pro | Asp | Tyr | Gln | Leu | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | gat | aag | aca | caa | aaa | ctt | ttt | gtg | cta | att | gat | aag | aga | aat | ggt | 192 |
| Tyr | Asp | Lys | Thr | Gln | Lys | Leu | Phe | Val | Leu | Ile | Asp | Lys | Arg | Asn | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| tgt | ttt | cag | aaa | gat | gat | aca | ggt | act | tgt | ctt | gca | ttt | aca | tta | aaa | 240 |
| Cys | Phe | Gln | Lys | Asp | Asp | Thr | Gly | Thr | Cys | Leu | Ala | Phe | Thr | Leu | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| caa | gct | cgt | gaa | ttt | aga | gaa | tat | gtt | tta | gct | aag | atg | att | gaa | ata | 288 |
| Gln | Ala | Arg | Glu | Phe | Arg | Glu | Tyr | Val | Leu | Ala | Lys | Met | Ile | Glu | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| gat | gtt | aga | ctt | gct | aag | gac | gac | tat | gga | aac | tac | gct | att | gaa | gag | 336 |
| Asp | Val | Arg | Leu | Ala | Lys | Asp | Asp | Tyr | Gly | Asn | Tyr | Ala | Ile | Glu | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| tta | cga | aaa | gct | ggg | gtt | acc | acg | gtt | aat | aaa | cca | att | aaa | act | aaa | 384 |
| Leu | Arg | Lys | Ala | Gly | Val | Thr | Thr | Val | Asn | Lys | Pro | Ile | Lys | Thr | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| aaa | gtt | ttt | gca | act | cca | gtt | aag | cag | att | gtc | ctt | gat | aga | aag | caa | 432 |
| Lys | Val | Phe | Ala | Thr | Pro | Val | Lys | Gln | Ile | Val | Leu | Asp | Arg | Lys | Gln | |
| | 130 | | | | | 135 | | | | | 140 | | | | | |

| | | | | | | | | | | | | | | | | |
|---|---|---|---|---|---|---|---|---|---|---|---|---|---|---|---|---|
| caa | tat | cac | ctt | gtt | aga | aaa | gaa | tat | gaa | ata | gat | tca | aat | ctt | gta | 480 |
| Gln | Tyr | His | Leu | Val | Arg | Lys | Glu | Tyr | Glu | Ile | Asp | Ser | Asn | Leu | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gca | atg | gtt | gtt | aat | gat | aaa | gaa | ggt | aaa | aaa | cgt | ata | aaa | gtt | gct | 528 |
| Ala | Met | Val | Val | Asn | Asp | Lys | Glu | Gly | Lys | Lys | Arg | Ile | Lys | Val | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| tat | act | gtt | gat | ttt | cct | ggc | tta | gag | aaa | gag | tat | agt | acc | gag | ctt | 576 |
| Tyr | Thr | Val | Asp | Phe | Pro | Gly | Leu | Glu | Lys | Glu | Tyr | Ser | Thr | Glu | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| aga | cca | ttt | att | att | gat | cca | gaa | tac | tta | tat | aca | cat | atg | act | att | 624 |
| Arg | Pro | Phe | Ile | Ile | Asp | Pro | Glu | Tyr | Leu | Tyr | Thr | His | Met | Thr | Ile | |
| | | 195 | | | | | 200 | | | | | 205 | | | | |

| | | | | | | | | | | | | | | | | |
|---|---|---|---|---|---|---|---|---|---|---|---|---|---|---|---|---|
| gac | gct | gtc | cat | gaa | gct | caa | ttc | atg | cag | aga | gat | gtt | atg | aag | agt | 672 |
| Asp | Ala | Val | His | Glu | Ala | Gln | Phe | Met | Gln | Arg | Asp | Val | Met | Lys | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| caa | aca | aat | gtc | aaa | aag | aaa | gtt | gat | gac | tat | ctt | aaa | gat | gtt | gtc | 720 |
| Gln | Thr | Asn | Val | Lys | Lys | Lys | Val | Asp | Asp | Tyr | Leu | Lys | Asp | Val | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gac | agc | gat | aaa | aaa | gat | aca | gga | tac | act | cac | caa | gaa | gtt | gca | agt | 768 |
| Asp | Ser | Asp | Lys | Lys | Asp | Thr | Gly | Tyr | Thr | His | Gln | Glu | Val | Ala | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| agt | gtc | gca | gcg | cta | gat | aac | gat | cta | ata | act | aag | gca | gat | gag | caa | 816 |
| Ser | Val | Ala | Ala | Leu | Asp | Asn | Asp | Leu | Ile | Thr | Lys | Ala | Asp | Glu | Gln | |
| | | | 260 | | | | | 265 | | | | | 270 | | | |

| | | | | | | | | | | | | | | | | |
|---|---|---|---|---|---|---|---|---|---|---|---|---|---|---|---|---|
| cgc | gaa | gac | aaa | gaa | acc | aca | cta | gca | agt | ggt | agt | agt | att | agt | act | 864 |
| Arg | Glu | Asp | Lys | Glu | Thr | Thr | Leu | Ala | Ser | Gly | Ser | Ser | Ile | Ser | Thr | |
| | | 275 | | | | | 280 | | | | | 285 | | | | |

| | | | | | | | | | | | | | | | | |
|---|---|---|---|---|---|---|---|---|---|---|---|---|---|---|---|---|
| ata | gcg | aaa | aag | cct | atc | aat | caa | gaa | agt | agt | ggt | agt | aca | ata | caa | 912 |
| Ile | Ala | Lys | Lys | Pro | Ile | Asn | Gln | Glu | Ser | Ser | Gly | Ser | Thr | Ile | Gln | |
| | 290 | | | | | 295 | | | | | 300 | | | | | |

-continued

```
aca gcc aca aaa act gct tca acc act caa gtt gat agc aat gat act     960
Thr Ala Thr Lys Thr Ala Ser Thr Thr Gln Val Asp Ser Asn Asp Thr
305             310                 315                 320 cca aaa aca act cta gca agt gac aat aaa tag                         993
Pro Lys Thr Thr Leu Ala Ser Asp Asn Lys
                325                 330
```

<210> SEQ ID NO 20
<211> LENGTH: 330
<212> TYPE: PRT
<213> ORGANISM: Francisella tularensis subsp. Tularensis SCHU S4

<400> SEQUENCE: 20

```
Met Glu Phe Ser Met Arg Asn Ile Phe Lys Lys Thr Leu Leu Ile Leu
1               5                   10                  15

Leu Leu Ser Val Ile Ile Ala Ser Cys Gly Met Leu Ser Asn Asp Gln
                20                  25                  30

Phe Val Tyr Leu Gly His Gly Glu Asn Ser Pro Asp Tyr Gln Leu Tyr
            35                  40                  45

Tyr Asp Lys Thr Gln Lys Leu Phe Val Leu Ile Asp Lys Arg Asn Gly
    50                  55                  60

Cys Phe Gln Lys Asp Asp Thr Gly Thr Cys Leu Ala Phe Thr Leu Lys
65                  70                  75                  80

Gln Ala Arg Glu Phe Arg Glu Tyr Val Leu Ala Lys Met Ile Glu Ile
                85                  90                  95

Asp Val Arg Leu Ala Lys Asp Asp Tyr Gly Asn Tyr Ala Ile Glu Glu
            100                 105                 110

Leu Arg Lys Ala Gly Val Thr Thr Val Asn Lys Pro Ile Lys Thr Lys
        115                 120                 125

Lys Val Phe Ala Thr Pro Val Lys Gln Ile Val Leu Asp Arg Lys Gln
    130                 135                 140

Gln Tyr His Leu Val Arg Lys Glu Tyr Glu Ile Asp Ser Asn Leu Val
145                 150                 155                 160

Ala Met Val Val Asn Asp Lys Glu Gly Lys Lys Arg Ile Lys Val Ala
                165                 170                 175

Tyr Thr Val Asp Phe Pro Gly Leu Glu Lys Glu Tyr Ser Thr Glu Leu
            180                 185                 190

Arg Pro Phe Ile Ile Asp Pro Glu Tyr Leu Tyr Thr His Met Thr Ile
        195                 200                 205

Asp Ala Val His Glu Ala Gln Phe Met Gln Arg Asp Val Met Lys Ser
    210                 215                 220

Gln Thr Asn Val Lys Lys Val Asp Asp Tyr Leu Lys Asp Val Val
225                 230                 235                 240

Asp Ser Asp Lys Lys Asp Thr Gly Tyr Thr His Gln Glu Val Ala Ser
                245                 250                 255

Ser Val Ala Ala Leu Asp Asn Asp Leu Ile Thr Lys Ala Asp Glu Gln
            260                 265                 270

Arg Glu Asp Lys Glu Thr Thr Leu Ala Ser Gly Ser Ser Ile Ser Thr
        275                 280                 285

Ile Ala Lys Lys Pro Ile Asn Gln Glu Ser Ser Gly Ser Thr Ile Gln
    290                 295                 300

Thr Ala Thr Lys Thr Ala Ser Thr Thr Gln Val Asp Ser Asn Asp Thr
305                 310                 315                 320

Pro Lys Thr Thr Leu Ala Ser Asp Asn Lys
                325                 330
```

<210> SEQ ID NO 21
<211> LENGTH: 486
<212> TYPE: DNA
<213> ORGANISM: Francisella tularensis subsp. Tularensis SCHU S4
<220> FEATURE:
<221> NAME/KEY: CDS
<222> LOCATION: (1)..(486)

<400> SEQUENCE: 21

```
atg ttg att ata atg att aga gtt tta aat aat gga gat aac aat atg    48
Met Leu Ile Ile Met Ile Arg Val Leu Asn Asn Gly Asp Asn Asn Met
1               5                   10                  15 gaa ctt caa tta gaa aat aaa caa gaa att att gat caa tta aat aaa    96
Glu Leu Gln Leu Glu Asn Lys Gln Glu Ile Ile Asp Gln Leu Asn Lys
                20                  25                  30 atc tta gaa ctc gaa atg tct gga gtt gtg cgt tat act cat tat tct   144
Ile Leu Glu Leu Glu Met Ser Gly Val Val Arg Tyr Thr His Tyr Ser
            35                  40                  45 tta atg att ata ggt cat aat aga att cct ata gtt agt tgg atg caa   192
Leu Met Ile Ile Gly His Asn Arg Ile Pro Ile Val Ser Trp Met Gln
        50                  55                  60 tct caa gca agt gaa agt tta act cat gct act gca gca ggt gaa atg   240
Ser Gln Ala Ser Glu Ser Leu Thr His Ala Thr Ala Ala Gly Glu Met
65                  70                  75                  80 ata act cac ttt ggt gag cat cca tct tta aaa ata gca gat tta aac   288
Ile Thr His Phe Gly Glu His Pro Ser Leu Lys Ile Ala Asp Leu Asn
                85                  90                  95 gaa act tat cag cat aat atc aat gat ata tta atc gaa agt cta gaa   336
Glu Thr Tyr Gln His Asn Ile Asn Asp Ile Leu Ile Glu Ser Leu Glu
                100                 105                 110 cat gag aaa aaa gct gtt tca gca tac tat gaa ctt cta aaa ctt gta   384
His Glu Lys Lys Ala Val Ser Ala Tyr Tyr Glu Leu Leu Lys Leu Val
            115                 120                 125 aat ggc aaa tca ata ata tta gaa gaa tat gca aga aaa ctc ata gtt   432
Asn Gly Lys Ser Ile Ile Leu Glu Glu Tyr Ala Arg Lys Leu Ile Val
        130                 135                 140 gaa gaa gaa acg cac att ggt gaa gta gaa aaa atg tta aga aaa cct   480
Glu Glu Glu Thr His Ile Gly Glu Val Glu Lys Met Leu Arg Lys Pro
145                 150                 155                 160 gca taa                                                           486
Ala
```

<210> SEQ ID NO 22
<211> LENGTH: 161
<212> TYPE: PRT
<213> ORGANISM: Francisella tularensis subsp. Tularensis SCHU S4

<400> SEQUENCE: 22

```
Met Leu Ile Ile Met Ile Arg Val Leu Asn Asn Gly Asp Asn Asn Met
1               5                   10                  15

Glu Leu Gln Leu Glu Asn Lys Gln Glu Ile Ile Asp Gln Leu Asn Lys
                20                  25                  30

Ile Leu Glu Leu Glu Met Ser Gly Val Val Arg Tyr Thr His Tyr Ser
            35                  40                  45

Leu Met Ile Ile Gly His Asn Arg Ile Pro Ile Val Ser Trp Met Gln
        50                  55                  60

Ser Gln Ala Ser Glu Ser Leu Thr His Ala Thr Ala Ala Gly Glu Met
65                  70                  75                  80

Ile Thr His Phe Gly Glu His Pro Ser Leu Lys Ile Ala Asp Leu Asn
```

```
                    85                  90                  95
Glu Thr Tyr Gln His Asn Ile Asn Asp Ile Leu Ile Glu Ser Leu Glu
            100                 105                 110

His Glu Lys Lys Ala Val Ser Ala Tyr Tyr Glu Leu Leu Lys Leu Val
            115                 120                 125

Asn Gly Lys Ser Ile Ile Leu Glu Glu Tyr Ala Arg Lys Leu Ile Val
        130                 135                 140

Glu Glu Glu Thr His Ile Gly Glu Val Glu Lys Met Leu Arg Lys Pro
145                 150                 155                 160

Ala

<210> SEQ ID NO 23
<211> LENGTH: 393
<212> TYPE: DNA
<213> ORGANISM: Francisella tularensis subsp. Tularensis SCHU S4
<220> FEATURE:
<221> NAME/KEY: CDS
<222> LOCATION: (1)..(393)

<400> SEQUENCE: 23 atg aaa tta aga aaa gta tta atc gcg aca tta tta gga gct tct gct      48
Met Lys Leu Arg Lys Val Leu Ile Ala Thr Leu Leu Gly Ala Ser Ala
1               5                   10                  15 tta tct tta agt agt tgt tgg tta ctt gtt ggt gca gct gtt ggt ggt      96
Leu Ser Leu Ser Ser Cys Trp Leu Leu Val Gly Ala Ala Val Gly Gly
            20                  25                  30 gga act gct gcg tat att tct ggt gag tat tca atg aat atg agt ggc     144
Gly Thr Ala Ala Tyr Ile Ser Gly Glu Tyr Ser Met Asn Met Ser Gly
        35                  40                  45 agt gta aaa gat att tac aat gct act tta aaa gct gtt caa agc aat     192
Ser Val Lys Asp Ile Tyr Asn Ala Thr Leu Lys Ala Val Gln Ser Asn
    50                  55                  60 gat gat ttt gta att act aaa aaa tct att act tct gtt gat gca gtt     240
Asp Asp Phe Val Ile Thr Lys Lys Ser Ile Thr Ser Val Asp Ala Val
65                  70                  75                  80 gtt gat ggt agt att aag gta gac tca aca agt ttc tat gtt aaa ata     288
Val Asp Gly Ser Ile Lys Val Asp Ser Thr Ser Phe Tyr Val Lys Ile
                85                  90                  95 gaa aaa ctt act gat aat gct tca aaa gtt aca att aag ttt ggt act     336
Glu Lys Leu Thr Asp Asn Ala Ser Lys Val Thr Ile Lys Phe Gly Thr
            100                 105                 110 ttt ggt gac caa gca atg tca gca aca tta atg gat caa atc caa aag     384
Phe Gly Asp Gln Ala Met Ser Ala Thr Leu Met Asp Gln Ile Gln Lys
        115                 120                 125 aat ctt taa                                                          393
Asn Leu
    130

<210> SEQ ID NO 24
<211> LENGTH: 130
<212> TYPE: PRT
<213> ORGANISM: Francisella tularensis subsp. Tularensis SCHU S4

<400> SEQUENCE: 24

Met Lys Leu Arg Lys Val Leu Ile Ala Thr Leu Leu Gly Ala Ser Ala
1               5                   10                  15

Leu Ser Leu Ser Ser Cys Trp Leu Leu Val Gly Ala Ala Val Gly Gly
            20                  25                  30

Gly Thr Ala Ala Tyr Ile Ser Gly Glu Tyr Ser Met Asn Met Ser Gly
        35                  40                  45
```

```
Ser Val Lys Asp Ile Tyr Asn Ala Thr Leu Lys Ala Val Gln Ser Asn
    50                  55                  60

Asp Asp Phe Val Ile Thr Lys Lys Ser Ile Thr Ser Val Asp Ala Val
65                  70                  75                  80

Val Asp Gly Ser Ile Lys Val Asp Ser Thr Ser Phe Tyr Val Lys Ile
                85                  90                  95

Glu Lys Leu Thr Asp Asn Ala Ser Lys Val Thr Ile Lys Phe Gly Thr
            100                 105                 110

Phe Gly Asp Gln Ala Met Ser Ala Thr Leu Met Asp Gln Ile Gln Lys
        115                 120                 125

Asn Leu
    130

<210> SEQ ID NO 25
<211> LENGTH: 199
<212> TYPE: PRT
<213> ORGANISM: Francisella tularensis subsp. Tularensis SCHU S4

<400> SEQUENCE: 25

Met Met Asp Phe Lys Asp Gln Tyr Asn Ile Ser Ser Asp Gly Lys Leu
1               5                   10                  15

Tyr Ile Asn Ala Lys Ile Met Ser His Ser Ser Ala Thr Ala Asn Val
            20                  25                  30

Thr Val Val Leu Gln Asp Gln Asn Gly Asn Gln Val Tyr Arg Lys Thr
        35                  40                  45

Asp Ile Gln Ile Ser Pro Met Asp Thr Tyr Asp Leu Ala Leu Ala Ile
    50                  55                  60

Asp Asn Ile Lys Ala Gly Asp Tyr Lys Leu Ile Ile Ser Ser Glu Leu
65                  70                  75                  80

Ala Gly Ala Glu Ala Trp Gln Lys Asp Met Asn Ile Lys Ala Val Ser
                85                  90                  95

Ser Glu Thr Ser Asp Asp Asn Asn Pro Pro Ala Asn Gln Asp
            100                 105                 110

Ile Asn Val Asn Ile Glu Ser Asn Thr Pro Tyr Tyr Gln Val Asn Pro
        115                 120                 125

Asn Asp Ser Val Thr Ala Arg Ala Trp Ala Ser Ser Leu Gly Asn Ile
    130                 135                 140

Asn Leu Ala Asn Asn Gln Val Thr Ile Ile Ala Trp Asn Lys Thr Leu
145                 150                 155                 160

Gln Ala Ser Gly Asn Asp Ser Ser Ala Tyr Val Lys Cys Pro Leu Pro
                165                 170                 175

Lys Asn Asn Gln Ile Ser Ile Thr Tyr Leu Val Ser Gly Asp Leu Asn
            180                 185                 190

Asn Val Asn Cys Thr Ile Lys
        195

<210> SEQ ID NO 26
<211> LENGTH: 270
<212> TYPE: PRT
<213> ORGANISM: Francisella tularensis subsp. Tularensis SCHU S4

<400> SEQUENCE: 26

Met Lys Leu Lys Lys Ile Val Ala Val Ile Ser Cys Ser Leu Leu Gly
1               5                   10                  15

Leu Ala Met Ser Ser Cys Ser Thr Asn Thr Asp Ser Val Asp Ser Thr
            20                  25                  30
```

Asn Ala Gln Gln Val Thr Lys Asn Thr Glu Ala Lys Gly Val Ala Thr
                35                  40                  45

Asn Lys Ser Ala Gln Asp Asn Pro Thr Ile Lys Met Gly Ala Asn Ala
 50                  55                  60

Ser Tyr Val Val Gly Tyr Gln Val Gly Ala Gly Ile Ala Lys Gln Asp
 65                  70                  75                  80

Phe Gly Leu Tyr Asp Lys Gln Thr Ile Ala Gly Phe Ala Asp Ala Ile
                85                  90                  95

Asn Gly Asn Lys Pro Arg Ile Ser Glu Ser Gln Ile Arg Arg Asn Met
               100                 105                 110

Glu Thr Leu Lys Asp Lys Met Ile Lys Gln Leu Asp Thr Ala Asn
               115                 120                 125

Leu Asn Lys Thr Lys Ser Gln Glu Phe Met Ala Gln Ile Ala Lys Met
130                 135                 140

Asp Asn Ala Ile Lys Val Asp Asp Gly Val Tyr Tyr Gln Met Ile Lys
145                 150                 155                 160

Gln Gly Asp Gly Lys Asn Pro Lys Ser Asp Ser Gln Val Thr Ile Ala
               165                 170                 175

Tyr Lys Gly Thr Thr Pro Val Ile Ala Tyr Glu Asp Lys Ser Lys
               180                 185                 190

Leu Asn Glu Val Lys Glu Ala Lys Leu Ile Gly Pro Thr Phe Asp Ser
               195                 200                 205

Ser Asp Ser Ala Thr Phe Pro Leu Arg Asn Leu Ile Glu Cys Trp Lys
               210                 215                 220

Asp Ala Ile Pro Gln Ile Pro Asn Gly Ser Thr Ile Ile Leu Tyr Cys
225                 230                 235                 240

Ser Pro Asp Lys Ala Tyr Gly Thr Arg Ala Pro Ala Val Ile Gly Pro
               245                 250                 255

Asn Gln Ala Leu Ser Phe Glu Ile Thr Leu Lys Asp Phe Lys
               260                 265                 270

<210> SEQ ID NO 27
<211> LENGTH: 456
<212> TYPE: PRT
<213> ORGANISM: Francisella tularensis subsp. Tularensis SCHU S4

<400> SEQUENCE: 27

Met Ser Lys His Ile His Ile Leu Gly Ile Cys Gly Thr Phe Met Gly
 1               5                  10                  15

Ser Leu Ala Val Leu Ala Lys Gln Lys Gly Tyr Lys Val Thr Gly Ser
                20                  25                  30

Asp Leu Asn Val Tyr Pro Pro Met Ser Thr Tyr Leu Glu Ser Gln Gly
                35                  40                  45

Ile Glu Ile Leu Gln Gly Phe Asp Cys Asp Gln Leu Asp Thr Asn Pro
 50                  55                  60

Asp Glu Ile Ile Ile Gly Asn Ile Met Lys Arg Gly Met Pro Ile Ile
 65                  70                  75                  80

Glu Lys Ile Leu Ala Glu Lys Leu Asn Tyr Phe Ser Gly Pro Glu Trp
                85                  90                  95

Leu Tyr Gln Asn Ile Leu Lys Tyr Lys Lys Val Ile Ala Ile Ala Gly
               100                 105                 110

Thr His Gly Lys Thr Thr Thr Thr Thr Met Thr Ile Lys Ile Leu Glu
               115                 120                 125

Gln Ala Gly Leu Asn Pro Ser Phe Leu Val Gly Gly Val Ser Ser Asp

```
                130                 135                 140
Phe Gly Val Ser Ser Arg Tyr Thr Asp Ser Glu Tyr Phe Val Ile Glu
145                 150                 155                 160

Ala Asp Glu Tyr Asp Thr Ala Phe Phe Asp Lys Arg Ser Lys Leu Ile
                165                 170                 175

His Tyr Asp Pro Ser Ile Phe Val Ile Asn Asn Ile Glu Phe Asp His
            180                 185                 190

Ala Asp Ile Phe Lys Asp Ile Asp Ala Ile Phe Trp Gln Phe His Gln
            195                 200                 205

Leu Leu Arg Lys Met Pro Ser Thr Ala Lys Ile Ile Tyr Asn Ala Lys
    210                 215                 220

Asp Asn Val Gln Lys Ile Ile Ser Met Gly Cys Trp Ser Glu Leu
225                 230                 235                 240

Val Lys Val Asn Ser Asp Leu Gly Ile Ser Ile Thr Lys His Thr Leu
                245                 250                 255

Asp Tyr Ser Lys Phe Glu Leu Cys Asp Ile Asn Gly Asn Ser Val Glu
            260                 265                 270

Val Ser Trp Gly Leu Ile Gly Glu His Asn Ala Leu Asn Ala Met Ser
            275                 280                 285

Ala Tyr Ala Val Ala Lys Gln Leu Asn Ile Ser Asp Glu Met Val Lys
    290                 295                 300

Asp Ala Leu Glu Ser Phe Arg Gly Val Lys Arg Arg Leu Glu Val Leu
305                 310                 315                 320

Ser His Gln Asp Asn Val Thr Leu Tyr Asp Asp Phe Ala His His Pro
                325                 330                 335

Thr Ser Ile Lys Leu Thr Leu Glu Ala Val Arg Asn Lys Ala Lys Asp
            340                 345                 350

Ala Tyr Val Val Ala Leu Ile Asp Pro Arg Ser Asn Thr Met Arg Gln
    355                 360                 365

Gly Asp Asn Lys Asp Asn Leu Pro Met Ser Ile Ile Glu Ala Asp Arg
370                 375                 380

Val Leu Leu Tyr Asn His Asn Leu Leu Lys Trp Asp Ala Lys Glu Val
385                 390                 395                 400

Leu Lys Asn Ser Asn Asn Val Asp Phe Ile Ala Asp Val Asp Asp Phe
                405                 410                 415

Val Asp Cys Val Asp Lys Leu Leu Thr Lys His Gln Ser Arg Asn Ile
            420                 425                 430

Gln Leu Val Met Met Ser Asn Gly Ser Phe Asp Gly Leu Arg Glu Lys
            435                 440                 445

Leu Val Lys Leu Leu Glu Ile Lys
    450                 455

<210> SEQ ID NO 28
<211> LENGTH: 424
<212> TYPE: PRT
<213> ORGANISM: Francisella tularensis subsp. Tularensis SCHU S4

<400> SEQUENCE: 28

Met Glu Val Met Leu Met Ser Lys Tyr Ala Thr Leu Lys Tyr Ala Asp
1               5                   10                  15

Lys Asn Ile Glu Ile Glu Leu Pro Val Tyr Ser Pro Ser Leu Gly Asn
            20                  25                  30

Asp Cys Ile Asp Val Ser Ser Leu Val Lys His Gly Ile Phe Thr Tyr
        35                  40                  45
```

Asp Pro Gly Phe Met Ser Thr Ala Ala Cys Glu Ser Lys Ile Thr Tyr
        50                  55                  60

Ile Asp Gly Gly Lys Gly Val Leu Leu His Arg Gly Tyr Pro Ile Glu
 65                  70                  75                  80

Glu Trp Thr Gln Lys Ser Asn Tyr Arg Thr Leu Cys Tyr Ala Leu Ile
                 85                  90                  95

Tyr Gly Glu Leu Pro Thr Asp Glu Gln Val Lys Ser Phe Arg Gln Glu
            100                 105                 110

Ile Ile Asn Lys Met Pro Val Cys Glu His Val Lys Ala Ala Ile Ala
        115                 120                 125

Ala Met Pro Gln His Thr His Pro Met Ser Ser Leu Ile Ala Gly Val
130                 135                 140

Asn Val Leu Ala Ala Glu His Ile His Asn Gly Gln Lys Glu Ser Gln
145                 150                 155                 160

Asp Glu Val Ala Lys Asn Ile Val Ala Lys Ile Ala Thr Ile Ala Ala
                165                 170                 175

Met Ala Tyr Arg His Asn His Gly Lys Lys Phe Leu Glu Pro Lys Met
            180                 185                 190

Glu Tyr Gly Tyr Ala Glu Asn Phe Leu Tyr Met Met Phe Ala Asp Asp
            195                 200                 205

Glu Ser Tyr Lys Pro Asp Glu Leu His Ile Lys Ala Met Asp Thr Ile
210                 215                 220

Phe Met Leu His Ala Asp His Glu Gln Asn Ala Ser Thr Ser Thr Val
225                 230                 235                 240

Arg Leu Ser Gly Ser Thr Gly Asn Ser Pro Tyr Ala Ala Ile Ile Ala
                245                 250                 255

Gly Ile Thr Ala Leu Trp Gly Pro Ala His Gly Gly Ala Asn Glu Ala
            260                 265                 270

Val Leu Lys Met Leu Ser Glu Ile Gly Ser Thr Glu Asn Ile Asp Lys
            275                 280                 285

Tyr Ile Ala Lys Ala Lys Asp Lys Asp Pro Phe Arg Leu Met Gly
290                 295                 300

Phe Gly His Arg Val Tyr Lys Asn Thr Asp Pro Arg Ala Thr Ala Met
305                 310                 315                 320

Lys Lys Asn Cys Glu Glu Ile Leu Ala Lys Leu Gly His Ser Asp Asn
                325                 330                 335

Pro Leu Leu Thr Val Ala Lys Lys Leu Glu Ile Ala Leu Gln Asp
            340                 345                 350

Glu Phe Phe Ile Glu Arg Lys Leu Phe Ser Asn Val Asp Phe Tyr Ser
            355                 360                 365

Gly Ile Ile Leu Lys Ala Met Gly Ile Pro Glu Asp Met Phe Thr Ala
370                 375                 380

Ile Phe Ala Leu Ala Arg Thr Ser Gly Trp Ile Ser Gln Trp Ile Glu
385                 390                 395                 400

Met Val Asn Asp Pro Ala Gln Lys Ile Gly Arg Pro Arg Gln Leu Tyr
                405                 410                 415

Thr Gly Ala Thr Asn Arg Asn Phe
            420

<210> SEQ ID NO 29
<211> LENGTH: 144
<212> TYPE: PRT
<213> ORGANISM: Francisella tularensis subsp. Tularensis SCHU S4

<400> SEQUENCE: 29

```
Met Lys Lys Ile Lys Leu Leu Ala Ala Tyr Thr Leu Ala Thr Leu Thr
1               5                   10                  15

Leu Val Ser Cys Ser Asn Asn Ala Ser Leu Ser Asn Asp Leu Asn Ser
            20                  25                  30

Ala Gly Asp Ser Ile Val Arg Phe Val Asn Gly Thr Phe Tyr Ala Glu
        35                  40                  45

Ile Tyr Asn Thr Ser Leu Gln Ser Val Tyr Asn Ala Thr Leu Leu Ala
    50                  55                  60

Leu Asn Asn Ser Asn Ile Tyr Ser Val Lys Asn Asn Thr Ile Asn Ser
65                  70                  75                  80

Lys Asp Ala Glu Ile Thr Gly Thr Tyr Ala Thr Asp Lys Asn Phe Phe
                85                  90                  95

Asn Lys Ser Gly Gln Asp Asp Phe Ala Ile Arg Leu Val Lys Gly Asn
            100                 105                 110

Gln Asp Thr Ile Asn Leu Phe Ile Lys Ile Gly Lys Leu Gly Asp Lys
        115                 120                 125

Gln Ala Ser Val Asp Leu Leu Ala Lys Ile Gln Thr Asn Leu Gly Ile
    130                 135                 140
```

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 30

```
Asn Cys Arg Leu Phe Ile Asp Ser Leu
1               5
```

<210> SEQ ID NO 31
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 31

```
Glu Met Ile Thr Arg Gln Gln Val Thr Ser Gly Glu Thr Ile His
1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 32

```
Arg Gln Gln Val Thr Ser Gly Glu Thr Ile His Val Arg Thr Asp
1               5                   10                  15
```

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 33

```
Thr Ser Gly Glu Thr Ile His Val Arg Thr Asp Pro Thr Ala Cys
1               5                   10                  15
```

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Thr Ile His Val Arg Thr Asp Pro Thr Ala Cys Ile Gly Ser His
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 35

Arg Thr Asp Pro Thr Ala Cys Ile Gly Ser His Pro Asn Cys Arg
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 36

Thr Ala Cys Ile Gly Ser His Pro Asn Cys Arg Leu Phe Ile Asp
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 37

Gly Ser His Pro Asn Cys Arg Leu Phe Ile Asp Ser Leu Thr Ile
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 38

Asn Cys Arg Leu Phe Ile Asp Ser Leu Thr Ile Ala Gly Glu Lys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 39

Phe Ile Asp Ser Leu Thr Ile Ala Gly Glu Lys Leu Asp Lys Asn
1               5                   10                  15

```
<210> SEQ ID NO 40
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 40

Leu Thr Ile Ala Gly Glu Lys Leu Asp Lys Asn Ile Val Ala Ile
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 41

Gly Glu Lys Leu Asp Lys Asn Ile Val Ala Ile Asp Gly Gly Glu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 42

Asp Lys Asn Ile Val Ala Ile Asp Gly Gly Glu Asp Val Thr Lys
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 43

Val Ala Ile Asp Gly Gly Glu Asp Val Thr Lys Ala Asp Ser Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 44

Gly Gly Glu Asp Val Thr Lys Ala Asp Ser Ala Thr Ala Ala Ala
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 45

Val Thr Lys Ala Asp Ser Ala Thr Ala Ala Ala Ser Val Ile Arg
1               5                   10                  15
```

```
<210> SEQ ID NO 46
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 46

Asp Ser Ala Thr Ala Ala Ala Ser Val Ile Arg Leu Ser Ile Thr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 47

Ala Ala Ala Ser Val Ile Arg Leu Ser Ile Thr Pro Gly Ser Ile
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 48

Val Ile Arg Leu Ser Ile Thr Pro Gly Ser Ile Asn Pro Thr Ile
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 49

Ser Ile Thr Pro Gly Ser Ile Asn Pro Thr Ile Ser Ile Thr Leu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 50

Gly Ser Ile Asn Pro Thr Ile Ser Ile Thr Leu Gly Val Leu Ile
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 51

Pro Thr Ile Ser Ile Thr Leu Gly Val Leu Ile Lys Ser Asn Val
1               5                   10                  15

<210> SEQ ID NO 52
```

```
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 52

Ile Thr Leu Gly Val Leu Ile Lys Ser Asn Val Arg Thr Lys Ile
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 53

Val Leu Ile Lys Ser Asn Val Arg Thr Lys Ile Glu Glu Lys Val
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 54

Ser Asn Val Arg Thr Lys Ile Glu Glu Lys Val Ser Ser Ile Leu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 55

Thr Lys Ile Glu Glu Lys Val Ser Ser Ile Leu Gln Ala Ser Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 56

Glu Lys Val Ser Ser Ile Leu Gln Ala Ser Ala Thr Asp Met Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 57

Ser Ile Leu Gln Ala Ser Ala Thr Asp Met Lys Ile Lys Leu Gly
1               5                   10                  15

<210> SEQ ID NO 58
<211> LENGTH: 15
```

```
<212> TYPE: PRT
<213> ORGANISM: Artificial Sequence
<220> FEATURE:
<223> OTHER INFORMATION: Synthetic polypeptide

<400> SEQUENCE: 58

Ala Ser Ala Thr Asp Met Lys Ile Lys Leu Gly Asn Ser Asn Lys
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 59

Asp Met Lys Ile Lys Leu Gly Asn Ser Asn Lys Lys Gln Glu Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 60

Lys Leu Gly Asn Ser Asn Lys Lys Gln Glu Tyr Lys Thr Asp Glu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 61

Ser Asn Lys Lys Gln Glu Tyr Lys Thr Asp Glu Ala Trp Gly Ile
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 62

Gln Glu Tyr Lys Thr Asp Glu Ala Trp Gly Ile Met Ile Asp Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 63

Thr Asp Glu Ala Trp Gly Ile Met Ile Asp Leu Ser Asn Leu Glu
1               5                   10                  15

<210> SEQ ID NO 64
<211> LENGTH: 15
<212> TYPE: PRT
```

```
<213> ORGANISM: Artificial Sequence
<220> FEATURE:
<223> OTHER INFORMATION: Synthetic polypeptide

<400> SEQUENCE: 64

Trp Gly Ile Met Ile Asp Leu Ser Asn Leu Glu Leu Tyr Pro Ile
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 65

Ile Asp Leu Ser Asn Leu Glu Leu Tyr Pro Ile Ser Ala Lys Ala
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 66

Asn Leu Glu Leu Tyr Pro Ile Ser Ala Lys Ala Phe Ser Ile Ser
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 67

Tyr Pro Ile Ser Ala Lys Ala Phe Ser Ile Ser Ile Glu Pro Thr
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 68

Ala Lys Ala Phe Ser Ile Ser Ile Glu Pro Thr Glu Leu Met Gly
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 69

Ser Ile Ser Ile Glu Pro Thr Glu Leu Met Gly Val Ser Lys Asp
1               5                   10                  15

<210> SEQ ID NO 70
<211> LENGTH: 15
<212> TYPE: PRT
<213> ORGANISM: Artificial Sequence
```

```
<220> FEATURE:
<223> OTHER INFORMATION: Synthetic polypeptide

<400> SEQUENCE: 70

Glu Pro Thr Glu Leu Met Gly Val Ser Lys Asp Gly Met Arg Tyr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 71

Leu Met Gly Val Ser Lys Asp Gly Met Arg Tyr His Ile Ile Ser
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 72

Ser Lys Asp Gly Met Arg Tyr His Ile Ile Ser Ile Asp Gly Leu
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 73

Met Arg Tyr His Ile Ile Ser Ile Asp Gly Leu Thr Thr Ser Gln
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 74

Ile Ile Ser Ile Asp Gly Leu Thr Thr Ser Gln Gly Ser Leu Pro
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 75

Asp Gly Leu Thr Thr Ser Gln Gly Ser Leu Pro Val Cys Cys Ala
1               5                   10                  15

<210> SEQ ID NO 76
<211> LENGTH: 15
<212> TYPE: PRT
<213> ORGANISM: Artificial Sequence
<220> FEATURE:
```

<223> OTHER INFORMATION: Synthetic polypeptide

<400> SEQUENCE: 76

Thr Ser Gln Gly Ser Leu Pro Val Cys Cys Ala Ala Ser Thr Asp
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 77

Ser Leu Pro Val Cys Cys Ala Ala Ser Thr Asp Lys Gly Val Ala
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 78

Cys Cys Ala Ala Ser Thr Asp Lys Gly Val Ala Lys Ile Gly Tyr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 79

Ser Thr Asp Lys Gly Val Ala Lys Ile Gly Tyr Ile Ala Ala Ala
1               5                   10                  15

<210> SEQ ID NO 80
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 80

Gly Val Ala Lys Ile Gly Tyr Ile Ala Ala Ala
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 81

Asn Cys Arg Leu Phe Ile Asp Ser Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic polypeptide -continued

<400> SEQUENCE: 82

Cys Arg Leu Phe Ile Asp Ser Leu Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 83

Arg Leu Phe Ile Asp Ser Leu Thr Ile
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 84

Leu Phe Ile Asp Ser Leu Thr Ile Ala
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 85

Phe Ile Asp Ser Leu Thr Ile Ala Gly
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 86

Ile Asp Ser Leu Thr Ile Ala Gly Glu
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 87

Asp Ser Leu Thr Ile Ala Gly Glu Lys
1               5

<210> SEQ ID NO 88
<211> LENGTH: 393
<212> TYPE: PRT
<213> ORGANISM: Francisella tularensis subsp. Tularensis SCHU S4

<400> SEQUENCE: 88

```
Met Met Arg Leu Lys Ser Ile Val Ile Ala Thr Thr Val Leu Leu Gly
1               5                   10                  15

Ser Ala Thr Ala Ser Ile Ala Ala Gly Ser Asp Asn Ile Asp Thr Leu
            20                  25                  30

Ala Asn Thr Asn Ser Ala Thr Thr Gln Ser Ser Gly Phe Ala Ala Asn
            35                  40                  45

Asn Phe Ile Ala Pro Phe Ala Asn Thr Tyr Ser Ala Leu Thr Asn Lys
            50                  55                  60

Asp Asn Thr Trp Gly Pro Gln Asp Arg Thr Gly Gln Trp Tyr Leu Gly
65                      70                  75                  80

Val Asp Ala Asn Gly Leu Ala Gly Thr Pro Asn Ser Pro Ser Gly Ala
                85                  90                  95

Gly Ala Asn Phe Thr Ile Gly Tyr Asn Ile Asn Lys Tyr Phe Ala Val
                100                 105                 110

Gln Tyr Asn Gln Leu Val Gly Arg Val Phe Ala Gly Leu Gly Glu Gly
            115                 120                 125

Val Val Asn Phe Ser Asn Asn Thr Met Phe Thr Pro Tyr Ala Ala Gly
            130                 135                 140

Gly Ala Gly Trp Ala Asn Leu Ala Gly Gln Ala Thr Gly Ala Trp Asp
145                 150                 155                 160

Val Gly Gly Gly Leu Lys Phe Glu Leu Ser Arg Asn Val Gln Ala Ser
                165                 170                 175

Val Asp Tyr Arg Tyr Ile Gln Thr Met Ala Pro Ser Asn Ile Ser Gly
            180                 185                 190

Ala Asn Gly Arg Ala Gly Thr Asn Met Ile Gly Ala Gly Leu Thr Trp
            195                 200                 205

Phe Phe Gly Gly Lys Asp Thr Thr Asn Asn Asp Thr Gly Asn Ile Gln
            210                 215                 220

Asp Asn Gly Ala Thr Thr Ala Ala Gln Thr Val Ala Met Pro Thr Ile
225                 230                 235                 240

Asp Glu Ser Lys Tyr Val Leu Pro Ala Gly Ile Lys Gln Cys Glu Gly
            245                 250                 255

Asn Phe Asn Leu Thr Glu Asp Gly Val Ala Cys Tyr Thr Ile Asn Gly
            260                 265                 270

Asp Asp Val Thr Val Tyr Leu Asp Thr Lys Phe Ala Tyr Asp Lys Ala
            275                 280                 285

Thr Leu Asn Ala Lys Gly Lys Ala Ile Ala Ser Phe Val Asn Phe
            290                 295                 300

Ile Lys Asp Ser Asn Ile Ser Ser Val Thr Val Lys Gly Tyr Ala Ser
305                 310                 315                 320

Gln Gly Gln Thr Gly Ser Glu Phe Asp Ile Tyr Asn Gln Lys Leu Ser
                325                 330                 335

Glu Lys Arg Ala Gln Ala Val Ala Asp Tyr Met Lys Gln Leu Gly Leu
            340                 345                 350

Asp Ser Glu Lys Ile Ile Thr Lys Gly Phe Gly Tyr Asn Asp Thr Leu
            355                 360                 365

Gly Gly Ile His Lys Ser Asp Pro Arg Asn Gln Arg Val Glu Ala Ser
            370                 375                 380

Val Ser Ala Pro Leu Lys Glu Ala Asn
385                 390
```

ANTIGENIC COMBINATIONS AGAINST *FRANCISELLA* BACTERIA AND RELATED NANOLIPOPROTEIN PARTICLES, COMPOSITIONS, METHODS AND SYSTEMS

CROSS REFERENCE TO RELATED APPLICATIONS

The present application is a continuation-in-part application of U.S. application Ser. No. 16/422,263 filed on May 24, 2019, which in turn, claims priority to U.S. Provisional Application No. 62/676,222, entitled "Antigenic Combinations against *Francisella* bacteria and related Nanolipoprotein Particles, Compositions, Methods and Systems" filed on May 24, 2018, the content of each of which is incorporated herein by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

The present disclosure relates to antigenic combinations for immunization against pathogenic *Francisella* bacteria and related nanolipoprotein particles, composition methods and systems.

BACKGROUND

Over the last few decades, there has been a constant drive towards developing a vaccine against *Francisella* species and in particular against *Francisella tularensis*. Despite the efforts, development of immunogenic compositions against bacterial infection caused by *Francisella*, bacteria and in particular of protective, stable and safe vaccines against more virulent *Francisella* species, is still challenging.

SUMMARY

Provided herein are antigenic combinations, and related nanolipoprotein particles, compositions, methods and systems which can be used to immunize an individual against a *Francisella* bacterium, which in several embodiments can provide improved immunostimulation and immunogenic response with respect to existing immunization methods.

According to a first aspect, an antigenic combination is described. The antigenic combination comprises an antigenic polysaccharide component from a *Francisella* bacterium capable of triggering a humoral immune response in an individual, a protein antigen component from the *Francisella* bacterium capable of triggering a cellular immune response in the individual, and an adjuvant. The antigenic *Francisella* polysaccharide component, the *Francisella* protein antigen component and the adjuvant are in a suitable amount to immunize an individual against the *Francisella* bacterium.

According to a second aspect, an immunogenic nanolipoprotein particle (NLP) is described, which presents the antigenic combination herein described. The immunogenic nanolipoprotein particle comprises: a scaffold protein, a membrane forming lipid, and the antigenic combination herein described, wherein the membrane forming lipids are arranged in a discoidal membrane lipid bilayer stabilized by the scaffold protein and the antigenic *Francisella* polysaccharide component, the *Francisella* protein antigen component, and the adjuvant are attached to the discoidal membrane lipid bilayer. In some embodiments, at least one of a *Francisella* antigenic polysaccharide or derivative thereof of the antigenic *Francisella* polysaccharide component, a protein antigen from *Francisella* or a derivative thereof of the *Francisella* protein antigen component, and the adjuvant, comprises a hydrophobic region and is attached to the membrane lipid bilayer through interaction of the hydrophobic region with the membrane lipid bilayer.

In some embodiments, the immunogenic nanolipoprotein particle further comprises a functionalized membrane-forming lipid presenting an anchor compound substrate, and at least one of the antigenic polysaccharide from the *Francisella* bacterium or derivative thereof, the protein antigen from the *Francisella* bacterium and the adjuvant, comprises an anchor compound attached to the anchor compound substrate of the functionalized amphipathic compound.

According to third aspect, an immunogenic composition is described. The immunogenic composition comprises the antigenic combination herein described together with a suitable vehicle, the antigenic combination in an amount effective to induce an immunogenic response against the *Francisella* bacterium in an individual. In some embodiments, in the composition the components of the antigenic combination are presented on a single same or different carrier (e.g. the composition comprises antigenic polysaccharide component, protein antigen component and adjuvant on a single NLP and/or antigenic polysaccharide component, protein antigen component and adjuvant on a microsphere). In some embodiments, in the composition the components of the antigenic combination are presented on separate same or different carriers (e.g. the composition comprises antigenic polysaccharide component on an NLP, the protein antigen component on a liposome and the adjuvant on a microsphere).

According to a fourth aspect, a method to provide an immunogenic nanolipoprotein particle is described. The method comprises: providing a membrane-forming lipid, a scaffold protein, the antigenic *Francisella* polysaccharide component, the *Francisella* protein antigen component, the adjuvant, and optionally a functionalized membrane-forming lipid presenting an anchor compound substrate.

In the method, an antigenic polysaccharide from the *Francisella* bacterium or derivative thereof of the antigenic *Francisella* polysaccharide component, a protein antigen from the *Francisella* bacterium or a derivative thereof of the *Francisella* protein antigen component, and the adjuvant comprise a hydrophobic region configured for attachment to a membrane lipid bilayer, and/or comprise an anchor compound presented for binding with the anchor compound substrate on the functionalized amphipathic compound.

The method comprises mixing the membrane-forming lipid, the scaffold protein, the functionalized membrane-forming lipid and optionally the functionalized amphipathic compound, together with the antigenic polysaccharide from the *Francisella* bacterium or derivative thereof, the protein antigen from the *Francisella* bacterium, and the adjuvant comprising a hydrophobic region, if any.

In the method the mixing is performed for a time and under conditions to allow self-assembly of the membrane-forming lipid, the scaffold protein, into a discoidal membrane lipid bilayer stabilized by the scaffold protein with the at least one of the *Francisella* antigenic polysaccharide or derivative thereof, the protein antigen from *Francisella* or derivative thereof and the adjuvant, if any, attached to the membrane lipid bilayer through interaction of the hydrophobic region with the membrane lipid bilayer to form a nanolipoprotein particle.

In embodiments wherein at least one of the antigenic polysaccharide from the *Francisella* bacterium or derivative thereof, the protein antigen from the *Francisella* bacterium or derivative thereof, and the adjuvant comprise an anchor compound presented for binding with the anchor compound substrate on the functionalized amphipathic compound, the method further comprises mixing a formed nanolipoprotein particle comprising a functionalized amphipathic compound presenting an anchor compound substrate with the at least one of the antigenic polysaccharide or derivative thereof, the protein antigen and the adjuvant for a time and under condition to allow the attaching to the nanolipoprotein particle through the binding of the anchor compound and the anchor compound substrate of the functionalized membrane-forming lipid.

According to a fifth aspect, a method to provide an immunogenic composition is described. The method comprises mixing an antigenic polysaccharide component from a *Francisella* bacterium, at least one protein antigen component from the *Francisella* bacterium and an adjuvant together with a suitable vehicle, the antigenic polysaccharide component, the protein antigen component, and the adjuvant in a suitable form and amount to immunize an individual against the *Francisella* bacterium.

According to a sixth aspect, a method of immunizing an individual against an infection of a *Francisella* bacterium is described. The method comprises administering to the individual an effective amount of the antigenic combination, the immunogenic nanoparticle and/or immunogenic composition described herein comprising an antigenic polysaccharide component from the *Francisella* bacterium, and a protein antigen component from the *Francisella* bacterium in a suitable form and amount to immunize an individual against the *Francisella* bacterium.

According to a seventh aspect, a system for immunizing an individual against an infection of a *Francisella* bacterium is described. The system comprises an antigenic combination herein described wherein the antigenic *Francisella* polysaccharide component, the *Francisella* protein antigen component are from the *Francisella* bacterium. In the system the antigenic polysaccharide component and the protein antigen component from the *Francisella* bacterium are comprised in separate compositions in a form and an amount for simultaneous, combined or sequential use in the method to immunize an individual against the *Francisella* bacterium described herein.

In antigenic combinations, and related nanolipoprotein particles, compositions, method and systems herein described, the antigenic *Francisella* polysaccharide component comprises an antigenic *Francisella* and/or a derivative thereof, and the antigenic *Francisella* protein antigen component comprises an antigenic *Francisella* protein antigen and/or a derivative thereof.

The antigenic combinations, and related nanolipoprotein particles, compositions, method and systems herein described allow in several embodiments to effectively immunize an individual as a result of a synergistic effect in protection against *Francisella* bacteria and in particular against bacteria of the species *Francisella tularensis* subspecies *tularensis*, particularly type A *Francisella tularensis*.

The antigenic combinations, and related nanolipoprotein particles, compositions, method and systems herein described allow in several embodiments induction of both humoral and cell mediated immunity in an immunized individual, thus leading to enhanced protective capacity against a virulent *Francisella* bacterium and in particular against virulent bacteria of the species *Francisella tularensis* over either component alone.

In particular, when the antigenic combinations are presented on a single carrier and in particular on an immunogenic nanolipoprotein particle, the co-localized presentation of the antigens results in an improved immunostimulation and immunogenic response with respect to known immunogenic compositions and other immunogenic compositions herein described.

The antigenic combinations, and related nanolipoprotein particles, compositions, method and systems herein described allow in several embodiments development of a safer vaccine with an effective protection against infections caused by *Francisella tularensis*.

The antigenic combinations, and related nanolipoprotein particles, compositions, method and systems herein described can be used in connection with various applications wherein use of antigens of a *Francisella* bacterium, and/or immunization of an individual against a *Francisella* bacterium are desired. For example, antigenic combinations, and related nanolipoprotein particles, compositions, method and systems herein described can be used in combination with compounds such as therapeutics to target *Francisella* bacterium in an individual, and in particular in combination with immunostimulating agents against infection of the individual by a *Francisella* bacterium, in vaccine development and use, and/or to treat and/or prevent a condition associated with an infection of a *Francisella* bacterium, such as *Francisella tularensis*. Additional exemplary applications include basic biology research, applied biology, bio-engineering, medical research, medical diagnostics, therapeutics, and additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure.

FIGS. 5A-E illustrate exemplary structures of *Francisella* LPS and its components from Okan 2013 [1]. In particular, FIG. 5A shows a representative structure of *Francisella* LPS having a major *Francisella* lipid A molecule with a polysaccharide core component. Chain length variation (16/18) indicates temperature regulation. FIG. 5B shows less abundant lipid variants having various modifications in sugar composition as shown in dashed circles. FIGS. 5C and 5D show the structure of *F. tularensis* O-antigen and *F. novicida* O-antigen, respectively. FIG. 5E shows the structure of *E. coli* Kdo2-lipid A.

FIG. 6 illustrates an exemplary embodiment of *F. tularensis* LVS lipid A from LVS *F. tularensis* from Okan 2013 [1].

In FIG. 21A, vaccine formulations were analyzed by SDS-PAGE to verify presence of appropriate protein constituents in the formulations to verify the presence of NLP (i.e. apoE in Groups 2-5) and antigen (i.e. IglC in Groups 3-6). In FIG. 21B, SDS-PAGE and Western blot (using anti F.t. LVS LPS antibody FB11) were used to verify presence of F.t. LPS in the appropriate formulation groups (i.e. Groups 2, 4-6).

FIG. 26 shows the search parameters and databases used for querying the protein sequences.

FIG. 27A shows a representation of the alignment hit table generated from the BLASTP search using SEQ ID NO: 2 as a query sequence.

FIG. 28A shows the alignment hit table generated from the BLASTP search using SEQ ID NO: 4 as a query sequence.

FIG. 29A shows a representation of the alignment hit table generated from the BLASTP search using SEQ ID NO: 6 as a query sequence.

FIG. 30A shows a representation of the alignment hit table generated from the BLASTP search using SEQ ID NO: 8 as a query sequence.

FIG. 31A shows a representation of the alignment hit table generated from the BLASTP search using SEQ ID NO: 88 as a query sequence.

FIG. 32A shows a representation of the alignment hit table generated from the BLASTP search using SEQ ID NO: 10 as a query sequence.

FIG. 33A shows a representation of the alignment hit table generated from the BLASTP search using SEQ ID NO: 14 as a query sequence.

FIG. 34A shows a representation of the alignment hit table generated from the BLASTP search using SEQ ID NO: 16 as a query sequence.

FIG. 35A shows a representation of the alignment hit table generated from the BLASTP search using SEQ ID NO: 18 as a query sequence.

FIG. 36A shows a representation of the alignment hit table generated from the BLASTP search using SEQ ID NO: 20 as a query sequence.

FIG. 37A shows a representation of the alignment hit table generated from the BLASTP search using SEQ ID NO: 22 as a query sequence.

FIG. 38A shows a representation of the alignment hit table generated from the BLASTP search using SEQ ID NO: 24 as a query sequence.

FIG. 39A shows a representation of the alignment hit table generated from the BLASTP search using SEQ ID NO: 25 as a query sequence.

FIG. 40A shows a representation of the alignment hit table generated from the BLASTP search using SEQ ID NO: 26 as a query sequence.

FIG. 41A shows a representation of the alignment hit table generated from the BLASTP search using SEQ ID NO: 27 as a query sequence.

FIG. 42A shows a representation of the alignment hit table generated from the BLASTP search using SEQ ID NO: 28 as a query sequence.

FIG. 43A shows a representation of the alignment hit table generated from the BLASTP search using SEQ ID NO: 29 as a query sequence.

DETAILED DESCRIPTION

Figure 1:
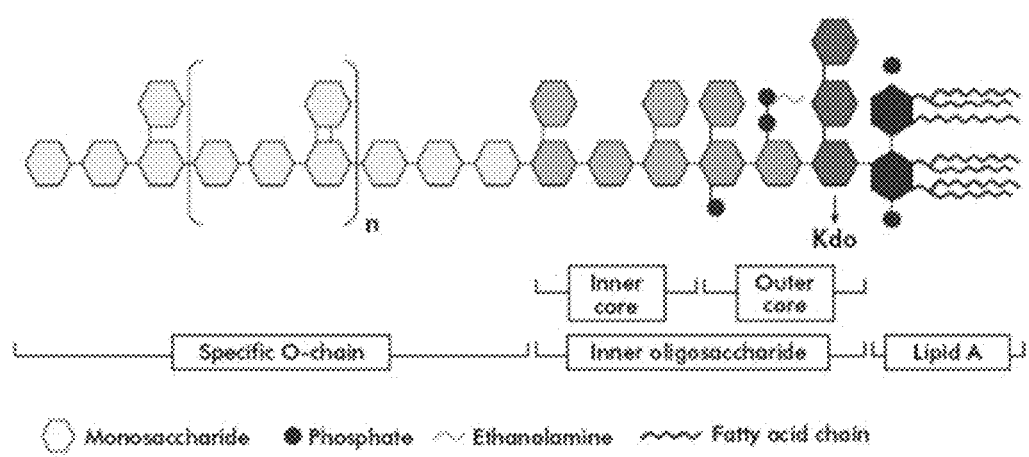
FIG. 1 shows a schematic illustrating the general chemical structure of bacterial lipopolysaccharides comprising Lipid A and a polysaccharide component. Different components of the bacterial lipopolysaccharides are indicated with symbols shown in different shades of gray as indicate in the figure.
Figures 2A, 2B, 2C:
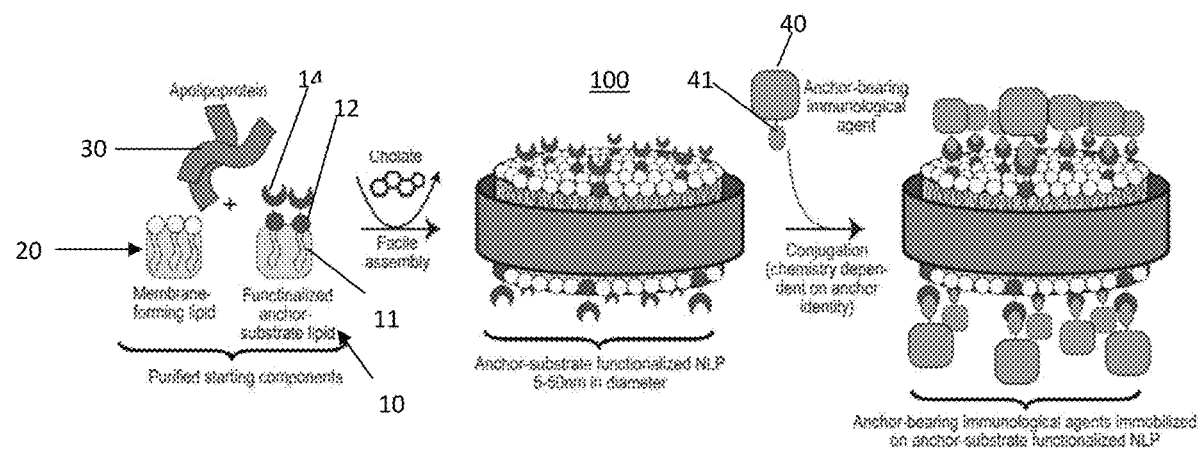
FIGS. 2A-C show a schematic representation of an NLP assembly process to provide an NLP comprising a functionalized membrane-forming lipid presenting at least one protein antigen according to some embodiments herein described. In the illustration of FIGS. 2A-C, the starting components, intermediate NLP and final NLP presenting an anchor bearing immunological agents are illustrated in FIGS. 2A to 2C respectively.

Provided herein are antigenic combinations, and related nanolipoprotein particles, compositions, method and systems which can be used to immunize an individual against a *Francisella* bacterium, and in particular against a bacterium of the species *Francisella tularensis*.

The term "*Francisella*" as used herein indicates a genus of pathogenic, Gram-negative bacteria. *Francisella* is the sole genus in the family Francisellaceae, falling within the class Gammaproteobacteria. *Francisella* bacteria are small coccobacillary or rod-shaped, nonmotile organisms, which are also facultative intracellular parasites of macrophages. Strict aerobes, *Francisella* colonies bear a morphological resemblance to those of the genus *Brucella*. *Francisella* contains two recognized species, *F. tularensis* and *F. philomiragia*, several recently identified species *F. noatunensis*, *F. hispaniensis*, and possibly *F. halioticida* as well as potentially other as yet unidentified species, underscoring the dynamic nature of *Francisella* taxonomy [3-6]. Accordingly, exemplary bacteria of the genus *Francisella* are *F. tularensis*, *F. novicida*, *F. hispaniensis*, *W. persica*, *F. noatunensis*, *F. philomiragia*, *F. halioticida*, *F. endociliophora*, *F. guangzhouensis*, and *F. piscicida*.

The term "*Francisella tularensis*" "*F. tularensis*" or "FT" as used herein indicates a small, highly pleomorphic, gram-negative coccobacillus. In particular, *Francisella tularensis* indicates a pathogenic species of Gram-negative, rod-shaped coccobacillus, an aerobe bacterium. FT is a non-spore forming, non-motile bacteria and the causative agent of tularemia, the pneumonic form of which is often lethal without treatment. When found in nature, *Francisella tularensis* can survive for several weeks at low temperatures in animal carcasses, soil, and water. In laboratory, *Francisella tularensis* appears as small rods (0.2 by 0.2 μm), and is grown best at 35-37 degrees Celsius. *F. tularensis* contains four recognized subspecies: *F. tularensis* subspecies *tularensis*, *F. tularensis* subspecies *holarctica*, *F. tularensis* subspecies *novicida* and *F. tularensis* subspecies *mediasiatica* [7].

The term "antigen" or "antigenic" as used herein indicates a substance that prompts the generation of antibodies and/or can cause an immune response in an individual. In particular, antigens in the sense of the present disclosure encompass all substances that can be recognized by an adaptive immune system. Exemplary antigens include exogenous antigens and endogenous antigens. Exogenous antigens are antigens that have entered the body from the outside, for example by inhalation, ingestion, or injection. Exogenous antigens are taken into the antigen-presenting cells (APCs) by endocytosis or phagocytosis, and processed into fragments. APCs then present the fragments to T helper cells (CD4⁺) by the use of class II histocompatibility molecules on their surface. Some T cells are specific for the peptide: MHC complex. T cells become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic CD8⁺ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. Antigens are also generated between normal cells.

In embodiments of the disclosure an antigenic combination described is configured to immunize an individual against a *Francisella* bacterium, and in particular against a *Francisella tularensis* bacterium.

The term "immunize" or "immunogenize" as used herein refers to the ability of a particular antigenic substance to provoke an immune response in an individual. In particular, an immune response indicates the reaction of the cells and fluids of the body of an individual to the presence of a substance that is not recognized as a constituent of the body itself. The immune response can be a humoral (antibody) response, or a cell-mediated response, or both.

The term "cell mediated response" in the sense of the disclosure indicates an immune response that does not involve antibodies, but rather involves the activation of phagocytes, antigen-specific cytotoxic T-lymphocytes, and the release of various cytokines in response to an antigen. The protective function of cell mediated immunity is typically associated with cells, such as CD4 cells or helper T cells and Naive T cells. Mature T cells that have yet to encounter an antigen, are converted into activated effector T cells after encountering antigen-presenting cells (APCs). These APCs, such as macrophages, dendritic cells, and B cells in some circumstances, load antigenic peptides onto the MHC of the cell, in turn presenting the peptide to receptors on T cells. The most important of these APCs are highly specialized dendritic cells; conceivably operating solely to ingest and present antigens. Activated Effector T cells can be placed into three functioning classes, detecting peptide antigens originating from various types of pathogen: The first class being Cytotoxic T cells, which kill infected target cells by apoptosis without using cytokines, the second class being TH1 cells, which primarily function to activate macrophages, and the third class being TH2 cells, which primarily function to stimulate B cells into producing antibodies. Cellular immunity protects the body by: i) T-cell mediated immunity or T-cell immunity activating antigen-specific cytotoxic T cells that are able to induce apoptosis in body cells displaying epitopes of foreign antigen on their surface, such as virus-infected cells, cells with intracellular bacteria, and cancer cells displaying tumor antigens; ii) activating macrophages and natural killer cells, enabling them to destroy pathogens; and iii) stimulating cells to secrete a variety of cytokines that influence the function of other cells involved in adaptive immune responses and innate immune responses.

Cell mediated immune responses triggered by an antigen can be detected using standard recall response assays using the antigen. The assays typically comprise harvesting spleens from vaccinated animals vaccinated with the antigen, processing the harvested spleen into single cell suspension and re-stimulating total splenocytes in the suspension with purified antigen for 24-72 hours. The assays further comprise collecting culture supernatants following re-stimulation and analyzing the collected culture supernatants for presence of TH1/Th2 cytokines such as IL-2 and IFN-γ to assess T cell responses. Alternatively, assays can comprise harvesting spleens from vaccinated mice, processing harvested spleens into a single cell suspension and purifying CD4+ and CD8+ T cells, e.g. using MACS bead sorting prior to re-stimulating the purified CD4+ and CD8+ T cells with purified antigen. The assays further comprise collecting culture supernatants and analyzing the collected culture supernatants for presence of IL-2 and IFN-γ to assess t cell responses. An additional assay that can be used to detect cell mediate immune response is the Enzyme-Linked Immuno-Spot (ELISPOT) assay is also widely used to monitor cell-mediated immune responses in animals.

The term "humoral immunity" in the sense of the disclosure indicates an immune response mediated by macromolecules found in extracellular fluids such as secreted antibodies, complement proteins, and certain antimicrobial peptides. Humoral immunity is so named because it involves substances found in the humors, or body fluids. It contrasts with cell-mediated immunity. Its aspects involving antibodies are often called antibody-mediated immunity. Humoral immunity refers to antibody production and the accessory processes that accompany it, including: Th2 activation and cytokine production, germinal center formation and isotype switching, affinity maturation and memory cell generation. It also refers to the effector functions of antibodies, which include pathogen and toxin neutralization, classical complement activation, and opsonin promotion of phagocytosis and pathogen elimination. In a humoral immune response, first the B cells mature in the bone marrow and gain B-cell receptors (BCR's) which are displayed in large number on the cell surface. These membrane-bound protein complexes have antibodies which are specific for antigen detection. Each B cell has a unique antibody that binds with an antigen. The matured B cells migrate from bone marrow to lymph nodes or other lymphatic organs, where they begin to encounter pathogens. The humoral response is typically divided in B cell activation, B cell proliferation and Antibody-antigen reaction. B cell action refers to the phase where when a B cell encounters an antigen, it is bound to the receptor and taken inside by endocytosis. The antigen is processed and presented on its surface again with MHC-II molecule. Be cell proliferation refers to the phase where the B cell waits for the $T_H$ cell to bind to the complex and this binding will activate $T_H$ cell and it releases cytokines that induce B cells to divide rapidly which make thousands of identical clones of B cell. These daughter cells either become plasma cells or memory cells. The memory B cells remain inactive here; later when these memory B cells encounter the same antigen due to reinfection, they divide and form Plasma cells. On the other hand, the plasma cells produce a large number of antibodies which are released free in the circulatory system. The antibody antigen reaction refers to the phase where these antibodies will encounter antigens and bind with them. This will either interfere with the chemical interaction between host and foreign cells, or they may form bridges between their antigenic sites hindering their proper functioning, or their presence will attract macrophages or killer cells to phagocytose them.

A humoral response can be qualitatively or quantitatively detected with standard ELISAs methods and other methods identifiable by a person of ordinary skill in the art.

Antigenic molecules capable of triggering a cellular and/or humoral comprise one or more epitopes. The term "epitope" as used herein, also known as an "antigenic determinant" refers to the part of an antigen that is recognized by the immune system, specifically by antibodies, B cells, or T cells. For example, the epitope is the specific piece of the antigen to which an antibody binds. The part of an antibody that binds to the epitope is called a paratope. Although epitopes are usually non-self proteins, sequences derived from the host that can be recognized (as in the case of autoimmune diseases) are also epitopes.

Epitopes of antigenic molecules can be conformational epitopes or linear epitopes, based on their structure and interaction with the paratope as will be understood by a skilled person. A conformational epitope is composed of discontinuous sections of the antigen's amino acid sequence and interacts with a corresponding paratope based on the 3-D surface features and shape or tertiary structure of the antigen. Linear epitopes interact with a corresponding paratope based on their primary structure. A linear epitope is typically formed by a continuous sequence of residues of an antigen.

Epitopes can be mapped, for example using protein microarrays, or with ELISA or ELISPOT techniques, among others known to those skilled in the art. Another technique involves high-throughput mutagenesis, an epitope mapping strategy developed to improve rapid mapping of conformational epitopes on structurally complex proteins [8]. In addition, MHC class I and II epitopes can be predicted by computational means [9]. Additional methods for identifying epitopes are described in U.S. Pat. Nos. 8,889,142, 8,486,411, 7,754,228 and 6,635,746 and will be understood by a person skilled in the art.

In the embodiments herein described, the antigenic combination comprises an antigenic polysaccharide component from a *Francisella* bacterium capable of triggering a humoral immune response, a protein antigen component from *Francisella* bacterium capable of triggering a cell-mediated immune response, and an adjuvant.

In particular, in antigenic combination herein described the antigenic polysaccharide component can comprise an antigenic polysaccharide from a *Francisella* bacterium capable of triggering a humoral immune response and/or a derivative thereof, and a protein antigen from *Francisella* bacterium capable of triggering a cell-mediated immune response and/or a derivative thereof.

The term "derivative" as used herein in connection with an antigenic polysaccharide or a protein antigen, indicates a fragment of the molecule which retains the immunogenicity of the original antigenic polysaccharide or protein with a same lower or higher degree. Typically, a derivative of an antigenic molecule comprises one or more epitopes of the original antigen which form the base for obtaining the derivative. Derivatives can be obtained by fragmentation of a base antigenic polysaccharides or protein antigen, or can be provided synthetically to reproduce part of the structure of the base antigenic polysaccharide or protein antigen as will be understood by a skilled person.

In some embodiments, rationally designed antigenic fragments and synthetic polysaccharides or peptides comprising one or more epitopes which maintain the immunogenicity of the original antigenic polysaccharides or protein antigens can serve as the derivatives. For example, polynucleotides can be designed to encode a protein fragment to include one or more epitopes of a protein antigen. In some embodiments, polynucleotides can be designed to encode a mutated protein from the original protein antigen with a same, lower or higher degree of immunogenicity. In some embodiments, the polynucleotide can be designed such that the resulting protein, protein fragment or mutated proteins is expressed as a fusion, or chimeric protein products by joining via a peptide bond to a heterologous protein sequence of a different protein to facilitate purification or detection. For example, a chimeric product can be made by ligating the appropriate nucleic acid sequences encoding the desired amino acid sequences to each other using standard methods and expressing the chimeric product. In particular, in some embodiments, the polynucleotide can be engineered so that the protein antigen is labeled or tagged. Labeling or tagging can be performed with methods that include, for example, FRET pairs, NHS-labeling, fluorescent dyes, and biotin as well as coding for a "His-tag" to enable protein isolation and purification via established Ni-affinity chromatography.

Derivatives of antigenic polysaccharides can be chemically synthesized through chemical polymerization as will be understood by a person skilled in the art. Examples of antigenic polysaccharide derivatives can comprise at least one tetrasaccharide repeating unit as described below.

Derivatives of original antigenic proteins and polysaccharides can be assessed for immunogenicity and protective capacity in a suitable animal model using approaches known to a person skilled in the art. Murine model systems can be employed where animals are vaccinated with the antigen of interest and the humoral and cell mediated immune response to vaccination is characterized. In the case of humoral responses, serum from vaccinated animals can be screened for the presence of antigen specific antibodies using traditional ELISA methodologies. Cell mediated immunity can be assessed using recall responses to quantify the ability of recombinant protein to elicit activation of T cells in vaccinated animals. Protection can then be assessed in vaccinated animals that are subsequently challenged with a lethal dose of *Francisella* and assessed for survival.

The term "polysaccharide" as used herein indicates a polymeric saccharide having different lengths and dimensions. In particular, polysaccharides in the sense of the disclosure encompass polymeric carbohydrate molecules composed of chains of monosaccharide units bound together by glycosidic linkages, which on hydrolysis give the constituent monosaccharides and/or oligosaccharides. A "glycosidic linkage" as used herein indicates an oxygen atom that joins an anomeric carbon atom of one monosaccharide to a designated carbon atom on an adjacent monosaccharide and is typically designed as an (L) as will be understood by a skilled person. The glycosidic linkage is denoted by α or β (m→n), wherein α or β represents a configuration of an anomeric carbon m of a monosaccharide and n represents the corresponding carbon on an adjacent monosaccharide to which the glycosidic linkage is connected. Polysaccharide in the sense of the disclosure range in structure from linear to highly branched and are often quite heterogeneous, containing slight modifications of the repeating unit. Polysaccharides, have a general formula of $C_x(H_2O)_y$ where x can be a number between 200 or lower and 2500 or higher.

In embodiments, herein described the antigenic polysaccharide component from a *Francisella* bacterium capable of triggering a humoral immune response comprises one or more antigenic polysaccharides from the *Francisella* bacterium and/or one or more derivative thereof. The one or more antigenic polysaccharides from the *Francisella* bacterium and/or one or more derivative thereof can be isolated from the *Francisella* bacterium or produced synthetically to include the type and number of saccharides of the polysaccharide from the *Francisella* bacterium or derivative thereof. Antigenic polysaccharides can be chemically synthesized through chemical polymerization using linear or convergent approaches as will be understood by a person skilled in the art.

In some embodiments, a *Francisella* polysaccharide component can comprise an antigenic *Francisella* polysaccharide having a Formula (XI):

$$\left\{ M_1-L_1-M_2-L_2-M_3-L_3-M_4-L_4 \right\}_n \quad (XI)$$

wherein

M1-M4 can each independently be selected from the group consisting of (Xa) to (Xw):

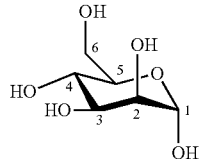

α-D-Mannose or α-D-Man (Xa)

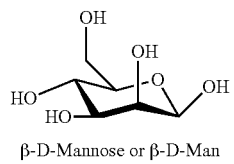

β-D-Mannose or β-D-Man (Xb)

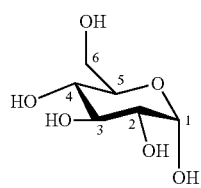

α-D-Glucose or α-D-Glc (Xc)

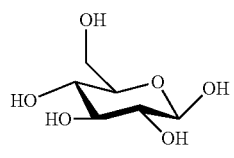

β-D-Glucose or β-D-Glc (Xd)

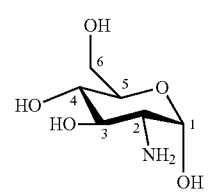

α-D-glucosamine or α-D-GlcN (Xe)

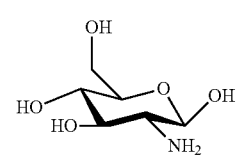

β-D-glucosamine or β-D-GlcN (Xf)

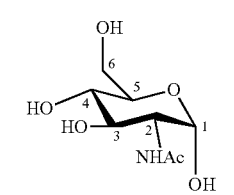

α-D-N-Acetylglucosamine or α-D-GlcNAc (Xg)

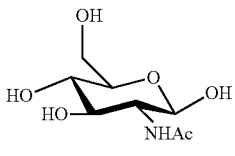

β-D-N-Acetylglucosamine or β-D-GlcNAc (Xh)

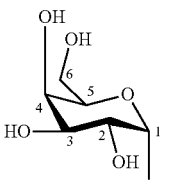

α-D-Galactose or α-D-Gal (Xi)

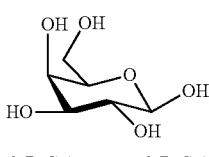

β-D-Galactose or β-D-Gal (Xj)

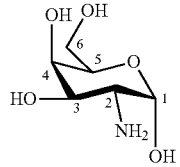

α-D-Galactosamine or α-D-GalN (Xk)

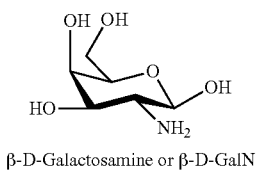

β-D-Galactosamine or β-D-GalN (Xl)

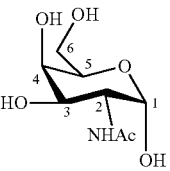

α-D-N-Acetylgalactosamine or α-D-GalNAc (Xm)

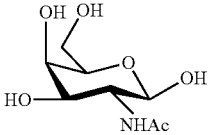

β-D-N-Acetylgalactosamine or β-D-GalNAc (Xn)

(Structures shown on left column:)

β-Kdo (β anomer of cyclized 3-Deoxy-D-manno-oct-2-ulsonic acid)

α-Kdo (α anomer of cyclized 3-Deoxy-D-manno-oct-2-ulsonic acid)

α-2-Acetamido-2-deoxy-D-galacturonamide or α-D-GalNAcAN

β-2-Acetamido-2-deoxy-D-galacturonamide or β-D-GalNAcAN

β-2-acetamido-2,6-dideoxy-D-glucose or β-D-QuiNAc

α-2-acetamido-2,6-dideoxy-D-glucose or α-D-QuiNAc

β-2-Diacetamido-2,4,6-trideoxy-D-glucose or β-D-Qui2NAc4NAc (Xo), (Xp), (Xq), (Xr), (Xs), (Xt), (Xu)

(Xv) α-2,N-Diacetamido-2,4,6-trideoxy-D-glucose or α-D-Qui2NAc4NAc (Xw) β-4-Formamido-4,6-dideoxy-D-glucose or β-D-Qui4NFm L1-L4 can be selected independently from the group consisting of:
α (1→2), α (1→3), α (1→4), α (1→5), α (1→6), β (1→2), β (1→3), β (1→4), β (1→5), and β (1→6); and n is 1 to 1250,
or a derivative thereof.

Derivatives of an antigenic *Francisella* polysaccharide of formula (XI) typically comprise at least one or two epitopes of the antigenic *Francisella* polysaccharide.

Epitopes of an antigenic polysaccharides such as the O-polysaccharide from *Francisella* can be provided by two tetrasaccharide repeats for antibodies recognizing internal O—Ag epitopes, and a single repeat for antibodies recognizing the terminal O—Ag [10] wherein a structural characterization (and molecular docking simulation) of the interaction between an internal O—Ag binding antibody and a 2-unit tetrasaccharide molecule. If the tetrasaccharide unit is represented as "a, c, b, d" (where each letter is a different monosaccharide comprising the tetrasaccharide, and "a, b, c, d, a, b, c, d" represents a 2-unit tetrasaccharide, the binding epitope for this particular Ab would be 6 residues represented as "b, c, d, a, b, c" [11].

In some embodiments, the antigenic polysaccharide of formula (XI) is a polysaccharide isolated from a *Francisella* bacterium as a polysaccharide molecule (e.g. as a Capsular Polysaccharide). In some embodiments, the antigenic polysaccharide of formula (XI) is a polysaccharide isolated from *Francisella* bacterium within a multicomponent *Francisella* molecule (such as lipopolysaccharide) which further comprises additional molecular components of a different chemical nature such as lipid or protein components.

A derivative of the antigenic polysaccharide of formula (XI) can be obtained from the polysaccharide following isolation of the polysaccharide from a *Francisella* bacterium whether said polysaccharide is isolated as a polysaccharide molecule or as a part of a multicomponent molecule. In particular, in some embodiments, a derivative of the antigenic polysaccharide of formula (XI) can be any moiety obtained from fragmentation (e.g. by hydrolysis or other suitable processing) of the polysaccharide molecule, and/or multicomponent molecule from the *Francisella* bacterium. In those embodiments the derivative also has an ability to trigger a humoral immune response which can be the same lower or higher than the one of the base antigenic polysaccharide of formula (XI).

In some embodiments, a derivative of the antigenic polysaccharide of formula (XI) can be obtained by synthetically producing any moiety of the polysaccharide of formula (XI).

In particular, in some of these embodiments, a derivative of the antigenic polysaccharide of formula (XI) comprises at least one tetrasaccharide repeat unit comprising monomers selected from the group consisting of Xa to Xw.

Polysaccharides and derivatives thereof can be chemically synthetized through chemical polymerization using linear or convergent approaches as will be understood by a person skilled in the art. For example, the polysaccharides can be extended by one monosaccharide unit selected from the group consisting of Xa to Xw at a time. An oligosaccharide can be build starting from either the non-reducing or the reducing end. The resulting disaccharide can be converted either into a new glycosyl donor or into a new glycosyl acceptor. The disaccharide is then coupled with another monosaccharide building block to provide a trisaccharide. The process is reiterated to provide a single tetrasaccharide of Formula (XI) or until an oligosaccharide of the desired length is obtained. Alternatively, in the convergent approach, tetrasaccharide building blocks are synthesized separately and subsequently used for the assembly of a larger polysaccharide.

In some embodiments, the antigenic *Francisella* polysaccharide of formula (XI) or of derivative thereof, can comprise one, two or more repeats of the tetrasaccharide of Formula (XI).

In some embodiments, herein described in the antigenic *Francisella* polysaccharide of formula (XI) or of derivative thereof, n can be 1 and the antigenic *Francisella* polysaccharide can be a tetrasaccharide as will be understood by a skilled person. The term "tetrasaccharide" as used herein refers to a moiety having four monosaccharide units joined sequentially by a glycosidic linkage.

In some embodiments, in the antigenic *Francisella* polysaccharide of formula (XI) or derivative thereof, M1-M4 can each independently be selected from the group consisting of α-D-Glc (Xc), α-D-GalNAc (Xm), α-D-GlcN (Xe), α-D-GlcNAc (Xg), α-D-GalNAcAN (Xq), β-D-QuiNAc (Xs), β-D-Qui2NAc4NAc (Xu), and β-D-Qui4NFm (Xw). In some preferred embodiments, M1-M4 are the following saccharides in this specific order: β-D-Qui4NFm (Xw), α-D-GalNAcAN (Xq), α-D-GalNAcAN (Xq), and β-D-QuiNAc (Xs).

In some embodiments, in the antigenic *Francisella* polysaccharide of formula (XI) or derivative thereof, M1-M4 can each independently be selected from the group consisting of α-D-GalNAc (Xm), β-D-QuiNAc (Xs), and β-D-Qui4NFm (Xw). Preferably M1 and M2 are the same, and more preferably M1 and M2 are α-D-GalNAc (Xm).

In some embodiments, in the antigenic *Francisella* polysaccharide the antigenic polysaccharide of formula (XI) or derivative thereof, L1, L2, L3 and L4 each independently be selected from the group consisting of α (1→4), α (1→3), β (1→2), and β (1→4), respectively. Preferably, L1 and L2 can be independently α (1→4), and α (1→3) and L3 and L4 can be independently β (1→2), and β (1→4).

In some embodiments, in the antigenic *Francisella* polysaccharide the antigenic polysaccharide of formula (XI) or derivative thereof, L1, L2, L3 and L4 each independently be α (1→4), α (1→3), β (1→2), and β (1→4), respectively.

In some embodiments herein described the antigenic *Francisella* polysaccharide the antigenic polysaccharide of formula (XI) or derivative thereof, n can be 1 to 10, 10 to 50, 50 to 100, 100 to 250, 250 to 500, or 500 to 1,000.

In some embodiments of the antigenic combination herein described, the antigenic *Francisella* polysaccharide or derivative of Formula (XI) can be an antigenic fragment of *Francisella* LPS herein described where the antigenic *Francisella* polysaccharide or derivative of Formula (XI) may or may not include an additional lipidic component.

In some embodiments herein described, the antigenic *Francisella* polysaccharide of formula (XI) or derivative thereof is a polysaccharide molecule which further comprises a lipidic component. In some of these embodiments, the antigenic *Francisella* polysaccharide herein described is an antigenic lipopolysaccharide (LPS) from a *Francisella* bacterium capable of triggering a humoral immune response or a derivative thereof.

The term "lipopolysaccharide" or "LPS" as used herein refers to an integral component of gram-negative bacteria cell walls. In particular, LPS is a macromolecule of molecular mass about 10-200 kDa and is composed of a lipid component (also referred to as "Lipid A") and a polysaccharide component comprising a core oligosaccharide attached to the lipid component by an eight-carbon sugar, 3-deoxy-D-manno-octulosonic acid (KDO) and an O-polysaccharide (also known as O-antigen), which contains a varying number of tetrasaccharide repeating units, typically from two to six sugars.

The lipid component of an LPS molecule or Lipid A is typically formed by a β-glucosamine-(1→6)-glucosamine-1-phosphate base with fatty acid esters attached to both carbohydrates. The acyl chain length and number of acyl groups can vary between bacterial species but are relatively conserved within a species. In an LPS molecule of a gram-negative bacteria the Lipid A typically anchors the LPS to the outer membrane. In *Francisella* bacteria lipid A typically has four long acyl chains with 16 and 18 carbons, whereas most bacterial lipid A has six acyl chains that are usually shorter, 12-14 carbons. Some *Francisella* lipid A exhibits temperature-regulated heterogeneity in their acyl chains (see Example 1 reporting exemplary LPS from Exemplary *Francisella* species).

The polysaccharide component of an LPS molecule typically includes an inner core and an outer core as well as an O-antigen portion. The inner core of the polysaccharide component typically contains between 1 and 4 molecules of the 3-deoxy-α-D-manno-octulosonic acid (KDO) attached to the disaccharide core. KDO is specifically associated with lipopolysaccharide, and biologically active lipid A is thought to require at least one KDO residue for bacterial survival. However, an *Escherichia coli* K-12 suppressor strain that is KDO deficient demonstrates that the KDO requirement is not absolute for viability. Typically, the inner core of the LPS polysaccharide component is also modified with heptulose (ketoheptose) monosaccharides, the most common of which is L-glycero-α-D-manno-heptopyranose. The inner core glycan residues are typically phosphorylated or modified with phosphate-containing groups, e.g., pyrophosphate or 2-aminoethylphosphate. The phosphate groups of lipopolysaccharides increase the overall negative charge of the cell membrane and help to stabilize the structure. Typically, the outer core of the polysaccharide component of the lipopolysaccharide contains more common hexoses, including glucose, galactose, and N-acetylglucosamine and is structurally more diverse than the inner core. In *Francisella* LPS the core is relatively small, and typically contains two mannose sugars in the inner core instead of the more commonly found heptoses. *Francisella* LPS differs from presence of different residues in this portion (see Example 1). *Francisella* LPS typically also has a single non-branched Kdo in its core region even though studies have shown that *Francisella* initially synthesizes its LPS with two Kdo sugars, one of which is removed by a novel Kdo hydrolase. The O-antigen portion comprises one or more repetitive units of an O-antigen which is a repeating oligosaccharide unit typically comprised of two to six sugars. The O-antigen is the primary structural constituent of lipopolysaccharide that differentiates bacteria. The distinctive 0-antigen structures have been used to identify and assign serogroups to *Escherichia coli, Salmonella enterica*, and *Vibrio cholerae*. Lipopolysaccharides from rough mutant strains of *E. coli* lack the O-antigen portion of the structure. Studies aimed at gaining insight into anti-Ft LPS antibodies demonstrated that four monoclonal anti-Ft LPS antibodies all are specific for the O-antigen of Ft LPS [12].

The polysaccharide section and the lipid A section of a lipopolysaccharide can have variability in structure, while the O-antigen has a high degree of structural variability as well as variability in the number of repeating units. These differences result in a degree of heterogeneity in LPS preparations.

LPS molecules are variable in length (and molecular weight), due to variability in the number of repeating O-antigen oligosaccharide side chains. The molecular weights of individual F.t. LPS molecules range from ~10,000 Da to >200,000 Da (as determined by sodium dodecyl sulfate polyacrylamide electrophoresis (SDS-PAGE).

Immune responses directed against *Francisella* LPS can be assessed by quantifying anti-Ft LPS antibodies present in serum from infected and/or vaccinated animals using standard Enzyme Linked Immunosorbant Assays (ELISA). Detectable antibody titers against Ft LPS would indicate that the molecule was immunogenic.

In some embodiments, the LPS from *Francisella* can be represented by a general formula (XZY)

$$X—Z—Y \qquad (XZY)$$

wherein X is the O antigen, Z is the inner oligosaccharide or core forming with the O antigen the polysaccharide component and Y is the Lipid A component.

In particular, in some embodiments, the O antigen X has formula (XII)

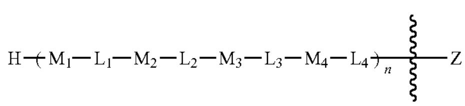

in which M1-M4 can each independently be selected from the group consisting of (Xa) to (Xw):

(Xa)

α-D-Mannose or α-D-Man (Xb)

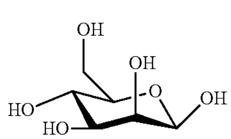

β-D-Mannose or β-D-Man

-continued (Xc)

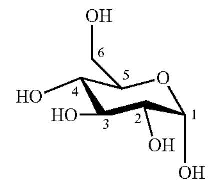

α-D-Glucose or α-D-Glc (Xd)

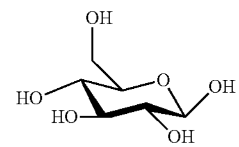

β-D-Glucose or β-D-Glc (Xe)

α-D-glucosamine or α-D-GlcN (Xf)

β-D-glucosamine or β-D-GlcN (Xg)

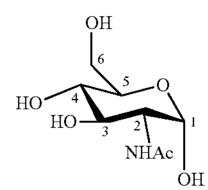

α-D-N-Acetylglucosamine or α-D-GlcNAc (Xh)

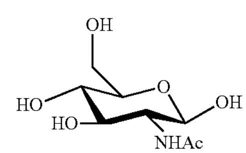

β-D-N-Acetylglucosamine or β-D-GlcNAc (Xi)

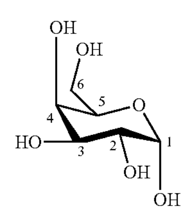

α-D-Galactose or α-D-Gal

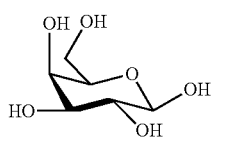
β-D-Galactose or β-D-Gal

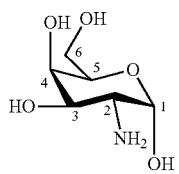
α-D-Galactosamine or α-D-GalN

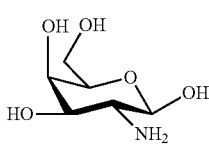
β-D-Galactosamine or β-D-GalN

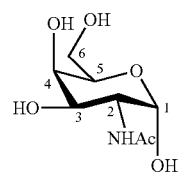
α-D-N-Acetylgalactosamine or α-D-GalNAc

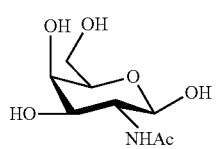
β-D-N-Acetylgalactosamine or β-D-GalNAc

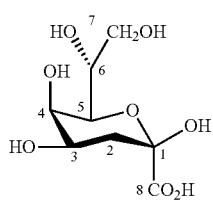
β-Kdo (β anomer of cyclized 3-Deoxy-D-manno-oct-2-ulsonic acid)

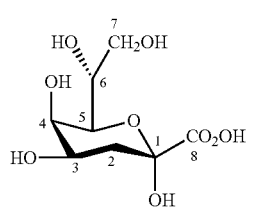
α-Kdo (α anomer of cyclized 3-Deoxy-D-manno-oct-2-ulsonic acid)

(Xj)

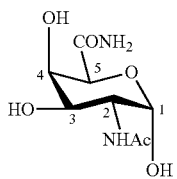
α-2-Acetamido-2-deoxy-D-galacturonamide or α-D-GalNAcAN (Xk)

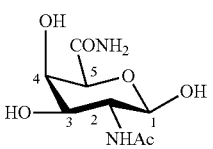
β-2-Acetamido-2-deoxy-D-galacturonamide or β-D-GalNAcAN (Xl)

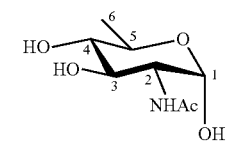
β-2-acetamido-2,6-dideoxy-D-glucose or β-D-QuiNAc (Xm)

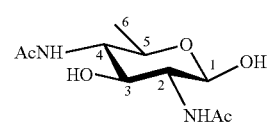
α-2-acetamido-2,6-dideoxy-D-glucose or α-D-QuiNAc (Xn)

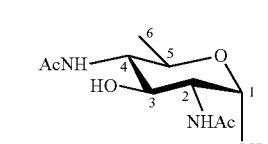
β-2-Diacetamido-2,4,6-trideoxy-D-glucose or β-D-Qui2NAc4NAc (Xo)

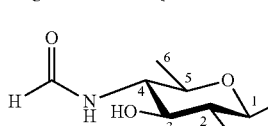
α-2,N-Diacetamido-2,4,6-trideoxy-D-glucose or α-D-Qui2NAc4NAc (Xp)

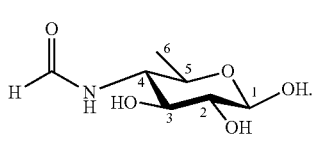
β-4-Formamido-4,6-dideoxy-D-glucose or β-D-Qui4NFm (Xq)

(Xr)

(Xs)

(Xt)

(Xu)

(Xv)

(Xw)

in which L1-L4 can be selected independently from the group consisting of:
α (1→2), α (1→3), α (1→4), α (1→5), α (1→6), β (1→2), β (1→3), β (1→4), β (1→5), and β (1→6); and
n is 1 to 250.

In LPS of Formula XZY, the core Z is a chemical moiety linking a lipid A to an O antigen. In some embodiments, a Z can be a trisaccharide represented by formula

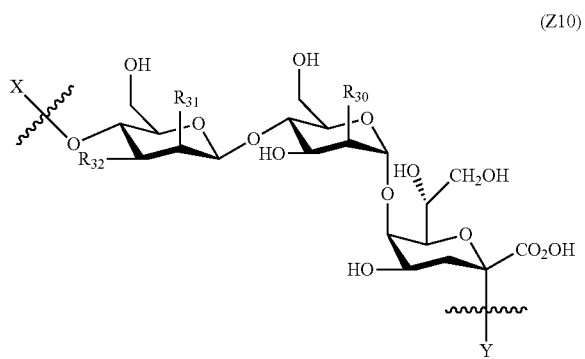

(Z10)

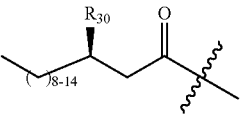

(Y11)

wherein R30 is hydrogen H, OH or represented by Formula (Y12):

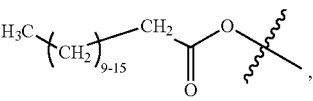

(Y12)

wherein
R30 to R32 are each independently a hydrogen H or represented by Formula (Z11):

R20 and R21 is represented by Formula (Y10):

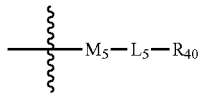

(Z11)

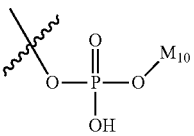

(Y10)

wherein M5 a monosaccharide selected from the group consisting of monosaccharide represented by Formulas (Xa) to (Xw), and R40 is a hydrogen H or a monosaccharide selected from the group consisting of monosaccharide represented by Formulas (Xa) to (Xw), wherein M5 and R40 are linked by linkage L5 selected from the group consisting of: α (1→2), α (1→3), α (1→4), α (1→5), α (1→6), β (1→2), β (1→3), β (1→4), β (1→5), and β (1→6).

In LPS from *Francisella* of formula XZY, the LPS further comprises a lipid A component Y. In some embodiments, Y is as a chemical moiety having at least one C12 to C18 lin (Y1a)

[Structure of Y1a showing disaccharide with phosphate groups, hydroxyl groups, and substituents R10, R11, R12, R13]

wherein R10, R11, R12 and R13 are defined as for Formula (Y10).

In some embodiments, the LPS comprises a tetrasaccharide repeat of (Qui4NFm-GalNAcAN-GalNAcAN-QuiNAc)$_n$, with Qui4NFm at the non-reducing end and n between 1 and 100.

In some embodiments herein described an antigenic *Francisella* polysaccharide further comprising a lipid component, can comprise an antigenic fragment of *Francisella* LPS which comprises at least the O-antigen domain. In some embodiments, an antigenic *Francisella* LPS fragment can further comprise an LPS core polysaccharide herein described in addition to the 0-antigen. In some embodiments, an antigenic *Francisella* LPS fragment can further comprise both a lipid A and a core polysaccharide herein described in addition to the O-antigen. An antigenic *Francisella* LPS fragment in accordance with the disclosure is capable of triggering a humoral immune response at a same, reduced or increased level compared to the *Francisella* LPS as will be understood by a skilled person.

In some embodiments, an antigenic *Francisella* LPS or fragments thereof herein described can be purified from any strain of *Francisella tularensis*. In some embodiments, *Francisella* LPS can be derived from *Francisella tularensis* subspecies *holarctica* Live Vaccine Strain (LVS). General methods of isolating LPS from a bacterial cell membrane can be found in [13-16], each incorporated by reference in its entirety.

One of the most common methods for isolation of LPS from bacterial cell walls involves disruption of the cell wall by sonication followed by proteinase and nuclease treatment. A hot phenol-mediated extraction step follows, which eliminates any residual amounts of enzymes added previously. Briefly, bacteria are disrupted by an overnight incubation with shaking at 37° C. in a buffer (pH 8.0) containing Lysozyme, followed by incubation with micrococcal nuclease. LPS is then precipitated and washed using Ethanol/Sodium Acetate. Purified LPS can be further characterized by SDS-PAGE electrophoresis followed by silver and commassie blue staining and HPLC according to techniques identifiable by a skilled person. Additional methods can be identified by a skilled person upon reading of the present disclosure.

In some embodiments herein described, the antigenic *Francisella* polysaccharide or derivative of formula (XI) can be an antigenic capsule polysaccharide (CPS) from a *Francisella* bacterium or a fragment thereof which is capable of triggering a humoral immune response or a derivative thereof.

The term "capsule polysaccharide (CPS)" as used herein indicates a macromolecule attached to the surface of *Francisella* having a molecular weight higher than 100 kDa and composed of a lipid component and a polysaccharide component comprising a varying number of tetrasaccharide repeating units. The characteristics of *F. tularenesis* CPS include 1) phenol resistance, 2) protease resistance, 3) ethanol precipitable, 4) high molecular weight (>100 kDa).

In some of those embodiments, the structure and composition of *F. tularensis* CPS can have a same or similar structure of the LPS O-antigen and therefore have formula (XII)

$$H-(M_1-L_1-M_2-L_2-M_3-L_3-M_4-L_4)_n\text{---}Z10$$

in which M1-M4 can each independently be selected from the group consisting of (Xa) to (Xw):

(Xa)

[Structure of α-D-Mannose]

α-D-Mannose or α-D-Man (Xb)

[Structure of β-D-Mannose]

β-D-Mannose or β-D-Man (Xc)

[Structure of α-D-Glucose]

α-D-Glucose or α-D-Glc (Xd)

[Structure of β-D-Glucose]

β-D-Glucose or β-D-Glc (Xe)

[Structure of α-D-glucosamine]

α-D-glucosamine or α-D-GlcN

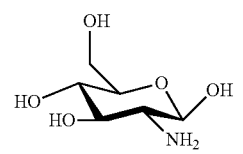

β-D-glucosamine or β-D-GlcN

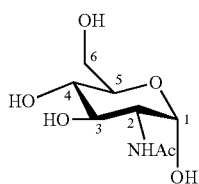

α-D-N-Acetylglucosamine or
α-D-GlcNAc

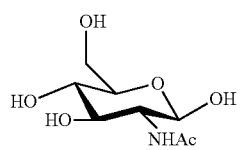

β-D-N-Acetylglucosamine or
β-D-GlcNAc

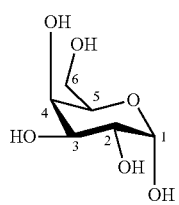

α-D-Galactose or α-D-Gal

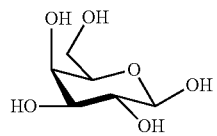

β-D-Galactose or β-D-Gal

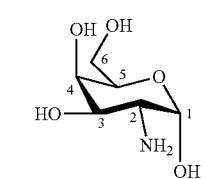

α-D-Galactosamine or α-D-GalN

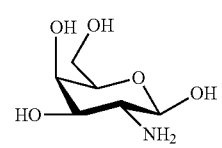

β-D-Galactosamine or β-D-GalN (Xf)

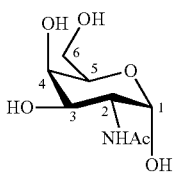

α-D-N-Acetylgalactosamine or
α-D-GalNAc (Xg)

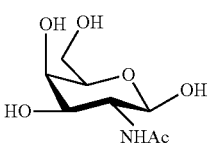

β-D-N-Acetylgalactosamine or
β-D-GalNAc (Xh)

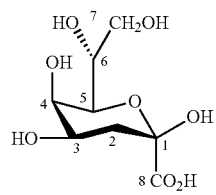

β-Kdo (β anomer of cyclized 3-Deoxy-
D-manno-oct-2-ulsonic acid)

(Xi)

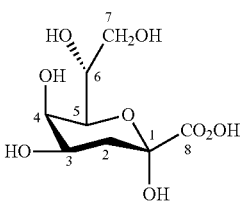

α-Kdo (α anomer of cyclized 3-Deoxy-
D-manno-oct-2-ulsonic acid)

(Xj)

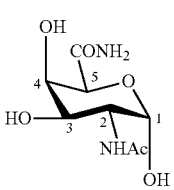

α-2-Acetamido-2-deoxy-D-
galacturonamide or α-D-GalNAcAN (Xk)

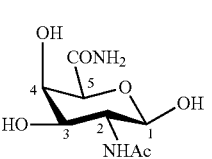

β-2-Acetamido-2-deoxy-D-
galacturonamide or β-D-GalNAcAN (Xl)

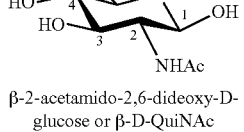

β-2-acetamido-2,6-dideoxy-D-
glucose or β-D-QuiNAc (Xm)

(Xn)

(Xo)

(Xp)

(Xq)

(Xr)

(Xs)

(Xt)

α-2-acetamido-2,6-dideoxy-D-
glucose or α-D-QuiNAc (Xu)

β-2, 4-Diacetamido-2,4,6-trideoxy-D-
glucose or β-D-Qui2NAc4NAc (Xv)

α-2, 4-Diacetamido-2,4,6-trideoxy-D-
glucose or α-D-Qui2NAc4NAc (Xw)

β-4-Formamido-4,6-dideoxy-D-glucose
or β-D-Qui4NFm in which L1-L4 can be selected independently from the group consisting of:
α (1→2), α (1→3), α (1→4), α (1→5), α (1→6), β (1→2), β (1→3), β (1→4), β (1→5), and β (1→6); and
n is 1 to 1000.

In some embodiments, the CPS comprises a tetrasaccharide repeat of (Qui4NFm-GalNAcAN-GalNAcAN-QuiNAc)$_n$, wherein n is greater than 100.

In particular, in some embodiments, F. tularensis capsule polysaccharide can comprise a tetrasaccharide repeat unit such as 2-acetamido-2,6-dideoxy-O-D-glucose (O-QuiNAc), 4,6-dideoxy-4-formamido-D-glucose (O-Qui4NFm), and/or 2-acetamido-2-deoxy-O-D-galacturonamide (0-GalNAcAN). In some embodiments, the F. tularensis CPS tetrasaccharide can have a molecular mass of approximately 790 Da, comprised of the following saccharides in this specific order: β-D-Qui4NFm (Xw), α-D-GalNAcAN (Xq), α-D-GalNAcAN (Xq), and β-D-QuiNAc (Xs).

In some embodiments of F. tularensis CPS, the tetrasaccharide units of formula (XII) are further covalently linked to a lipid component. The CPS lipid moiety has the structural properties characteristic of F. tularensis lipid A, but with a composition distinct from the free lipid A. In particular, the CPS Lipid A-like anchors have molar ratios of 3-OH-18:0/3-OH-16:0 less than 3 compared to >5 for Lipid A or LPS. The most prominent non-hydroxylated fatty acid present in CPS Lipid A-like anchors is C14:0 compared to C16:0 for LipidA or LPS.

Methods of extraction and purification of a F. tularensis CPS are identifiable by a skilled person as well as methods for the related characterization. A specific example can be found in related references such as in Apicella et al. [17] however other procedures can be used as will be understood by a skilled person (see also Example 19 of the present disclosure).

In some embodiments, the antigenic Francisella polysaccharide component can comprise more than one antigenic polysaccharide from the Francisella bacterium or derivative thereof in the sense of the disclosure. In particular in some embodiment the antigenic Francisella polysaccharide to be included in the antigenic combination of the disclosure can comprise an antigenic Francisella lipopolysaccharide (LPS) and/or a fragment thereof and an antigenic capsule Francisella polysaccharide (CPS) or a fragment thereof in various combinations as will be understood by a skilled person.

In antigenic combination herein described an antigenic Francisella polysaccharide component is comprised together with at least one protein antigen component from the Francisella bacterium.

The term "protein antigen" refers to a protein that is an antigen with respect to the immune system of an individual. In embodiments herein described, a protein antigen incorporated in the antigenic composition is a protein antigen isolated from a Francisella bacterium or recombinantly produced to obtain protein antigen with the primary, secondary and tertiary structure of a protein antigen isolated from a Francisella bacterium as will be understood by a skilled person.

In embodiments herein described a Francisella protein antigen component comprises one or more Francisella protein antigens and/or one or more derivatives thereof.

Suitable Francisella protein antigens in the sense of the present disclosure comprise any protein antigen from a Francisella bacterium that can confer cell mediated immune response. In particular, in some embodiments, suitable Francisella protein antigens comprise antigens capable of inducing a robust T cell response in vivo in an INF-7 dependent manner. A variety of in vitro and in vivo assays such as cell-based assays and assay in animals, can be used for identification and selection of protein antigens as will be understood by a person of ordinary skill in the art upon reading of the present disclosure.

In some embodiments, the Francisella protein antigen comprised in the antigenic combination can be selected from a group consisting of IglC, DnaK, OmpA, SucB, LpnA, FopA, Lpp3, Type IV pilus fiber building block protein, FopB, FTT_1676, FTT_1441, and FTT_1778c.

A list of exemplary coding sequences of the above-mentioned Francisella protein antigens from Francisella tularensis subsp. tularensis SCHU S4 is reported in Table 1 below. The sequences are available from public databases such as NCBI gene database (see e.g. the web addresses for the exemplary sequences indicated in the table) at the date of filing of the present disclosure as will be understood by a person of ordinary skill in the art.

TABLE 1

Exemplary Francisella protein antigen gene sequences from Francisella tularensis subsp. tularensis SCHU S4

| Annotation | Gene sequences | SEQ ID NO | Number of TM helices |
|---|---|---|---|
| Ig1C1 and Ig1C2 (FTT1357c and FTT_1712c): Web page ncbi.nlm.nih. gov/gene/?term= iglC+AND+ francisella | atgattatgagtgagatgataacaagacaacaggtaacaagtggcgagaccattc<br>atgtgagaactgatcctactgcatgtataggatctcatcctaattgtagattatt<br>tattgattctttaactatagctggggagaaacttgataaaaatatcgttgctata<br>gatggtgagaggatgtcacgaaagctgattcggctacagctgctgctagtgtaa<br>tacgtttatctataacgccaggctctataaatccaacaataagtattactcttgg<br>tgttctaattaaatcaaatgttagaactaaaattgaagagaaagtttcgagtata<br>ttacaagcaagtgctacagatatgaaaattaagttaggtaattctaataaaaaac<br>aagagtataaaactgatgaagcatggggtattatgatagatctatctaatttaga<br>gttatatccaataagtgctaaggcttttagtattagtatagagccaacagaactt<br>atgggtgtttcaaaagatggaatgagatatcatattatatctatagatggtctta<br>caacatctcaaggaagtttgccagtatgttgcgcagctagcacagataaaggagt<br>tgctaaaataggatatattgcagctgcatag | 1 | 0 |
| DnaK (FTT_1269c) Web page ncbi.nlm.nih. gov/gene/3191531 | ATGGGAAAAATAATAGGTATAGATTTAGGTACTACTAACTCTTGTCTTGCTATTA<br>TGGATGCAAGACTGCTAAAGTTATTGAGAATGCTGAAGGACATAGAACAACACC<br>TTCAGTTGTGGCATATACTGATAGCGGTGAAATATTAGTAGGTCAAGCTGCTAAA<br>AGACAAGCTGTAACTAACCCTGATAATACATTCTTTGCTATCAAGAGACTTATAG<br>GTCGTAAGTACGATGATAAAGCTGTACAAGAAGATATTAAAAAGAAAGTACCTTA<br>TGCGGTAATTAAAGCTGATAATGGTGATGCTTGGGTTGCTACTAAAGAAGGCAAA<br>AAAATGGCTCCACCACAAGTTTCTGCAGAAGTTCTAAGAAAAATGAAAAAAACAG<br>CAGAAGACTATCTAGGTGAACCAGTTACAGAAGCTGTAATTACAGTGCCAGCATA<br>CTTTAACGATAGTCAAAGACAAGCTACAAAAGATGCTGGTAAAATAGCAGGTCTT<br>GAAGTTAAAAGAATTATCAACGAGCCTACAGCGGCAGCGCTGGCATATGGTAG<br>ACTCTAAGAAAGGTGAGCAAACTGTAGCGGTGTATGACCTAGGTGGTGGTACATT<br>CGATATCTCAATTATTGAGATTGCTGATGTTGATGGCGATAACCAAATCGAAGTA<br>TTATCAACCAATGGTGATACTTTCTTAGGTGGTGAAGACTTCGACTTGGCTTTAA<br>TGAACTATCTAATTGACGAGTTCAAAAAGAGCAAGGTATAGATCTTCACAATGA<br>TAAGCTTGCTTTACAAAGAGTTAGAGAGGCTGCTGAGAAAGCTAAAGTAGAATTA<br>TCTTCAGCACAACAAACTGATGTTAACCTACCTTACATCACAGCAGATGCTACTG<br>GACCTAAGCACTTAAATATCAAAGTAACTAGAGCTAAGTTTGAGTCTTTAGTTTC<br>TGATCTTGTAATGAGATCACTTGAGCCTTGTAAGAAAGCTCTTGAAGATGCTGGT<br>TTAAGTAAGTCTGATATTACAGAAGTATTACTAGTGGGTGGACAAGCTGCTATGC<br>CTCTAGTACAAGAGAAAGTAAAAGAGTTTTTTGGTAAAGAGCCACGTAAAGATGT<br>GAACCCTGATGAAGCTGTTGCAGTTGGTGCGGCTATTCAAGGTGGTGTATTAGCA<br>GGTGATGTTAAAGATATTCTTTTATTGGATGTAACACCGCTTTCTCTAGGTATTG<br>AGACTATGGGAGGTGTTATGACTAAGCTTATCGAGAGAAATACTACGATTCCTAC<br>TAAGAAGTCGCAAGTATTCTCAACAGCTGAAGATAACCAGCCTGCGGTAACTATT<br>CATGTACTTCAAGGTGAGCGTGAAATGGCTTCTGCAAACAATCTTTAGGTAGAT<br>TTGATCTGGCAGATATTCCACCAGCGCCACGTGGTATGCCACAAATTGAGGTTAC<br>TTTTGATATAGATGCTAACGGTATATTAAATGTGTCTGCTAAAGATAAAGCTACT<br>GGTAAAGAGCAAAATATTGTGATTAAGTCTTCAAGTGGTTTATCTGAAGAGGATA<br>TCGAAAAAATGGTACAAGACGCTGAAGCTAATGCAGAAGCAGATAAAAAGTTCCA<br>TGATTTAGTTACTGCTAGAAATACTGCTGATAACTTAATTCATAGCTCAAGAAAA<br>GCAATTCAAGAACTGGGTGACAAAGTAACAGCAGCAGAAAAAGAAAAAATCGAAG<br>AAGCTTGTAAAGAGCTTGAAGCAGCAACTAAAGGTGATGATAAGCAAGCGATTGA<br>ATCTAAAACTAAGGCTCTAGAAGAAGCATTTGCGCCAATAGCTCAAAAAGCTTAT<br>GCTGAGCAAGCTCAAGCTGCTGTTGCCCAAGGTGGTGCTAAAGCTGAAGAACCTA<br>AGAAAGAAGAAGATGTTGTTGATGCTGACTTTGAGGATGTTGAAGACGACAAAAA<br>ATAA | 3 | 0 |
| OmpA (FTT_0831c) Web page ncbi.nlm.nih. gov/gene/3191752 | ATGAAAAAAATTACTGAAACTATGCTTAATGACATCATTAATTACAACACTCTCAG<br>CCTGCCAAACACTAGATGATAAAGATAAAGATAGTGGTCCACTAACATTTCCAAC<br>ATTGAACCTTGTACTGCCGAGCTACTTCAATCAAATCAATCTTTTATATGTGTA<br>AAAGAACAAACAGGACCTGATCTAATCGAAACAAATATAAAATTTGATGCTGATA<br>GCTATACATTAAACACTCAGGCTAAAGAAGTTTTAGATAAGCTTTTTGCTTATTT<br>GAAACTAACTGATACTACAAATTTCACAATTAAAGGTTATGCTGGAAAAGTTGAA<br>TCAAAAATTCTCACAGATCAGAAAATCCTAACCGACTATAATATTAGACTATCAA<br>AAAACCGTGCTAGTAGTGTCGAAGAATACCTTGTAAACAAAGGTCTTGGCTCTAG<br>TGATGGAATTACTATTAAAGCCTTAGGTTATCAAGATCCTATCGCCCCTAATGAC<br>TCAACCTCAAGTAGAGCTATAAATCAGCGCGTTGAAATTACTCTAAAAAGTAGAC<br>TTATAGAGCAAATTGATAATATTGAAAATAACTTAGAGCATGTCAGCACAGCTGA<br>ATATACAAAATTCTTCTCAAATGTATATTTACTTAATGATAATCAGATAGACAAT<br>ATTTCAAGAATATACAATTCTAGAGAGAAACGCCCAATACTCGGAATTAACTTTA<br>AAATCTTTGCTAACAAAGAATATACAGCAGCCAAGGATAACAGTAACTTCATAAT<br>AATATCCGAACCAAAACCAATATCTTCATTTAATGATGATAAAAAAGTCTATAGA<br>CTAGGCTCAGCAAAATATGATTATACCTTTAAAGGTATAACAGCATTGACGATAA<br>CTAATTTAAGTCGTGAAGCTAGTGTAGGCAATTATGTAATACCTAATGATATTGT<br>TTCACAACAACTGCCAGAACAAACTTTTAAAATGAAAGTAAAATAACAGCTAAT<br>GTACTTGAAGATGTAATGAATACTAATACATTCTCATCTTCTAATAATAGTATTC<br>TATTGAACAAAGGCGCTGCTGATGGCTTGAAAGTAGGCGCTCAAGTTATTTTATA<br>TGAACCAGAAACCAGAGTAGATGGTTTTCCAGTCCCACCTAAATATATTGGTTAT<br>GGTTTTATCTATAGAGAATCTCAACACTACTCTATAGCCCTAATTGTCAATTCAC<br>TACAAGAAATTACAAATAATTCAATGGCAACGACTATTTTATAA | 5 | 0 |

TABLE 1-continued

Exemplary *Francisella* protein antigen gene sequences from *Francisella tularensis* subsp. *tularensis* SCHU S4

| Annotation | Gene sequences | SEQ ID NO | Number of TM helices |
|---|---|---|---|
| SucB (FTT_0077) Web page ncbi.nlm.nih. gov/gene/?term= SucB+ *francisella* | ATGGTTGAATTAAAAGTACCTATGTTCCCAGAGTCTGTAGCAGATGGCACATTAG CTCAATGGAATAAAAACGAAGGTGACTTTGTAAATGAGGGCGATATCTTGGCAGA GATTGAGACTGATAAAGTTGTTCTAGAAGTACCTGCAACATCTAGTGGTGTTTTA AAAGGGATAAAAAAACATGCTGGTGATACAGTGCTTTCAGAAGAGTCATTAGCGA TCATTGATACTGCTGTTTCTACATCTGAACCTAACCAACAAACTACTAATCAAGG AAATGCTTCAGAAGCAACTGCTACTGGGCAAGAAATTGATATTAAGGCGCCTGTA TTTCCAGAGTCTGTAGCAGATGGCACGATCTCAGAGTGGCATAAGAAAGAGGGTG AGGCTGTTTCTGAGGGTGATATCTTAGCAGAGATTGAGACTGATAAGGTTGTTCT AGAGGTTCCGGCAACATCAAATGGTGTTTTGACAAAAATATTAAAAACAGCAGGA GAGACTGTACTATCTGCAGAGCTTATCGCTAAGATTACAGCAGGAGGCGCAACTG CTACTACGAAATCAGAAGCTTCGGTGGGAGTTTCTCAAGCAAATAATGATCCGCA TCTAGTACCTTCAGCACGTAAAGCTTTTAATGCAAGCGGCTTGGATACTGCTGCT AATATCGAAGGTACAGGTAAAAAAGGGCGTATAACTTCTGAAGATGTCAAAAAAG CAGTTGCATCAGTAAATAAACCTCAACAACAGACAGTTGTTATAAATCAAGGTGC TAGATATGAAAAAGAGTCAAGATGACTCGTCTGCGTCAGACTATAGCAAATAGG TTAGTTGAGGTTCAACATACTAATGCAATCTTAACTACTTTCAATGAAGTAGATA TGAGTGCAGTTATGGAGCTTAGAAACAAATATAAAGATATGTTTGTCAAAGAACA TGATACTAAGCTTGGCTTTATGTCTTTCTTTATCAAAGCAGCAACAGAAGCACTT AAGAAATTCCCAGATGTAAATGCCTCTATTGATGGTGATGAGATTGTTTACCATA ATTATTTTGATATTGGTATTGCTGTAGGTACTGATAGGGGTCTAGTGGTACCTGT ACTAAGAGATACAGATACTAAATCTCTAGCTGAATTAGAAGCCGATGTTTTAGAC AAAGCGATTAAAGGTCGTGATGGTAAATTAAGCCTTGAAGATATGCAAGGTGGTA CATTTACGATTACAAATGGCGGAACTTATGGTTCGATGTTATCTACGCCTATTAT TAATTCACCGCAAAGTGCTATTTTAGGTATGCATAATATTGTTGAGCGTCCTGTA GTTGTTAAGGGTGAGATTAAGATTCGTCCAATTATGTATTTAGCGTTATCTTACG ACCATAGAATCATTGATGGCGGTACATCTGTAAGATTCTTGAAGATGATCAAAGA GCTAATTGAAGATCCAAATAGAATTCTTCTACAAGTATAG | 7 | 0 |
| LpnA/Tu14 (FTT_0901) Web page ncbi.nlm.nih. gov/gene/3191792 | ATGAAAAAAATAATTGAGCTTAGTCTTTTATCTTTATCAATCGCAGGTTTAGCGA GCTGTTCTACTCTAGGGTTAGGTGGCTCTGATGATGCAAAAGCTTCAGCTAAAGA TACTGCTGCTGCTCAGACAGCTACTACTGAGCAAGCTGCTGCTGATCTAAGCCA ACTGCAAAAGTAAGTTTAAATAAACTTGGTCAGGATAAAATAAAAGCAACTGTAT ATACAACATACAATAATAACCCACAAGGAAGTGTAAGATTACAATGGCAGGCTCC AGAAGGTTCTAAGTGCCATGATACAAGCTTCCCAATTACTAAGTATGCTGAGAAG AACGATAAAACTTGGGCAACTGTAACAGTTAAGCAAGGTAATAACTTCTGTAGCG GTAAGTGGACAGCTAATGTAGTTTATGACAAAGAAGTAATCGCTTCTGATTCAAT AAATATTTAA | 9 | 1 |
| FopA1 (FTT_0583) Web page ncbi.nlm.nih. gov/gene/3192005 | TTGATGAGATTAAAAAGTATTGTTATAGCTACAACTGTATTATTAGGTTCAGCTA CAGCATCTATCGCTGCAGGTTCAGATAATATCGATACATTAGCAAACACTAATTC AGCTACTACACAAAGCAGTGGTTTTGCAGCTAATAATTTCATTGCTCCTTTTGCA AATACTTATAGCGCTTTGACTAACAAGGACAATACTTGGGGTCCTCAAGATAGAA CTGGCCAGTGGTACTTAGGTGTAGATGCTAACGGTCTAGCTGGAACTCCTAACTC TCCATCAGGTGCTGGTGCTAACTTCACAATCGGTTATAACATCAATAAATACTTC GCTGTACAGTACAACCAATTAGTTGGTAGAGTATTTGCTGGTTTAGGTGAAGGTG TTGTAAACTTTAGTAATAATACTGTTTACTCCATATGCTGCAGGTGGTGCTGG TTGGGCAAATCTAGCAGGTCAAGCAACAGGTGCTTGGGATGTGGGTGGTGGTCTT AAGTTTGAACTATCTAGAAATGTTCAAGCAAGTGTTGACTACAGATATATCCAAA CAATGGCACCTAGTAATATTTCTGGTGCTAATGGCAGAGCGGGTACTAACATGAT TGGTGCTGGTTTAACATGGTTCTTTGGTGGCAAAGATACTACTAATAATGACACT GGTAATATTCAGGATAATGGTGCGACTACAGCTGCTCAAACTGTTGCTATGCCAA CTATTGATGAGTCTAAGTATGTTTTACCTGCTGGTATTAAGCAATGTGAAGGCAA CTTTAATCTAACTGAAGATGGTGTCGCGTGCTATACAATAAATGGTGATGATGTA ACAGTTTACCTAGATACTAAGTTTGCTTATGATAAAGCTACTTTAAATGCTAAAG GTAAAAAAGCTATTGCATCTTTTGTTAATTTTATCAAGGATAGTAACATTAGCTC TGTAACAGTTAAAGGTTATGCTTCTCAAGGTCAAACTGGTAGCGAGTTTGATATA TATAACCAAAACTTTCTGAGAAGAGAGCACAAGCTGTTGCTGATTACATGAAGC AATTAGGTTTAGATAGTGAGAAATAATTACTAAAGGTTTTGGCTATAATGATAC TTTAGGTGGTATTCATAAGTCTGATCCGCGTAACCAGCGTGTAGAAGCTAGCGTA TCAGCTCCACTTAAAGAAGCTAACTAA | 11 | 1 |
| Lpp3 (FTT_1416c) Web page ncbi.nlm.nih. gov/gene/3191965 | ATGAAAGGATTAAAAGCAAAATATATATAATTTTTTTGGCTGCAGTGCTAGCGG TTATTTCAGGCTGTGCTACTGACAAAGGAACCCAGTATAAAGATGGTTATTATAT AACTACGCTTAACTATAATTTTAATACGGTTTATAATGCTACTCTGCAAGCAATA CAAAACGGACAAACATTTGATTATAAGAGTAACCCATATGATATATCAGTTAACA AAAATAATGGAACTGATGCTGAGATAGTTTCTGCTAGTGATAGCGATTCTACAGA CTCTCTACAAGTAGCAATGAAGAAGTTACCTAATAATGCTACAAGGATTTCAATT AAAATATGGTAGCCAAGGAAATTCGATTAGATCTTCAGCGCTAATAGGCATAATAG AAGGAAATATTCGCTACGCTAATACAA | 13 | 1 |

TABLE 1-continued

Exemplary *Francisella* protein antigen gene sequences from *Francisella tularensis* subsp. *tularensis* SCHU S4

| Annotation | Gene sequences | SEQ ID NO | Number of TM helices |
|---|---|---|---|
| Type IV pilus fiber building block protein (FTT_0890c) Web page ncbi.nlm.nih.gov/gene/?term=FTT_0890c+ francisella | ATGAAAAAGAAAATGCAAAAAGGTTTCTCACTAGTTGAGTTAATGGTAGTGATCG CGATCATCGCTATCCTAGCAGCTGTAGCGATCCCGATGTACTCTAACTACACTAC ACGTGCTCAGTTAGGCTCTGATCTATCTGCTCTAGGTGGTGCTAAAGCTACAGTA GCTGAAAGAATAGCTAACAACAATGGTGATGCATCTCAAGTTACAATTCTTCAAG CTAATGCCGCTGCAAATGGTCTTCCAAGTGGTGCTTCAGTTGCTGCTGGTACTAT TAGTTATCCATCAACAGTATCTGGTGCAACAATTCAATTAGCTCCTACAGTAAGT TCCGGTGCTATTACTTGGACTTGTAATATTTCAGGTGTATCAGCATCTCAAGTAC CATCTAACTGTAATGCTATCTAA | 15 | 1 |
| FopB (FTT_1747) Web page ncbi.nlm.nih.gov/gene/?term=FTT_1747+ francisella | ATGTTTTATAAACTAAACAAGCAAGGAAGAAAAATTATGAAAAAAACTATACTAG GAGCAATGATTGCTGGTGGTTTGATGGTTTCTGCAACTACAGCTATGGCTGGTGG GGTAGGTTTTGCTAATGTCCAAGATATTTTTGAAACTTCACCTCTTGGTAAAGCA AAGGTAACAGCTGATGAGAAAAAGCTAAAGCCACAGATGGATCAACTTAAGCAAA ACATCACTGCTTTACAAGAGAAAGTAAATGCATACACTCAAGAAAAAGATGATGT TCAAACAGATGATTCTAAAGGCGATACTAAAGATGCACAGTCAGCAGACAAAGTA GAAAATCAAGATAAGCAACAAGCTCAAGCAGATCTTGAAAAAGCAATGAAAGATT ACCAAAACCTAATGAATCAGGTTCAAAAAATGGCTTCTGACGATGCTGATGCGTT CAAAGATGCTTTGACTAAGGCTTCTGCTCAAGTTGCTAAAGAGAAGCAACTTGAT GCTATTTTACCTGCTGAAATGAGTCTATATAATGTTGATAGTATTGATGTTACTA AAGATGTTATAGCTAAGATGCAATAA | 17 | 1 |
| Hypothetical protein (FTT_1676) Web page ncbi.nlm.nih.gov/gene/?term=FTT_1676+ francisella | ATGGAATTTAGTATGCGCAATATATTCAAAAAAACATTATTAATATTATTACTAA GCGTAATTATAGCATCATGTGGTATGCTATCTAACGACCAGTTTGTTTATCTAGG TCATGGTGAGAACTCTCCTGACTATCAGCTCTATTACGATAAGACACAAAAACTT TTTGTGCTAATTGATAAGAGAAATGGTTGTTTTCAGAAAGATGATACAGGTACTT GTCTTGCATTTACATTAAAACAAGCTCGTGAATTTAGAGAATATGTTTTAGCTAA GATGATTGAAATAGATGTTAGACTTGCTAAGGACGACTATGGAAACTACGCTATT GAAGAGTTACGAAAGCTGGGGTTACCACGGTTAATAAACCAATTAAAACTAAAA AAGTTTTTGCAACTCCAGTTAAGCAGATTGTCCTTGATAGAAAGCAACAATATCA CCTTGTTAGAAAAGAATATGAAATAGATTCAAATCTTGTAGCAATGGTTGTTAAT GATAAAGAAGGTAAAAAACGTATAAAAGTTGCTTATACTGTTGATTTTCCTGGCT TAGAGAAAGAGTATAGTACCGAGCTTAGACCATTTATTATTGATCCAGAATACTT ATATACACATATGACTATTGACGCTGTCCATGAAGCTCAATTCATGCAGAGAGAT GTTATGAAGAGTCAAACAATGTCAAAAAGAAAGTTGATGACTATCTTAAAGATG TTGTCGACAGCGATAAAAAAGATACAGGATACACTCACCAAGAAGTTGCAAGTAG TGTCGCAGCGCTAGATAACGATCTAATAACTAAGGCAGATGAGCAACGCGAAGAC AAAGAAACCACACTAGCAAGTGGTAGTAGTATTAGTACTATAGCGAAAAAGCCTA TCAATCAAGAAAGTAGTGGTAGTACAATACAAACAGCCACAAAAACTGCTTCAAC CACTCAAGTTGATAGCAATGATACTCCAAAAACAACTCTAGCAAGTGACAATAAA TAG | 19 | 1 |
| Hypothetical protein (FTT_1441) Web page ncbi.nlm.nih.gov/gene/?term=FTT_1441+ francisella | ATGTTGATTATAATGATTAGAGTTTTAAATAATGGAGATAACAATATGGAACTTC AATTAGAAAATAAACAAGAAATTATTGATCAATTAAATAAAATCTTAGAACTCGA AATGTCTGGAGTTGTGCGTTATACTCATTATTCTTTAATGATTATAGGTCATAAT AGAATTCCTATAGTTAGTTGGATGCAATCTCAAGCAAGTGAAAGTTTAACTCATG CTACTGCAGCAGGTGAAATGATAACTCACTTTGGTGAGCATCCATCTTTAAAAAT AGCAGATTTAAACGAAACTTATCAGCATAATATCAATGATATATTAATCGAAAGT CTAGAACATGAGAAAAAAGCTGTTTCAGCATACTATGAACTTCTAAAACTTGTAA ATGGCAAATCAATAATATTAGAAGAATATGCAAGAAAACTCATAGTTGAAGAAGA AACGCACATTGGTGAAGTAGAAAAAAATGTTAAGAAAACCTGCATAA | 21 | 0 |
| Hypothetical protein (FTT_1778c) Web page ncbi.nlm.nih.gov/gene/?term=FTT_1778c+ francisella | ATGAAATTAAGAAAGTATTAATCGCGACATTATTAGGAGCTTCTGCTTTATCTT TAAGTAGTTGTTGGTTACTTGTTGGTGCAGCTGTTGGTGGTGGAACTGCTGCGTA TATTTCTGGTGAGTATTCAATGAATATGAGTGGCAGTGTAAAAGATATTTACAAT GCTACTTTAAAAGCTGTTCAAAGCAATGATGATTTTGTAATTACTAAAAAATCTA TTACTTCTGTTGATGCAGTTGTTGATGGTAGTATTAAGGTAGACTCAACAAGTTT CTATGTTAAAATAGAAAAACTTACTGATAATGCTTCAAAAGTTACAATTAAGTTT GGTACTTTTGGTGACCAAGCAATGTCAGCAACATTAATGGATCAAATCCAAAAGA ATCTTTAA | 23 | 1 |

A list of exemplary protein sequences of the *Francisella* protein antigens is reported in Table 2 below. The sequences are available from public databases ((see e.g. the web addresses for the exemplary sequences indicated in the table) at the date of filing of the present disclosure as will be understood by a person of ordinary skill in the art.

TABLE 2

Exemplary *Francisella* protein antigen protein sequences from *Francisella tularensis* subsp. *tularensis* SCHU S4

| Annotation | Gene sequences | SEQ ID NO |
|---|---|---|
| FTT_1357c and FTT_1712c (IglC) Web page uniprot.org/ uniprot/Q5NEC5) | MIMSEMITRQQVISGETIHVRTDPTACIGSHPNCRLFIDSLTIAGEKLDKNIVAIDGGEDVIKADS ATAAASVIRLSITPGSINPTISITLGVLIKSNVRTKIEEKVSSILQASATDMKIKLGNSNKKQEYK TDEAWGIMIDLSNLELYPISAKAFSISIEPTELMGVSKDGMRYHIISIDGLITSQGSLPVCCAAST DKGVAKIGYIAAA | 2 |
| FTT_1269c (DnaK) Web page uniprot.org/ uniprot/Q5NFG7) | MGKIIGIDLGTINSCLAIMDGKTAKVIENAEGHRTIPSVVAYTDSGEILVGQAAKRQAVINPDNIF FAIKRLIGRKYDDKAVQEDIKKKVPYAVIKADNGDAWVATKEGKKMAPPQVSAEVLAKMKKTAEDY LGEPVTEAVITVPAYFNDSQRQATKDAGKIAGLEVKRIINEPTAAALAYGVDSKKGEQTVAVYDLG GGIFDISIIEIADVDGDNQIEVLSINGDIFLGGEDFDLALMNYLIDEFKKEQGIDLHNDKLALQRV REAAEKAKVELSSAQQTDVNLPYITADATGPKHLNIKVIRAKFESLVSDLVMRSLEPCKKALEDAG LSKSDITEVLLVGGQTRMPLVQEKVKEFFGKEPRKDVNPDEAVAVGAAIQGGVLAGDVKDILLLDV TPLSLGIETMGGVMTKLIERNITIPIKKSQVFSTAEDNQPAVTIHVLQGEREMASANKSLGRFDLA DIPPAPRGMPQIEVTFDIDANGILNVSAKDKATGKEQNIVIKSSSGLSEEDIEKMVQDAEANAEAD KKFHDLVTARNTADNLIHSSRKAIQELGDKVTAAEKEKIEEACKELEAATKGDDKQAIESKTKALE EAFAPIAQKAYAEQAQAAVAQGGAKAEEPKKEEDVVDADFEDVEDDKK | 4 |
| FTT_0831c (OmpA) Web page uniprot.org/ uniprot/Q5NGK6) | MKKLLKLCLMTSLITTLSACQTLDDKDKDSGPLTFPTLEPCTAELLQSNQSFICVKEQTGPDLIET NIKFDADSYTLNTQAKEVLDKLFAYLKLTDTTNFTIKGYAGKVESKILTDQKILTDYNIRLSKNRA SSVEEYLVNKGLGSSDGITIKALGYQDPIAPNDSTSSRAINQRVEITLKSRLIEQIDNIENNLEHV RPAEYTKFFSNVYLLNDNQIDNISRIYNSREKRPILGINFKIFANKEYTAAKDNSNFIIISEPKPI SSFNDDKKVYALGSAKYDYTFKGITALTITNLSREASVGNYVIPNDIVSQQLPEQTFKMKSKITAN VLEDVMNTNTFSSSYNSILLNKGAADGLKVGAQVILYEPETRVDGFPVPPKYIGYGFIYRESQHYS IALIVNSLQEITNNSMATTIL | 6 |
| FTT_0077 (SucB) Web page uniprot.org/ uniprot/Q5NIJ0) | MVELKVPMFPESVADGTLAQWNKNEGDFVNEGDILAEIETDKVVLEVPATSSGVLKGIKKHAGDTV LSEESLAIIDTAVSTSEPNQQTTNQGNASEATATGQEIDIKAPVFPESVADGTISEWHKKEGEAVS EGDILAEIETDKVVLEVPATSNGVLTKILKTAGETVLSAELIAKITAGGATATTKSEASVGVSQAN NDPHLVPSARKAFNASGLDTAANIEGTGKKGRITSEDVKKAVASVNKPQQQTVVINQGARYEKRVK MTRLRQTIANALVEVQHTNAILTTFNEVDMSAVMELANKYKDMFVKEHDTKLGEMSFFIKAATEAL KKEPDVNASIDGDEIVYHNYFDIGIAVGTDRGLVVPVLADTDTKSLAELEADVLDKAIKGRDGKLS LEDMQGGTFTITNGGTYGSMLSTPIINSPQSAILGMHNIVERPVVVKGEIKIRPIMYLALSYDHRI IDGGTSVRFLKMIKELIEDPNRILLQV | 8 |
| FTT_0583 (FopA) Web page uniprot.org/ uniprot/Q5NH85) | MMALKSIVIATTVLLGSATASIAAGSDNIDTLANTNSATTQSSGFAANNFIAPFANTYSALTNKDN TWGPQDRTGQWYLGVDANGLAGTPNSPSGAGANFTIGYNINKYFAVQYNQLVGRVFAGLGEGVVNF SNNTMFTPYAAGGAGWANLAGQATGAWDVGGGLKFELSRNVQASVDYRYIQTMAPSNISGANGRAG TNMIGAGLTWFFGGKDTTNNDTGNIQDNGATTAAQTVAMPTIDESKYVLPAGIKQCEGNFNLTEDG VACYTINGDDVTVYLDTKFAYDKATLNAKGKKAIASFVNFIKDSNISSVTVKGYASQGQTGSEFDI YNQKLSEKRAQAVADYMKQLGLDSEKIITKGFGYNDTLGGIHKSDPRNQRVEASVSAPLKEAN | 88 |
| FTT_0901 (LpnA/Tu14) Web page uniprot.org/ uniprot/Q5NGE4) | MKKIIELSLLSLSIAGLASCSTLGLGGSDDAKASAKDTAAAQTATTEQAAAVSKPTAKVSLNKLGQ DKIKATVYTTYNNNPQGSVALQWQAPEGSKCHDTSFPITKYAEKNDKTWATVTVKQGNNFCSGKWT ANVVYDKEVIASDSINI | 10 |
| FTT_1416c (Lpp3/ hypothetical lipoprotein) Web page uniprot.org/ uniprot/Q5NF33) | MKGLKAKIYIIFLAAVLAVISGCATDKGTQYKDGYYITTLNYNENTVYNATLQAIQNGQTFDYKSN PYDISVNKNNGTDAEIVSASDSDSTDSLQVAMKKLPNNATRISIKYGSQGNSIRSSALIGIIEGNI RYANT | 14 |
| FTT_0890c (Type IV pili fiber building block protein) Web page uniprot.org/ uniprot/Q5NGF5) | MKKKMQKGFSLVELMVVIAIIAILAAVAIPMYSNYTTRAQLGSDLSALGGAKATVAERIANNNGDA SQVTILQANAAANGLPSGASVAAGTISYPSTVSGATIQLAPTVSSGAITWTCNISGVSASQVPSNC NAI | 16 |
| FTT_1747 (FcpB outer membrane protein) Web page uniprot.org/ uniprot/Q5NEA1) | MFYKLNKQGRKIMKKTILGAMIAGGLMVSATTAMAGGVGFANVQDIFETSPLGKAKVTADEKKLKP QMDQLKQNITALQEKVNAYTQEKDDVQTDDSKGDTKDAQSADKVENQDKQQAQADLEKAMKDYQNL MNQVQKMASDDADAFKDALTKASAQVAKEKQLDAILPAEMSLYNVDSIDVTKDVIAKMQ | 18 |
| FTT_1676 (Hypothetical | MEFSMANIFKKILLILLLSVIIASCGMLSNDQFVYLGHGENSPDYQLYYDKTQKLEVLIDKRNGCF QKDDIGICLAFTLKQAREFREYVLAKMIEIDVALAKDDYGNYAIEELRKAGVTIVNKPIKTKKVFA | 20 |

TABLE 2-continued

Exemplary Francisella protein antigen protein sequences from Francisella tularensis subsp. tularensis SCHU S4

| Annotation | Gene sequences | SEQ ID NO |
|---|---|---|
| membrane protein) Web page uniprot.org/ uniprot/Q5NEG0) | TPVKQIVLDRKQQYHLVRKEYEIDSNLVAMVVNDKEGKKRIKVAYTVDFPGLEKEYSTELRPFIID PEYLYTHMTIDAVHEAQFMQRDVMKSQINVKKKVDDYLKDVVDSDKKDIGYTHQEVASSVAALDND LITKADEQREDKETTLASGSSISTIAKKPINQESSGSTIQTATKTASTIQVDSNDTPKTTLASDNK | |
| FTT_1441 (Hypothetical protein) Web page uniprot.org/ uniprot/Q5NF13) | MLIIMIRVLNNGDNNMELQLENKQEIIDQLNKILELEMSGVVRYTHYSLMIIGHNRIPIVSWMQSQ ASESLTHATAAGEMITHFGEHPSLKIADLNETYQHNINDILIESLEHEKKAVSAYYELLKLVNGKS IILEEYARKLIVEEETHIGEVEKMLRKPA | 22 |
| FTT_1778c (Hypothetical protein) Web page uniprot.org/ uniprot/Q5NE75) | MKLAKVLIAILLGASALSLSSCWLLVGAAVGGGTAAYISGEYSMNMSGSVKDIYNATLKAVQSNDD FVITKKSITSVDAVVDGSIKVDSTSFYVKIEKLIDNASKVTIKFGTFGDQAMSATLMDQIQKNL | 24 |
| FTT_0814c (Hypothetical protein) Web page uniprot.org/ uniprot/Q5NGM1) | MMDFKDQYNISSDGKLYINAKIMSHSSATANVIVVLQDQNGNQVYRKTDIQISPMDTYDLALAIDN IKAGDYKLIISSELAGAEAWQKDMNIKAVSSETSDDNNNPPPANQDINVNIESNIPYYQVNPNDSV TARAWASSLGNINLANNQVIIIAWNKTLQASGNDSSAYVKCPLPKNNQISITYLVSGDLNNVNCTI K | 25 |
| FTT_1043 (Mip/Peptidyl-prolyl cis-trans isomerase) Web page uniprot.org/ uniprot/Q5NG16) | MKLKKIVAVISCSLLGLAMSSCSINTDSVDSTNAQQVIKNTEAKGVAINKSAQDNPTIKMGANASY VVGYQVGAGIAKQDFGLYDKQTIAGFADAINGNKPRISESQIRRNMETLKDKMIKKQLDTANLNKT KSQEEFMAQIAKMDNAIKVDDGVYYQMIKQGDGKNPKSDSQVTIAYKGTTPVIAYEDDKSKLNEVKE AKLIGPTEDSSDSATFPLANLIECWKDAIPQIPNGSTIILYCSPDKAYGTRAPAVIGPNQALSFEI TLKDFK | 26 |
| FTT_0438 (Mpl/UDP-N-acetylmuramate-L-alanyl-gamma-D-glutamyl-meso-2,6-diamincheptan dioate ligase) Web page uniprot.org/ uniprot/Q5NHL4) | MSKHIHILGICGTFMGSLAVLAKQKGYKVIGSDLNVYPPMSTYLESQGIEILQGFDCDQLDINPDE IIIGNIMKRGMPIIEKILAEKLNYFSGPEWLYQNILKYKKVIAIAGTHGKITITTMTIKILEQAGL NPSFLVGGVSSDFGVSSRYTDSEYFVIEADEYDTAFFDKRSKLIHYDPSIFVINNIEFDHADIFKD IDAIFWQFHQLLRKMPSTAKIIYNAKDDNVQKIISMGCWSESELVKVNSDLGISITKHILDYSKFELC DINGNSVEVSWGLIGEHNALNAMSAYAVAKQLNISDEMVKDALESERGVKARLEVLSHQDNVTLYD DFAHHPTSIKLTLEAVANKAKDAYVVALIDPRSNIMRQGDNKDNLPMSIIEADRVLLYNHNLLKWD AKEVLKNSNNVDFIADVDDFVDCVDKLLIKHQDRNIQLVMMSNGSFDGLREKLVKLLEIK | 27 |
| FTT_0071 (GltA/Citrate synthase) Web page uniprot.org/ uniprot/Q5NIJ6) | MEVMLMSKYAILKYADKNIEIELPVYSPSLGNDCIDVSSLVKHGIFTYDPGFMSTAACESKITYID GGKGVLLHRGYPIEEWTQKSNYRTLCYALIYGELPTDEQVKSFRQEIINKMPVCEHVKAAIAAMPQ HTHPMSSLIAGVNVLAAEHIHNGQKESQDEVAKNIVAKIATIAAMAYRHNHGKKFLEPKMEYGYAE NFLYMMFADDESYKPDELHIKAMDTIFMLHADHEQNASTSTVALSGSTGNSPYAAIIAGITALWGP AHGGANEAVLKMLSEIGSTENIDKYIAKAKDKDDPERLMGFGHAVYKNIDPRATAMKKNCEEILAK LGHSDNPLLTVAKKLEEIALQDEFFIERKLFSNVDFYSGIILKAMGIPEDMFTAIFALARTSGWIS QWIEMVNDPAQKIGRPRQLYTGATNRNF | 28 |
| FTT_0289c (Hypothetical lipoprotein) Web page uniprot.org/ uniprot/Q5NI03) | MKKIKLLAAYTLATLILVSCSNNASLSNDLNSAGDSIVRFVNGTFYAEIYNTSLQSVYNATLLALN NSNIYSVKNNTINSKDAEITGIYATDKNFFNKSGQDDFAIRLVKGNQDTINLFIKIGKLGDKQASV DLLAKIQTNLGI | 29 |

The above sequences and additional sequences of protein antigens according to the present disclosure in different *Francisella* species and/or strains, are identifiable from sequences available in public databases such as Uniprot database (Web page uniprot.org/uniprot/) (see e.g. Annotation\in the Tables 1 and 2) at the date of filing of the present disclosure as will be understood by a person of ordinary skill in the art.

In some embodiments, the protein antigen from the *Francisella* bacterium comprises DnaK, OmpA, SucB and LpnA (Tul4) preferably on a Tobacco Mosaic Virus (TMV) as an antigen carrier as such combination from *Francisella* Schu S4 provided complete protection in mice when used as a vaccine [18].

In some embodiments, the protein antigen from the *Francisella* bacterium can comprise DnaK and Tul4 in combination in particular in embodiments wherein the *Francisella* bacterium is Schu S4 (see Ashketar et al. [19])

In some embodiments, the protein antigen from the *Francisella* bacterium comprises immunogenic proteins FopA, LpnA, Lpp3 and Type IV pilus fiber, in particular in embodiments wherein the *Francisella* bacterium is Schu S4 (see [20].)

In some embodiments, the protein antigen from the *Francisella* bacterium comprises individual IglC, Ft proteins (FTT-1747 (FopB), FTT-1676, FTT-1441, or FTT-1778c) in particular in embodiments wherein the *Francisella* bacterium is SchuS4 in view of data showing that such combination of protein antigens induced a strong CMI response and provided, significant, albeit partial, protection against an aerosol challenge with Ft SCHU S4.

In some embodiments, the protein antigen from the *Francisella* bacterium, can comprise DnaK, OmpA, SucB LpnA (Tul4), FopA, Lpp3 and Type IV pilus fiber, IglC, and Ft proteins (FTT-1747 (FopB), FTT-1676, FTT-1441, and/or FTT-1778c either individually or in any combination.

In some embodiments the *Francisella* bacterium is *Francisella tularensis*, and the protein antigen from *Francisella tularensis* comprises intracellular growth locus protein C or IglC.

Figure 25:
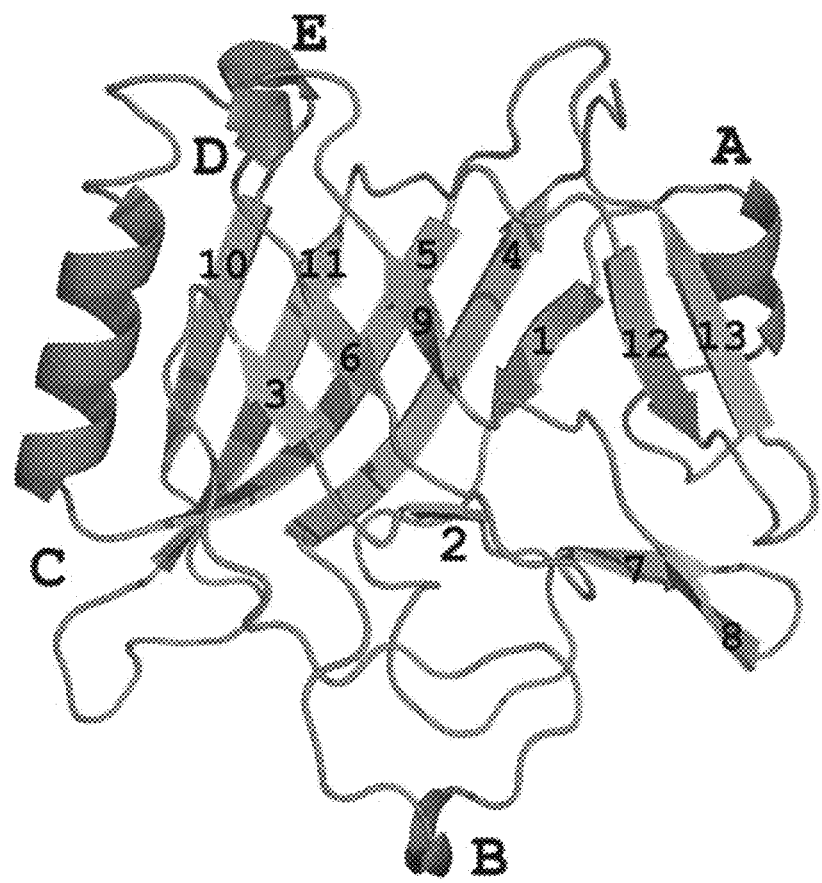
FIG. 25 illustrates a stereoview of the crystal structure of an exemplary *Francisella* protein antigen IglC. The 13 β-strands are numbered and the helices are labeled A-E (including α-helices A and C and $3_{10}$-helices B, D, and E). The image is taken from Sun et al. [2].
Figure 27B:
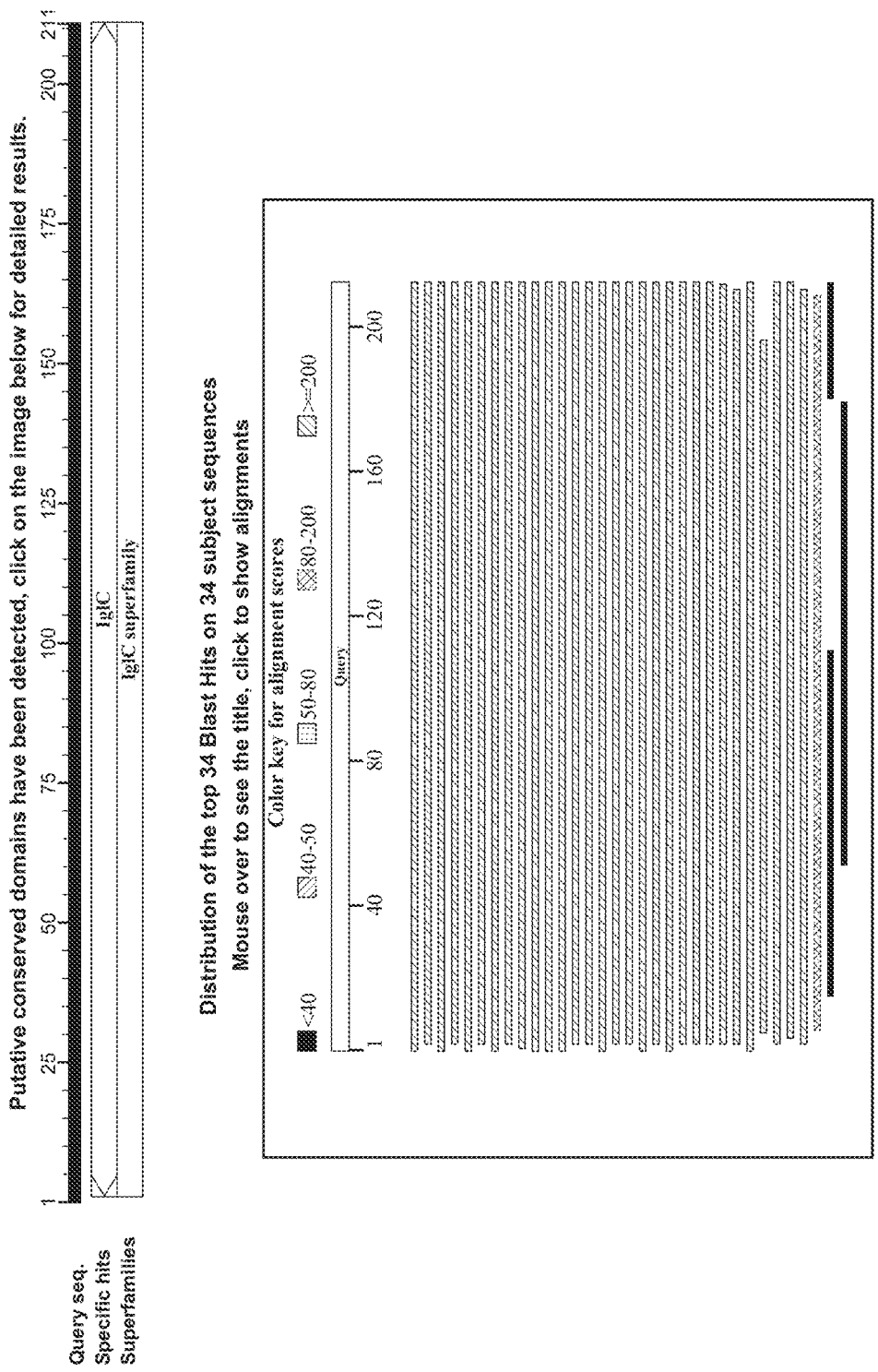
FIG. 27B is a grayscale representation of a graphic summary of the BLASTP search results using IglC protein having SEQ ID NO: 2 as a query sequence.
Figure 28B:
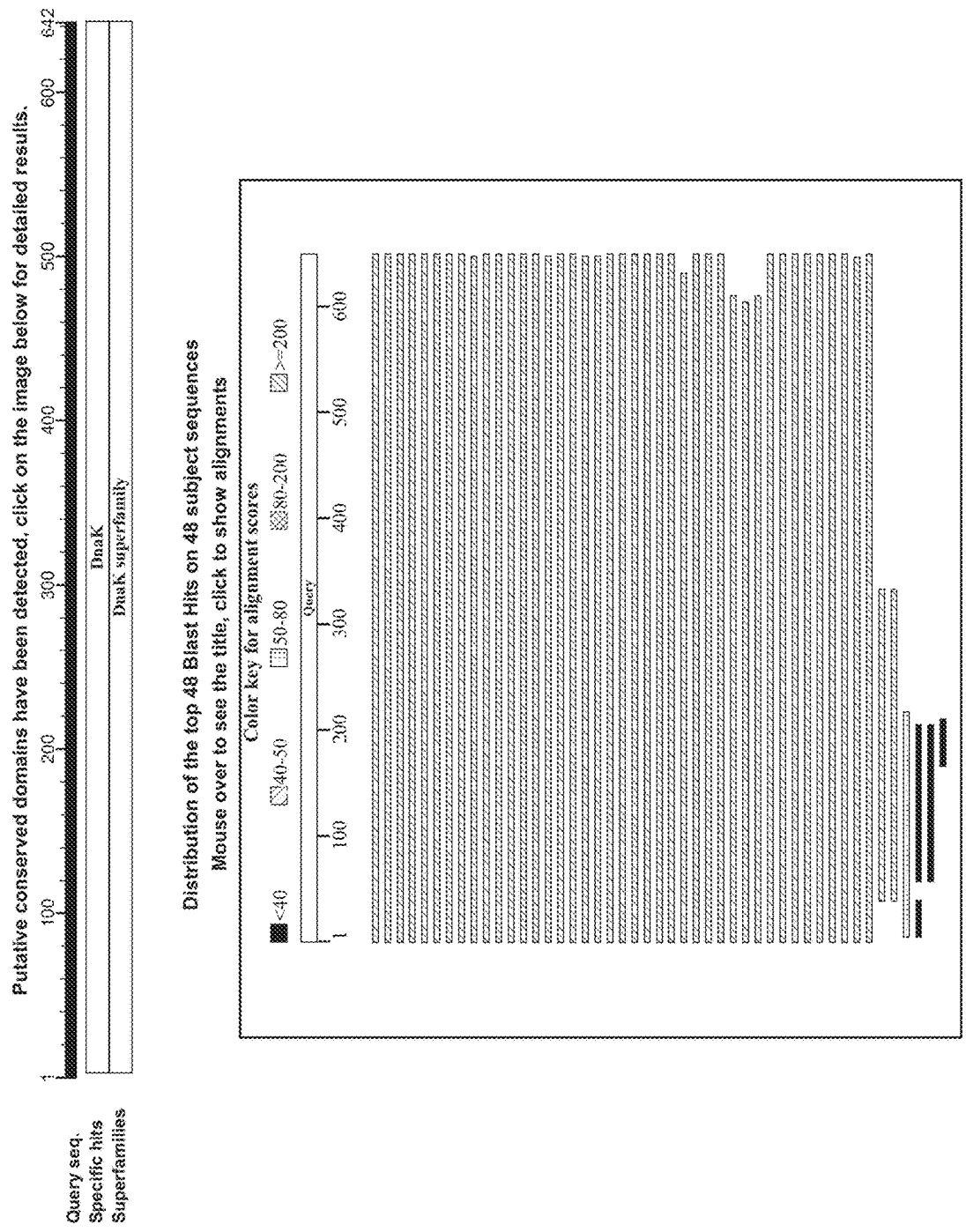
FIG. 28B is a grayscale representation of a graphic summary of the BLASTP search results using DnaK protein SEQ ID NO: 4 as a query sequence.
Figure 29B:
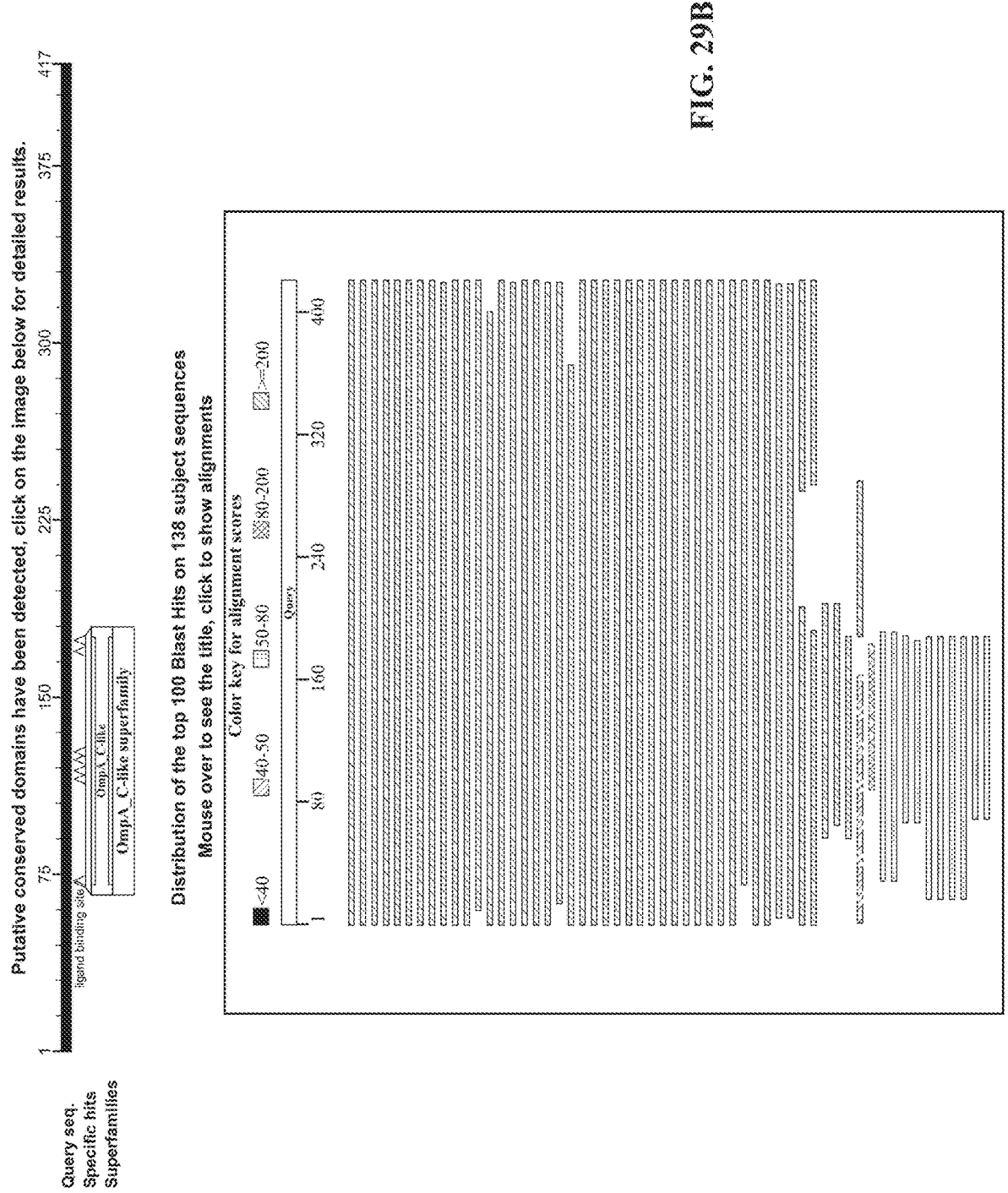
FIG. 29B is a grayscale representation of a graphic summary of the BLASTP search results using OmpA protein SEQ ID NO: 6 as a query sequence.
Figure 30B:
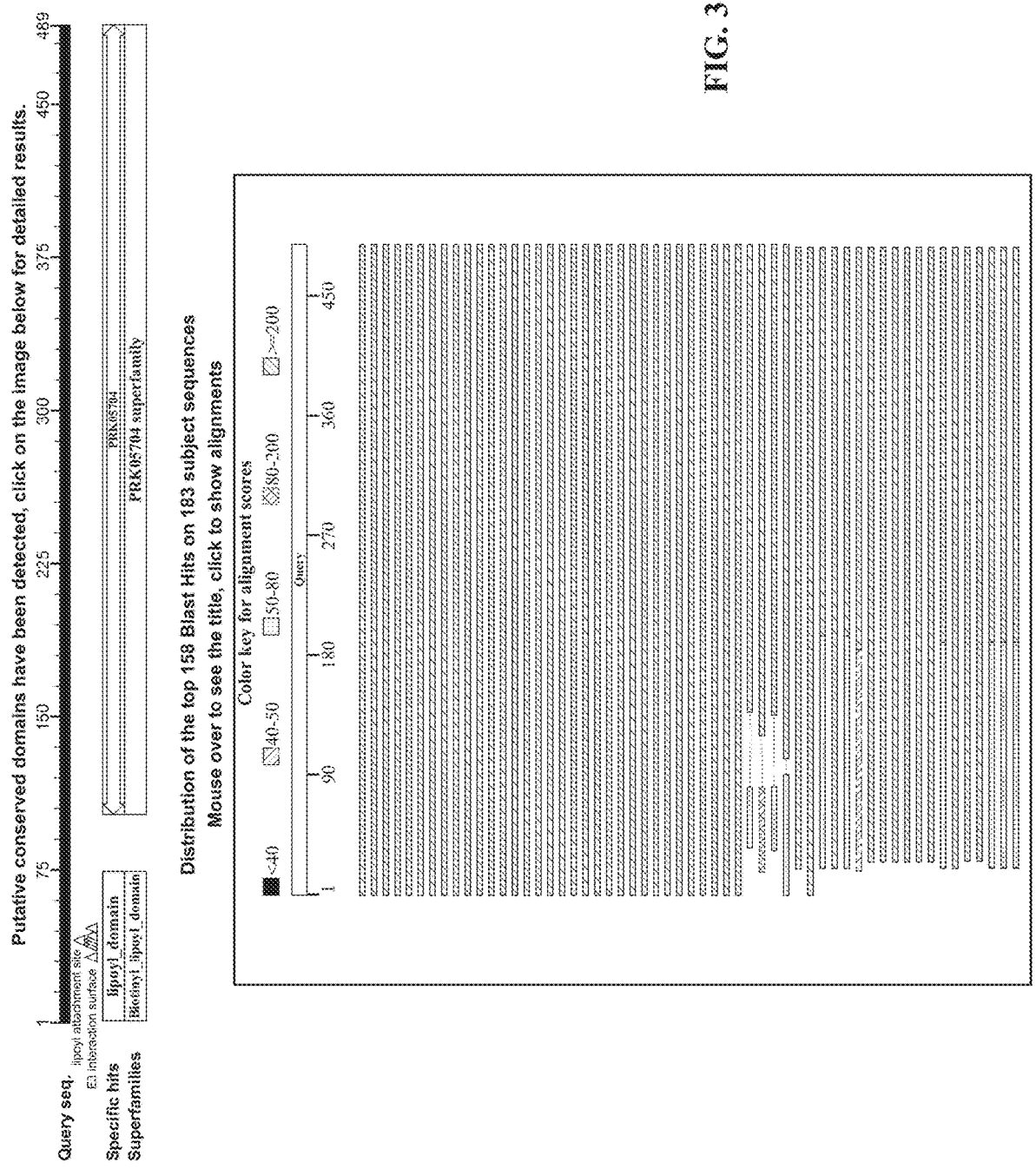
FIG. 30B is a grayscale representation of a graphic summary of the BLASTP search results using SucB protein SEQ ID NO: 8 as a query sequence.
Figure 31B:
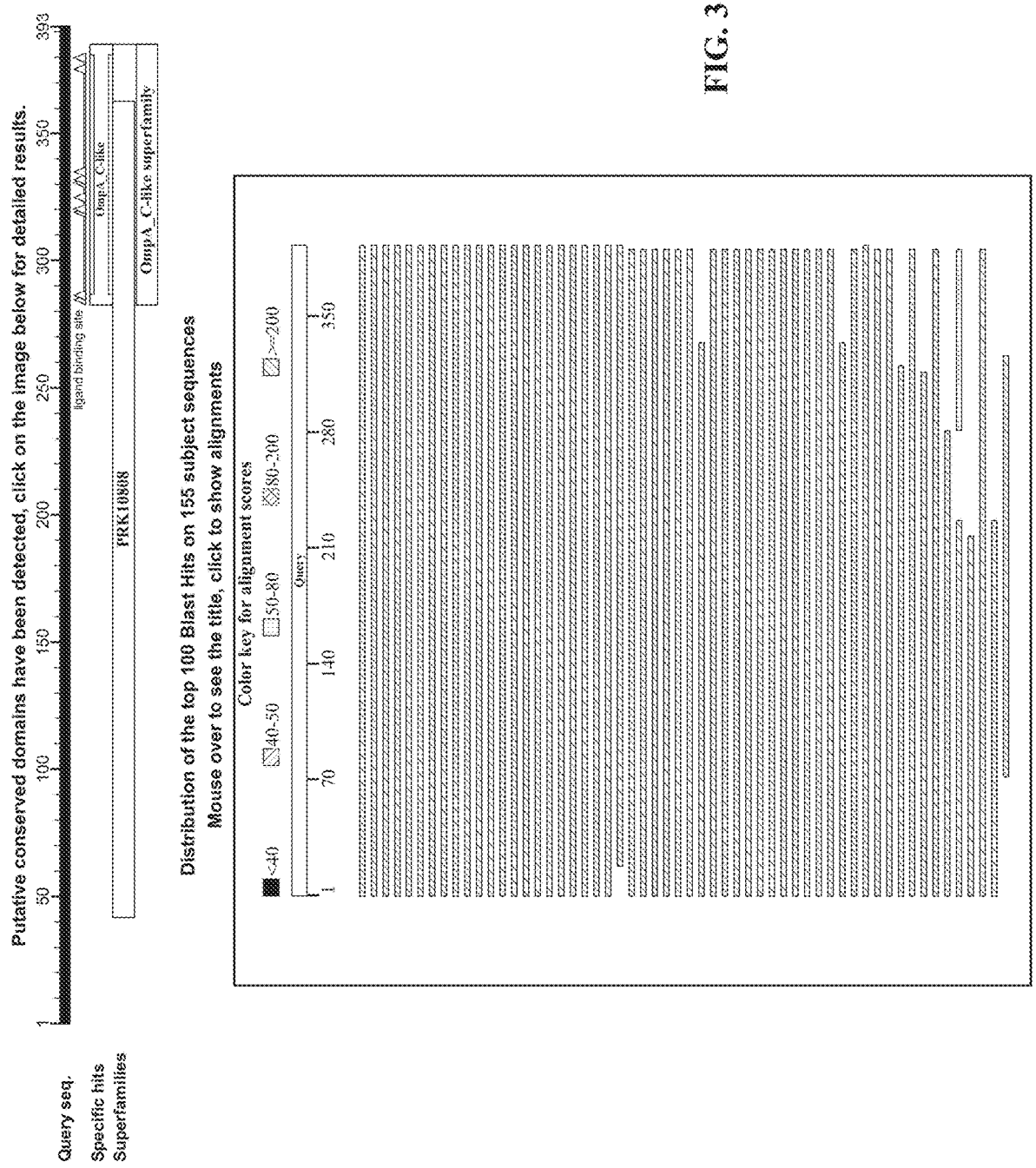
FIG. 31B is a grayscale representation of a graphic summary of the BLASTP search results using FopA protein SEQ ID NO: 88 as a query sequence.
Figure 32B:
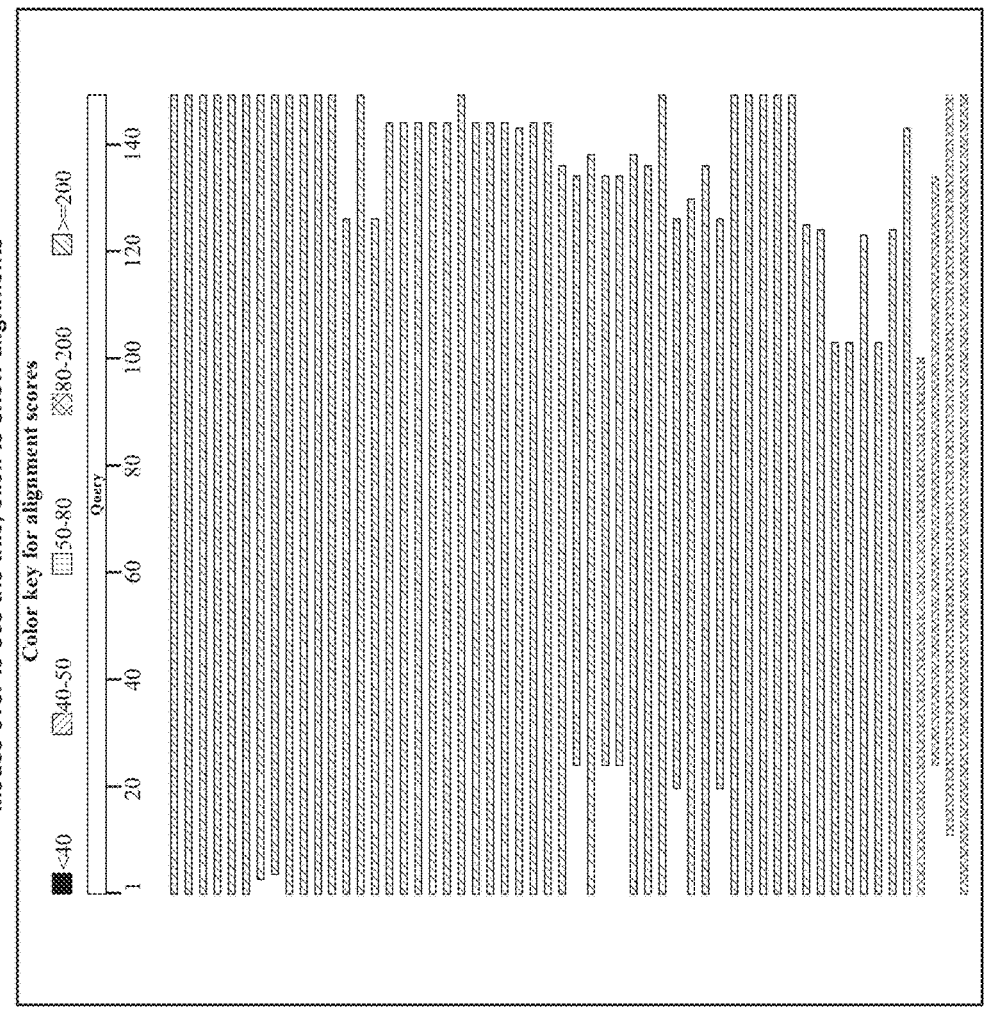
FIG. 32B is a grayscale representation of a graphic summary of the BLASTP search results using LpnA/Tul4 protein SEQ ID NO: 10 as a query sequence.
Figure 33B:
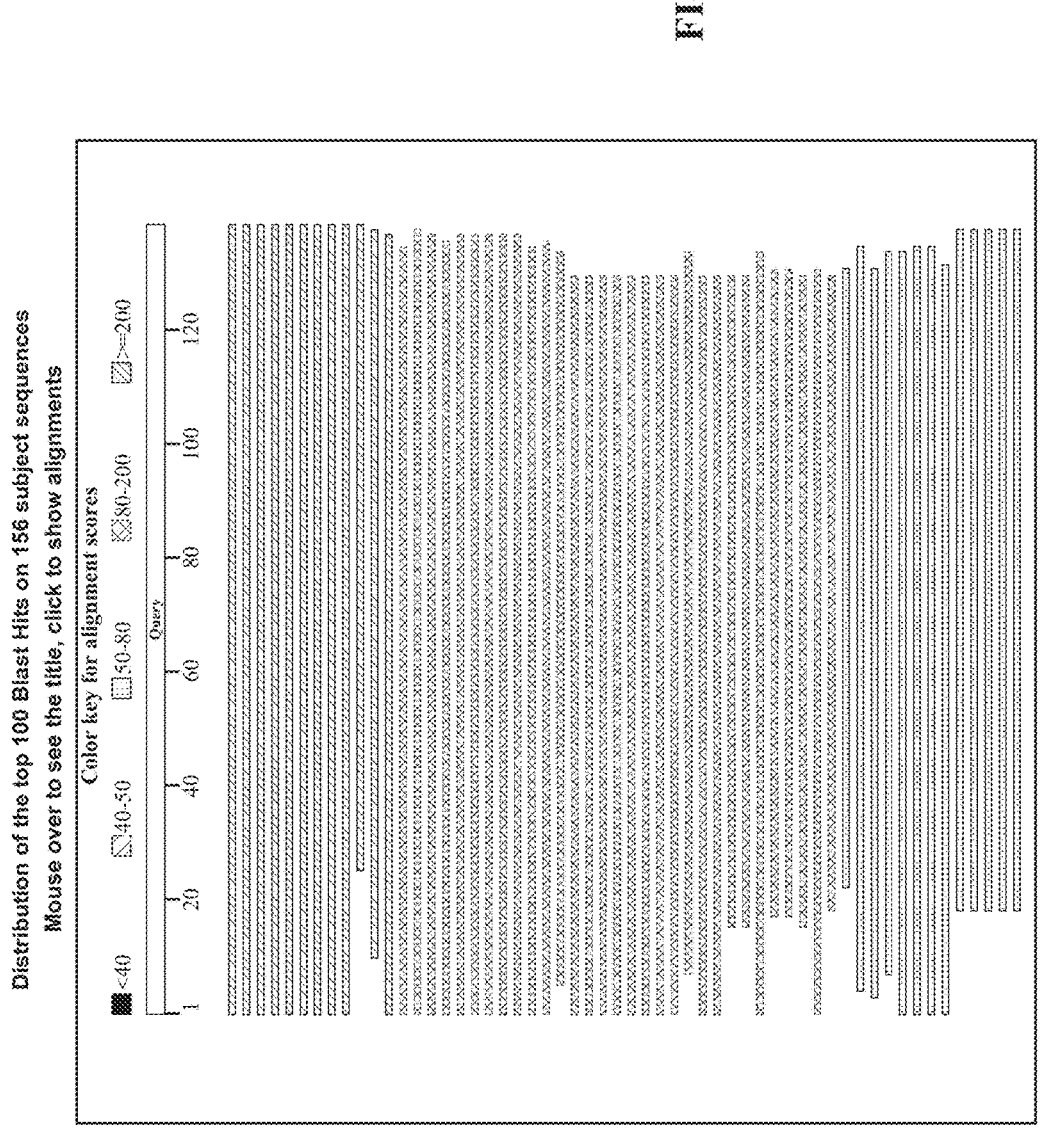
FIG. 33B is a grayscale representation of a graphic summary of the BLASTP search results using FTT1416c protein SEQ ID NO: 14 as a query sequence.
Figure 34B:
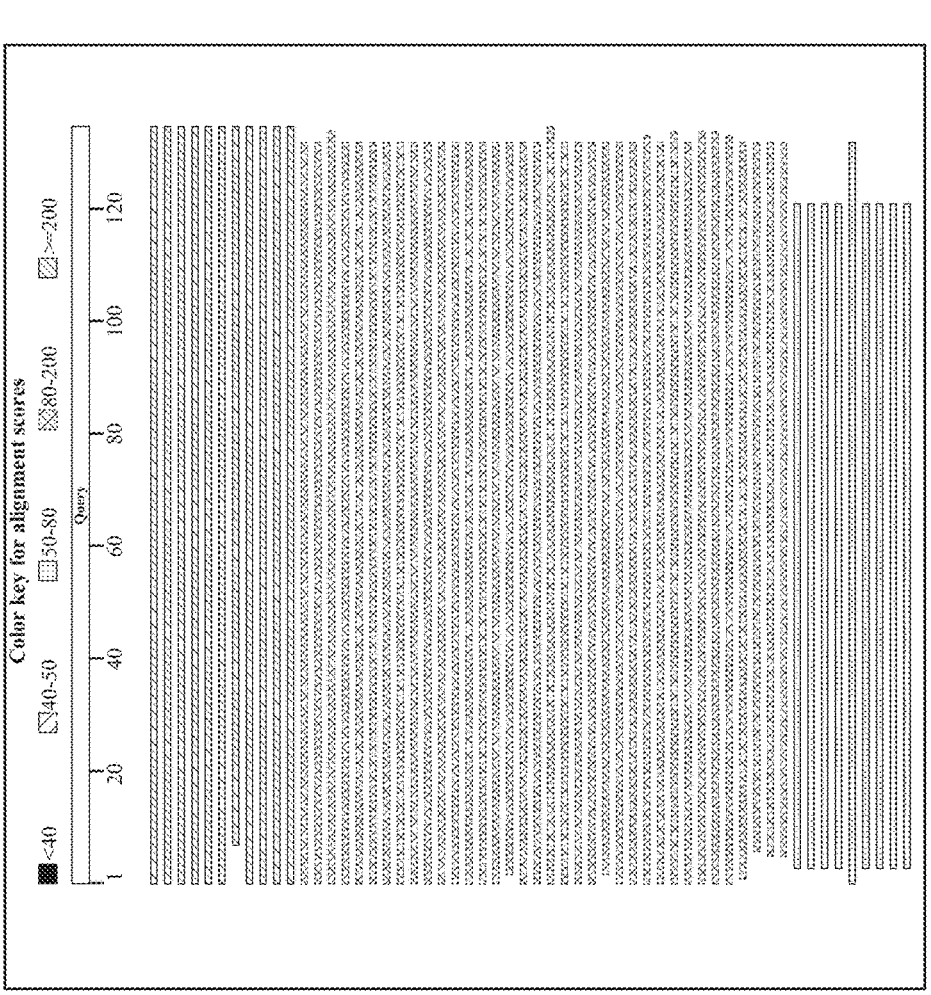
FIG. 34B is a grayscale representation of a graphic summary of the BLASTP search results using FTT0890c protein SEQ ID NO: 16 as a query sequence.
Figure 35B:
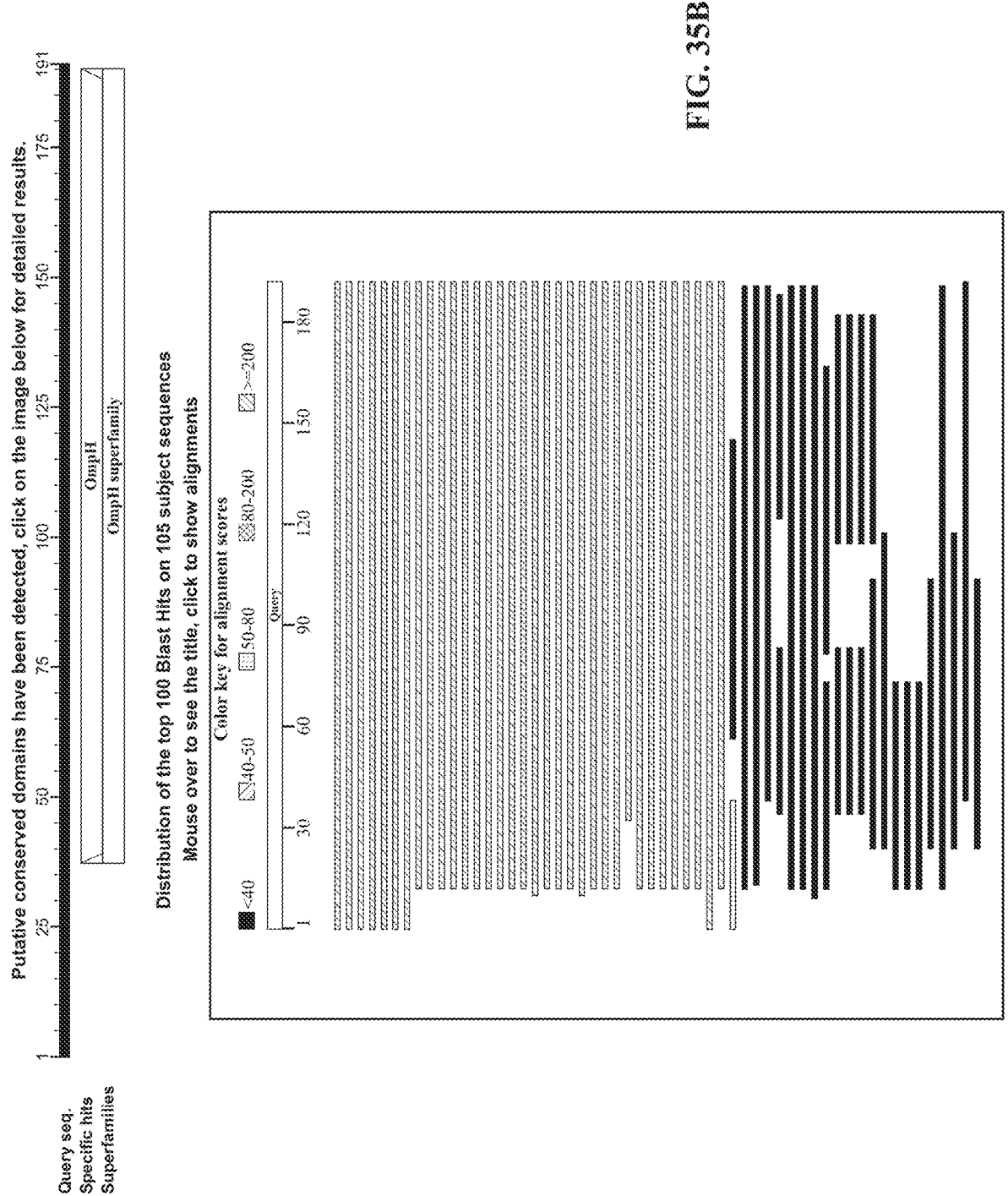
FIG. 35B is a grayscale representation of a graphic summary of the BLASTP search results using FopB protein SEQ ID NO: 18 as a query sequence.
Figure 36B:
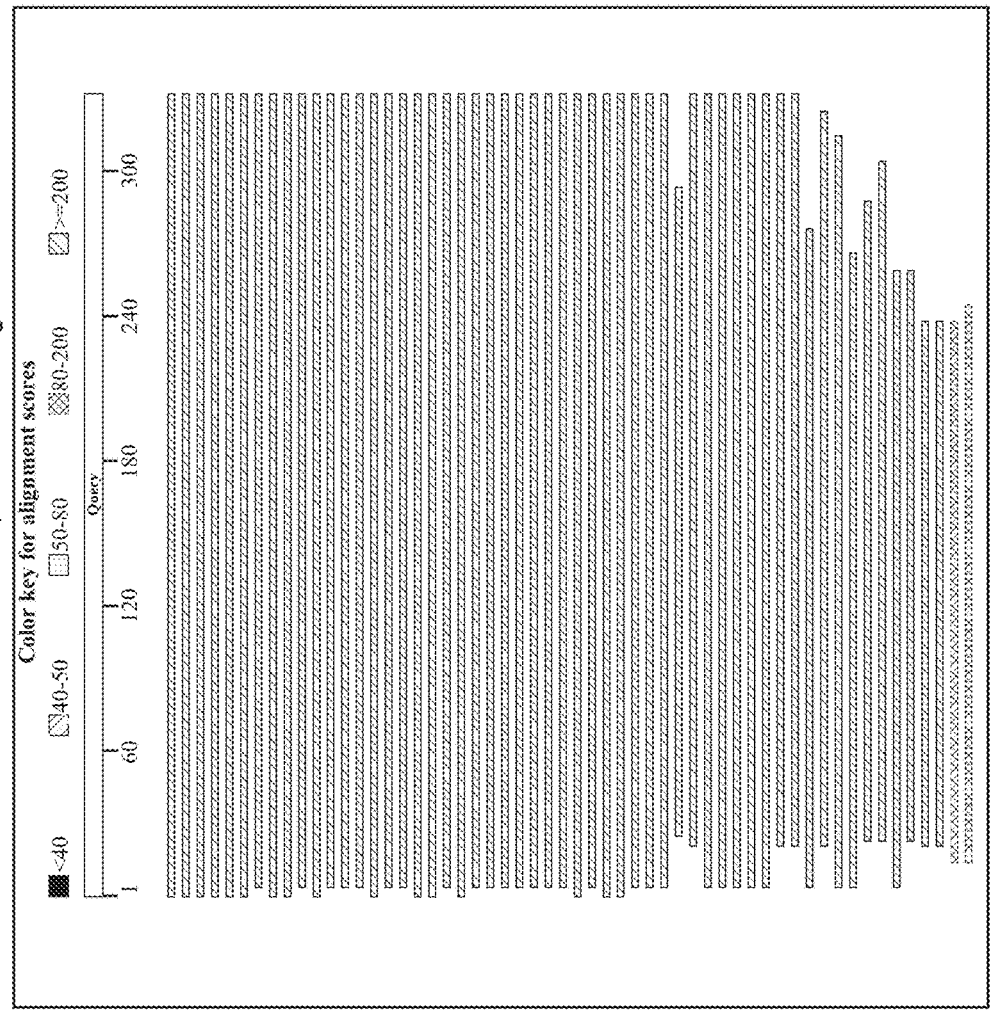
FIG. 36B is a grayscale representation of a graphic summary of the BLASTP search results using FTT1676 protein SEQ ID NO: 20 as a query sequence.
Figure 37B:
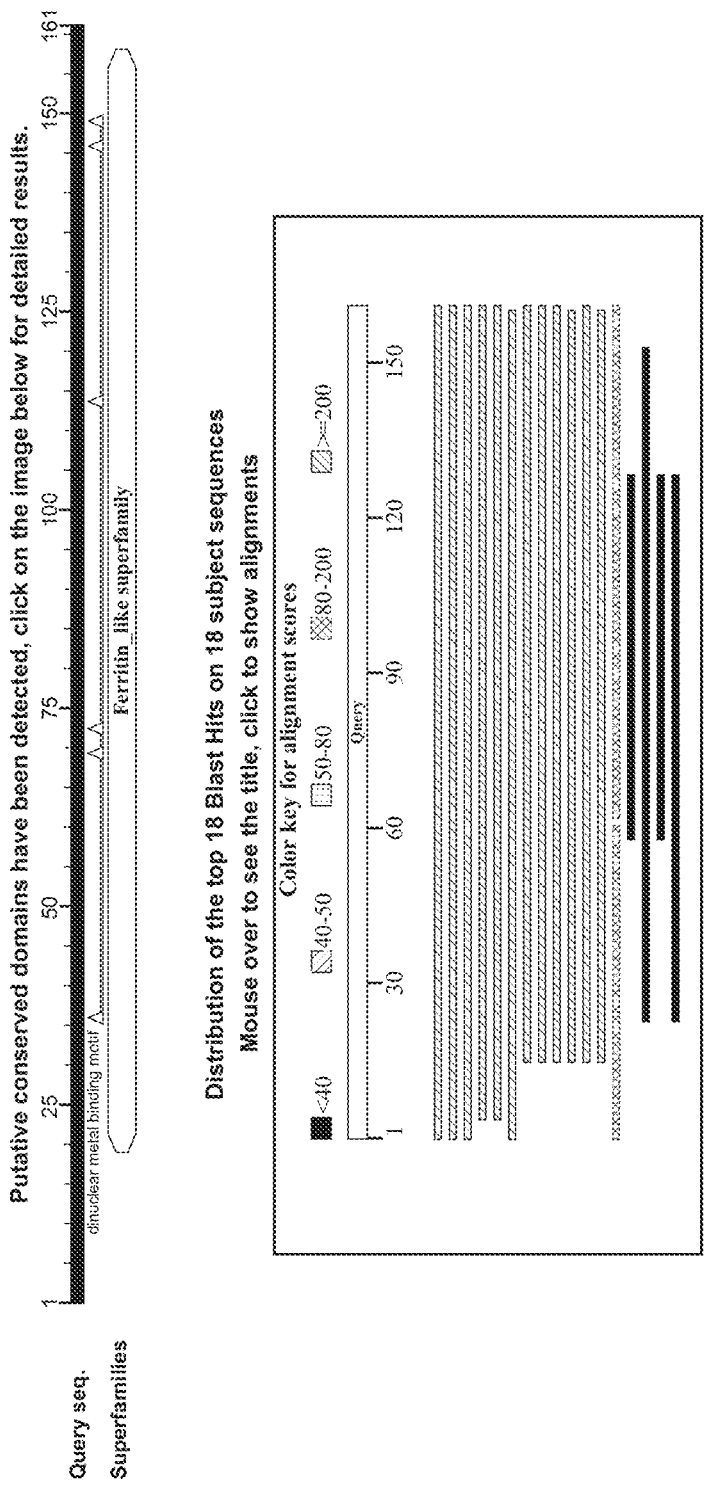
FIG. 37B is a grayscale representation of a graphic summary of the BLASTP search results using FTT1441 protein SEQ ID NO: 22 as a query sequence.
Figure 38B:
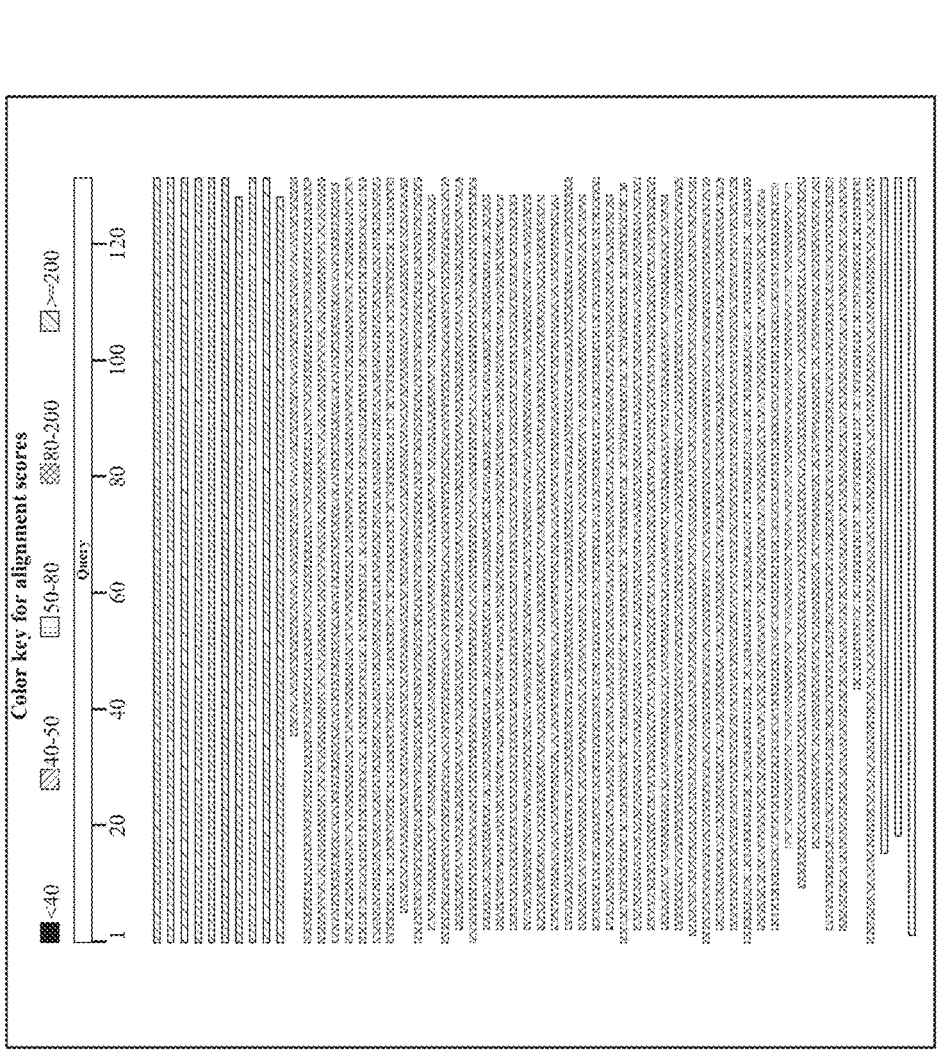
FIG. 38B is a grayscale representation of a graphic summary of the BLASTP search results using FTT1778c protein SEQ ID NO: 24 as a query sequence.
Figure 39B:
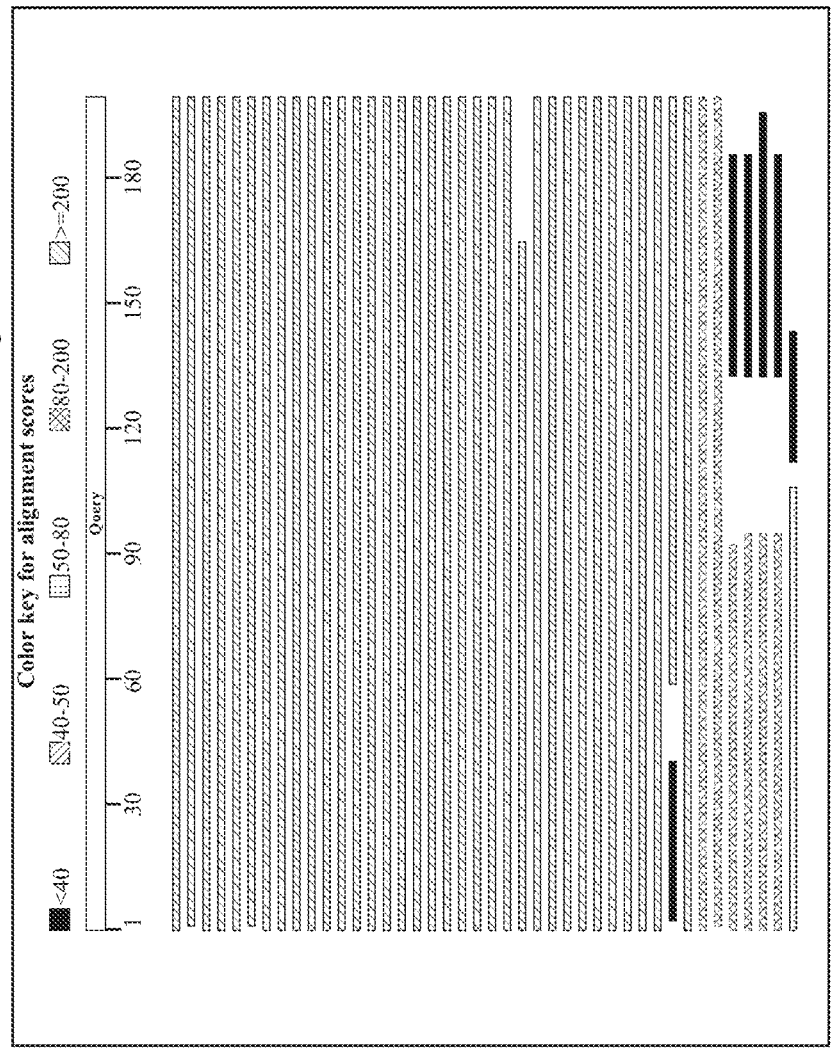
FIG. 39B is a grayscale representation of a graphic summary of the BLASTP search results using FTT0814c protein SEQ ID NO: 25 as a query sequence.
Figure 40B:
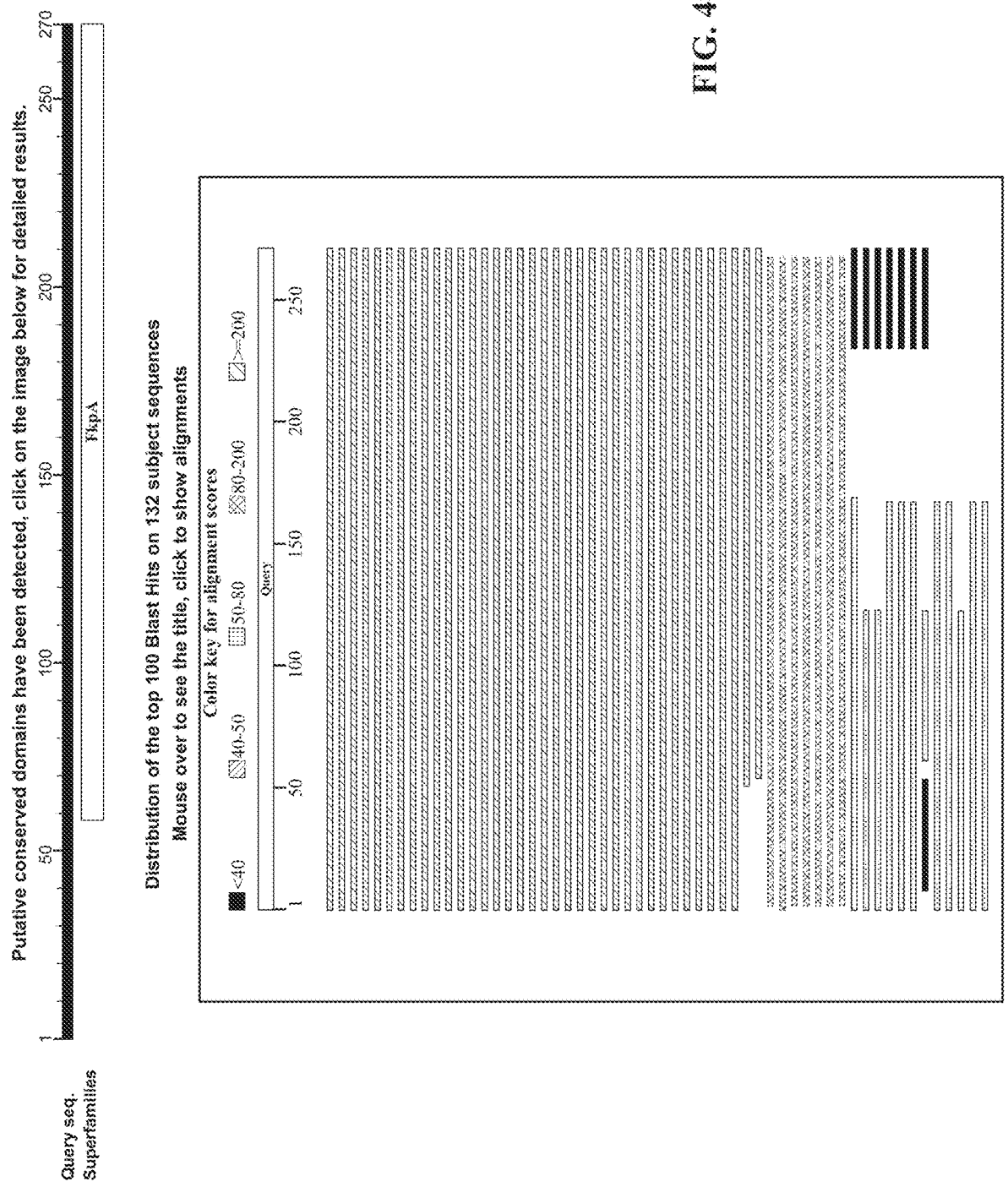
FIG. 40B is a grayscale representation of a graphic summary of the BLASTP search results using FTT1043 protein SEQ ID NO: 26 as a query sequence.
Figure 41B:
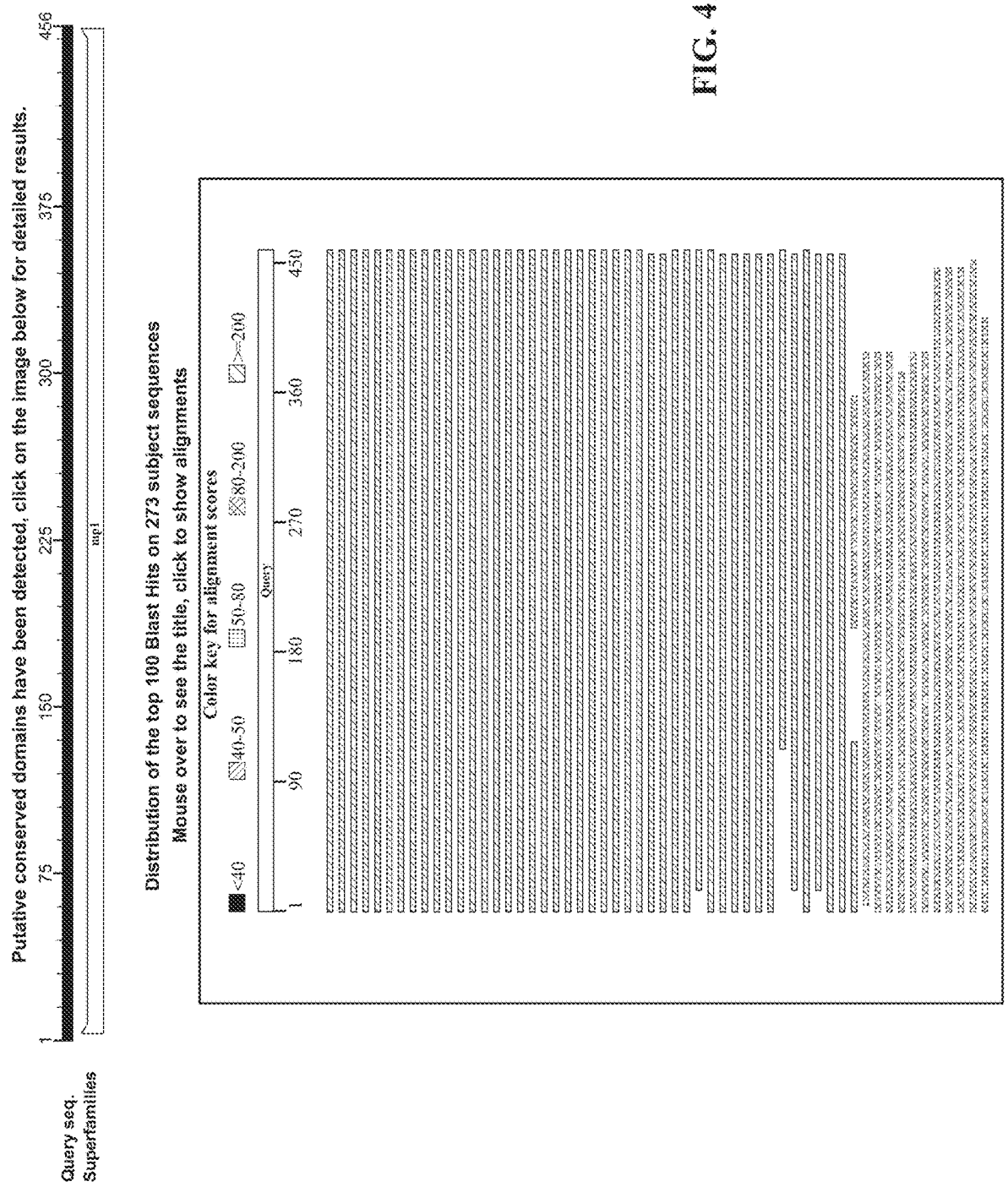
FIG. 41B is a grayscale representation of a graphic summary of the BLASTP search results using FTT0438 protein SEQ ID NO: 27 as a query sequence.
Figure 42B:
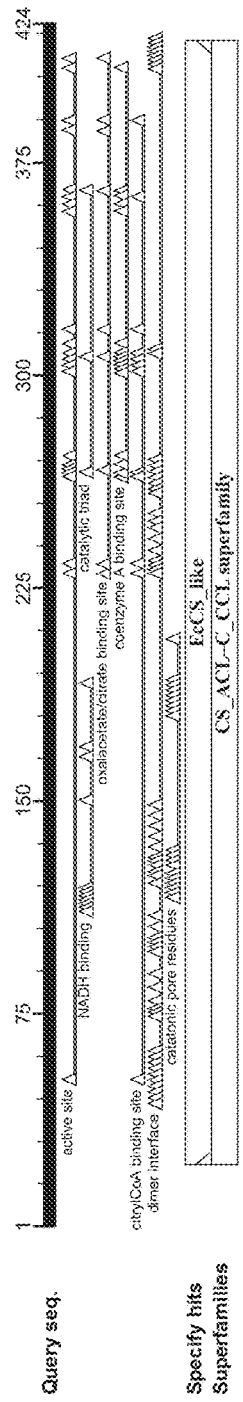
FIG. 42B is a grayscale representation of a graphic summary of the BLASTP search results using FTT0071 protein SEQ ID NO: 28 as a query sequence.
Figure 42B:
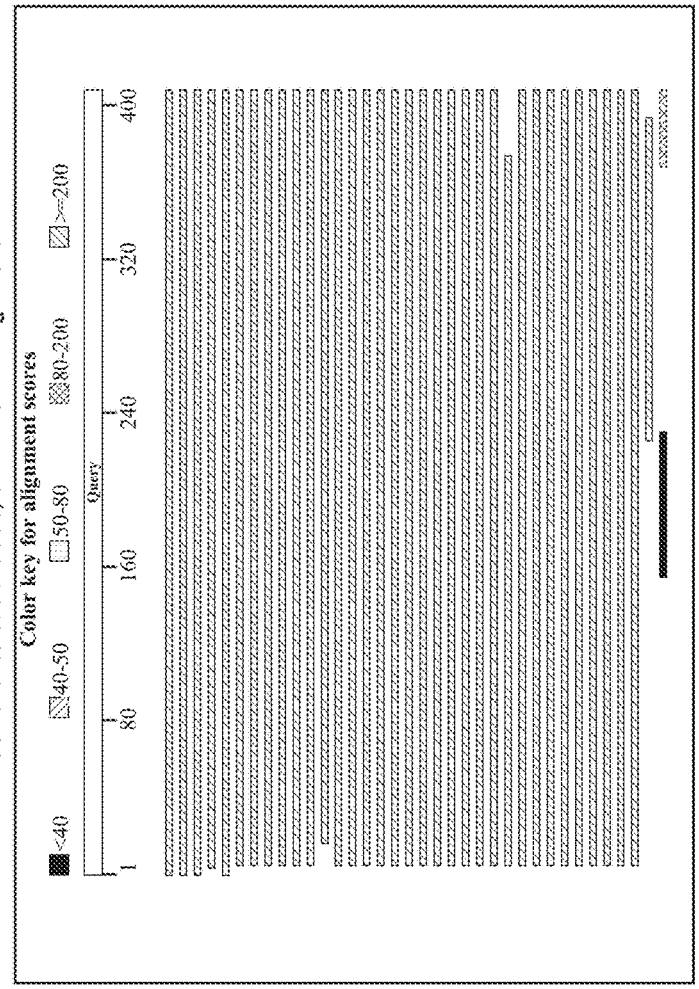
Figure 43B:
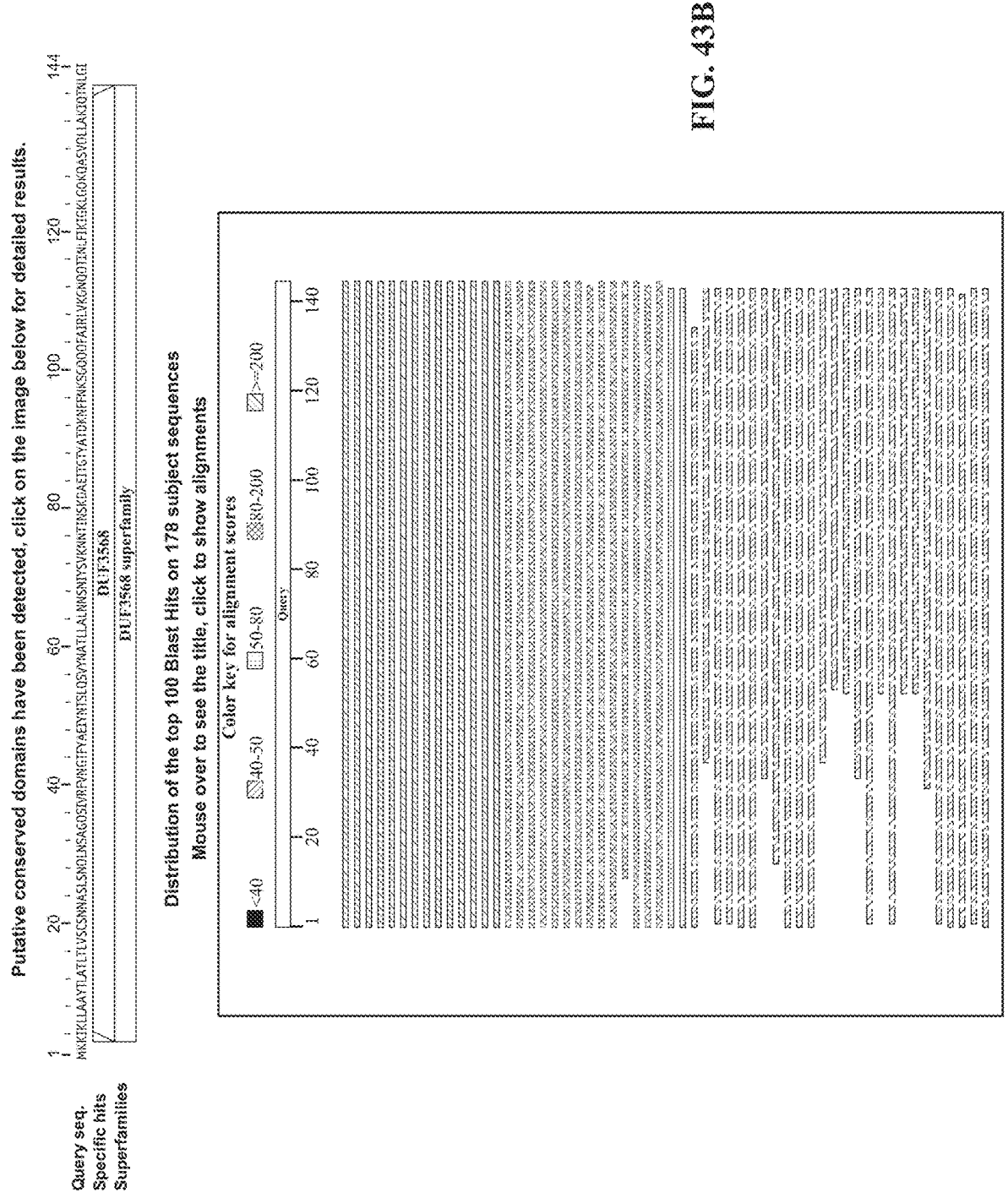
FIG. 43B is a grayscale representation of a graphic summary of the BLASTP search results using FTT0289c protein SEQ ID NO: 29 as a query sequence.

The term "intracellular growth locus protein C" or "IglC" as used herein indicates a 23-kDa protein encoded by the ig1ABCD operon in the *Francisella* Pathogenicity Island (FPI) in the genome of a *Francisella* bacterium. IglC is a β-sandwich plate comprising thirteen β sheets with approximate dimensions of 50×50×25 Å$^3$. The β-sandwich is augmented by two α-helices and three $3_{10}$-helices around its periphery. One layer of the β-sandwich is composed of six antiparallel β-strands with a strand order of β1/β2-β4-β5-β11-β10. The other layer is composed of three antiparallel b-strands: β3-β6-β9, β7-β8, and β12/β13. The two layers of the β-sandwich are packed together by virtue of extensive hydrophobic interactions at their interface. IglC is one of the most upregulated *F. tularensis* proteins during transcellular infection of macrophages, and is required for intracellular survival, replication and phagosome escape of *F. tularensis*. Studies on IglC mutants in *F. tularensis* subsp. *novicida*, *holarctica*, and *tularensis* demonstrated that IglC is essential for virulence in mice. A schematic structure of an exemplary IglC is shown in FIG. 25 which illustrates a stereoview of the crystal structure of an IglC. The 13 β-strands are numbered, and the helices are labeled A-E (including α-helices A and C and $3_{10}$-helices B, D, and E).

In some embodiments, the IglC protein antigen of an antigenic combination herein described has a protein sequence of SEQ ID NO:1 shown in Table 1. SEQ ID NO:1 corresponding to an intracellular growth locus subunit C from *Francisella tularensis* subsp. *tularensis* SCHU S4.

In some embodiments, the antigenic combination herein described can comprise a *Francisella* protein antigen component comprising one or more derivatives of a protein antigen of a *Francisella* bacterium capable of inducing a cell mediated immune response in the individual.

In some of these embodiments, the *Francisella* protein antigen component comprises one or more protein antigens having a gene sequence of SEQ ID NOs: 1, 3, 5, 7, 9, 11, 13, 15, 17, 19, 21, and 23 or a protein sequence of SEQ ID NOs: 2, 4, 6, 8, 88, 10, 14, 16, 18, 20, 22, 24-29. In some embodiments, the *Francisella* protein antigen component comprises one or more protein antigens having at least 30% identity with the *Francisella* protein antigen having SEQ ID NOs: 1-11, 88, and 13-29 and shows ability to trigger a cell-mediated immune response at a same, reduced or increased level compared to the original *Francisella* protein antigens. In some embodiments, the *Francisella* protein antigen component comprises one or more protein antigens having at least 80% identity with the *Francisella* protein antigen having SEQ ID NOs: 1-11, 88, and 13-29.

The term "percent identity" refers to a quantitative measurement of the similarity between sequences of a polypeptide or a polynucleotide and, in particular, indicates the amount of characters that match between two different sequences. Commonly used similarity searching programs, like BLAST, PSI-BLAST [21], SSEARCH [22, 23] FASTA [24] and the HMMER [25] can produce accurate statistical estimates, ensuring that protein sequences that share significant similarity also have similar structures.

The identity between sequences is typically measured by a process that comprises the steps of aligning the two polypeptide or polynucleotide sequences to form aligned sequences, then detecting the number of matched characters, i.e. characters similar or identical between the two aligned sequences and calculating the total number of matched characters divided by the total number of aligned characters in each polypeptide or polynucleotide sequence, including gaps. The similarity result is expressed as a percentage of identity.

In some embodiments, the *Francisella* protein antigen component comprises one or more protein antigens having a particular BLAST score with respect to the *Francisella* protein antigen having SEQ ID NOs: 2, 4, 6, 8, 88, 10, 14, 16, 18, 20, 22, 24-29 and shows ability to trigger a cell-mediated immune response at a same, reduced or increased level compared to the original *Francisella* protein antigens.

The term "BLAST" or "Basic Local Alignment Search Tool" is an algorithm for comparing primary biological sequence information, such as the amino-acid sequences of proteins or the nucleotides of DNA sequences. A BLAST search enables a researcher to compare a query sequence with a library or database of sequences, and identify library sequences that resemble the query sequence above a certain threshold. Accordingly, BLAST or Basis Local Alignment Search Tool uses statistical methods to compare a DNA or protein input sequence, also referred to as a query sequence to a database of nucleotide and protein (subject sequences) and returns sequences hits that have a level of similarity to the query sequence ranked based on the score.

The term "score" in the context of sequence alignments, indicates a numerical value that describes the overall quality of an alignment. Higher scores correspond to higher similarity and lower scores correspond to lower similarity. The score scale depends on the scoring system used for conducting the sequence alignment.

A BLAST score, also referred to as bit score or max score in the BLAST output is a normalized score with respect to the scoring system provided by the BLAST algorithm. The BLAST score defines the highest alignment score of a set of aligned segments from the same subject (database) sequences. The score is calculated from the sum of the match rewards and the mismatch, gap open an extend penalties independently for each segment. The BLAST score normally gives the same sorting order as the expect value (E value) in the BLAST alignment output.

A BLAST score can be obtained using BLAST software suite at the NCBI website and related references and in particular at the website Web page blast.ncbi.nlm.nih.gov/Blast.cgi?PROGRAM=blastp&PAGE_TYPE=BlastSearch&LINK_LOC=blasthome at the date of filing of the present disclosure, as will be understood to a person skilled in the art.

In some of these embodiments, the *Francisella* protein antigen component comprises one or more protein antigens having a BLAST score in a range between 112 and 427 with the *Francisella* protein antigen having SEQ ID NO: 2, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 1294 and 5740 with the *Francisella* protein antigen having SEQ ID NO: 4, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 192 and 846 with the *Francisella* protein antigen having SEQ ID NO: 6, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 112 and 427 with the *Francisella* protein antigen having SEQ ID NO: 8, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 104 and 795 with the *Francisella* protein antigen having SEQ ID NO: 88, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 36.2 and 302 with the *Francisella* protein antigen having SEQ ID NO: 10, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 38.1 and 273 with the *Francisella* protein antigen having SEQ ID NO: 14, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 37.7 and 264 with the *Francisella* protein antigen having SEQ ID NO: 16, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 79 and 375 with the *Francisella* protein antigen having SEQ ID NO: 18, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 59.7 and 678 with the *Francisella* protein antigen having SEQ ID NO: 20, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 122 and 323 with the *Francisella* protein antigen having SEQ ID NO: 22, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 38.1 and 256 with the *Francisella* protein antigen having SEQ ID NO: 24, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 69.3 and 399 with the *Francisella* protein antigen having SEQ ID NO: 25, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 42 and 551 with the *Francisella* protein antigen having SEQ ID NO: 26, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 42.4 and 941 with the *Francisella* protein antigen having SEQ ID NO: 27, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 95.1 and 889 with the *Francisella* protein antigen having SEQ ID NO: 28, and shows ability to trigger a cell-mediated immune response at a same, reduced or increased level compared to the original *Francisella* protein antigens.

In some of these embodiments, the *Francisella* protein antigen component comprises one or more protein antigens having a BLAST score in a range between 37.7 and 281 with the *Francisella* protein antigen having SEQ ID NO: 29, and shows ability to trigger a cell-mediated immune response at a same, reduced or increased level compared to the original *Francisella* protein antigens.

In some embodiments of the antigenic combination herein described a *Francisella* protein antigen component comprises one or more derivatives of a *Francisella* protein antigen herein. The derivatives of a *Francisella* protein antigen can be an immunogenic fragment of a *Francisella* protein antigen with retained immunogenicity. In particular, a derivative of a *Francisella* protein antigen comprises an epitope capable of eliciting a same, lower or higher cell-mediated immune response.

Accordingly, a derivative of a protein antigen having any one of SEQ ID NOs: 1-11, 88, and 13-29 or a sequence with at least 30% identity thereof is a fragment of said protein antigen comprising one or more epitopes of the antigen capable of eliciting a cell-mediated immune response in an individual. In general, an epitope, when discussed in connection with proteins refers to the shortest amino acid sequence in a protein that maintains stimulatory capacity for T cells. T cell epitopes of a protein antigen can be presented on the surface of an antigen-presenting cell, where they are bound to MHC molecules. In humans, antigen-presenting cells are specialized to present MHC class II peptides, whereas most nucleated somatic cells present MHC class I peptides. T cell epitopes presented by MHC class I molecules are typically peptides between 8 and 11 amino acids in length, whereas MHC class II molecules present longer peptides, 13-17 amino acids in length, and non-classical MHC molecules also present non-peptidic epitopes such as glycolipids.

A possible approach for identifying epitopes of an antigen, is that of synthesizing a complete panel of peptides, with a given length and a predetermined overlapping sequence, such that it encompasses an entire protein antigen. Once peptide panels have been produced, T cells can be tested with different methods to determine the stimulatory immunodominant peptides using assays that predict T-cell immunity. Using such assays, a functional T-cell response to stimulatory peptides can be demonstrated by upregulation of activation markers, cytokine synthesis, T-cell proliferation, cytolytic, and helper T cell function as described in Pira et al., 2010 [26]. Exemplary methods for T epitope mapping include MHC-peptide multimers, solid phase MHC-peptide complexes, lymphoproliferation, activation markers induced on specific T cells, ELIspot, intracytoplasmic cytokine staining (ICS), cytokine secretion and cell surface capture, cytokine secretion and well surface capture (cell-ELISA) and others identifiable by a skilled person. For example, several activation markers have been used for identification, enumeration, and selection of antigen specific CD4 and CD8 T cells. These markers for antigen activated T cells include CD137 for detection of CD8 cells and CD154 for detection of CD4 cells. Coexpression of CD25 and CD134 also identifies antigen specific CD4 T cells. Therefore, the same markers can also be applied for epitope mapping. In addition, T cells that secrete a given cytokines as a consequence of antigen recognition on APC can be detected by ELIspot as will be understood by a skilled person.

In some embodiments, synthesizing a complete panel of peptides, with a given length and a predetermined overlapping sequence, such that it encompasses an entire protein antigen can be performed by dividing the original protein antigen into protein antigen overlapping peptides with preset peptide length and offset number (the number of overlapping amino acids between two adjacent peptides) the protein antigen overlapping peptides having a sequence such that the protein antigen overlapping peptides encompass the entire protein antigen sequence. The offset number reflects the degree of overlapping. In general, the peptide length is selected between 8 to 20 amino acids and the offset number can be from 1 to 7.

In some embodiment, the protein antigen overlapping peptides can be designed to be 15 amino acids in length and sequentially shifted in sequence by 5 residues. For optimization experiments, peptides can be designed with a shorter length, such as 9 amino acids, and shifted in sequence by 1 residue (see Example 21 wherein the *Francisella* protein antigen is Ig1C). In some embodiments the protein antigen overlapping peptides can be designed to have a sequence covering only a portion of the protein antigen as will be understood by a skilled person.

A library of protein antigen overlapping peptides can then be generated for example by solid phase peptide synthesis on a solid support such as a resin, as well as with other techniques identifiable by a skilled person and the synthesized protein antigen overlapping peptides can then be tested for their immunogenicity as will be understood by a skilled person (see Example 22). Additional peptides can be designed and tested in view of the results of the immunogenicity tests (see e.g. the fine mapping of immunogenic peptide 9 in Example 22). In general, even in presence of negative results in a round of immunogenicity tests the process of designing and synthesizing peptide library can be repeated until epitopes of a protein antigen are identified.

Exemplary peptides from *Francisella* protein antigen Ig1C of SEQ ID NO: 2 comprise immunogenic T cell epitopes, TSGETIHVRTDPTAC (SEQ ID NO: 33), GSHPNCRLFIDSLTI (SEQ ID NO: 37) NCRLFIDSLTI-AGEK (SEQ ID NO: 38), VTKADSATAAASVIR (SEQ ID NO: 45), DSATAAASVIRLSIT (SEQ ID NO: 46), YPI-SAKAFSISIEPT (SEQ ID NO: 67), AKAFSISIEPTELMG (SEQ ID NO: 68), SKDGMRYHIISIDGL (SEQ ID NO: 72), MRYHIISIDGLTTSQ (SEQ ID NO: 73). In some embodiments, the exemplary peptides from *Francisella* protein antigen Ig1C of SEQ ID NO: 2 comprise NCRLFIDSL (SEQ ID NO: 81).

Peptides comprising immunogenic epitopes of additional protein antigens herein described, such as protein antigens having SEQ ID NO:4, 6, 8, 88, 10, 14, 16, 18, 20, 22, and 24 to SEQ ID NO: 29, can be identified with the above approach as will be understood by a skilled person.

*Francisella* protein antigens herein described comprise protein antigens obtained from recombinant protein expression as will be understood by a person of ordinary skill in the art.

Recombinant *Francisella* protein antigen can be created artificially using recombinant DNA technology identifiable by a person skilled in the art of molecular biology. In general, polynucleotides encoding *Francisella* protein antigens can be cloned using commercially available reagents from vendors such as Qiagen, Invitrogen, Applied Biosystems, Promega, and others, following standard molecular biology methods known in the art, such as those described in Sambrook and Russell (2001) Molecular Cloning, A Laboratory Manual. Synthetic DNA. Genomic DNA or cDNA encoding pyocyanin demethylase derivatives can be cloned into an expression vector. Expression vectors can comprise plasmid DNA, viral vectors, or non-viral vectors, among others known to those skilled in the art, comprising appropriate regulatory elements such as promoters, enhancers, and post-transcriptional and posttranslational regulatory sequences, as would be understood by a skilled person. Promoters can be constitutively active or inducible. RNA can be isolated from a cell, such as *Francisella tularensis* and cDNA produced by reverse transcription using standard techniques and commercial kits. Alternatively, genomic DNA can be purified from the cell, and cDNA or genomic DNA encoding one or more pyocyanin demethylases isolated, following methods known to those in the art. PCR-based amplification of the gene of interest can be performed using appropriately designed primer pairs (e.g. using PrimerDesign or other programs known to those skilled in the art). An encoded tag can be incorporated into the primer design (e.g. encoding a His-tag designed to be fused to the N- or C-terminus of the recombinant enzyme) to facilitate protein purification (e.g. using commercially-available His-tagged protein purification columns/kits), as described below. PCR-based amplification can be followed by ligation (e.g. using T4 DNA ligase) of the amplicon into an appropriate expression cassette in a plasmid suitable for propagation in bacteria or other cells, such as transformation-competent *E. coli*, followed by growth of transformed cell cultures, purification of the plasmid for confirmation of the cloned pyocyanin demethylase by DNA sequence analysis, among other methods known to those skilled in the art.

Cloned recombinant *Francisella* protein antigens can be expressed using cell-based methods or cell-free methods, following standard techniques and using commercially available kits. Cell-based methods for expression of recombinant *Francisella* protein antigens can include expression in prokaryotic or eukaryotic cell cultures, such as *E. coli* or other bacterial cells, yeast strains, insect cells, or mammalian cells, among other known to those skilled in the art.

An antigenic *Francisella* protein, an antigenic *Francisella* polysaccharide and/or derivative thereof, either experimentally identified or computationally predicted, can be assessed for immunogenicity and protective capacity in a suitable animal model using approaches known to a person skilled in the art. Murine model systems can be employed where animals are vaccinated with the antigen of interest and the humoral and cell mediated immune response to vaccination is characterized. In the case of humoral responses, serum from vaccinated animals can be screened for the presence of antigen specific antibodies using traditional ELISA methodologies. Cell mediated immunity can be assessed using recall responses to quantify the ability of recombinant protein to elicit activation of T cells in vaccinated animals. Protection can then be assessed in vaccinated animals that are subsequently challenged with a lethal dose of *Francisella* and assessed for survival.

In some embodiments, the antigenic combination comprising a *Francisella* protein antigen from a specific *Francisella* bacterium or a protein antigen having at least 30% identity with the *Francisella* protein antigen from a specific *Francisella* bacterium, together with an antigenic *Francisella* polysaccharide has protective effects against the specific *Francisella* bacterium itself.

In some embodiments, the antigenic combination comprising a *Francisella* protein antigen from a specific *Francisella* bacterium together with an antigenic *Francisella* polysaccharide is expected to have a protective effect against a different *Francisella* bacterium which has a protein antigen having at least 30% identity with respect to the *Francisella* protein antigen from a specific *Francisella* bacterium.

In some embodiments, the target *Francisella* bacteria is a human pathogen selected from subspecies *tularensis*, subspecies *holarctica* and *novicida*.

In some embodiments, the polysaccharide of the antigenic combination is from the target *Francisella* bacteria. In some embodiments, the polysaccharide of the antigenic combination is from a *Francisella* bacteria other than the target *Francisella* bacteria. the polysaccharide of the antigenic combination is synthetic.

In some embodiments, the antigenic combination comprising a *Francisella* protein antigen from a *Francisella tularensis* subspecies *tularensis* together with an antigenic *Francisella* polysaccharide provides protection effects against a *Francisella novicida* F6168 bacterium which has a protein antigen having at least 71% identity with respect to the *Francisella* protein antigen from the *Francisella tularensis* subspecies *tularensis*.

In some other embodiments, the antigenic combination comprising a *Francisella* protein antigen from a *Francisella tularensis* subspecies *tularensis* together with an antigenic *Francisella* polysaccharide provides protection effects against a *Francisella holarctica* bacterium which has a protein antigen having at least 90% identity with respect to the *Francisella* protein antigen from the *Francisella tularensis* subspecies *tularensis*.

In antigenic combination herein described, at least one antigenic *Francisella* polysaccharide (LPS and/or CPS) and at least one protein antigen from a *Francisella* bacterium are comprised together with at least one adjuvant.

The term "adjuvant" as used herein indicates an agent that stimulates the immune system but that is not antigenic in itself. Typically, adjuvants are used in connection with antigens and/or vaccine composition to increase the response to one or more antigen of choice. Adjuvants can be added to an antigenic combination to modify the immune response by boosting it such as to give a higher amount of antibodies and a longer-lasting protection, thus minimizing the amount of injected foreign material. Adjuvants can also be added to an antigenic combination to enhance the efficacy of the related antigens by helping to modify the immune response to particular types of immune system cells: for example, by activating T cells instead of antibody-secreting B cells depending on the purpose of the vaccine. Adjuvants are also used in the production of antibodies from immunized animals. There are different classes of adjuvants that can push immune response in different directions as will be understood by a skilled person.

In some embodiments, adjuvants that can be comprised in antigenic combinations herein described include naturally occurring hydrophobic or amphipathic adjuvants, immunostimulatory peptides (e.g. f-Met-Leu-Phe), muramyl dipeptide (including the analog muroctasin), saponins (e.g. gylcosidic terpenes from *Qillaja saponaria*), toxins (e.g. tetanus, cholera), oligonucleotide CpG motifs (e.g. Agatolimod), organic compounds (e.g. squalene, soribitol oleate esters), alpha-galactosyl ceramide, and lipotichoic acid (LTA), or hydrophilic adjuvants synthetically appended with a hydrophobic moiety, including microbial derivatives (e.g. muramyl dipeptide (MDP), flagellin), plant derivatives (e.g. saponins), and immunostimulatory proteins (e.g. cytokines, chemokines, flagellin, toxins, and derivative peptides), immunostimulatory carbohydrates and polysaccharides, and immunostimulatory nucleic acids (e.g. cholesterol-tagged CpG oligonucleotides).

Additional adjuvant suitable to be used in antigenic combination in the sense of the current disclosure include AddaVax™, Adju-Phos® adjuvant, Alhydrogel® adjuvant 2%, CFA, IFA, Quil-A® adjuvant, 2'3'-cGAMP VacciGrade™, 3'3'-cGAMP VacciGrade™, c-di-AMP VacciGrade™, 2'3'-c-di-AM(PS)2 (Rp,Rp) VacciGrade™, c-di-GMP VacciGrade™, Chitosan VacciGrade™, CL401 VacciGrade™, CL413 VacciGrade™, CL429 VacciGrade™, Flagellin FliC VacciGrade™, Gardiquimod VacciGrade™, Imiquimod VacciGrade™, LPS-EB VacciGrade™, MPLA-SM VacciGrade™, MPLA Synthetic VacciGrade™, N-Glycolyl-MDP VacciGrade™, ODN 1585 VacciGrade™, ODN 1826 VacciGrade™, ODN 2006 Vaccigrade™ ODN 2395 VacciGrade™, Pam3CSK4 VacciGrade™, Poly(I:C) (HMW) VacciGrade™, R848 VacciGrade™, TDB VacciGrade™, and others identifiable to a person skilled in the art.

The antigenic combination herein described can comprise an antigenic *Francisella* polysaccharide (e.g. LPS and/or CPS, and/or one or more derivatives thereof) in an amount from about 0.1 µg antigen/vaccination to about 100 µg antigen/vaccination, preferable 2-20 µg antigen/vaccination. The antigenic combination also comprises at least a *Francisella* protein antigen, each protein antigen in an amount from about 0.1 µg antigen/vaccination to about 100 µg antigen/vaccination, preferably 5-50 µg antigen/vaccination. The antigenic combination also comprises an adjuvant in an amount from about 0.001 µg to 200 µg, preferably between 0.5 and 50 µg.

A variety of factors will affect the dose of the antigenic *Francisella* polysaccharide, the *Francisella* protein antigen and the adjuvant, including the type of adjuvant and antigens being used, the administration route, the animal model used for testing, and whether the adjuvant is conjugated to the NLPs as will be understood by a person skilled in the art. Methods for dose conversion from animal model to humans and estimation of starting does for clinical trials can be found in related references such as Nair, A. B et al., [27] as will be understood by the skilled person.

Optimal vaccine composition and immunization regimen can be determined empirically by a skilled person. The general approach is to select and modify one parameter of the vaccine composition or immunization regimen while keeping all other parameters unchanged. The effect of the modification can be evaluated by immunizing separate groups of animals with the unmodified and modified vaccines and then challenging the vaccinated animals with a lethal dose of aerosolized *Francisella tularensis* SCHU S4 strain. The stringency of the test can be increased with larger challenge doses. Modifications that significantly improve survival, bacterial burden, or other measurable physiological parameters such as body weight, temperature, etc. compared to the unmodified vaccine will be selected for further development. Similar approaches can be used to optimize other parameters and to optimize the vaccine composition or immunization regimen for other animal species, including humans.

In particular, the antigenic combination herein described can comprise the *Francisella* LPS and *Francisella* protein antigen at a ratio between 1:0.1 and 1:10 by mass. In particular, the ratio between *Francisella* antigens and adjuvants herein described can range from 1:0.00001 and 1:2000 by mass. In some embodiments, the LPS to protein antigen ratio is 1:4 by mass. In some embodiments, the immunogenic composition comprises about 20 µg of protein antigen and about g of LPS (see Examples 12-17).

In embodiments herein described, the antigenic combination can comprise more than one protein antigen or derivative thereof, included in an antigenic combination together with one or more *Francisella* LPS and one or more adjuvants. In some embodiments, up to five different protein antigens can be included in the antigenic combination herein described. In some preferred embodiments, the antigenic combination comprises one LPS and one protein antigen, from the *Francisella* bacterium. For example in some embodiments an antigenic component of an antigenic combination herein described can comprise peptides of SEQ ID NO: 33, SEQ ID NO: 37, SEQ ID NO: 38, SEQ ID NO: 45, SEQ ID NO: 46, SEQ ID NO: 67, SEQ ID NO: 68, SEQ ID NO: 72, SEQ ID NO: 73 alone or in combination one with the other and/or with protein antigens such as IglC, SucB, OmpA, and DnaK in Table 1 or derivatives thereof in combination with any one of the adjuvants of the disclosure and preferably also in combination with one or more *Francisella* LPS.

In some embodiments, the antigenic combination herein described can further comprise one or more additional immunogenic agents. The term "immunological agent" as used herein indicates a compound that is able to interfere with the immune system of an individual, and in particular provoke, reduce, enhance or impair a response of the immune system under same or comparable conditions. Exemplary immunological agents comprise antigen and adjuvants.

In some embodiments herein described, the components of the antigenic combination herein described can be presented on a carrier.

A "carrier' in the sense of the disclosure indicates a substrate used in the process of delivery of an active principle which serves to improve the selectivity, effectiveness, and/or safety of the administration of the active principle. Carriers in the sense of the disclosure can encompass substrates selected to control the release of the active principle into systemic circulation of an individual, for example by slow release of the active principle over a long period of time (typically diffusion) or by triggered release at the active principle's target by some stimulus, such as changes in pH, application of heat, and activation by light. Carriers in the sense of the disclosure encompass substrates selected to improve the pharmacokinetic properties, specifically the bioavailability, of an active principle with poor water solubility and/or membrane permeability. Exemplary carriers in the sense of the disclosure include liposomes, polymeric micelles, microspheres, and nanoparticles. Methods and techniques to attach an active principle to a carrier are identifiable by a skilled person and comprise adsorption, integration into the bulk structure, encapsulation, and covalent bonding. Different types of carriers utilize different methods of attachment, and some carriers can even implement a variety of attachment methods as will be understood by a skilled person.

In some embodiments, at least one of the antigenic polysaccharide from the *Francisella* bacterium or derivative thereof, the protein antigen from the *Francisella* bacterium, and the adjuvant can be presented on a single or on separate carriers. In particular, in some of these embodiments, at least two of the protein antigens from the *Francisella* bacterium, the antigenic polysaccharide from the *Francisella* bacterium or derivative thereof and the adjuvant can be jointly presented on a single carrier which can be of a same or different type. In some embodiments the protein antigen from the *Francisella* bacterium, the antigenic polysaccharide from the *Francisella* bacterium or derivative thereof and the adjuvant can be presented on separate carriers.

In some embodiments, the antigenic polysaccharide, protein antigens, and/or adjuvants comprised in the antigenic combination herein described can be carried by a membrane-containing platform configured to provide a controllable and stable environment for the antigens to be incorporated while preserving their native conformations. The membrane-containing platform can also allow co-localized presentation of the antigens and/or adjuvants thus resulting in enhanced immunogenic response. Membrane containing platform can be isolated from existing membrane (e.g. cell membranes) or assembled from a number of components in vitro. Examples of membrane-containing platform include liposomes, micelles, membrane bilayers, nanolipoprotein particles and others identifiable by a person skilled in the art. In some embodiments the carrier can be provided by a nanolipoprotein particle.

In some embodiments, the antigenic polysaccharide from the *Francisella* bacterium or derivative thereof, the protein antigen from the *Francisella* bacterium, and/or the adjuvant can comprise a hydrophobic region configured to attach to a membrane lipid bilayer of a membrane derived platform.

For example, membrane proteins can be detergent solubilized and incorporated into membrane-derived platform during platform formation. In another example, a hydrophilic adjuvant (e.g. CpG oligonucleotide) that appended with a hydrophobic moiety (e.g. cholesterol) can be added to an aqueous solution of pre-formed membrane-containing platform. The cholesterol moiety of the adjuvant molecule will anchor the adjuvant into the membrane bilayer.

In some embodiments, *Francisella* lipopolysaccharides having a lipid A component, a core polysaccharide component and an O-antigen domain can be attached to a membrane-containing platform via the interactions between hydrophobic lipid A component and a membrane lipid bilayer of a membrane derived platform. The lipid A component of the *Francisella* LPS can be embedded into the membrane-containing platform and the polysaccharide and the O-antigen components are presented on the surface of the membrane-containing platform. In general, LPS can be incorporated into membrane-containing platform during platform formation. For example, LPS-liposomes can be formed by rehydrating dried lipid films in an aqueous solution containing LPS. During subsequent vortexing or sonication, the LPS will embed within the formed liposomes. Generic procedure for incorporating LPS into liposomes can be found in Watanabe et al 2013 [28].

In some embodiments, one or more of the antigenic polysaccharide from the *Francisella* bacterium or derivative thereof, the protein antigen from the *Francisella* bacterium, and/or the adjuvant, can comprise an anchor compound presented for binding with a corresponding anchor compound substrate on the carrier. In particular, in some embodiments the antigenic polysaccharide lacking a lipid A or lipid-A like moiety can be modified to present an anchor compound suitable for attachment to the anchor compound substrate of the carrier.

For example, soluble protein antigens that incorporate a poly-histidine peptide tag can be conjugated to a lipid-containing platform that features a lipid chelating nickel at the polar headgroup. The polyhistidine-tagged antigen will bind to the chelated nickel at the lipid platform surface and remain tethered. Similarly, protein adjuvants (e.g. flagellin) that incorporate a poly-histidine peptide tag can be conjugated to a lipid-containing platform that features a lipid chelating nickel at the polar headgroup.

In some embodiments, *Francisella* polysaccharide derivatives lacking a lipid component, *Francisella* protein antigens and/or adjuvants can be appended with a lipidic moiety or compound and then anchored in a membrane-derived platform. Exemplary lipidic compound include acyl chains, hydrophobic carbon chains, and others identifiable to a person skilled in the art. For example, CpG can be modified to include a cholesterol moiety. The cholesterol moiety anchors the highly-polar CpG molecule to the membrane-derived platform.

In some embodiments, *Francisella* polysaccharide, derivatives thereof, protein antigens, derivatives thereof, and/or adjuvants can be attached to a phospholipid functionalized with an anchor compound substrate through binding of an anchor compound attached to the *Francisella* polysaccharide, protein antigen and/or adjuvant and the corresponding anchor compound substrate.

In some embodiments where the antigen is a derivative of a *Francisella* protein antigen, the structure of the derivative can be identified using bioinformatics tools such as TMHMM Server 2.0 (Web page www.cbs.dtu.dk/services/TMHMM/ at the date of filing of the present disclosure) which can be used to predict transmembrane helices in protein sequences in order to ascertain a mode of NLP conjugation for each antigen listed in Table 1. In particular, accordance with an exemplary approach based on such predictions, the derivative *Francisella* protein antigen can be binned into two groups: 1) proteins with no putative transmembrane domains, and 2) proteins with one or more transmembrane domains. This binning allows one to tailor the vaccine formulations, especially with regards to formulation into a Nanolipoprotein Particle (NLP) or other lipidic particle carrier described herein.

Based on the TMHMM predictions, seven of the proteins listed in Table 1 contain at least one TM helix. For those proteins lacking putative transmembrane domains, including FTT_1441, DnaK, OmpA and SucB, these proteins can be recombinantly expressed to incorporate a functional anchor (e.g. poly-his tag) that will be used to anchor the soluble Ft protein to the NLP surface using a cognate anchor compound on the NLP bilayer surface as described for IglC below. For those proteins with putative membrane domains, including FopA, LpnA/Tul4, Lpp3, Type IV pilus fiber building block protein, FopB, FTT_1676 and FTT_1778c, recombinantly expressed Ft protein can be incorporated during the assembly process of NLP or other lipidic platform described herein such that the transmembrane domains of the Ft protein are embedded within the lipid bilayer.

In some embodiments, the antigenic combinations herein described are incorporated into nanolipoprotein particles to provide immunogenic nanolipoprotein particles.

The term "nanolipoprotein particle" "nanodisc" "rHDL" or "NLP" as used herein indicates a supramolecular complex formed by a membrane forming lipid arranged in a lipid bilayer stabilized by a scaffold protein. The membrane forming lipids and scaffold protein are components of the NLP. In particular, the membrane forming lipid component is part of a total lipid component (herein also membrane lipid component or lipid component) of the NLP together with additional lipids such as functionalized lipids and/or lysolipids, that can further be included in the NLPs as will be understood by a skilled person upon reading of the present disclosure. The scaffold protein component is part of a protein component of the NLP together with additional proteins such as membrane proteins, target proteins and other proteins that can be further included as components of the NLPs as will be understood by a skilled person upon reading of the present disclosure. Additional components can be provided as part of the NLP herein described as will be understood by a skilled person. In particular, the membrane lipid bilayer can attach membrane proteins or other amphipathic compounds through interaction of respective hydrophobic regions with the membrane lipid bilayer. The membrane lipid bilayer can also attach proteins or other molecule through anchor compounds or functionalized lipids as will be understood by a skilled person upon reading of the disclosure. In a nanolipoprotein particle, the membrane lipid bilayer can be confined in a discoidal configuration by the scaffold protein. Predominately discoidal in shape, nanolipoprotein particles typically have diameters between 5 to 25 nm, share uniform heights between 3 to 6 nm and can be produced in yields ranging between 30 to 90%.

In particular, in embodiments herein described the nanolipoprotein particle can be formed by a lipid bilayer confined in a discoidal configuration by a scaffold protein. In this configuration, the lipid bilayer confined by the scaffold protein can be 3-6 nanometers in thickness, the nanolipoprotein particle can have an overall diameter of 5-25 nanometers, and the scaffold protein on the particle can have a thickness of 1-2 nanometers. In some embodiments, an entire NLP structure can be up to 600 kilodaltons in weight.

The particular membrane forming lipid, scaffold protein, the lipid to protein ratio, and the assembly parameters determine the size and homogeneity of nanolipoprotein particles as will be understood by a skilled person. In the nanolipoprotein particle, the membrane forming lipid are typically arranged in a membrane lipid bilayer confined by the scaffold protein in a discoidal configuration as will be understood by a skilled person.

The term "membrane forming lipid" or "amphipathic lipid" as used herein indicates a lipid possessing both hydrophilic and hydrophobic moieties that in an aqueous environment assembles into a lipid bilayer structure that consists of two opposing layers of amphipathic molecules known as polar lipids. Each polar lipid has a hydrophilic moiety, i.e. a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols, alkylphosphocholines and the like. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC). In a preferred embodiment, the lipid is dioleoylphosphatidylcholine (DOPC).

The term "scaffold protein" as used herein indicates any amphipathic protein that is capable of self-assembly with amphipathic lipids in an aqueous environment, organizing the amphipathic lipids into a bilayer disc, and comprise apolipoproteins, lipophorins, derivatives thereof (such as truncated and tandemly arrayed sequences) and fragments thereof (e.g. peptide fragments and synthetic peptides) which maintains the amphipathic nature and capability of self-assembly, such as apolipoprotein E4 (22 kD fragment), lipophorin III, apolipoprotein A-1 and the like. In general, scaffold proteins have an alpha helical secondary structure in which a plurality of hydrophobic amino acids form a hydrophobic face and a plurality of hydrophilic amino acids form an opposing hydrophilic face. In some embodiments, rationally designed amphipathic peptides and synthetic apolipoproteins which maintain an amphipathic structure and capability of self-assembly can serve as a scaffold protein of the NLP.

The term "apolipoprotein" as used herein indicates an amphipathic protein that binds lipids to form lipoproteins. The term "amphipathic" pertains to a molecule containing both hydrophilic and hydrophobic properties. Exemplary amphipathic molecules comprise molecules having hydrophobic and hydrophilic regions/portions in its structure. Examples of biomolecules which are amphipathic include but not limited to phospholipids, cholesterol, glycolipids, fatty acids, bile acids, saponins, and additional lipids identifiable by a skilled person. A "lipoprotein" as used herein indicates a biomolecule assembly that contains both proteins and lipids. In particular, in lipoproteins, the protein component surrounds or solubilizes the lipid molecules enabling particle formation. Exemplary lipoproteins include the plasma lipoprotein particles classified under high-density (HDL) and low-density (LDL) lipoproteins, which enable fats and cholesterol to be carried in the blood stream, the transmembrane proteins of the mitochondrion and the chloroplast, and bacterial lipoproteins. In particular, the lipid components of lipoproteins are insoluble in water, but because of their amphipathic properties, apolipoproteins such as certain Apolipoproteins A and Apolipoproteins B and other amphipathic protein molecules can organize the lipids in a bilayer orientation with exposed hydrophilic moieties, creating the lipoprotein particle that is itself water-soluble, and can thus be carried through water-based circulation (e.g. blood, lymph in vivo or in vitro). Apolipoproteins known to provide the protein components of the lipoproteins can be divided into six classes and several sub-classes, based on the different structures and functions. Exemplary apolipoprotein known to be able to form lipoproteins comprise Apolipoproteins A (apo A-I, apo A-II, apo A-IV, and apo A-V), Apolipoproteins B (apo B48 and apo B100), Apolipoproteins C (apo C-I, apo C-II, apo C-III, and apo C-IV), Apolipoproteins D, Apolipoproteins E, and Apolipoproteins H. For example, apolipoproteins B can form low-density lipoprotein particles, and have mostly beta-sheet structure and associate with lipid droplets irreversibly, while Apolipoprotein A1 comprise alpha helices and can associate with lipid droplets reversibly forming high-density lipoprotein particles.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—$NH_2$) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In some embodiments, an immunogenic nanolipoprotein particle comprises and presents the antigenic combination herein described. The immunogenic nanolipoprotein particle herein described comprises: a scaffold protein, a membrane forming lipid, at least one antigenic *Francisella* polysaccharide (e.g. LPS and/or CPS and/or derivatives thereof in any combination), at least one protein antigen from *Francisella*, and an adjuvant, wherein the membrane forming lipids are arranged in a discoidal membrane lipid bilayer stabilized by the scaffold protein and the at least one *Francisella* polysaccharide or derivative thereof, at least one protein antigen from *Francisella*, and an adjuvant are attached to the discoidal membrane lipid bilayer. Accordingly, in these embodiments the NLPs herein described are provided as carriers for presenting *Francisella* polysaccharide, protein antigens and adjuvants.

The term "present" as used herein with reference to a compound or functional group indicates attachment performed to maintain the chemical reactivity of the compound or functional group as attached. Accordingly, a functional group presented on a molecule is able to perform under the appropriate conditions the one or more chemical reactions that chemically characterize the functional group. A compound presented on a particle is able to perform under the appropriate conditions the one or more chemical reactions that chemically characterize the compound. In embodiments, where the compound is or comprises an immunological agent, the immunological agent presented maintains the complex of reactions that are associated with the immunological activity characterizing the agent at issue. Accordingly, presentation of an immunological agent indicates attachment such that the immunological activity associated to the immunological agent attached is maintained.

The term "attach" or "attached" as used herein, refers to connecting or uniting by a bond, link, force or tie in order to keep two or more components together, which encompasses either direct or indirect attachment such that for example where a first compound is directly bound to a second compound or material, and the embodiments wherein one or more intermediate compounds, and in particular molecules, are disposed between the first compound and the second compound or material.

In some embodiments, at least one of the *Francisella* antigenic polysaccharide, derivative thereof, protein antigen from *Francisella*, derivative thereof and the adjuvant, comprises a hydrophobic region and is attached to the membrane lipid bilayer through interaction of the hydrophobic region with the membrane lipid bilayer.

In particular, in some embodiments wherein the antigenic *Francisella* polysaccharide component comprises at least one *Francisella* polysaccharide and/or derivative thereof comprising a hydrophobic moiety (such as hydrophobic lipid A or lipid A-like moiety of LPS), the antigenic *Francisella* polysaccharide component is attached to the NLPs via the hydrophobic moiety, which anchors the polysaccharide (e.g. LPS and/or CPS) and/or the derivative thereof to the NLP. In particular, in those embodiments the polysaccharide molecules forming the antigenic polysaccharide component from the *Francisella* bacterium, comprise a lipid component embedded into the nanolipoprotein particle and a polysaccharide component presented on the surface of the nanolipoprotein particle. Similarly, *Francisella* protein antigen components comprising one or more *Francisella* protein antigens and/or derivative thereof having a hydrophobic region (such as LpnA/Tul4, FopA1, Lpp3, Type IV pilus fiber building block protein and hypothetical proteins in Table 1 or derivative thereof having at least one transmembrane domain) can be embedded into the NLPs via the hydrophobic transmembrane domain with the epitope domain presented on the surface of the nanolipoprotein particle.

In some embodiments, a lipid component of a *Francisella* polysaccharide or derivative thereof can be replaced with a lipidic moiety to anchor the polysaccharide component and/or the O-antigen to the NLP during self-assembly.

In some embodiments, a *Francisella* polysaccharide or derivative thereof lacking a lipid component, a *Francisella* protein antigen or derivative thereof and/or an adjuvant can also be appended with a lipidic moiety or compound. Exemplary lipidic compound include acyl chains, hydrophobic carbon chains, and others identifiable to a person skilled in the art. For example, a *Francisella* polysaccharide derivative lacking a lipid component can be appended with a hydrophobic carbon chain to anchor the O-antigen or O-antigen together with a core polysaccharide to the membrane lipid bilayer. Similarly, *Francisella* protein antigens that do not have a transmembrane domain (such as IglC, SucB, OmpA, and DnaK in Table 1) or derivatives thereof such as peptides of SEQ ID NO: 33, SEQ ID NO: 37, SEQ ID NO: 38, SEQ ID NO: 45), SEQ ID NO: 46, SEQ ID NO: 67, (SEQ ID NO: 68, SEQ ID NO: 72, SEQ ID NO: 73. can be appended with a lipidic moiety or compound such as a hydrophobic carbon chain to anchor the *Francisella* protein antigens to the membrane lipid bilayer as will be understood by a skilled person.

In some embodiments, adjuvants having a hydrophobic region can be attached to an NLP through interaction of the hydrophobic region with the membrane lipid bilayer. Exemplary adjuvants falling in this group comprise amphipathic adjuvants such as cholesterol-tagged CpG can be added to preformed NLPs and will be anchored by the cholesterol moiety. Other adjuvants (for example Fsl-1, which is a peptide with acyl chains) can be added to preformed discs.

Other adjuvants, like monophosphoryl Lipid A are incorporated during the assembly process since they are highly non-polar.

In some embodiments, the NLP can comprise a functionalized amphipathic compound and at least one of the antigenic *Francisella* polysaccharide, derivatives thereof, *Francisella* protein antigens, derivatives thereof and/or adjuvants can be attached to functionalized membrane-forming lipids through binding of an anchor compound attached to the antigenic *Francisella* polysaccharide, antigen and/or adjuvant and a corresponding anchor compound substrate attached to the functionalized membrane-forming lipids.

The terms "functionalize" and "functionalization" as used herein, indicates the appropriate chemical modifications of a molecular structure (including a substrate or a compound) resulting in attachment of a functional group to the molecular structure. The term "functional group" as used herein indicates specific groups of atoms within a molecular structure that are responsible for the characteristic chemical reactions of that structure. Exemplary functional groups include, hydrocarbons containing halogen groups, hydrocarbons containing oxygen groups, hydrocarbons containing nitrogen groups, hydrocarbons containing phosphorus groups and hydrocarbons containing sulfur groups, all identifiable by a skilled person.

The term "functionalized amphipathic compounds" in the sense of the disclosure indicate compound having a hydrophobic portion and a hydrophilic portion in a configuration where the hydrophobic portion anchor is capable to anchor the compound to the lipid bilayer of the NLP and the hydrophilic portion (typically consisting or comprising a hydrophilic functional group) presented on the NLP bilayer face following NLP assembly.

The use of functionalized amphipathic compounds enables attachment of various peptides or other biologics to the surfaces of the lipid of the NLP that allows some desired target features to be obtained, such as stability, affinity for a target molecule, and the like. Non-limiting examples of functional groups presented on functionalized lipids include: chelated Ni atoms, azide, anhydride, alkynes, thiols, halogens, carboxy, amino, hydroxyl, and phosphate groups, and the like.

In some embodiments, the functional group on the functionalized amphipathic compound can be a reactive chemical groups (e.g. azide, chelated nickel, alkyne, and additional reactive chemical group identifiable by a skilled person), a biologically active compound (e.g. DNA, peptide, carbohydrate, and additional biologically active group identifiable by a skilled person) or a small molecule (e.g. cellular targeting compound, adjuvant, drug, and additional small molecules identifiable by a skilled person). In some embodiments the functionalized amphipathic compound is a functionalized lipid compound. Functional groups that enhance the lipid solubility are referred to as hydrophobic or lipophilic functional groups. Functional groups that lack the ability to either ionize or form hydrogen bonds tend to impart a measure of lipid solubility to a drug molecule. The functional group can be attached to the lipid polar head through covalent or ionic bonds and "weak bonds" such as dipole-dipole interactions, the London dispersion force and hydrogen bonding, preferably covalent. Moreover, functionalization of the lipid can involve hydrophobic quantum dots embedded into the lipid bilayer. The following article is incorporated by reference in its entirety: R. A. Sperling, and W. J. Parak. "Surface modification, functionalization and bioconjugation of colloidal inorganic nanoparticles". Phil. Trans. R. Soc. A 28 Mar. 2010 vol. 368 no. 1915 1333-1383.

In some embodiments, functionalized amphipathic compounds can comprise one or more of 1,2-dipalmitoyl-sn-glycero-3-phosphoethanolamine-N-(6-((folate)amino) hexanoyl), 1,2-dipalmitoyl-sn-glycero-3-phosphoethanolamine-N-(6-azidohexanoyl), 1,2-dipalmitoyl-sn-glycero-3-phosphoethanolamine-N-(succinyl), 1,2-dioleoyl-sn-glycero-3-phosphoethanolamine-N-(succinyl), 1,2-dipalmitoyl-sn-glycero-3-phosphoethanolamine-N-(glutaryl), 1,2-dioleoyl-sn-glycero-3-phosphoethanolamine-N-(glutaryl), 1,2-dioleoyl-sn-glycero-3-phosphoethanolamine-N-(dodecanyl), 1,2-Dipalmitoyl-sn-Glycero-3-Phosphoethanolamine-N-(hexanoylamine), 1,2-dipalmitoyl-sn-glycero-3-phosphoethanolamine-N-(dodecanylamine), 1,2-Dipalmitoyl-sn-Glycero-3-Phosphothioethanol, 1,2-dioleoyl-sn-glycero-3-phosphoethanolamine-N-[4-(p-maleimidomethyl)cyclohexane-carboxamide], 1,2-dioleoyl-sn-glycero-3-phosphoethanolamine-N-[4-(p-maleimidophenyl)butyramide], 1,2-dioleoyl-sn-glycero-3-phosphoethanolamine-N-[3-(2-pyridyldithio)propionate], 1,2-dioleoyl-sn-glycero-3-phosphoethanolamine-N-(biotinyl), 1,2-Dioleoyl-sn-Glycero-3-Phospho(Ethylene Glycol), 1,2-dioleoyl-sn-glycero-3-phosphoethanolamine-N-lactosyl, 1,2-distearoyl-sn-glycero-3-phosphoethanolamine-N-[dibenzocyclooctyl(polyethylene glycol)-2000], 1,2-distearoyl-sn-glycero-3-phosphoethanolamine-N-[succinyl (polyethylene glycol)-2000], 1,2-distearoyl-sn-glycero-3-phosphoethanolamine-N-[carboxy(polyethylene glycol)-2000], 1,2-distearoyl-sn-glycero-3-phosphoethanolamine-N-[maleimide(polyethylene glycol)-2000], 1,2-distearoyl-sn-glycero-3-phosphoethanolamine-N-[PDP(polyethylene glycol)-2000], 1,2-distearoyl-sn-glycero-3-phosphoethanolamine-N-[amino(polyethylene glycol)-2000], 1,2-distearoyl-sn-glycero-3-phosphoethanolamine-N-[biotinyl (polyethylene glycol)-2000], 1,2-distearoyl-sn-glycero-3-phosphoethanolamine-N-[cyanur(polyethylene glycol)-2000], 1,2-distearoyl-sn-glycero-3-phosphoethanolamine-N-[folate(polyethylene glycol)-2000], cholesterol modified oligonucleotides, cholesterol-PEG2000-azide, cholesterol-PEG2000-Dibenzocyclooctyl, cholesterol-PEG2000-maleimide, cholesterol-PEG2000-N-hydroxysuccinimide esters, cholesterol-PEG2000-thiol, cholesterol-azide, cholesterol-Dibenzocyclooctyl, cholesterol-maleimide, cholesterol-N-hydroxysuccinimide esters, cholesterol-thiol, C18 modified oligonucleotides, C18-PEG2000-azide, C18-PEG2000-Dibenzocyclooctyl, C18-PEG2000-maleimide, C18-PEG2000-N-hydroxysuccinimide esters, C18-PEG2000-thiol, C18-azide, C18-Dibenzocyclooctyl, C18-maleimide, C18-N-hydroxysuccinimide esters, C18-thiol. In some embodiments one or more functionalized amphipathic compounds are comprised together with non-functionalized membrane forming lipids in the lipid component of the NLP also comprising one or more polymerizable lipids. In some embodiments functionalized amphipathic compounds can be functionalized membrane forming lipid. In some embodiments, one or more functionalized membrane forming lipids are added or replace the membrane forming lipids in the lipid component of the NLP herein described also comprising one or more polymerizable lipids.

In several embodiments of the nanolipoprotein particle here described, the amphipathic compound is a membrane forming lipid at least a portion or all of the membrane-forming lipid is functionalized with an anchor substrate compound that is presented for binding with a target molecule. In particular, the ratio between functionalized membrane-forming lipid and membrane-forming lipids is dependent on the identity of the functionalized membrane-forming lipid, and it can be as low as 1% or even lower and as high as 100% as NLPs have been successfully formed with 100% functionalized membrane-forming lipid such as DOGS-NTA-Ni (1,2-di-(9Z-octadecenoyl)-sn-glycero-3-[(N-(5-amino-1-carboxypentyl)iminodiacetic acid)succinyl] (nickel salt)). This suggests that NLPs can be formed with any percentage of functionalized membrane-forming lipid (from 0 to 100%), depending on the specific functionalized membrane-forming lipid used.

In general, assembly of NLPs according to the present disclosure can be accomplished with a wide range of ratios of total membrane-forming lipids to scaffold proteins. For example, NLPs have been successfully formed with lipid to scaffold protein molar ratios of about 15:1 up to about 400:1. A typical assembly uses a lipid to scaffold protein molar ratio of about 100:1.

The term "anchor compound substrate" as used herein indicates a functional group capable to bind a corresponding functional group, herein also indicated as "anchor compound", presented on another molecule, and in particular on an antigen comprising molecule or an adjuvant molecule to be attached to the nanolipoprotein particle.

The term "bind", "binding", "conjugation" as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure includes both non-covalent binding and, covalent binding. Non-covalent binding as used herein indicates a type of chemical bond, such as protein protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities. An example of an electrostatic interaction includes using a charged lipid as the functional membrane lipid and binding an oppositely charged target molecule through electrostatic interactions.

Anchor compound substrates and corresponding anchor compound capable of binding through non-covalent binding include but are not limited to those listed in Table 3 below.

TABLE 3

| Non-Covalent Interactions | |
|---|---|
| Anchor (on a target molecule) | Anchor substrate (on functionalized lipid within NLP bilayer) |
| Poly-histidine (2-10 residues) 2-10 residue polypeptide | Chelated metal cations $Ni^{2+}$, $Co^{2+}$, $Cu^{2+}$, $Zn^{2+}$ chelated on NTA, IDA |
| Poly-arginine (5-6 residues) 5-6 residue polypeptide | Negatively charged surface e.g. carboxylates, phosphates, sulfonates |
| Proteins | Biological tags |
| Avidin (Streptavidin, neutravidin) | Biotin |
| Glutathione S-transferase (GST) fusion proteins | Glutathione |
| Strep-Tactin | Strep-tag II |

A covalent bond is instead a form of chemical bonding that is characterized by the sharing of pairs of electrons between atoms, or between atoms and other covalent bonds. In short, attraction-to-repulsion stability that forms between atoms when they share electrons is known as covalent bonding. Covalent bonding includes many kinds of interaction, including σ-bonding, π-bonding, metal to non-metal bonding, agostic interactions, three-center two-electron bonds, and the like.

Anchor compound substrates and corresponding anchor compounds capable of binding through covalent binding include but are not limited to those listed in Table 4 below.

TABLE 4

| Covalent Interactions | |
|---|---|
| Anchor (or anchor substrate) | Anchor substrate (or anchor) |
| Amine-reactive moieties Active esters (e.g. succinimidyl, tetrafluorophenyl) Carbodiimide (+/− NHS)-Carboxylic acids Isothiocyanates Sulfonyl chlorides Dichlorotriazines Aryl halides Acyl azides | Amines |
| Thiol-reactive reagents Maleimides (and derivatives) Haloacetamides (e.g. iodoacetamide) Pyridyldithio-propionate Thiosulfates | Sulfhydryls |
| Azides ("Click Chemistry" - formation of 1,2,3-triazol groups, ref. 7) | Acetylenes |
| Hydrazines/hydroxylamines/aromatic amines | Aldehydes and ketones |

Accordingly, exemplary functionalized membrane-forming lipids include, but are not limited to, chelated metal-bearing lipids, azide bearing lipids, maleimide bearing lipids, quaternary amine bearing lipids, carboxylate bearing lipids, propargyl bearing lipids, biotin bearing lipids, streptavidin and/or avidin bearing lipids, S-protein bearing lipids, and the like.

In some embodiments, binding or conjugation of the anchor compound can be performed by chelation. The term "chelation" as used herein indicates the binding or complexation of a bi- or multidentate ligand with a single metal ion. In particular, in some embodiments, the bi or multidentate ligand is part of the lipid and is capable of binding a metal ion. The ligands, which are often organic compounds, are called chelants, chelators, chelating agents, or sequestering agents. Chelating agents form multiple bonds with a single metal ion. The term "chelants" as used herein indicates a molecule that forms a stable complex with certain metal ions. Examples of chelating moieties include, but are not limited to, nitrilotriacetic acid (NTA), iminodiacetic acid (IDA), and diethylenetriamine penta-acetic acid (DTPA).

In the nanolipoprotein particles herein described, the anchor substrate compound is attached to the functionalized membrane-forming lipid so that upon assembly of the functionalized membrane-forming lipid in the nanolipoprotein particle, the anchor substrate compound is presented on the nanolipoprotein particle. Similarly, the anchor compound is attached to an immunological molecule to be presented on said NLP.

In several embodiments, the functionalized membrane-forming lipids are functionalized to present the anchor substrate compound on a hydrophilic moiety of the membrane-forming lipid to ensure presentation of the anchor substrate compound on a surface of the nanolipoprotein particle. The term "surface" as used herein indicates the exterior or upper boundary of a body or object. In particular with reference to the NLPs the term "surface" indicates they are defined by the discoidal faces. Surfaces of the NLPs form the hydrophilic portion of the NLP membrane bilayer.

Successful binding of an immunological agent to the NLP can be readily verified and quantified through a range of techniques that include but are not limited to centrifugal filtration, size exclusion chromatography, fluorescence correlation spectroscopy, cantilever-based sensing, force spectroscopy, fourier transform infrared spectroscopy, surface plasmon resonance, total internal reflection fluorescence, raman spectroscopy and additional techniques identifiable by a skilled person. In addition, binding specifically to the surface can be verified using atomic force microscopy and transmission electron microscopy and additional techniques identifiable by a skilled person.

The structure of nanolipoprotein particles herein described is illustrated in FIG. 2 which shows a schematic representation of an NLP assembly comprising a functionalized membrane-forming lipid according to some embodiments herein described.

As exemplified in the illustration of FIG. 2, panel A, purified starting components are provided that comprise a functionalized membrane-forming lipid (10), a membrane-forming lipid (20), and a scaffold protein (30). The functionalized membrane-forming lipid (10) comprises a hydrophobic moiety (11) and a hydrophilic moiety (12) and attached an anchor compound substrate (14) capable of binding to a corresponding anchor compound (41) presented on the immunological agent (40) of interest. In particular, the anchor compound substrate (14) is presented on the hydrophilic moiety (12) of the functionalized membrane-forming lipid (10). The functionalized membrane-forming lipid (10), the membrane-forming lipid (20), and the scaffold protein (30) are contacted for a time and under conditions to allow assembly of the NLP containing the functionalized membrane-forming lipid (100), shown in FIG. 2, panel A. In particular, spontaneous interaction of purified scaffold proteins, e.g. apolipoproteins, and membrane-forming lipids under appropriate conditions results in formation of nanolipoprotein particles with the nanometer-sized dimensions that are herein identified as NLPs.

In the illustration of FIG. 2, panel B, the nanolipoprotein particle (100) formed by the assembly of the functionalized membrane-forming lipid (10), the membrane-forming lipid (20) and the scaffold protein (30) is configured to present the anchor compound substrate (14) on a surface of the nanolipoprotein particle. In particular, as shown in the illustration of FIG. 2 anchor compound substrate moieties are appended to the headgroups of the functionalized membrane-forming lipid, and are presented into solution.

The amount of anchor-substrate moieties on the NLP bilayer surface can be controlled by the input ratios of membrane-forming and functionalized anchor-substrate lipids during assembly, allowing control of immunological agent loading on NLP. Generally, if 10 molar percent of the total lipid used for an assembly is a functionalized membrane-forming lipid, then approximately 10 molar percent of the total lipid within the NLP lipid bilayer will be functionalized membrane-forming lipid. This has been verified in the case of NLPs prepared with 90 molar percent DMPC and 10 molar percent of DOGS-NTA-Ni. The feed ratio to incorporated ratio of the anchor substrate moiety can further be quantitatively assesses after completion of NLP assembly using normal phase and reverse phase high performance liquid chromatography and subsequent ratios can be adjusted to achieve the desired input ratio.

Although other reagents might be added according to the desired experimental design, no other reagents have to be added to impart functionality to the NLPs since the functionalized membrane-forming lipids containing the necessary reactive group for conjugation.

As schematically shown in FIG. 2, Panel C, an immunological agent (40) bearing the appropriate corresponding anchor compound (41) (an anchor compound able to bind and accordingly be defined as complementary to the anchor-compound substrate (14)) can be attached on the NLP bilayer surface of the NLP (100).

In particular, the immunological agent (40) and the nanolipoprotein (100) are contacted for a time and under conditions to allow binding of the anchor compound (41) with the anchor compound substrate (14), which depends on the conjugation chemistry between the anchor compound and the anchor substrate compound.

Attachment of antigens and/or other immunological agents (such as adjuvants) to nanolipoprotein particles can be accomplished using any number of functionalization strategies and orientations. For example, using click chemistry, an acetylene-functionalized lipid can be conjugated with an azide-functionalized protein, or an azide-functionalized lipid can be conjugated with an acetylene-functionalized protein.

For example, attachment of antigens and/or other immunological agents (such as adjuvants) to nanolipoprotein particles can be accomplished by incorporating the molecule during NLP self-assembly. This is achieved with molecules that are hydrophobic (e.g. monophosphoryl lipid A (MPLA)) or amphipathic (e.g. LPS).

In addition, attachment of antigens and/or other immunological agents (such as adjuvants) to nanolipoprotein particles can be accomplished by adding amphipathic molecule to preformed NLP. The molecules can be inherently amphipathic (such as FSL-1) or be engineered to be amphipathic (such as CpG oligonucleotides that have been appended with a cholesterol moiety). The conjugation of azides with acetylenes (herein also indicated as click chemistry) can be achieved in buffered aqueous solution over a broad pH range for about 1 to about 24 hours to form a covalent 1, 2, 3 triazole. This reaction can be catalyzed by copper (I), typically introduced by addition of copper (II) in the presence of a reductant (e.g. ascorbic acid) to generate copper (I) in situ.

In other exemplary embodiments where attachment of a polyhistidine functionalized target molecule to a bivalent metal functionalized lipid is desired, conjugation of the poly-histidine anchor compound to the chelated metal ($Ni^{2+}$, $Co^{2+}$, $Cu^{2+}$, $Zn^{2+}$) anchor compound substrate (NTA or IDA) can be achieved over the course of an incubation ranging in time from about 5 minutes to about 2 hours at room temperature without the need of any additional components. According to this approach, no additional chelating agents (e.g. EDTA) are present in solution.

In other exemplary embodiments, where attachment of a poly-arginine functionalized immunological agent to an anionic functionalized lipid is desired, conjugation of the poly-arginine anchor compound to an anionic surface anchor compound substrate can be achieved over the course of an incubation ranging in time from about 5 minutes to about 2 hours at room temperature without the need of any additional components.

In other exemplary embodiments where attachment of an immunological agent functionalized with a protein anchor, to a lipid functionalized with a cognate biological tag is desired, conjugation of the protein anchor compounds, e.g. avidin (and derivatives such as neutravidin and the like), glutathione S-transferase (GST) and Strep-Tactin, to the cognate biological tag anchor compound substrates biotin, glutathione, and strept-tag II, respectively, can be achieved over the course of an incubation ranging in time from about 5 minutes to about 2 hours at room temperature without the need of any additional components.

In other exemplary embodiments, where attachment of an immunological agent to a functionalized lipid is performed through conjugation of active esters to amine, conjugation of the active esters to the amines is achieved in amine-free buffered aqueous solution at a pH of about 7.0 for about 1 to about 24 hours to form a covalent amide bond. Reaction can then be quenched upon addition of free amines at neutral to basic pH. No other reagents are needed to perform conjugation in those embodiments.

In other exemplary embodiments, where attachment of an immunological agent to a functionalized lipid is performed through conjugation of carboxylic acids to amine, conjugation of the carboxylic acids to the amines can be achieved by activating the carboxylic acid to an active ester, using commercially available reagents, e.g. N-hydroxysuccinimide (NHS). This can be accomplished by combining the NHS and a dehydrating agent (e.g. carbodiimides like 1-Ethyl-3-β-dimethylaminopropyl)carbodiimide (EDC)) with the target carboxylic acid. The EDC reacts with the carboxylic moiety to form a transient amine-reactive O-acylisourea, whereby NHS converts the amine-reactive O-acylisourea to an amine-reactive NHS-ester. A covalent amide bond is can then be achieved in amine-free buffered aqueous solution at a pH of 7.0 for 1 to 24 hours. Reaction can then be quenched upon addition of free amines at neutral to basic pH.

In other exemplary embodiments where attachment of an immunological agent to a functionalized lipid is performed through conjugation of isothiocyanate to amine, conjugation of the isothiocyanates to the amines is achieved in amine-free buffered aqueous solution at a pH of about 7.0 for about 1 to about 24 hours to form a covalent thiourea. Reaction can then be quenched upon addition of free amines at neutral to basic pH. According to this approach, no other reagents are needed to obtain conjugation.

In other exemplary embodiments where attachment of an immunological agent to a functionalized lipid is performed through conjugation of maleimides (and maleimide derivatives) to sulfhydryls, conjugation of the maleimides (and maleimide derivatives) to sulfhydryls can be achieved in thiol-free buffered aqueous solution at a pH between about 6.5 and about 0.5 for about 1 to about 24 hours to form a covalent thioether linkage. Maleimides can then be quenched at the completion of the reaction by the addition of free thiol. Reducing agents (e.g. tris(2-carboxyethyl) phosphine) may be used to produce free, reactive sulfhydryls, which may also be stabilized by the addition of ethylenediaminetetraacetic acid (EDTA).

In other exemplary embodiments, where attachment of an immunological agent to a functionalized lipid is performed through conjugation of halocetamide to sulfhydryls, conjugation of the haloacetamides to the sulfhydryls can be achieved in thiol-free buffered aqueous solution at a pH of about 8.3 for about 1 to about 24 hours to form a covalent thioether linkage by nucleophilic substitution of the halogen with the thiol. According to this approach no other reagents are needed to achieve conjugation.

In other exemplary embodiments, where attachment of an immunological agent to a functionalized lipid is performed through conjugation of pyridil disulfides to sulfhydryls, conjugation of the pyridyl disulfides to the sulfhydryls can be achieved in thiol-free buffered aqueous solution over a broad pH range for about 1 to about 24 hours to form disulfide bonds. According to this approach no other reagents are needed to achieve conjugation.

In other exemplary embodiments, where attachment of an immunological agent to a functionalized lipid is performed through conjugation of thiosulfate to sulfhydryls, conjugation of thiosulfates with sulfhydryls can be achieved in thiol-free buffered aqueous solution over a broad pH range for 1 to 24 hours to form disulfide bonds. No other reagents are needed in those embodiments.

In all those exemplary embodiments, conjugation of the immunological agent with the functionalized NLP can be monitored using techniques/methods such as the ones described above.

Exemplary immunological molecule that can be presented through conjugation with any one of the anchor compounds herein described comprise peptides of SEQ ID NO: 33, SEQ ID NO: 37, SEQ ID NO: 38, SEQ ID NO: 45), SEQ ID NO: 46, SEQ ID NO: 67, (SEQ ID NO: 68, SEQ ID NO: 72, SEQ ID NO: 73 alone or in combination one with the other and/or with protein antigens such as IglC, SucB, OmpA, and DnaK in nanolipoprotein particles further comprising at least one adjuvant and preferably at least one *Francisella* LPS. In particular the peptides, protein antigens and/or adjuvant can be attached to a functionalized amphipathic lipid comprising one or more of 1,2-dipalmitoyl-sn-glycero-3-phosphoethanolamine-N-(6-((folate)amino)hexanoyl), 1,2-dipalmitoyl-sn-glycero-3-phosphoethanolamine-N-(6-azidohexanoyl), 1,2-dipalmitoyl-sn-glycero-3-phosphoethanolamine-N-(succinyl), 1,2-dioleoyl-sn-glycero-3-phosphoethanolamine-N-(succinyl), 1,2-dipalmitoyl-sn-glycero-3-phosphoethanolamine-N-(glutaryl), 1,2-dioleoyl-sn-glycero-3-phosphoethanolamine-N-(glutaryl), 1,2-dioleoyl-sn-glycero-3-phosphoethanolamine-N-(dodecanyl), 1,2-Dipalmitoyl-sn-Glycero-3-Phosphoethanolamine-N-(hexanoylamine), 1,2-dipalmitoyl-sn-glycero-3-phosphoethanolamine-N-(dodecanylamine), 1,2-Dipalmitoyl-sn-Glycero-3-Phosphothioethanol, 1,2-dioleoyl-sn-glycero-3-phosphoethanolamine-N-[4-(p-maleimidomethyl)cyclohexane-carboxamide], 1,2-dioleoyl-sn-glycero-3-phosphoethanolamine-N-[4-(p-maleimidophenyl)butyramide], 1,2-dioleoyl-sn-glycero-3-phosphoethanolamine-N-[3-(2-pyridyldithio)propionate], 1,2-dioleoyl-sn-glycero-3-phosphoethanolamine-N-(biotinyl), 1,2-Dioleoyl-sn-Glycero-3-Phospho(Ethylene Glycol), 1,2-dioleoyl-sn-glycero-3-phosphoethanolamine-N-lactosyl, 1,2-distearoyl-sn-glycero-3-phosphoethanolamine-N-[dibenzocyclooctyl(polyethylene glycol)-2000], 1,2-distearoyl-sn-glycero-3-phosphoethanolamine-N-[succinyl (polyethylene glycol)-2000], 1,2-distearoyl-sn-glycero-3-phosphoethanolamine-N-[carboxy(polyethylene glycol)-2000], 1,2-distearoyl-sn-glycero-3-phosphoethanolamine-N-[maleimide(polyethylene glycol)-2000], 1,2-distearoyl-sn-glycero-3-phosphoethanolamine-N-[PDP(polyethylene glycol)-2000], 1,2-distearoyl-sn-glycero-3-phosphoethanolamine-N-[amino(polyethylene glycol)-2000], 1,2-distearoyl-sn-glycero-3-phosphoethanolamine-N-[biotinyl (polyethylene glycol)-2000], 1,2-distearoyl-sn-glycero-3-phosphoethanolamine-N-[cyanur(polyethylene glycol)-2000], 1,2-distearoyl-sn-glycero-3-phosphoethanolamine-N-[folate(polyethylene glycol)-2000], cholesterol modified oligonucleotides, cholesterol-PEG2000-azide, cholesterol-PEG2000-Dibenzocyclooctyl, cholesterol-PEG2000-maleimide, cholesterol-PEG2000-N-hydroxysuccinimide esters, cholesterol-PEG2000-thiol, cholesterol-azide, cholesterol-Dibenzocyclooctyl, cholesterol-maleimide, cholesterol-N-hydroxysuccinimide esters, cholesterol-thiol, C18 modified oligonucleotides, C18-PEG2000-azide, C18-PEG2000-Dibenzocyclooctyl, C18-PEG2000-maleimide, C18-PEG2000-N-hydroxysuccinimide esters, C18-PEG2000-thiol, C18-azide, C18-Dibenzocyclooctyl, C18-maleimide, C18-N-hydroxysuccinimide esters, C18-thiol.

In some embodiments, attachment of one or more antigens and/or other immunological agents in a same functionalized NLP can be performed using different anchor compounds and corresponding anchor substrate for a same NLP where the selection of compatible anchor/anchor substrate pair can be performed by the skilled person in view of the immunological agent(s) to be attached, the chemistry of the compounds involved and the experimental design.

In particular, compatibility of the anchor/substrate pair of choice with all the NLP components has to be considered in selecting a suitable NLP for attaching a target molecule of interest, especially if conjugation to the lipid bilayer, rather than the scaffold protein, is performed. For example, in some embodiments amine-based conjugation is not compatible with certain scaffold proteins. If the scaffold protein in question contains a free amine group, then amine-reactive compounds will conjugate to the scaffold proteins. Similarly, compounds functionalized with reactive maleimides would react with any available sulfhydryl moieties present in cysteine-containing scaffold proteins. A skilled person will be able to identify and sort components according to a desired experimental design.

In some embodiments immunogenic NLP comprises a scaffold protein, a membrane forming lipid, a functionalized amphipathic compound, and the antigenic combination herein described. In the immunogenic NLPs, at least one protein antigen from the *Francisella* bacterium of the *Francisella* protein antigen component (either derived to comprise an anchor or attached to an anchor compound to form an anchored protein antigen) presents an anchor portion attached to the anchor compound substrate of the functionalized amphipathic compound. Antigenic polysaccharides of the antigenic *Francisella* polysaccharide component, such as derivatives of the antigenic LPS and/or CPS lacking the Lipid A or Lipid-A like moiety can be modified to present an anchor compound suitable for attachment to the anchor compound substrate of the functionalized amphipathic compound.

In some embodiments, the antigenic *Francisella* polysaccharide component and the NLP are assembled at a ratio about 1 to 50 LPS molecules per NLP, preferably 2-10 LPS molecules per NLP (see Example 5).

In some embodiments, the *Francisella* protein antigen component and the NLP are assembled at a ratio about 1 to 50 protein antigen molecules per NLP, preferably 2-10 protein antigen molecules per NLP (see Example 5).

In some embodiments, the adjuvant and the NLP are assembled at a ratio about 1 to 50 adjuvant molecules per NLP, preferably 2-10 adjuvant molecules per NLP.

In some embodiments, the immunogenic NLPs herein described comprise the NLPs, adjuvants, the antigenic *Francisella* polysaccharide component and the *Francisella* protein antigen component at a ratio range of 1:1:1:1: to 1:50:50:50, preferably at a ratio range of 1:2:2:2 to 1:10: 10:10.

Figure 3:
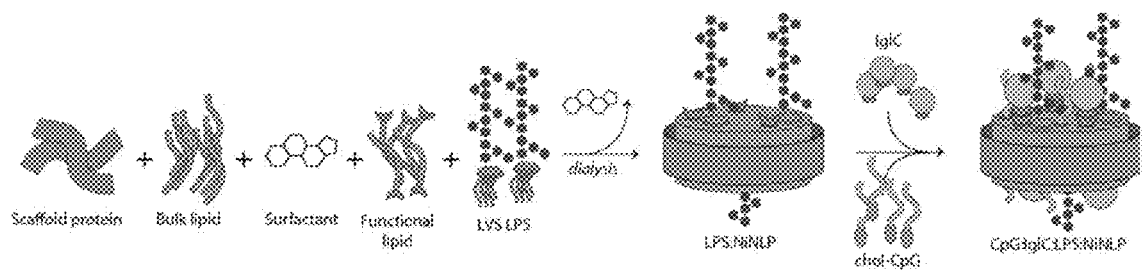
FIG. 3 shows a schematic representation of an NLP assembly with the incorporation of an adjuvant, a LPS and a protein antigen both from *Francisella tularensis*.

FIG. 3 shows a schematic illustration of nanoparticle incorporating a *Francisella* LPS and an exemplary protein antigen IglC wherein the incorporation of the IglC occurs through binding of an anchor compound with a corresponding anchor compound substrate. In particular, the illustration of FIG. 3 schematically shows the coupling of the protein antigen to the surface of a functionalized NLP bilayer. The lipid component of the LPS (lipid A) is embedded into the bilayers of the NLP acting as an anchor to conjugate the LPS molecule to the NLP, while the polysaccharide component of the LPS is presented on the surface of the NLP. As such, the LPS can be added to the NLP during the self-assembly process. NLPs assembled with a fraction of headgroup-functionalized lipids, providing a means of either covalently or noncovalently coupling the adjuvant to the surface of the NLP bilayer.

As a person skilled in the art will understand, LPS is an amphipathic molecule. In solution, LPS alone typically forms very high molecular weight aggregates. These aggregates must be dissociated into monomeric units so that individual LPS molecules (not aggregates) are available for incorporation into the NLP bilayer during self-assembly (see FIGS. 8 and 9).

In some immunogenic nanoparticles herein described, an adjuvant herein described is incorporated into the NLP. The incorporation of an adjuvant into NLPs can be achieved through binding of an anchor compound with a corresponding anchor compound substrate in a similar way a protein antigen is presented on NLPs.

Exemplary adjuvants that can be attached to an NLP herein described through anchor binding include, but are not limited to, immunostimulatory peptides (e.g. f-Met-Leu-Phe), muramyl dipeptide (including the analog muroctasin), saponins (e.g. gylcosidic terpenes from *Qillaja Saponaria*), toxins (e.g. tetanus, cholera), oligonucleotide CpG motifs (e.g. Agatolimod), immunostimulatory carbohydrates and polysaccharides, and immunostimulatory protein or peptide molecules (e.g. cytokines, chemokines, flagellin, and derivatives thereof).

Alternatively, an adjuvant can be synthetically appended with a long chain fatty acid, or other hydrophobic or amphipathic moieties, to form an amphipathic adjuvant having a hydrophilic portion and a hydrophobic portion. For example, a CpG molecule can be modified to include a cholesterol moiety. The cholesterol moiety anchors the highly-polar CpG molecule to the NLP. Any lipidic compound can be used with similar anchoring effect. Exemplary lipidic compound include acyl chains, hydrophobic carbon chains, and others identifiable to a person skilled in the art. Due to the amphipathic nature of this molecule, it can be added both during NLP self-assembly or after NLPs have been formed. In some preferred embodiments, the adjuvants are added after NLPs have been formed (see FIG. 3).

The immunogenic NLPs herein described can further comprise other immunological agents such as other carbohydrate antigen. For example, O-antigens of LPS can be conjugated or incorporated into the immunogenic NLPS.

In several embodiments, immunogenic NLPs herein described can be formed with a variety of phospholipids including but not limited to: dimyristoylphospatidylcholine (DMPC), dioleoylphosphoethanolamine (DOPE), dioleoylphophatidylcholine (DOPC), dioleoylphosphoserine (DOPS), dioleoylphosphoserine (DOPS), dioleoyl-glycero-3-[(N-(5-amino-1carboxypentyl) iminodiacetic acid)succinyl] (DOGS-NTA).

In several embodiments, immunogenic NLPs herein described can be formed with apolipoproteins that include human ApoE4 22K and insect lipophorins from *Bombyx mori* and *Manduca sexta*, apoA-1, and ApoA-1 derivatives.

In several embodiments the functionalized membrane-forming lipid of the immunogenic NLP can include but is not limited to dioleoyl-glycero-3-[(N-(5-amino-1-carboxy-pentyl)iminodiacetic acid)succinyl] (DOGS-NTA) and DOGS-NTA(Ni), 1,2-di-(9Z-octadecenoyl)-sn-glycero-3- phosphoethanolamine-N-[4-(p-maleimidophenyl)butyramide] (18:1 MPB PE), and 1,2-di-(9Z-octadecenoyl)-sn-glycero-3-phosphoethanolamine-N-(cap biotinyl) (sodium salt), and azido- and propargyl-modified lipids.

In particular, in some of those embodiments, where binding is performed by interaction with a chelated bivalent metal ion, the chelant is a modified lipid molecule, e.g. dioleoyl-glycero-3-[(N-(5-amino-1-carboxypentyl)iminodiacetic acid)succinyl] (DOGS-NitriloTriaceticAcid) and DOGS-NTA(bivalent metal ion) to which His-tagged proteins can be specifically and directly conjugated.

Embodiments based on the bivalent metal ion-chelating ability of NiNLPs allow conjugation of any (His)-tagged protein, opening the door to thousands of potential immunological agents. Bivalent metal ions comprise Ni and additional transition metals bound or chelated by polyhistidine sequences. Exemplary bivalent metal ions include but are not limited to $Co^{2+}$, $Ni^{2+}$, $Cu^{2+}$ and $Zn^{2+}$. Corresponding polyhistidine tags can be comprised at either one of the ends of the target molecule to be attached. For example, a His-tag can be added at either the N- or C-terminus of recombinantly expressed proteins to enable rapid isolation and purification.

In other embodiments, the membrane-forming lipid can be functionalized to contain an azide group that can react with an immunological agent (e.g. a protein) specifically modified to contain a propargyl group. The reaction product between the azide and acetylene group forms a 1,2,3-triazole moiety. The product of this cycloaddition reaction or "click chemistry" is a covalent association between the immunological agent and the NLP.

Still in other embodiments, a thiol group is added to the immunological agent and is then reacted with a maleimide group presented on a functionalized membrane-forming lipid. Maleimide bearing lipids (functionalized anchor substrate lipid), are available commercially. In this case, an anchor-bearing immunological agent would be configured to present a free thiol group that could add to the maleimide moiety forming a covalent bond.

In particular, metal chelating lipids, such as 1,2-di-(9Z-octadecenoyl)-sn-glycero-3-[(N-(5-amino-1-carboxypentyl)iminodiacetic acid)succinyl] (ammonium salt), and the like, that are suitable in forming NLPs herein described, are commercially available or synthesizable by a skilled person using techniques known in the art. In embodiments where metal chelating lipids are used in a functionalized NLP, the corresponding immunological agents are configured to contain a polyhistidine tag for conjugation. Attachment of a polyhistidine tag to the immunological agent can be achieved through molecular biological approaches and techniques identifiable by a skilled person.

Also negatively charged headgroup lipids, such as phosphatidic acid-, phosphatidylserine, phosphatidylglycerol-bearing lipids, and the like, that are suitable in forming NLPs herein described are commercially available or synthesizable by a skilled person using techniques known in the art. In embodiments where negatively charged headgroup lipids are used in a functionalized NLP, the corresponding immunological agents are configured to contain a polyarginine tag for conjugation. Attachment of a polyarginine tag to the immunological agent can be achieved through molecular biological approaches and techniques identifiable by a skilled person. Further, immunological agents that are inherently positively charged require no further modification.

Positively charged headgroup lipids, such as 1,2-di-(9Z-octadecenoyl)-3-trimethylammonium-propane (chloride salt), and the like, that are suitable in forming NLPs herein described are commercially available or synthesizable by a skilled person using techniques known in the art. In embodiments where positively charged headgroup lipids are used in a functionalized NLP, the corresponding target molecules are configured to contain an overall negative charge for conjugation sufficient to allow binding with the headgroup. In some of those embodiments the negatively charged immunological agents require no further modification to allow conjugation with the functionalized NLP.

Biotinylated lipids, such as 1,2-dihexadecanoyl-sn-glycero-3-phosphoethanolamine-N-(biotinyl) (sodium salt), and the like, that are suitable in forming NLPs herein described are commercially available or synthesizable by a skilled person using techniques known in the art. In embodiments where biotinylated lipids are used in a functionalized NLP, the corresponding immunological agents are configured to contain avidin (and/or derivatives thereof), via an additional biotin moiety.

Glutathione-derivatized lipids such as phosphatidylethanolamine-bearing lipid that are suitable in forming NLPs herein described be formed through coupling of glutathione to an appropriate lipid. In embodiments where glutathione-derivatized lipids are used in a functionalized NLP, the corresponding immunological agents are configured to contain a glutathione S-transferase fusion protein tag for conjugation. Attachment of a glutathione S-transferase fusion protein tag to the immunological agent can be achieved through molecular biological approaches and techniques identifiable by a skilled person.

Strep-tag II-derivatized lipids that are suitable in forming NLPs herein described can be formed through coupling of synthetic strep-tag II to an appropriate lipid, such as. phosphatidylethanolamine-bearing lipid, according to techniques identifiable by a skilled person. In embodiments where glutathione-derivatized lipids used in a functionalized NLP, the corresponding immunological agents are configured to contain a compound such as Strep-Tactin, which is commercially available.

Amine-bearing lipids, such as phosphatidylethanolamine that are suitable in forming NLPs herein described are commercially available or synthesizable by a skilled person using techniques known in the art. In embodiments where amine bearing lipids are used in a functionalized NLP, the corresponding immunological agents are configured to contain an amine-reactive moiety, (e.g. active esters, isothiocyanates, sulfonyl chlorides, dichlorotriazines, aryl halides, acyl azides, and the like). Attachment of an amine reactive moiety to the immunological agent can be achieved through previously established coupling chemistries and techniques identifiable by a skilled person.

Carboxylic acid-bearing lipids, such as. 1,2-dihexadecanoyl-sn-glycero-3-phosphoethanolamine-N-(succinyl) (sodium salt), that are suitable in forming NLPs herein described are commercially available or synthesizable by a skilled person using techniques known in the art. In embodiments where carboxylic acids are used in a functionalized NLP, the corresponding immunological agents are configured to contain a reactive primary amine, e.g. lysine side chain presented on the immunological agent for binding with the carboxylic acid-bearing lipids.

Thiol-reactive lipids, such as 1,2-dihexadecanoyl-sn-glycero-3-phosphoethanolamine-N-[4-(p-maleimidophenyl)butyramide] (sodium salt), that are suitable in forming NLPs herein described are commercially available or synthesizable by a skilled person using techniques known in the art. In embodiments where thiol-reactive lipids are used in a functionalized NLP, the corresponding immunological agents are configured to contain a reduced sulfhydryl moiety, such as reduced cysteine residue.

Free sulfhydryl-bearing lipids, such as 1,2-Dipalmitoyl-sn-Glycero-3-Phosphothioethanol (Sodium Salt), that are suitable in forming NLPs herein described are commercially available or synthesizable by a skilled person using techniques known in the art. In embodiments where free sulfhydryl-bearing lipids are used in a functionalized NLP, the corresponding immunological agents are configured to contain thiol-reactive moieties, such as maleimides (and derivatives), haloacetamides, pyridyldithio-propionate, and thiosulfates.

Azide- and alkyne-bearing lipids that are suitable in forming NLPs herein described can be prepared from commercially available components that react with phosphatidylethanolamine-bearing lipids, e.g. 3-(azidotetra(ethyleneoxy))propionic acid, succinimidyl ester and 3-propargyloxypropanoic acid, succinimidyl ester, respectively. In embodiments where azide- and alkyne-bearing lipids are used in a functionalized NLP, the corresponding immunological agents are configured to contain either an acetylene- or azide reactive group, respectively, to form a stable 1, 2, 3 triazole reaction product.

In any of the above embodiments, one or more additional same or different adjuvant and/or antigen can be attached to the immunostimulatory nanoparticle through binding the anchor compound-anchor substrate compound and/or through self-assembly of the additional amphipathic or hydrophobic adjuvant and/or antigen in the nanoparticle assembly process and/or through binding lipidic-anchored adjuvant and/or antigen to preformed NLPs.

For example, in several embodiments, NLPs made from apolipoprotein and a mixture of DOGS-NTA (Ni) [1-50%] and DMPC, DOPC form nanoparticles containing nickel ions on the surface or face of the particle (Ni-NLPs). In some of those embodiments, protein conjugation between these Ni containing NLPs bind antigens formed by His labeled proteins (see Examples 1-3 wherein conjugation has been shown with particular reference to the major envelope protein from West Nile Virus (WNV—Env).

Accordingly, in some embodiments, the antigens and/or other immunological agents herein described including LPS and protein antigens from *Francisella tularensis*, and adjuvants can be presented on an NLP allowing assembly of customized immunogenic platforms comprising a combination of selected antigens and/or other immunological agents immobilized on the surface of the lipid bilayer.

A schematic exemplary representation of an immunogenic nanolipoprotein particle is illustrated in FIG. 3. In particular, FIG. 3 shows an NLP assembly with the incorporation of an adjuvant, a LPS and a protein antigen both from *Francisella tularensis*.

In some embodiments of the immunogenic NLPs, at least one *Francisella* LPS together with at least one protein antigen from *Francisella* are contained on an NLP with at least one adjuvant molecule. In some other embodiments, *Francisella* LPS and protein antigens are separately contained on NLPs with at least one adjuvant molecule. In the embodiments herein described, each NLP is conjugated with an adjuvant and preferably contains at least one *Francisella* LPS and/or at least one *Francisella* protein antigen.

Accordingly, in a population of immunogenic NLPs comprising *Francisella* LPS, *Francisella* protein antigens and adjuvants, the population of immunogenic NLPs can comprise a subpopulation of immunogenic NLPs each containing at least one protein antigen from *Francisella*, at least one LPS from *Francisella*, and at least one adjuvant molecule, and/or a subpopulation of immunogenic NLPs each containing a *Francisella* LPS and an adjuvant molecule, and/or a subpopulation of immunogenic NLPs each containing a *Francisella* protein antigen and an adjuvant molecule, and/or a subpopulation of immunogenic NLPs each containing a *Francisella* LPS and *Francisella* protein antigen.

The amount of antigens and immunological agents on the NLP biolayer surface can be controlled by the input ratios of the antigens and immunological agents, membrane-forming lipids and the functionalized membrane-forming lipids, allowing the control of immunological agent loading in the NLP.

In some embodiments, the immunogenic NLP comprises *F. tularensis* LVS LPS, *F. tularensis* protein antigen IglC, and an adjuvant CpG. The LPS is anchored to the NLP bilayer during NLP self-assembly via the hydrophobic Lipid A moiety of LPS, which anchors the LPS to the NLP. The protein antigen is conjugated to the pre-formed NLP via a polyhistidine tag on the NLP and the cognate chelated nickel present on the NLP bilayer surface. The CpG molecule is modified with a cholesterol moiety. The modified amphipathic molecule is added to pre-formed NLP, whereby the cholesterol moiety inserts into the NLP bilayer and anchors the CpG moiety to the bilayer surface. In some embodiments, the preferred ratio of NLP:LPS:protein:adjuvant is 1:2:2:2.

Immunogenic nanolipoprotein particle according to the present disclosure and NLP carrier presenting at least one of the antigenic polysaccharide from the *Francisella* bacterium or derivative thereof forming the antigenic *Francisella* polysaccharide component, the protein antigen from the *Francisella* bacterium or derivative thereof of the *Francisella* protein antigen component, the adjuvant, can be provided according to methods identifiable by a skilled person upon reading of the present disclosure.

In some embodiments a method to provide an NLP comprises: providing a membrane-forming lipid, a scaffold protein and optionally a functionalized membrane-forming lipid presenting an anchor compound substrate, together with at least one molecule of the antigenic *Francisella* polysaccharide component, the *Francisella* protein antigen component, and the adjuvant.

In these embodiments the antigenic LPS from the *Francisella* bacterium or derivative thereof, the protein antigen from the *Francisella* bacterium, and the adjuvant comprise a hydrophobic region configured for attachment to a membrane lipid bilayer, and/or comprise an anchor compound presented for binding with the anchor compound substrate on the functionalized amphipathic compound.

In embodiments, wherein the method is directed to provide NLPs presenting at least one molecule of the antigenic *Francisella* polysaccharide component and the *Francisella* protein antigen component and the adjuvant, comprising a hydrophobic region configured for attachment to a membrane lipid bilayer, the method comprises mixing the membrane-forming lipid, the scaffold protein, and optionally the functionalized amphipathic compound, together with the antigenic LPS from the *Francisella* bacterium or derivative thereof, the protein antigen from the *Francisella* bacterium, and the adjuvant comprising a hydrophobic region.

In the method the mixing is performed for a time and under condition to allow self-assembly of the membrane-forming lipid and the scaffold protein into a discoidal membrane lipid bilayer stabilized by the scaffold protein with the at least one molecule of the antigenic *Francisella* polysaccharide component, the *Francisella* protein antigen component and the adjuvant, if any, attached to the membrane lipid bilayer through interaction of the hydrophobic region with the membrane lipid bilayer to form a nanolipoprotein particle. For example, NLPs can incorporate LPS (consisting of lipid A, core, and o-antigen), a membrane protein antigen, and a cholesterol-tagged CpG adjuvant. The LPS, membrane protein, and scaffold protein are added to surfactant-solubilized lipids. The surfactant is removed to initiate NLP self-assembly and the LPS and membrane protein are anchored to the NLP lipid bilayer by either the lipid A moiety or hydrophobic polypeptide region of the LPS or membrane protein respectively. The cholesterol-tagged CpG adjuvant can then be added to these pre-formed NLPs, whereby the cholesterol moiety will anchor the molecule to the NLP lipid bilayer.

In embodiments wherein at least one molecule of the antigenic *Francisella* polysaccharide component, the *Francisella* protein antigen component, and the adjuvant comprise an anchor compound presented for binding with the anchor compound substrate on the functionalized amphipathic compound, the method further comprises mixing a formed nanolipoprotein particle comprising a functionalized amphipathic compound presenting an anchor compound substrate with the at least one molecule of the antigenic *Francisella* polysaccharide component, the *Francisella* protein antigen component and the adjuvant for a time and under condition to allow the attaching to the nanolipoprotein particle through the binding of the anchor compound and the anchor compound substrate of the functionalized membrane-forming lipid.

In some embodiments, the method comprises providing a membrane-forming lipid, a scaffold protein, a functionalized membrane-forming lipid attached with an anchor compound substrate, and an antigenic *Francisella* polysaccharide component comprising a polysaccharide from *Francisella* or derivative thereof, the polysaccharide or derivative thereof further comprising a lipid component and a polysaccharide component; mixing the membrane-forming lipid, the scaffold protein, the functionalize membrane-forming lipid, and the antigenic *Francisella* polysaccharide component for a time and under condition to allow self-assembly of the membrane-forming lipid, the scaffold protein, the functionalize membrane-forming lipid into a nanolipoprotein particle with the lipid component of the *Francisella* polysaccharide embedded into the nanolipoprotein particle and the polysaccharide component of the *Francisella* polysaccharide on the surface of the nanolipoprotein particle.

The method further comprises attaching a protein antigen and/or a derivative thereof of a *Francisella* protein antigen component to an anchor compound thus providing an anchored *Francisella* protein antigen component; mixing the formed nanolipoprotein particle with the anchored *Francisella* protein antigen component for a time and under condition to allow the anchored a protein antigens and/or a derivative thereof of the anchored *Francisella* protein antigen attaching to the nanolipoprotein particle through the binding of the anchor compound and the anchor compound substrate of the functionalized membrane-forming lipid. For example, soluble protein antigens that incorporate a polyhistidine peptide tag (anchor compound) can be conjugated to a lipid-containing platform that features a lipid chelating nickel at the polar headgroup (anchor compound). The polyhistidine-tagged antigen will bind to the chelated nickel at the lipid platform surface and remain tethered.

As exemplified in the illustration of FIG. 3, purified starting components are provided, which comprise F.t. LPS, a membrane-forming lipid, a functionalized membrane-forming lipid, and a scaffold protein. The F.t. LPS comprises a hydrophilic component (polysaccharide component) and a hydrophobic component (lipid A component). The starting components are contacted for a time and under conditions to allow assembly of the LPS:NLP.

The *Francisella* LPS is first heated in cholate or some other surfactants prior to the addition to the NLP to ensure that monomeric LPS is present during the self-assembly reaction.

In some embodiments, the dispersed *Francisella* LPS, membrane-forming lipids, functionalized membrane-forming lipids, and scaffold proteins are incubated for about 30-600 minutes at a temperature ranging from 15-35° C. In some preferred embodiments, the contact time is about 60-120 minutes and the incubation temperature is from 20-25° C. (see Example 5).

The formed LPS:NLP are further mixed with a protein antigen from *Francisella tularensis* attaching an anchor compound and, optionally, an amphipathic adjuvant having a hydrophobic moiety and a hydrophilic moiety. The protein antigen from *Francisella tularensis* is attached with an anchor compound which allows the protein antigen to be attached to the NLP through the binding of the anchor compound and the anchor compound substrate from the functionalized membrane-forming lipids. The hydrophobic moiety of the adjuvant can be appended to a hydrophilic adjuvant using synthetic procedures identifiable by a skilled person or be naturally occurring. The LPS:NLP, the protein antigen from *Francisella tularensis* and the amphipathic adjuvant are contacted for a time and under conditions to allow assembly of the immunogenic NLP. The protein antigen and the amphipathic adjuvant are incubated for at least 5 minutes, preferably 30 minutes. The incubation can be done at temperature ranges between +2° C. and +37° C., preferably at +20° C.

As illustrated in FIG. 3, the immunogenic NLPs formed by the assembly of the membrane-forming lipids, the functionalized membrane-forming lipids, the scaffold protein, the FT LPS, the protein antigen from *Francisella tularensis* and optionally the adjuvant is configured to present the polysaccharide portion of the FT LPS and the protein antigen from *Francisella tularensis* on the surface of the nanolipoprotein particle.

Other membrane-derived vesicles such as membrane microparticles can also be used as carriers in place of NLPs for incorporating the antigens and/or adjuvants.

In some embodiments herein described, an immunogenic composition is described. The immunogenic composition comprises the antigenic combination described together with a suitable vehicle.

The term "vehicle" as used herein indicates any of various media acting usually as solvents, carriers, binders or diluents for antigens and/or NLPs comprised in the composition as an active ingredient.

The term "excipient" as used herein indicates an inactive substance used as a carrier for the active ingredients of a medication. Suitable excipients for the pharmaceutical compositions herein disclosed include any substance that enhances the ability of the body of an individual to absorb the immunogenic composition. Suitable excipients also include any substance that can be used to bulk up formulations with the composition herein described to allow for convenient and accurate dosage. In addition to their use in the single-dosage quantity, excipients can be used in the manufacturing process to aid in the handling of the immunogenic compositions. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent includes any substance that can decrease the viscosity of a medicinal preparation.

In some embodiments, the components of the antigenic combination are comprised in an amount effective to induce immunogenic responses in a subject. The term "effective amount" refers to a nontoxic but sufficient amount of one or more active ingredients of the antigenic combination to provide a desired effect. Accordingly, an effective amount associated with inducing immunogenic responses in a subject against bacterial infections caused by *Francisella* refers to non-toxic but sufficient amount of the at least one *Francisella* LPS and the at least one *Francisella* protein antigen.

The immunogenic composition can comprise an antigenic *Francisella* polysaccharide component (e.g. a *Francisella* LPS) in an amount from about 0.1 µg antigen/vaccination to about 100 µg antigen/vaccination, preferable 2-20 µg antigen/vaccination. The immunogenic composition also comprises *Francisella* protein antigen component in an amount from about 0.1 g antigen/vaccination to about 100 µg antigen/vaccination, preferable 5-50 µg antigen/vaccination.

Optimal vaccine composition and immunization regimen can be determined empirically by skilled person. The general approach is to select and modify one parameter of the vaccine composition or immunization regimen while keeping all other parameters unchanged. The effect of the modification can be evaluated by immunizing separate groups of animals with the unmodified and modified vaccines and then challenging the vaccinated animals with a lethal dose of aerosolized *Francisella tularensis* SCHU S4 strain. The stringency of the test can be increased with larger challenge doses. Modifications that significantly improves survival, bacterial burden, or other measurable physiological parameters such as body weight, temperature, etc. compared to the unmodified vaccine will be selected for further development. Similar approaches can be used to optimize other parameters and to optimize the vaccine composition or immunization regimen for other animal species, including humans.

In particular, the immunogenic composition herein described can comprise the antigenic *Francisella* polysaccharide component and the *Francisella* protein antigen component at a ratio between 1:0.1 and 1:10 by mass. In some embodiments, the immunogenic composition comprises about 5 µg of LPS antigen and about 20 µg of protein antigen (see Examples 12-17).

In some embodiments, the components of the antigenic combination and/or related subcomponents are comprised in the composition presented on one or more same or different carriers. In particular in some embodiments the antigenic *Francisella* polysaccharide component and the *Francisella* protein antigen component and/or related antigenic *Francisella* polysaccharides and derivatives thereof and *Francisella* protein antigens and derivatives thereof can be presented on single same or different carrier. In some embodiments the components and/or subcomponents of the antigenic combination can be presented on separate same or different carriers. In particular, in some embodiments, the carrier can comprise one or more membrane-derived platform. In some embodiments, the membrane derived platform carrier can be a nanolipoprotein particle.

In embodiments herein described, the immunogenic composition further comprises one or more compatible and pharmaceutically acceptable vehicles, excipients or diluents selected to provide the composition in a particular form, for example, aerosol, aqueous or oily suspension, solutions, emulsions, syrups or elixirs, for various routes of administration.

In some embodiments, the immunogenic composition herein described are provided as pharmaceutical compositions such as a vaccine for preventing tularemia in a subject. The term "vaccine" as used herein indicates a composition, and in particular a biological preparation, that establishes or improves immunity to a particular external pathogenic assault, or an inherent transformational incident resulting in a cancerous condition in mammals. Vaccines in the sense of the present description can be prophylactic, or therapeutic.

In some embodiments herein described, the combination of the antigenic *Francisella* polysaccharide component and the *Francisella* protein antigen component can cause a synergistic effect in protection against *Francisella tularensis*, particularly type A *Francisella tularensis*. In particular, the immunogenic composition herein described can induce both a humoral immunity and a cellular immunity, thus resulting in an increase in the potency of the vaccine and enhanced protective capacity against virulent *Francisella* over either component alone.

In some exemplary embodiments described herein, a vaccine formulation comprising either a LPS antigen or a protein antigen from *Francisella tularensis* provides no protection or only marginal protection effect against *Francisella tularensis*. By contrast, animals vaccinated with a formulation comprising both the LPS antigen and the protein antigen from *Francisella tularensis* achieve significantly higher survival rate (Example 14 and 18) and less severity of symptoms such as less severe pathology (Example 13 and 18) against aerosol challenge with type A *F. tularensis*.

In some embodiments, when the LPS and the protein antigen from *Francisella* are presented in a carrier, such as a nanolipoprotein particle, to form an immunogenic nanolipoprotein particle, the immunogenic nanolipoprotein particle allows co-localized presentation of the antigens thus resulting in even more enhanced immunostimulation and immunogenic response (Examples 17 and 18). The NLP formulation appears to be superior in that animals vaccinated with NLP formulations exhibited much less severe disease as evidenced by minimal weight loss after challenge and showed much faster resolution of disease after the onset of clinical signs.

In several embodiments, the immunogenic compositions comprising antigenic combinations alone or in combination with membrane-derived platforms encapsulate key requirements for vaccine formulation: non-virulence; immunostimulation; clustered antigen presentation; simple, rapid, inexpensive production; and the means to accommodate a wide range of select-agent antigens.

In several embodiments, the immunogenic compositions herein described and related compositions, methods and systems allow cost effective and rapid development of *Francisella* vaccines that are safe, enable immunization with multivalent/or broad-spectrum response and at the same time, are able to elicit a high levels protection following an adequate stimulation of a host immune response.

Accordingly, in some embodiments, a method of immunizing a subject against an infection of *Francisella tularensis* is described. The method comprises administering an effective amount of the immunogenic compositions herein described to the subject. The term "subject" "individual" or "host" as used herein in the context of immunization includes a single biological organism wherein an immune response can occur such as animals and in particular higher animals and in particular vertebrates such as mammals and in particular human beings.

The immunogenic compositions herein described can be formulated as pharmaceutical compositions such as vaccines for administration in any suitable manner, such as intranasally, intramuscularly, intradermally, intratracheal or by other routes such as subcutaneously, intravenously, or even orally to a host. More than one route can be used to administer the immunogenic composition herein described. Some routes such as intranasal, intramuscular, or subcutaneous routes can provide a more immediate and more effective reaction than other regimens.

The dose administered to a subject should be sufficient to induce a beneficial therapeutic response in the subject over time. Amounts effective for therapeutic use depend on for example the antigen composition, the routes of administration, the weight and general state of health of the subject and other factors identifiable to a person skilled in the art. Single or multiple dosage of the immunogenic compositions can be administered simultaneously or subsequently.

In some embodiments, more than one-time immunization is required for conferring optimal protection against *Francisella* infections. A subsequent boost vaccination can be administered 3-four weeks after the initial prime vaccination. Up to 6 immunizations can be administered in a 2-year time period. Optimal vaccine composition and immunization regimen can be determined empirically by skilled person. The general approach is to select and modify one parameter of the vaccine composition or immunization regimen while keeping all other parameters unchanged. The effect of the modification can be evaluated by immunizing separate groups of animals with the unmodified and modified vaccines and then challenging the vaccinated animals with a lethal dose of aerosolized *Francisella tularensis* SCHU S4 strain. The stringency of the test can be increased with larger challenge doses. Modifications that significantly improves survival, bacterial burden, or other measurable physiological parameters such as body weight, temperature, etc. compared to the unmodified vaccine will be selected for further development. Similar approaches can be used to optimize other parameters and to optimize the vaccine composition or immunization regimen for other animal species, including humans.

In general, administration to an individual begins prior to the first sign of disease, or possibly at the first sign of possible exposure to *F. tularensis*. In some cases, administration can also be given to an individual who is early diagnosed with *Francisella* infection.

In certain embodiments, the immunogenic compositions and, in particular, pharmaceutical compositions, can be formulated for systemic administration, which includes parenteral administration and more particularly intravenous, intradermic, and intramuscular administration.

In some embodiments, the compositions herein described are administered to humans or animals by intranasal inhalation. The intranasal formulations can include vehicles that neither cause irritation to the nasal mucosa nor significantly disturb ciliary functions. Diluents such as water, aqueous saline or other substances can be employed. The nasal formulations can also contain preservatives as will be identified by those skilled in the art. A surfactant can also be included to enhance absorption of the active ingredients in the vaccine by the nasal mucosa. In some exemplary embodiments, intranasal formulations are prepared in pharmaceutical grade saline and 50 µl instilled into the nose (25 µl per nare) using a micropipette while animals were under anesthesia.

In some embodiments, the compositions herein described are administrated to humans or animals by intramuscular administration. Exemplary intramuscular formulations can be prepared in pharmaceutical grade saline and 100 µl injected into the hindleg using a TB syringe.

Exemplary compositions for parenteral administration include sterile aqueous solutions, injectable solutions or suspensions including the immunogenic composition herein described. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance.

Lyophilization can also causes less damage to the substance than other dehydration methods using higher temperatures. Freeze-drying does not usually cause shrinkage or toughening of the material being dried. In addition, flavors and smells generally remain unchanged, making the process popular for preserving food. However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. Lyophilization can also be used to increase the shelf life of some pharmaceuticals for many years.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection.

The antigens and/or other immunological agents of the present disclosure may be also formulated in separate dosage forms which are provided as a system that can be in the form of a kit of parts comprising any of the active ingredients and any of the formulations described herein.

Accordingly, in some embodiments, a system for immunizing a subject against an infection of *Francisella* is described, the system comprising at least one *Francisella* LPS, at least one *Francisella* protein antigen, and optionally an adjuvant, alone or incorporation within a membrane-derived platform for simultaneous, combine or sequential used in the methods described herein.

The system herein disclosed can be provided in the form of kits of parts. For example, the components herein described can be included as a molecule alone or in a composition together with suitable vehicle carrier or auxiliary agents.

Additional components can also be included and comprise microfluidic chip, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

EXAMPLES

The methods and systems herein disclosed are further illustrated in the following examples, which are provided by way of illustration and are not intended to be limiting. In particular, the immunogenic compositions comprising various LPS, protein antigens, adjuvants as well as nanolipoprotein particles were prepared at various combination and concentrations and characterized in vitro and tested in vivo. A skilled person will be able to use other lipopolysaccharides, protein antigens, adjuvants, other NLPs including different scaffold proteins and membrane-forming lipids, or other non-NLP membrane vesicles herein described.

Example 1: Exemplary LPS from a *Francisella* Bacterium

LPS from *Francisella* bacteria share structural features as illustrated by the exemplary LPS herein described.

With reference to the lipid component of the *Francisella* LPS, the tetraacyl lipid A was shown to be present in all *F. tularensis* subspecies, *F. novicida* and *F. philomiragia* when bacteria were grown at 37° C. [29, 30]. The tetra-acylation of *Francisella* Lipid A severely limits its ability to activate innate immune cells via Toll-like receptor 4 (TLR4), in contrast to other bacterial LPS molecules.

Some *Francisella* lipid A exhibits temperature-regulated heterogeneity in their acyl chains such as lipid A from *F. novicida* lipid A. When *F. novicida* is grown at 18° C. (environmental temperature), lipid A acyl chains at the 2- and 2'-positions are composed primarily of C16:0 (3-OH). Conversely, when the bacterium is grown at 37° C. (mammalian host temperature), lipid A has longer acyl chains C18:0 (3-OH). Minor lipid A species with acyl chain variations include C14:0 or C18:0 fatty acyl branches instead of a C16:0 secondary chain at the 2'-position.

FIG. 5 shows exemplary *Francisella* LPS structure comprising lipid A and a polysaccharide core component in comparison with *E. coli* Kdo2-lipid A.

Different from lipid A of other gram-negative bacteria, *Francisella* lipid A include 1) absence of phosphate at the 4' position as well as the modification of 1-phosphate with GalN and 2) tetraacylation of lipid A with longer acyl chains (16-18 carbons) (FIG. 5, panels A and E).

In particular, the lipid A of *Francisella* LPS contains a β-(1-6)-linked diglucosamine (GlcN) backbone with four long fatty acyl groups that are amide-linked with C18:0 (3-OH) at the 2- and 2'-positions and ester-linked with C18:0 (3-OH) at the 3-position (FIG. 5). The hydroxy group of the 2'-linked fatty acyl chain is further esterified with C16:0.

Unlike lipid A from other gram-negative species such as *E. coli*, which has two phosphates at the 1- and 4'-positions (FIG. 5, panel E), *Francisella* lipid A has an α-linked galactosamine (GalN) addition at the 1-position and lacks phosphate at the 4'-position (FIG. 5, panel A).

This major tetraacyl lipid A, typically observed at m/z 1665 by negative ion MALDI mass spectrometry (MS), is present in all *F. tularensis* subspecies, *F. novicida* and *F. philomiragia* when bacteria were grown at 37° C. The absence of negatively charged phosphate groups affects the overall charge of LPS and has implications in the organism's resistance to antimicrobial peptides.

Figure 6:
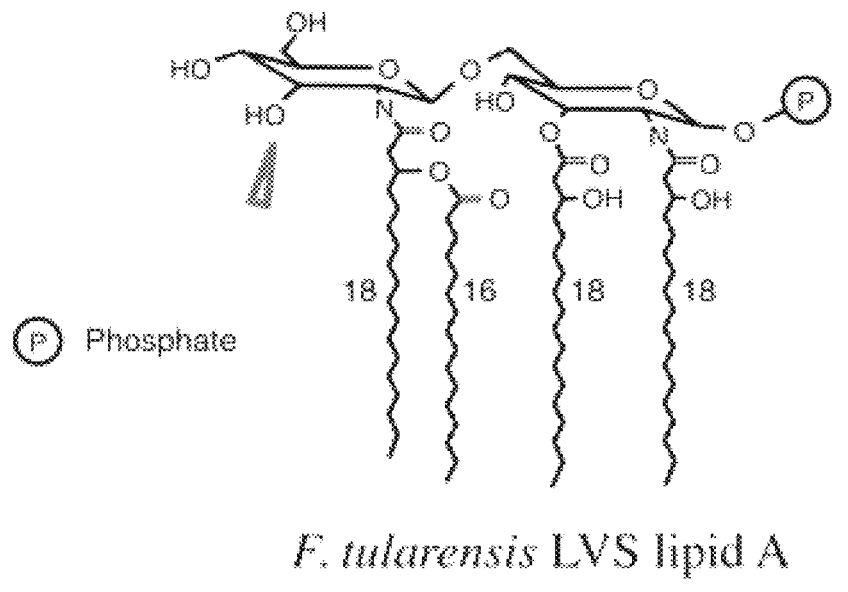

An exemplary Lipid A of a *Francisella* LPS is shown in FIG. 6.

With reference to the polysaccharide component the antigenic combination can comprise LPS from LVS strain 15, OSU10, and SchuS4 strain (members of either subsp. *tularensis* or subsp. *holarctica*) with the O-antigen repeating units-2)-β-D-Qui4NFm-(1-4)-α-D-GalNAcAN-(1-4)-α-D-GalNAcAN-(1-3)-β-D-QuiNAc-(1-(FIG. 5, panel C). In some embodiments the antigenic combination can comprise LPS from *F. novicida* strain U112 which has an antigenically distinct repeating O-antigen unit of -4)-α-D-GalNAcAN-(1-4)-α-D-GalNAcAN-(1-4)-α-D-GalNAcAN-(1-3)-β-D-Qui2NAc4NAc-(1).

Reflecting the structural variation, the O-antigen gene clusters of *F. tularensis* and *F. novicida* differ in a number of genes involved in the biosynthesis of individual O-antigen sugars. The O-antigen gene cluster of *F. tularensis* contains 19 putative O-antigen genes. The O-antigen gene cluster of *F. novicida* contains 14 putative O-antigen genes. Functional differences demonstrate that Ft LPS is important for maintaining an intracellular niche whereas *F. novicida* LPS appears to be important for serum stability [31, 32].

Several *Francisella* bacteria also comprise lipid A in free form and not attached to Kdo, core oligosaccharide, or O-antigen. The sugar and fatty acid composition of this free lipid A is very similar to lipid A with O-antigen. Both *F. tularensis* and *F. novicida* are reported to have free lipid A. In *F. novicida*, a small amount of free lipid A contains an α-linked glucose at the 6'-position of distal glucosamine. However, the presence of O-antigen is expected to be the key determinant of a protective antigen. While some lipid A in free form may be present in the preparations of LPS isolated from *Francisella tularensis*, this proportion relative to molecules consisting of lipid A, core-oligosaccharide, and O-antigen is low.

Example 2: Biosynthesis of *Francisella* LPS

Figure 4:
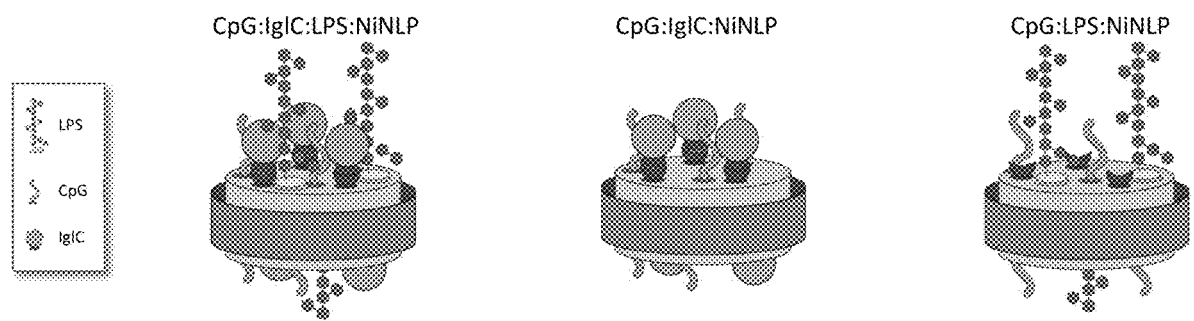
FIG. 4 illustrates exemplary embodiments of the immunogenic agents herein described loaded in a nanolipoprotein particle carrier.
Figure 7:
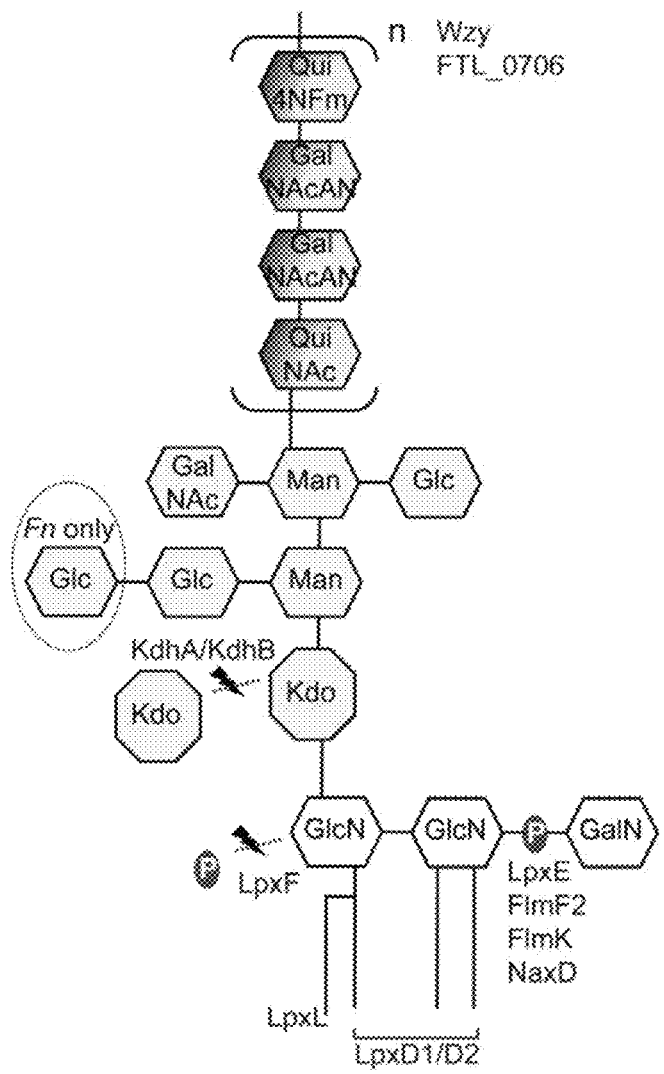
FIG. 7 illustrates a cartoon representation of *Francisella* LPS and its modifying proteins.
Figure 8A:
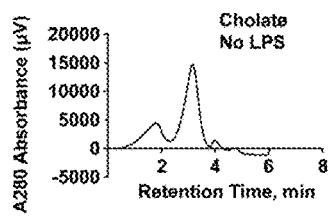
FIGS. 8A-H show in some embodiments size exclusion chromatography analysis of various NLP assemblies with or without LPS at different temperatures. As monomeric LPS species should incorporate more readily into NLPs than large aggregates, conditions were screened to dissociate large LPS aggregates typically found in aqueous preparations of LPS. Cholate (60 mM) (left column) or Z3-14 (60 mM) (right column) were first added to LPS stock (LPS rehydrated in water) and incubated for about 2 minutes at elevated temperatures prior to mixing with NLP assembly reaction components. Three incubation temperatures were tested: 37° C., 55° C. and 95° C. After thorough dialysis to remove residual cholate, the assembly was analyzed by size exclusion chromatography. The results show that incubating LPS in detergent at 95° C. results in NLP formation. As a control, NLP formation in the absence is shown in the top two chromatograms, using either cholate (left column) or the surfactant Z3-14 (right column) to solubilize lipidic components of the reaction into aqueous solution.
Figure 8B:
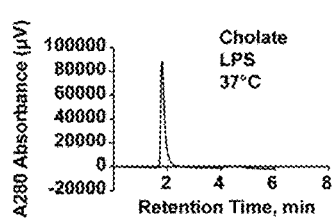
Figure 8C:
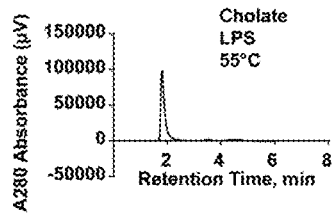
Figure 8D:
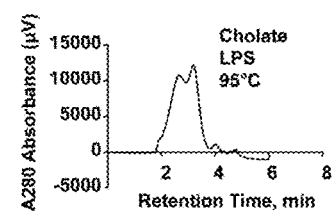
Figure 8E:
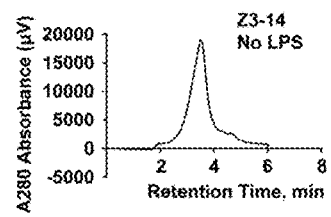
Figure 8F:
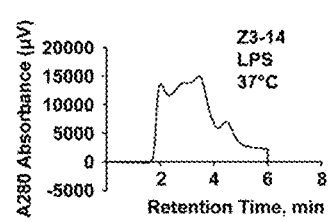
Figure 8G:
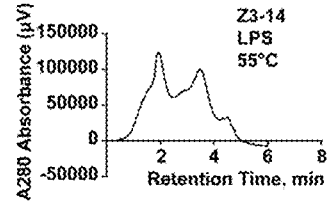
Figure 8H:
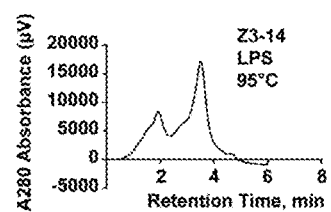
Figure 9A:
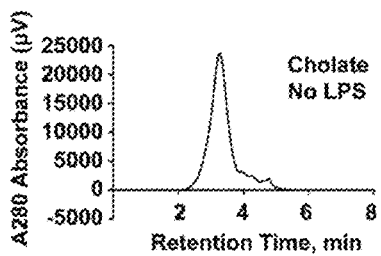
FIGS. 9A-D show in some embodiments size exclusion chromatography analysis of various NLP assemblies prepared with LPS that has been incubated in cholate at 95° C. for various times. Cholate at 60 mM was added to LPS stock and incubated at 95° C. for different incubation times: 2 minutes, 5 minutes, and 15 minutes. The LPS stock mixed with cholate was then added to lipid, and then mixed with scaffold protein. After thorough dialysis to remove residual cholate, the assembly was analyzed by size exclusion chromatography. The results show that incubating LPS in cholate at 95° C. for 15 minutes was optimal for NLP formation.
Figure 9B:
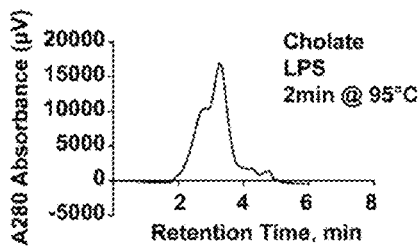
Figure 9C:
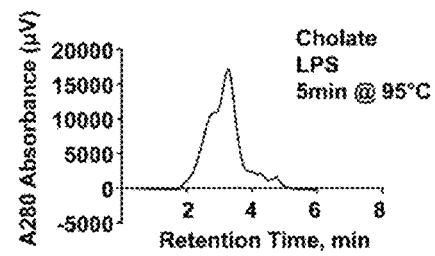
Figure 9D:
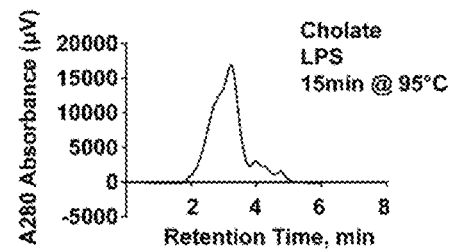

FIG. 7 illustrates a cartoon representation of *Francisella* LPS and its modifying proteins. For example, LpxD1 and LpxD2 are identified as N-acyltransferases whose expression and activity increases at 37° C. and 18° C., respectively. LpxL is identified as a Kdo-dependent acyltransferase responsible for modifying the secondary chain on the 2'-acyl group (FIG. 4). This function has been confirmed by demonstration of the ability of *Francisella* LpxL to complement the acylation of lipid A in an *E. coli* lpxL mutant.

A Kdo hydrolase system in *Francisella* is composed of kdhA and kdhB gene products. [33] and [34] In particular, in *Francisella* the Kdo hydrolase system is involved in removing the second side chain of two Kdo sugars initially synthesized with the *Francisella* LPS. More particularly, KdhA and KdhB are inner-membrane proteins and are both required for Kdo hydrolase activity in *Francisella*. KdhA catalyzes the cleavage of the side-chain Kdo and has homology to sialidase-family enzymes KdhB's function is unknown, but it is predicted to contain a number of alpha-helical transmembrane domains. A similar two-component Kdo hydrolase system has been identified in two other pathogens, *Helicobacter pylori* and *Legionella pneumophila*. [33] [35] [1]

Example 3: Biology of *Francisella* LPS

The lack of immune recognition of *Francisella* lipid A has been attributed to several structural differences compared to *E. coli* lipid A, a potent immune activator. These include 1) absence of phosphate at the 4' position as well as the modification of 1-phosphate with GalN and 2) tetraacylation of lipid A with longer acyl chains (16-18 carbons); *E. coli*'s lipid A is hexaacylated with shorter acyl chains (12-14 carbons) (FIGS. 5A & E). The lack of phosphate affects the overall charge of lipid A, a frequent target of cationic antimicrobial peptides. Supporting this notion that charge is important to the biology of lipid A, lpxD1, flmK, and naxD mutants of *F. novicida*, which are unable to modify 1- or 4'-phosphate, show increased sensitivity to polymyxin B and attenuation in mice.

Dynamic regulation of lipid A acyl chain length by LpxD1/LpxD2 at varying temperatures appears to be important in maintaining membrane permeability and susceptibility to cationic antimicrobial peptides as well. Consistent with LpxD1's optimum activity at 37° C., the lpxD1 mutant is unable to modify lipid A with longer acyl groups and is severely attenuated in mice, whereas the lpxD2 mutation has no effect.

Example 4: Preparation of *Francisella* LPS

LPS can be prepared by extraction from TCA, phenol, or phenol-chloroform-petroleum ether (for rough strains). TCA extracted lipopolysaccharides are structurally similar to the phenol extracted ones, with similar electrophoretic patterns and endotoxicity. The primary differences are in the amounts of nucleic acid and protein contaminants remaining after extraction. The TCA extracts contain ~2% RNA and ~10% denatured proteins, while phenol extracts contain up to 60% RNA and <1% protein. Subsequent purification by gel filtration chromatography removes much of protein present in the phenolextracted LPS, but results in a preparation that contains 10-20% nucleic acids. Further purification using ion exchange chromatography yields a lipopolysaccharide product which contains <1% protein and <1% RNA.

In an exemplary embodiment, *Francisella* LPS can be purified from *F. tularensis* LVS as follows. Briefly, a 1.5-liter culture of Ft LVS is grown in 4-liter flasks at 37° C. for 48 hours in Trypticase soy broth supplemented with cysteine. Following centrifugation and PBS, methanol and acetone washes, the samples are lyophilized. LPS is then extracted by the hot phenol method followed by enzymatic treatment to remove contaminants. Pellets are harvested by centrifugation for 12 hours [36].

Example 5: Assembly Tests with *F. tularensis* Live Vaccine Strain (LVS) LPS

Preliminary experiments were firstly conducted to incorporate LPS into NLPs using *F. tularensis* LVS LPS as a surrogate to evaluate if NLPs are formed and if HPLC can be used to detect the LPS in the NLP samples.

A number of assembly tests on *F. tularensis* LPS were then conducted following these preliminary experiments. The *F. tularensis* LPS were isolated from the LVS strain.

In the first set of assembly test, LPS rehydrated in water was added to cholate-solubilized lipids (30 mM cholate). Three different LPS:NLP ratios were tested: no LPS (0 μg LPS/μg rE4), a low amount of LPS (0.29 μg LPS/μg rE4), and a high amount of LPS (0.86 μg LPS/μg rE4).

In the second set of assembly test, LPS rehydrated in water was added to lipids solubilized in cholate (30 mM or 60 mM) or Z3-14 detergent (30 mM). Three different LPS:NLP rations were tested: no LPS (0 μg LPS/μg rE4), a low amount of LPS (0.29 μg LPS/μg rE4), and a high amount of LPS (0.86 μg LPS/μg rE4).

For each assembly test, scaffold protein was then added to the solubilized LPS-lipid and allowed to incubate for 1 hour at room temperature. After thorough dialysis to remove residual cholate, the assemblies were analyzed by size exclusion chromatography.

The results show opalescent solutions, which is an indication that there are significantly large lipid particles in solution, much large than the NLPs. This suggests that the assembly reaction did not result in NLP formation.

A third assembly test was then conducted in which detergents (cholate at 60 mM or Z3-14 at 60 mM) were first added to LPS stock (LPS rehydrated in water) and incubated for about 2 minutes at elevated temperatures prior to mixing with NLP assembly reaction components. Three incubation temperatures were tested: 37° C., 55° C. and 95° C. After thorough dialysis to remove residual cholate, the assembly was analyzed by size exclusion chromatography. The results show that incubating LPS in detergent at 95° C. results in NLP formation (FIG. 8).

A fourth assembly test was then conducted in which cholate at 60 mM was added to LPS stock and incubated at 95° C. for different incubation times: 2 minutes, 5 minutes and 15 minutes. The LPS stock mixed with cholate was then added to lipid, and then mixed with scaffold protein. After thorough dialysis to remove residual cholate, the assembly was analyzed by size exclusion chromatography. The results show that incubating LPS in cholate at 95° C. for 15 minutes was optimal for NLP formation (FIG. 9).

Figure 10:
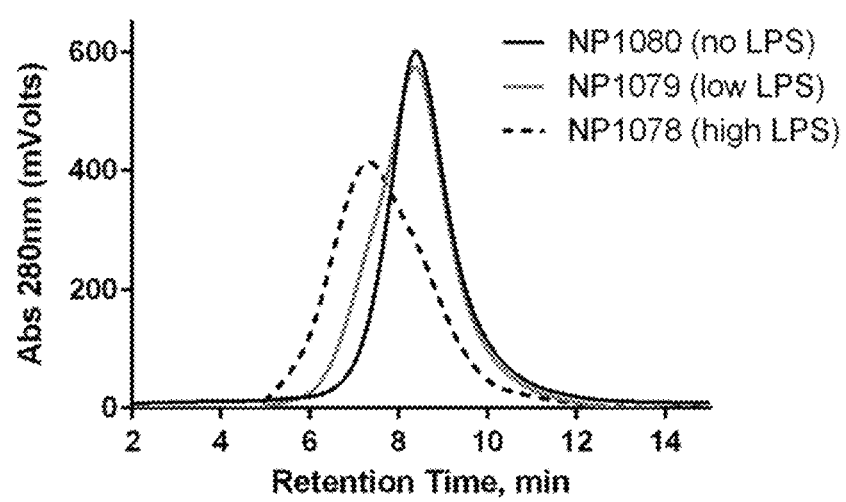
FIG. 10 shows size exclusion chromatography analysis of three exemplary NLP assemblies with LPS and NLP at different ratios: no LPS (0 μg LPS/μg rE4, NP1080) (black solid trace), a low amount of LPS (0.29 μg LPS/μg rE4, NP1079) (gray solid trace), and a high amount of LPS (0.86 μg LPS/μg rE4, NP1078) (black dashed trace).

A fifth assembly test was then conducted in which cholate at 60 mM was added to LPS stock and incubated at 95° C. for 15 minutes. The LPS stock mixed with cholate was then added to dry lipid. Three different LPS:NLP ratios were tested: no LPS (0 μg LPS/μg rE4, NP1080), a low amount of LPS (0.29 μg LPS/μg rE4, NP1079), and a high amount of LPS (0.86 μg LPS/μg rE4, NP1078). After thorough dialysis to remove residual cholate, the assembly was analyzed by size exclusion chromatography. The results show successfully NLP formation in all three cases (FIG. 10). In particular, a higher amount of LPS results in larger NLP in size.

Example 6: RP-HPLC Quantification of LVS-LPS

In this example, a method was developed to characterize the incorporation of LPS into the NLP in order to quantify and control the amount of LPS incorporated in the final vaccine formulation.

This method is based on reversed-phase high-performance liquid chromatography (RP-HPLC). Using a C8 RP column, methods were developed using an aqueous buffer and two organic buffers (acetonitrile and isopropanol) to successfully separate LPS from other NLP constituents. An evaporative light scattering detector was used to detect the LPS. Standards of pure F.t. LPS were used to prepare a standard curve for quantification of unknown samples.

Figure 11A:
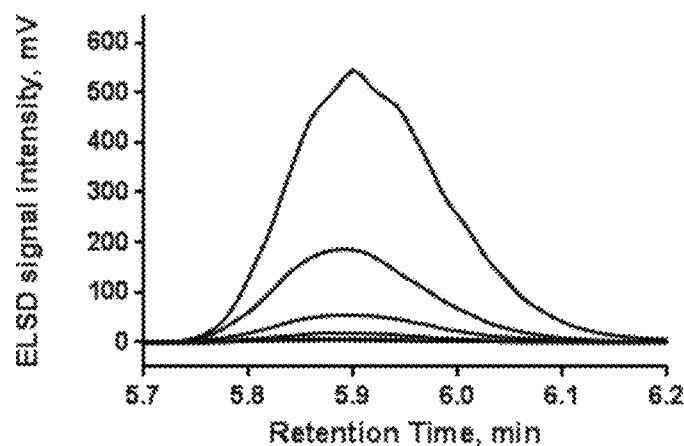
FIG. 11A shows representative RP-HPLC traces of pure F.t LVS LPS standards at different concentrations. LPS samples were diluted in water and injected onto the C8 RP column, using an aqueous buffer and two organic buffers (acetonitrile and isopropanol) to provide appropriate resolution. An evaporative light scattering detector was used to detect the LPS. The peak areas were calculated to prepare a standard curve for quantification of unknown samples.
Figure 11B:
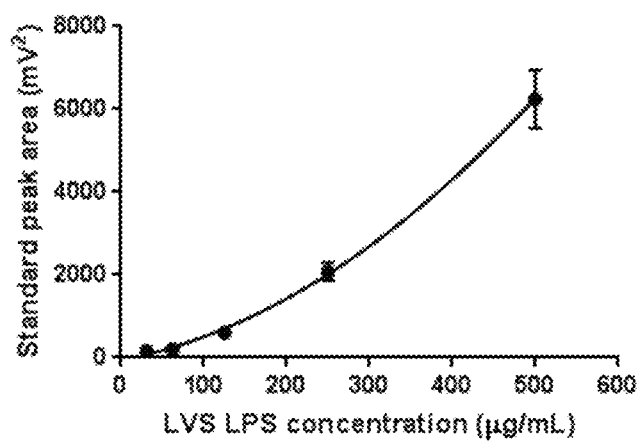
FIG. 11B shows a standard curve based on the peak area of known LPS standards. This standard curve enables the quantification of LPS in unknown samples by correlating LPS peak area values with LPS concentration.
Figure 12:
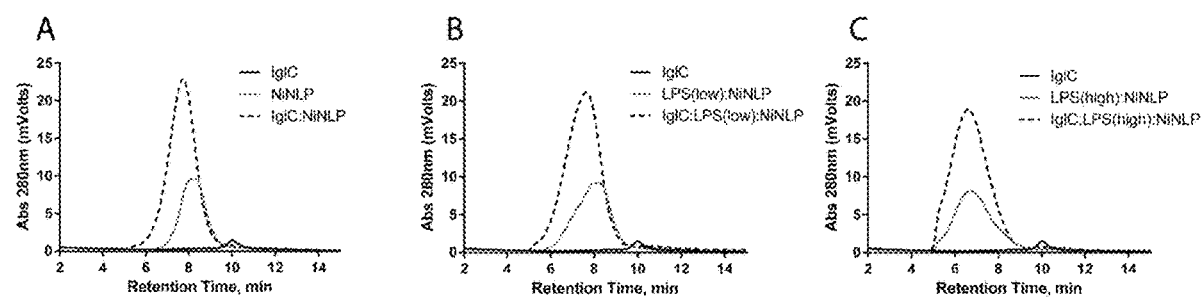
FIG. 12 shows representative SEC traces of NiNLPs prepared with LPS (at three different amounts: no LPS, low LPS incorporation, high LPS incorporation, shown in FIG. 10) are able to bind his-tagged protein. His-tagged protein (black trace) is incubated with the NiNLP (gray trace) to form protein:NiNLP complex (dashed trace). The increased absorbance intensity of the protein:NiNLP complex, as well as the shift to earlier retention times, indicates that conjugation was successful. Protein conjugation was successfully demonstrated using NiNLP with no LPS, with low amounts of incorporated LPS, and high amounts of incorporated LPS. This demonstrates that the presence of LPS in the NLP does not interfere with the incorporation or conjugation of additional biomolecules.
Figure 13A:
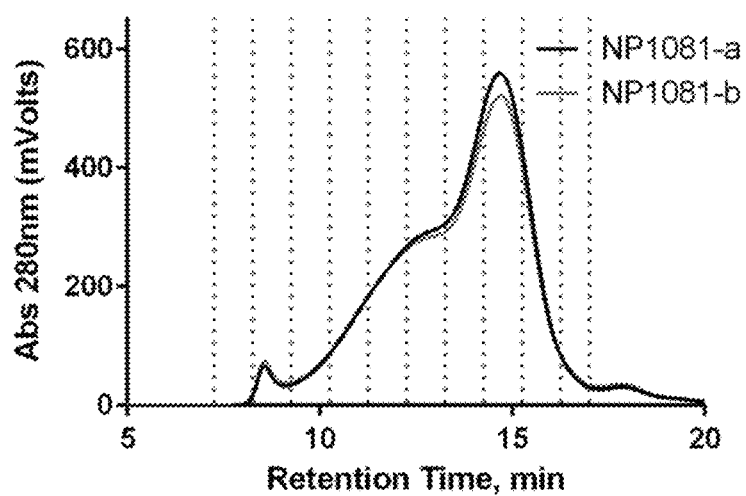
FIG. 13A shows exemplary SEC traces of a scaled-up assembly of LPS:NiNLPs in two purification runs. Samples were purified on a Superose 6 SEC column (10 mm×30 cm column dimensions, 1 ml/min PBS flow rate). Both purification runs were identical with respect to chromatogram intensity and elution profile. 1 mL fractions were collected from 7 to 17 minutes for subsequent analysis. Appropriate fractions corresponding to NLPs were pooled for subsequent analysis.
Figure 13B:
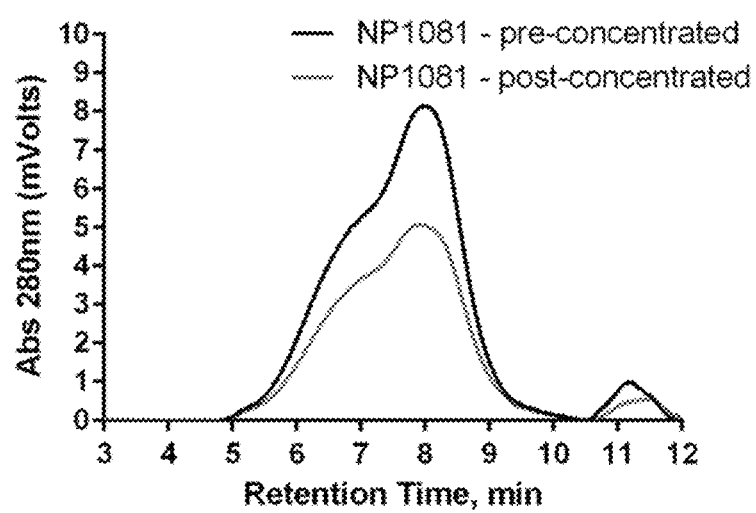
FIG. 13B shows exemplary SEC analysis of pre-concentrated and post-concentrated LPS:NiNLPs. Some material is lost during the purification status (as indicated by the decrease is chromatogram intensity post-concentrated), but the peak shape remains. This indicates that the NLP remain intact after the concentration process.

In particular, FIG. 11A shows the chromatograms of LPS standards at different concentrations. Peak areas were calculated for each standard. FIG. 11B shows the standard curve correlating LPS peak area with concentration of LPS. This standard curve was used to quantify LPS amounts in unknown samples.

NLPs prepared with or without increasing amount of LPS were purified by SEC. Fractions corresponding to the NLP peak were pooled and analyzed by RP-HPLC. The presence of LPS in the NLP peak fractions was verified, and subsequently quantified (FIGS. 11A-B).

Successful LVS LPS incorporation was detected as shown in Table 5.

TABLE 5

Exemplary LVS:NLP quantification

| Formed NLPs | μg in rxn | μg in NLP | Yield |
|---|---|---|---|
| NP1078 | 422 | 101 | 24% |
| NP1079 | 84 | 36 | 43% |
| NP1080 | 0 | 0 | n/a |

Figure 14:
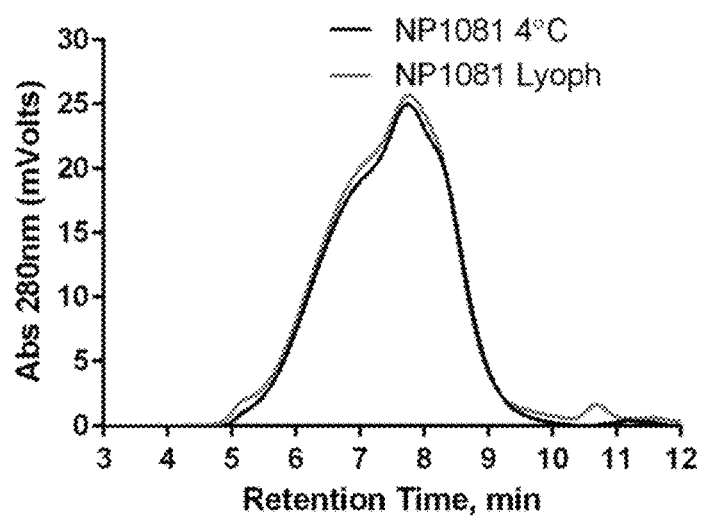
FIG. 14 shows exemplary SEC analysis of lyophilized and non-lyophilized NLPs samples. To verify that LPS:NiNLPs could be lyophilized while maintaining particle integrity, LPS:NiNLPs were formulated with trehalose and either stored at 4° C. in solution (control) or lyophilized. These samples were stored overnight. The lyophilized sample was subsequently rehydrated in water and analyzed by analytical SEC. LPS:NiNLPs stored at 4° C. in solution (black trace) and lyophilized, rehydrated LPS:NiNLPs (gray trace) exhibited identical peak shape and overall chromatogram intensity.

For example, in NP1078, 422 μg LVS LPS were added to the self-assembly reaction mixture and 101 μg was measured in the resultant NLPs purified by SEC. This represents a 24% yield under these conditions. In NP1079, 84 μg LVS LPS were added to the self-assembly reaction mixture and 36 μg was measured in the resultant NLPs purified by SEC. This represents a 43% yield under these conditions.

Example 7: The Binding of LPS-Bearing NiNLPs to IglC

To demonstrate that NLPs containing LPS can be used for vaccination tests in conjunction with protein antigens, NLPs were prepared with nickel-chelating lipid to form NiNLPs. The NiNLPs are able to conjugate any his-tagged protein antigens for the vaccination tests. The LPS-bearing NiNLPs with LPS at different amount were prepared according to Table 4.

It is demonstrated by using size exclusion chromatography to look at the retention of individual components and the complexes formed by adding the IglC to the NiNLP (+/− LPS) (FIG. 12A) that NiNLPs with increasing amounts of LPS are able to immobilize the His-tagged F.t. protein antigen IglC. When IglC is added to the NiNLPs, an increase in the NLP peak intensity was observed. No free IglC was observed. A shift to decreased retention times was also observed, indicating larger NLP species due to protein binding. For the NLPs with high amounts of LPS, the shift to larger size is less apparent, due to the decreased resolution of the SEC column at this size regime. These data demonstrate that the presence of LPS in the NLP does not interfere with the incorporation or conjugation of additional biomolecules.

Example 8: Concentration of LPS-NLPs

LPS-bearing NLPs are different in physical and chemical composition than traditional non-LPS-bearing NLPs. The large polysaccharide chains extending from the surface of the NLP into solution can conceivably impact the ability to concentrate the NLP solutions.

In this example, the recovery of apolipoprotein E and LPS after concentrating NLPs with increasing amounts of LPS was assessed. 200 μl of dilute NLP (pooled) was used to test effects of concentration. Vivaspin concentrators were used for concentration of samples. Scaffold protein and LPS were quantified by nanodrop and RP-HPLC, respectively. The results are shown in Table 6.

TABLE 6

ApoE and LPS recovery percentage in exemplary LPS-bearing NLPs

| | LPS-bearing NLPs | Pre-con, μg | Post-con, μg | % recovery | LPS:apoE ratio (mg/mg) |
|---|---|---|---|---|---|
| apoE | NP1080 | 35.9 | 35.8 | 100% | 0.00 |
| | NP1079 | 41.0 | 39.5 | 96% | 0.21 |
| | NP1078 | 41.5 | 37.9 | 91% | 0.38 |
| LPS | NP1080 | 0.0 | 0.0 | n/a | |
| | NP1079 | 9.6 | 8.4 | 88% | |
| | NP1078 | 27.0 | 14.6 | 54% | |

The results show that NLPs can be successfully concentrated with an acceptable loss in material. In particular, ApoE recovery is above 90% in all cases. LPS recovery decreased as more LPS was present in the NLP. This could indicate that some of the LPS molecules may be pulled out of the NLP during the concentration process.

Example 9: Scale-Up Assembly of LVS LPS:NLP

In this example, the assembly process of forming the LPS-NiNLP was scaled up to verify that this process could be scaled for subsequent use in animal experiments.

The following parameters were used in the scale-up assembly: rE4.22k 65:35 DOPC:DOGS-NTA-Ni, 5 mg assembled with 2.7 mg LVS LPS, 15 min boil in 60 mM cholate then added to dry lipid. The mixture is then purified on semi-prep Superose6 SEC column.

In general, the results show that the scale of the assemblies was increased ~10-fold. The large assembly was split into two SEC purification runs, which appear identical (FIG. 13A). Concentrating pooled NLP fractions did not impact the shape of the SEC chromatogram (FIG. 13B). Yields were assessed as shown in Table 7.

TABLE 7

Yield in scale-up assembly of LVS LPS:NLP

| | NLP assembly | NLP product | Yield |
|---|---|---|---|
| rE4 | 5 mg | 2.4 mg | 48% |
| LVS LPS | 2.7 mg | 0.37 mg | 14% |
| LPS:rE4 Ratio (w/w) | 0.54 | 0.15 | n/a |

Example 10: Lyophilization Test of LPS:NiNLPs

Identifying appropriate storage conditions is paramount for ensuring material is available for animal experiments. In this example, two samples, lyophilized NLPs ample and non-lyophilized NLPs sample were prepared as follows. For the lyophilized NLPs sample, 4.5 μL NLP was formulated with 1M trehalose (0.5 μL) to reach a final concentration of 0.1M trehalose. The sample is then frozen on dry ice and lyophilized. The lyophilized LPS:NiNLPs were rehydrated in 5 μL and assessed on an analytical Superose 6 SEC column. For the non-lyophilized NLPs sample, 4.5 μL NLP was formulated with 0.5 uL H₂O, stored at 4° C., and assessed on INaSUP6 SEC column. The SEC results in FIG. 14 show no difference between the lyophilized NLPs sample and the non-lyophilized NLPs sample, suggesting that LPS:NiNLPS can be successfully lyophilized.

Example 11: Verification of Final NLP Vaccine Formulations

The final vaccine formulations to be tested are comprised of NLPs containing LPS, IglC, and the adjuvant CpG. It was previously demonstrated that His-tagged IglC could readily conjugate to LPS:NiNLPs. In this example, it is demonstrated that cholesterol-tagged CpG could also be included in the NLP formulation. In particular, IglC and CpG can be conjugated to control NLPs (NiNLPs, no LPS) (FIG. 15A) and LPS:NiNLPs (FIG. 15B).

Figure 15A:
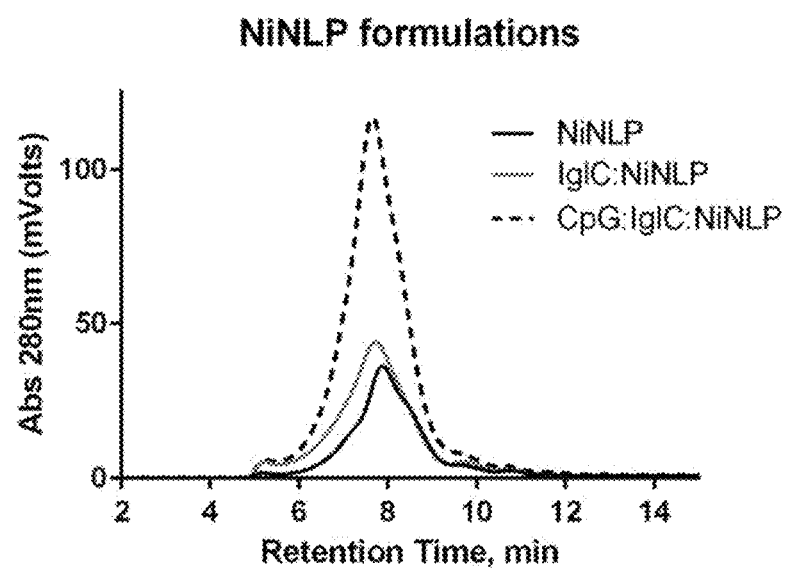
FIG. 15A shows exemplary SEC analysis of IglC and CpG conjugation to NiNLPs (in the absence of incorporated LPS) to form CpG:IglC:NiNLP formulations. IglC conjugates to NiNLPs (black trace) to form IglC:NiNLP (gray trace). Subsequent addition of cholesterol-tagged CpG forms CpG:IglC:NiNLP (dashed trace).

FIG. 15A shows the his-tagged protein antigen (IglC) and cholesterol-tagged CpG can be successfully conjugated to NiNLPs. This is the control NiNLP sample that does not contain LPS, and demonstrates the expected trend in the chromatogram upon conjugation of his-tagged protein and CpG adjuvant.

Figure 15B:
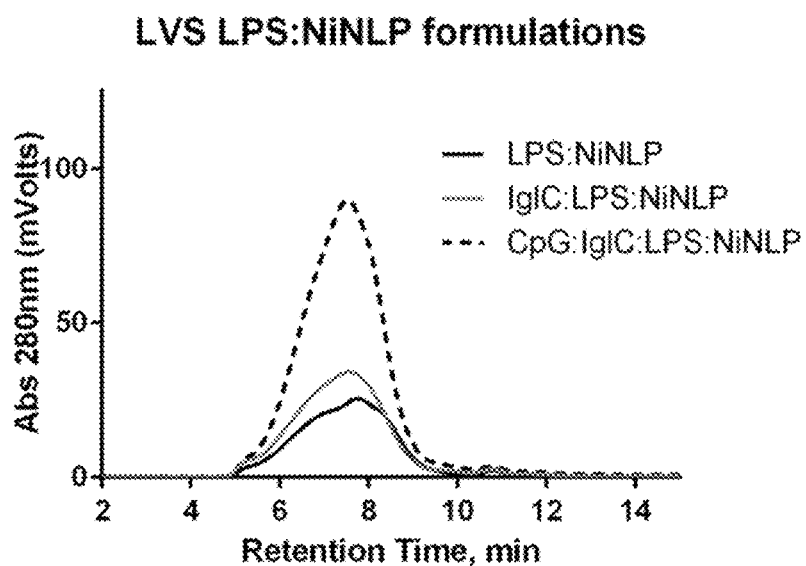
FIG. 15B shows exemplary SEC analysis of IglC and CpG conjugation to LPS:NiNLPs (in the presence of incorporated LPS) to form CpG:IglC:LPS:NiNLP formulations. IglC conjugates to LPS:NiNLPs (black trace) to form IglC:LPS:NiNLP (gray trace). Subsequent addition of cholesterol-tagged CpG forms CpG:IglC:LPS:NiNLP (dashed trace). These tests demonstrate that vaccine formulations co-localizing LPS antigen, protein antigen, and adjuvant can be successfully prepared.
Figure 16:
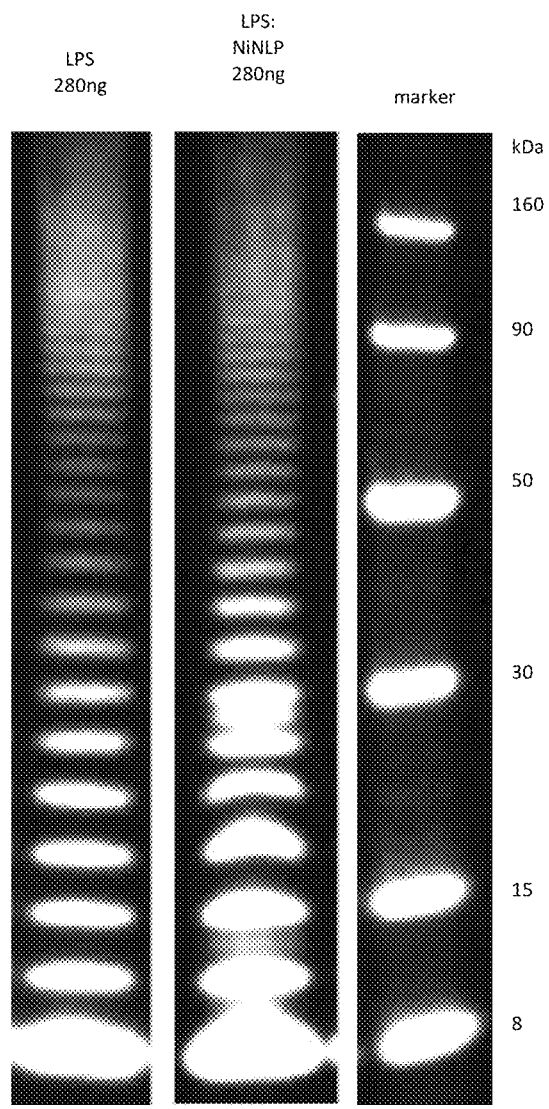
FIG. 16 shows in some embodiments SDS polyacrylamide gel electrophoresis (SDS-PAGE) analysis of LPS, both unincorporated and incorporated in NiNLPs. For each sample, an equivalent amount of LPS (280 ng) was loaded on an SDS-polyacrylamide gel to compare band intensities and pattern. For Western analysis, samples were transferred to a membrane and probed with the anti-F.t. LPS antibody FB11, and imaged using a fluorescent secondary antibody. Marker corresponds to a protein standard marker included for general comparisons of molecular weights. The banding pattern is identical between the unincorporated LPS and the LPS incorporated in the NLP.
Figure 17A:
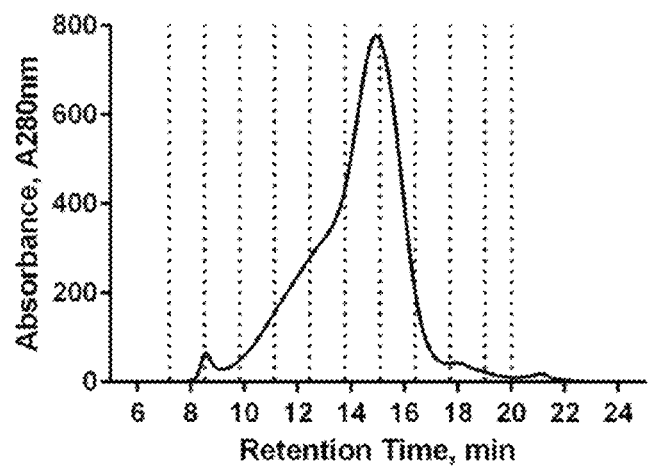
FIG. 17A shows an exemplary SEC of an LPS:NiNLP assembly. Fractions were purified on a Superose 6 SEC column (10 mm×30 cm column dimensions, 1 mL/min PBS flow rate) collected every 1.3 minutes between 7 and 20 minutes.
Figure 17B:
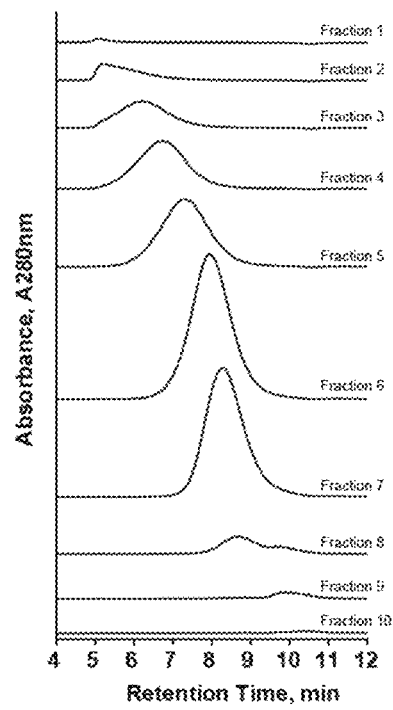
In FIG. 17B, these fractions are further analyzed by analytical SEC (Superose 6 column, 10 mm×30 cm, 0.2 mL/min PBS flow rate) to demonstrate the relative size of the NLPs in each purified fraction.
Figure 17C:
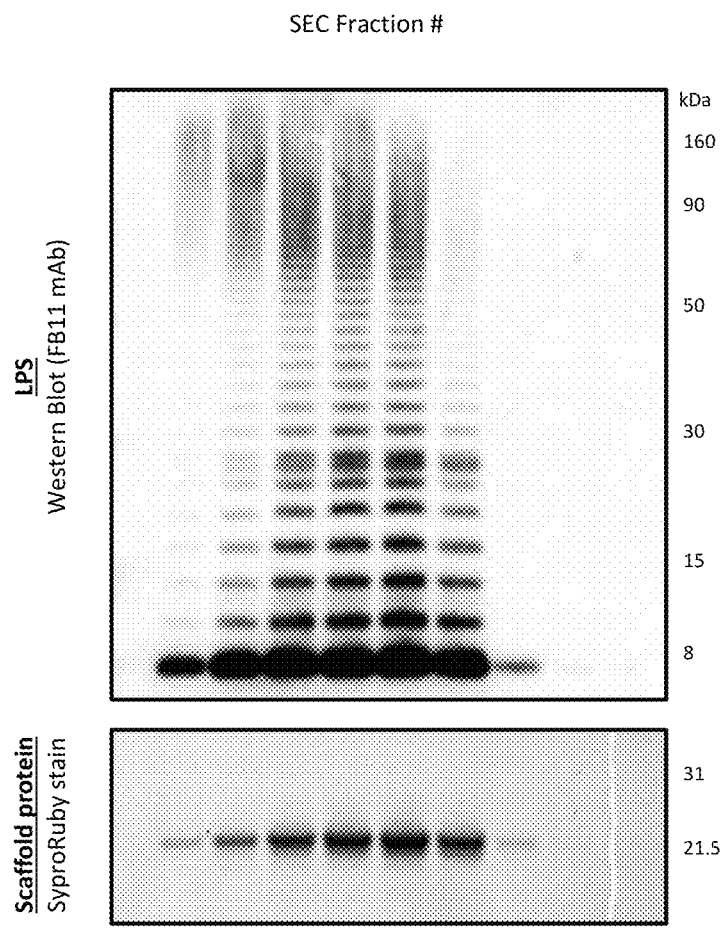
FIG. 17C shows exemplary SDS-PAGE analysis of SEC fractions. Fractions were either stained for protein constituents (i.e. apoE) using the fluorescent stain SyproRuby, or transferred to a membrane and probed by Western analysis with the anti-F.t. LPS antibody FB11. These gels demonstrate that fractions corresponding to NLPs (f2-f7) exhibit the presence of both LPS and apoE. In addition, the distribution of LPS molecules correlates with the size of the NLP. Larger NLP (collected in early fractions) are predominated by LPS species of high molecular weight, whereas smaller NLPs (collected in later fractions) are predominated by LPS species of lower molecular weight.

FIG. 15B shows the his-tagged protein antigen (IglC) and cholesterol-tagged CpG can be successfully conjugated to LPS:NiNLPs. The same trend in the chromatogram (e.g. increase in absorbance intensity and shift to earlier elution times) is observed in NiNLP in the presence or absence of incorporated LPS. This verifies that the LPS incorporated into the NiNLP does not negatively impact the incorporation of other biomolecules.

In each case, the IglC and CpG readily conjugate to the NLP. Accordingly, desired vaccine formulation that contains NLPs functionalized with LPS, IglC, and CpG can be prepared.

Example 12: SDS-PAGE and Western Blot Analysis of LPS and LPS:NiNLPs

To further verify that LPS was incorporated into the NLP, an LPS standard and LPS:NLPs were analyzed by SDS polyacrylamide gel electrophoresis (SDS-PAGE) and probed with an antibody that specifically binds to F.t. LPS (Western Blot). The LPS:NLPs were first purified by SEC, and the fractions corresponding to the NLP peak were pooled prior to loading on the SDS-PAGE gel.

Both LPs and LPS:NLPs exhibited the expected banding pattern, indicating that a LPS molecules spanning a significant size range were present in both samples (FIG. 16). The results confirm that LPS:NLPs contain LPS and encompass the full size range of the LPS species present in the purified LPS samples used for the assembly.

A more in-depth study was also conducted to identify the types of LPS molecules that were incorporated in NLPs of different sizes. The LPS:NLPs were run on an SEC column to separate out the NLP species by size (larger species eluting first, smaller NLP species eluting later). Each of the NLP fractions was again run on analytical SEC to demonstrate the relative size of the NLPs in each purified fraction (FIG. 17B). As expected, NLPs in the earlier fractions are larger (earlier elution) than the later fractions. These fractions were also analyzed by SDS-PAGE and western blot (FIG. 17C). Based on the western blot analysis, the larger NLPs were enriched in the larger LPS species (primarily higher MW bands were observed in those fractions). In the smaller NLPs, only shorter LPS species were observed. Also, the NLP scaffold protein (ApoE) was observed in the NLP species, verifying the present of all NLP components in the purified fractions. This observation suggests a way of separating large LPS species from small LPS species.

Example 13: NLP Vaccine Formulation and Design of In Vivo Preliminary Experiments Various experiments were designed to identify if the full NLP vaccine formulation that incorporates the protein antigen (IglC), the polysaccharide antigen (LPS) and the adjuvant (cholesterol-modified CpG) can protect the animal model (Fischer 344 rats) against a lethal challenge of virulent F.t. Adjuvanted NLPs that contained only the IglC antigen or only the LPS antigen were also tested. Two separate routes of vaccination were tested for the full NLP formulation: intranasal (i.n.) and intramuscular (i.m.). The details about the experimental design are listed in Table 8.

TABLE 8

Experimental design of exemplary vaccine formulations

| Vaccination Group # | Vaccination Group ID | Formulation Antigen | Formulation Adjuvant | Formulation Platform | Vaccination Route | Vaccination volume (μL) | Anti-LPS mAb | Animal numbers (F344 rat) |
|---|---|---|---|---|---|---|---|---|
| 1 | Naïve | | PBS | | I.N./I.N. | 50 | | 6 |
| 2 | CpG:LPS:NLP | LPS (5 μg) | CpG ODN 1826 (5 μg) | NLP | I.N./I.N. | 50 | | 8 |
| 3 | CpG:IglC:NLP | IglC (20 μg) | CpG ODN 1826 (5 μg) | NLP | I.N./I.N. | 50 | | 8 |
| 4 | CpG:IglC:LPS: NLP | LPS (5 μg); IglC (20 μg) | CpG ODN 1826 (5 μg) | NLP | I.N./I.N. | 50 | | 8 |
| 5 | CpG:IglC:LPS: NLP | LPS (5 μg); IglC (20 μg) | CpG ODN 1826 (5 μg) | NLP | I.M./I.M. | 100 | | 8 |

At day 0, the 344 rats in groups 1-5 were administered with the formulations listed in Table 8. At day 28, a second administration was performed with the same formulation. At day 35, the serum of the 344 rats were collected for analysis. All rats were challenged with either intranasally or intramuscularly on day 56 with 130±65 colony forming units (CFUs) F. t. aerosol as assessed by lung deposition from three animals exposed at the same time. Survival was monitored for 21 days after challenge, at which point the lungs and spleens of the rats were collected for further analysis and assessment.

Female Fischer F344 rats (8 animals/group) were allotted into five vaccination groups: 1) PBS control, intranasal vaccination (IN); 2) CpG:LPS:NLP, IN; 3) CpG:IglC:NLP, IN; 4) CpG:IglC:LPS:NLP, IN; 5) CpG:IglC:LPS:NLP, intramuscular vaccination (IM). Animals were vaccinated with an initial prime on day 0 followed by an additional vaccination, or boost, 4 weeks later (day 28). Serum was collected from vaccinated animals one week after the boost by tail vein bleeds. Animals were challenged with 130±65 CFUs of aerosolized F. tularensis SCHU S4 four weeks after the boost (day 56). Animals were monitored for signs of clinical disease over the course of 21 days at which point the study was terminated (day 77). Surviving animals were euthanized and bacterial burdens were quantified in lungs and spleen.

Example 14: Test of Animal Survival Rate Over Time

Figure 18:
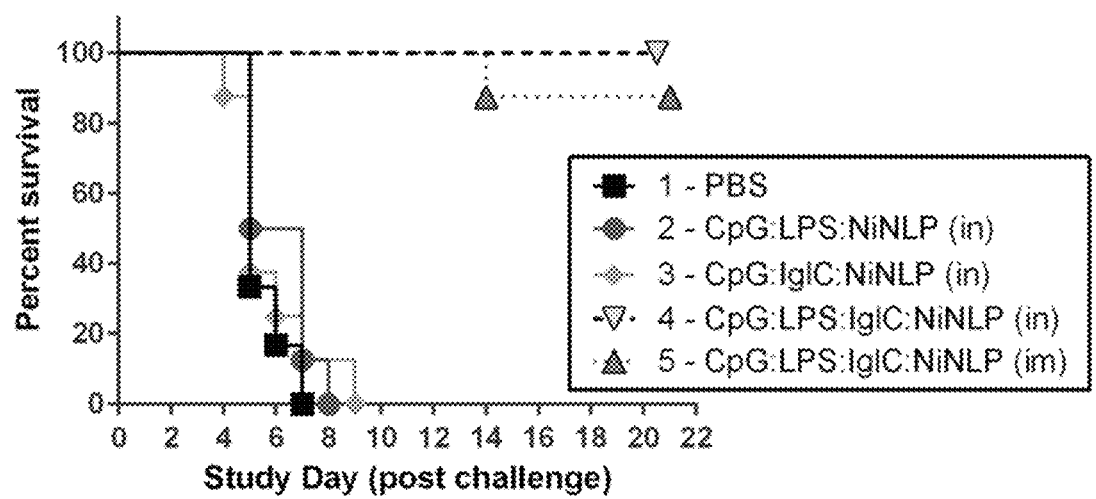
FIG. 18 illustrates in some embodiments percent survival of the tested animals after being challenged with *Francisella tularensis* aerosol.

Animals were monitored daily after challenge for survival and weights. As shown in FIG. 18, only animals vaccinated with LPS:IglC:CpG:NLPs were protected, with intranasal vaccination achieving 100% survival. Single antigen formulations using only the IglC antigen or only the LPS antigen were not protected. The data suggests that vaccine formulations were protected only when both LPS and IglC antigens were included.

Example 15: Test of Animal Weight Loss Over Time

Figure 19A:
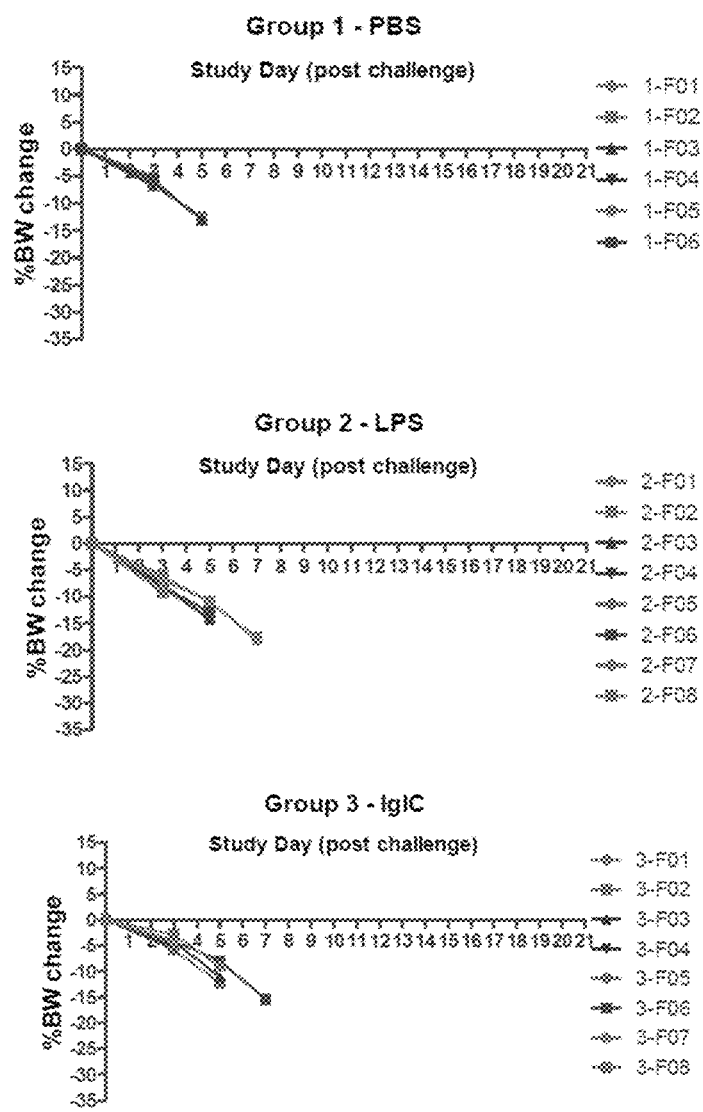
FIGS. 19A-B illustrate in some embodiments the individual animal weight measured over the course of the experiments for experimental groups 1-3 (FIG. 19A) and group 4-5 (FIG. 19B).
Figure 19B:
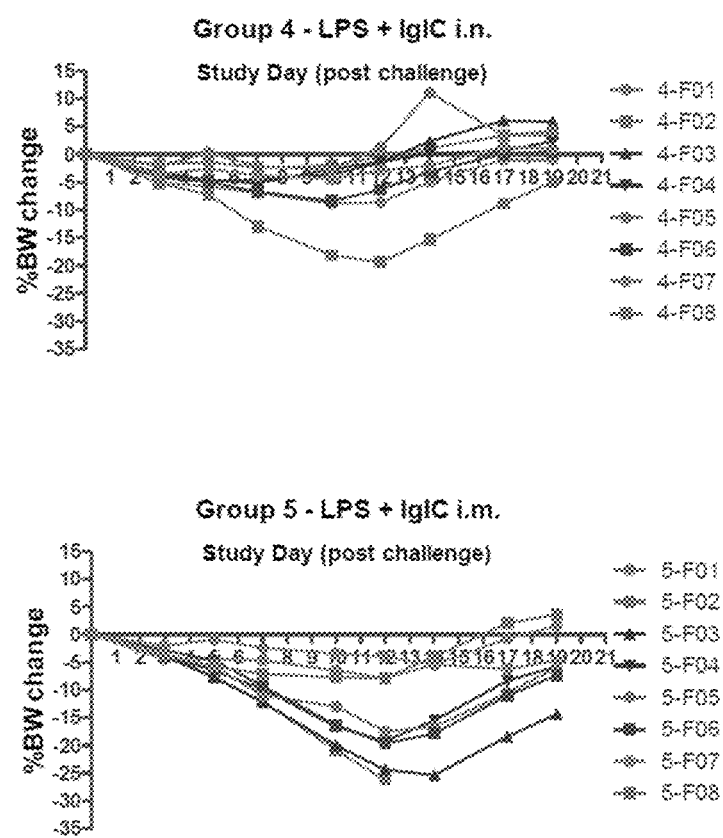

In additional to survival rate, individual animal weights were measured over the course of the experiment. These are plotted in FIGS. 19A-B for each experimental group. Each trace corresponds to the weights of an individual animal over time. In animals that did not survive (e.g. groups 1, 2, and 3) (FIG. 19A), weights dropped significantly before animals died. For the two survival groups with complete or significant survival (groups 4 and 5) (FIG. 19B), weights also dropped, but not as dramatically as in groups 1-3. In general, the weight loss over time for the intranasal (i.n.) groups was less severe than for the intramuscular (i.m.) group. The data in this example indicates that not only is survival outcome greater for the animals vaccinated with the full formulation via the i.n. route, but symptoms (i.e. weight loss) were also substantially ameliorated.

Example 16: Bacterial Tissue Burdens in Surviving Animal

After the conclusion of the 21-day survival window of the in vivo experiment, animals were culled and the lungs and spleens of the survivors were collected. These organs were assessed for the presence of bacteria by plating organ homogenates on agar plates, and resulting bacterial colonies were counted.

Figure 20:
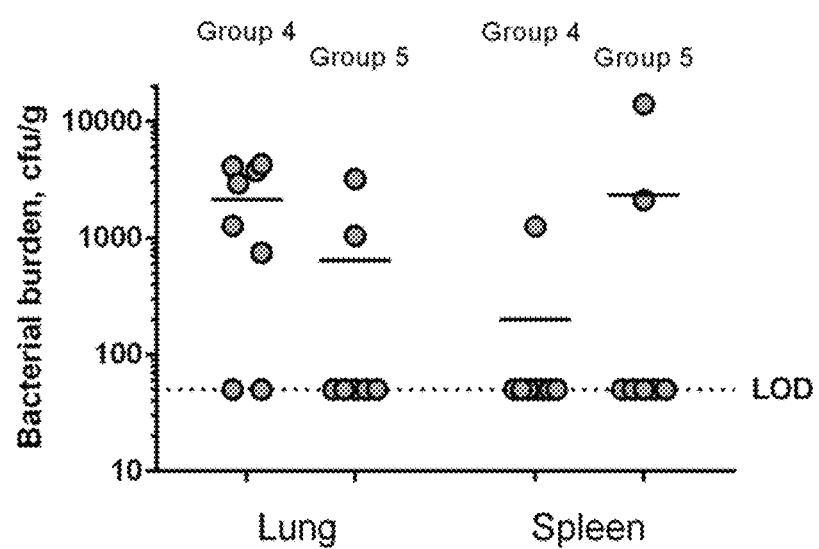
FIG. 20 illustrates in some embodiments bacterial burden in cfu/g measured in lungs and spleens 21 days post challenge in two survival groups (groups 4 and 5).

As shown in FIG. 20, low bacterial burdens were measured in lungs and spleens 21-days post challenge in both survival groups (groups 4 and 5). The low numbers of bacteria suggest that the animals were clearing the infection and historical data suggests that the bacterial burden would have continued to decline over time. Bacteria assessment was not performed on the animals in Groups 1-3, but typically animals that died from tularemia usually have $10^9$ or $10^{10}$ bacteria present in the lungs and spleen.

Example 17: NLP Vaccine Formulation and Design of In Vivo Confirmatory Experiments The goal of this confirmatory experiment was to repeat the in vivo preliminary study in its entirety. In addition to the five groups tested, a non-NLP control group (group 6) was included. This group included the LPS, IglC, and CpG, but in the absence of the NLP. This group was included to demonstrate that these vaccine formulations are superior when incorporated on an NLP platform. In particular, the vaccination formulation of Group 6 comprises 20 μg IglC, 5 μg LVS LPS and 5 μg cCpG1826 and was administrated by i.n.

At day 0, the 344 rats in groups 1-6 were administered with the formulations listed in Table 8 and described above. At day 28, a second administration was performed with the same formulation. At day 35, the serum of the 344 rats were collected for analysis. All rats were challenged with either intranasally or intramuscularly on day 56 with 130±65 CFUs F. t. aerosol. Survival was monitored for 21 days after challenge, at which point the lungs and spleens of the rats were collected for further analysis and assessment.

Female Fischer F344 rats (8 animals/group) were allotted into six vaccination groups: 1) PBS control, intranasal vaccination (IN); 2) CpG:LPS:NLP, IN; 3) CpG:IglC:NLP, IN; 4) CpG:IglC:LPS:NLP, IN; 5) CpG:IglC:LPS:NLP, intramuscular vaccination (IM); 6) CpG+IglC+LPS, IN. Animals were vaccinated with an initial prime on day 0 followed by an additional vaccination, or boost, 4 weeks later (day 28). Serum was collected from vaccinated animals one week after the boost by tail vein bleeds (day 35). Animals were challenged with 130±65 CFUs of aerosolized F. tularensis SCHU S4 four weeks after the boost (day 56). Animals were monitored for signs of clinical disease over the course of 21 days at which point the study was terminated (day 77). Surviving animals were euthanized and bacterial burdens were quantified in lungs and spleen.

Figure 21A:
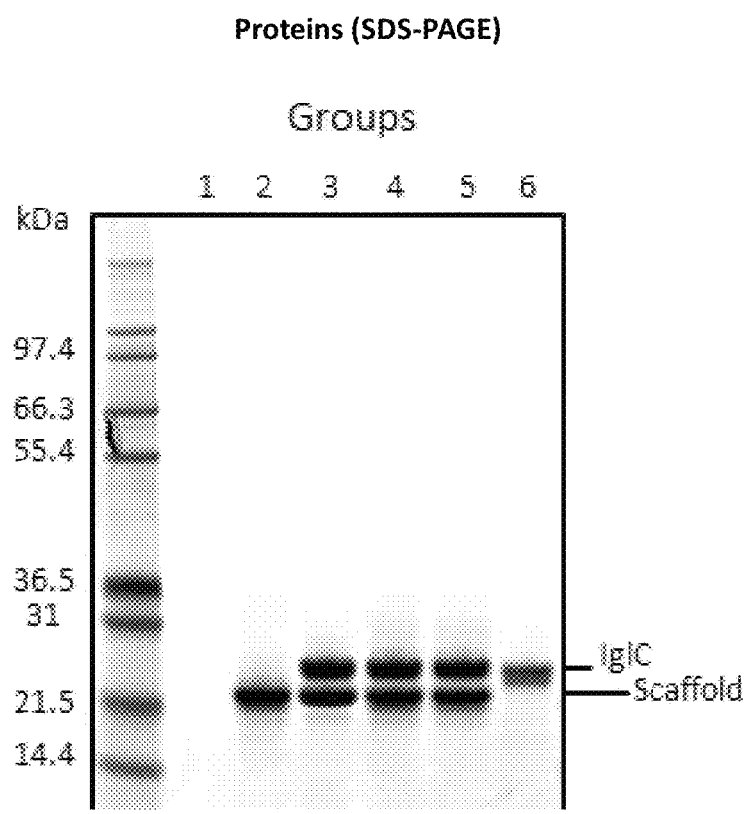
FIGS. 21A-B show in an exemplary SDS-PAGE and Western blot analysis of the vaccine formulations used in the animal tests. Group 1: PBS vehicle only (intranasal vaccination); Group 2: CpG:LPS:NiNLP (intranasal vaccination); Group 3: CpG:IglC:NiNLP (intranasal vaccination); Group 4: CpG:IglC:LPS:NiNLP (intramuscular vaccination); Group 5: CpG:IglC:LPS:NiNLP (intranasal vaccination); Group 6: CpG+IglC+LPS (intranasal vaccination).
Figure 21B:
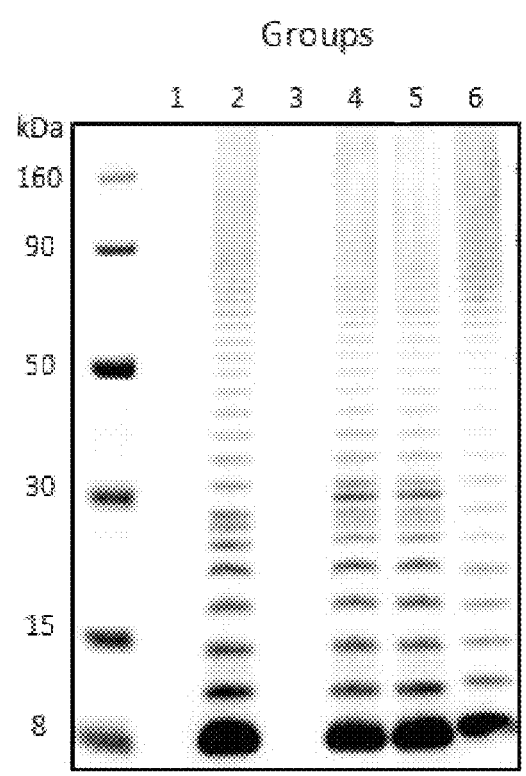

The results from the quality control assessment of the vaccine formulations were shown in FIGS. 21A-B. The formulations were assessed by SDS-PAGE and probed with either a protein stain (FIG. 21A) or an antibody against F.t. LPS (Western blot, FIG. 21B). Each formulation contained the appropriate constituents, depending on the formulation. For example, the NLP formulations 2, 3, 4 and 5 all exhibited the scaffold protein by SDS-PAGE (FIG. 21A). Formulations 3, 4, 5 and 6 contained the IglC protein antigen, as verified by SDS-PAGE (FIG. 21A). Formulations 2, 4, 5 and 6 were confirmed to contain LPS by Western blot (FIG. 21B). Therefore, it is verified that the components in the formulations were present in the vaccine material used to inject the animals.

Example 18: Animal Test Results from In Vivo Confirmatory Experiments

Figure 22:
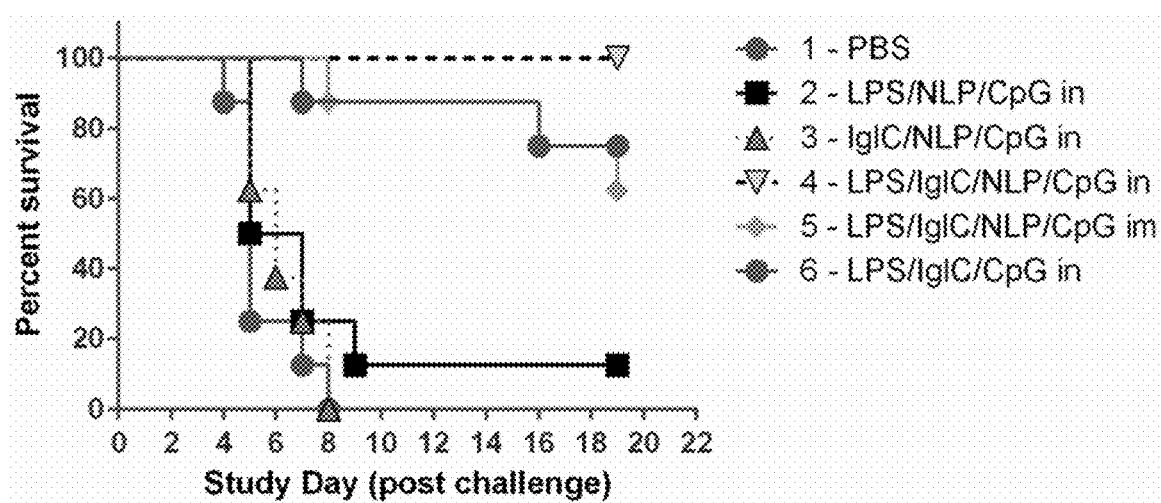
FIG. 22 illustrates in some embodiments percent survival of the tested animals after being challenged with *Francisella tularensis* aerosol. Group 1: PBS vehicle only (intranasal vaccination); Group 2: CpG:LPS:NiNLP (intranasal vaccination); Group 3: CpG:IglC:NiNLP (intranasal vaccination); Group 4: CpG:IglC:LPS:NiNLP (intramuscular vaccination); Group 5: CpG:IglC:LPS:NiNLP (intranasal vaccination); Group 6: CpG+IglC+LPS (intranasal vaccination).

As shown in FIG. 22, the results from animal survival test confirm the preliminary results, indicating that only animals vaccinated with formulations containing LPS, IglC and cpG were protective. Intranasal (i.n.) vaccination achieved 100% survival, but only when conjugated to NLP. Non-NLP formulations administered i.n. were ~85% protective. Intramuscular (i.m.) administration of the complete NLP formulation provided ~65% protection. Single antigen formulations using only the IglC antigen or only the LPS antigen were not protective or only marginally protective.

The results from these confirmatory experiments further indicate that vaccine formulations were protected only when both LPS and IglC antigens were included. NLP formulations were more protective than non-NLP formulations administered by i.n.

Figure 23:
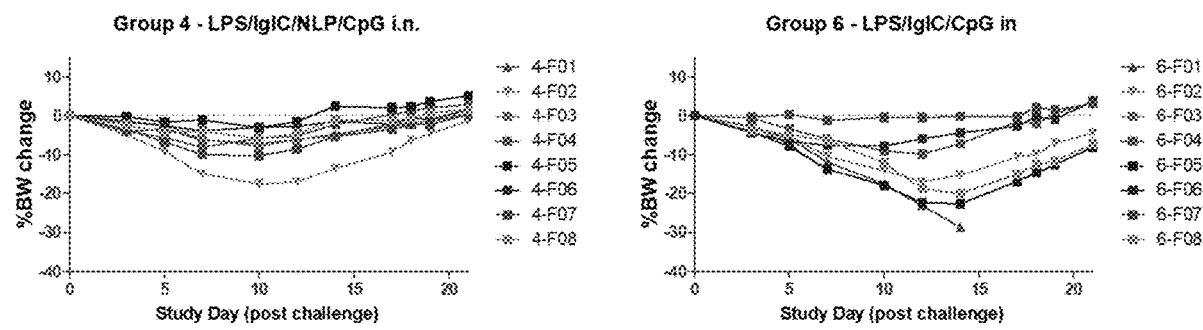
FIG. 23 illustrates in some embodiments the individual animal weight measured over the course of the experiments for experimental group 4 and group 6. Group 4: CpG:IglC: LPS:NiNLP (intramuscular vaccination); Group 6: CpG+ IglC+LPS (intranasal vaccination).

As shown in FIG. 23, the results from the animal weight loss test between the preliminary experiments and the confirmatory experiments follow nearly identical trends. The comparison between group 4 and group 6 also suggests that animals vaccinated i.n. with the full NLP formulation overall had less severe weight loss than those receiving the non-NLP formulation i.n.

Figure 24A:
FIGS. 24A-B show an exemplary graphical representation of the daily clinical scores recorded during the 21-day observation period after the *Francisella tularensis* aerosol challenge.
Figure 24B:
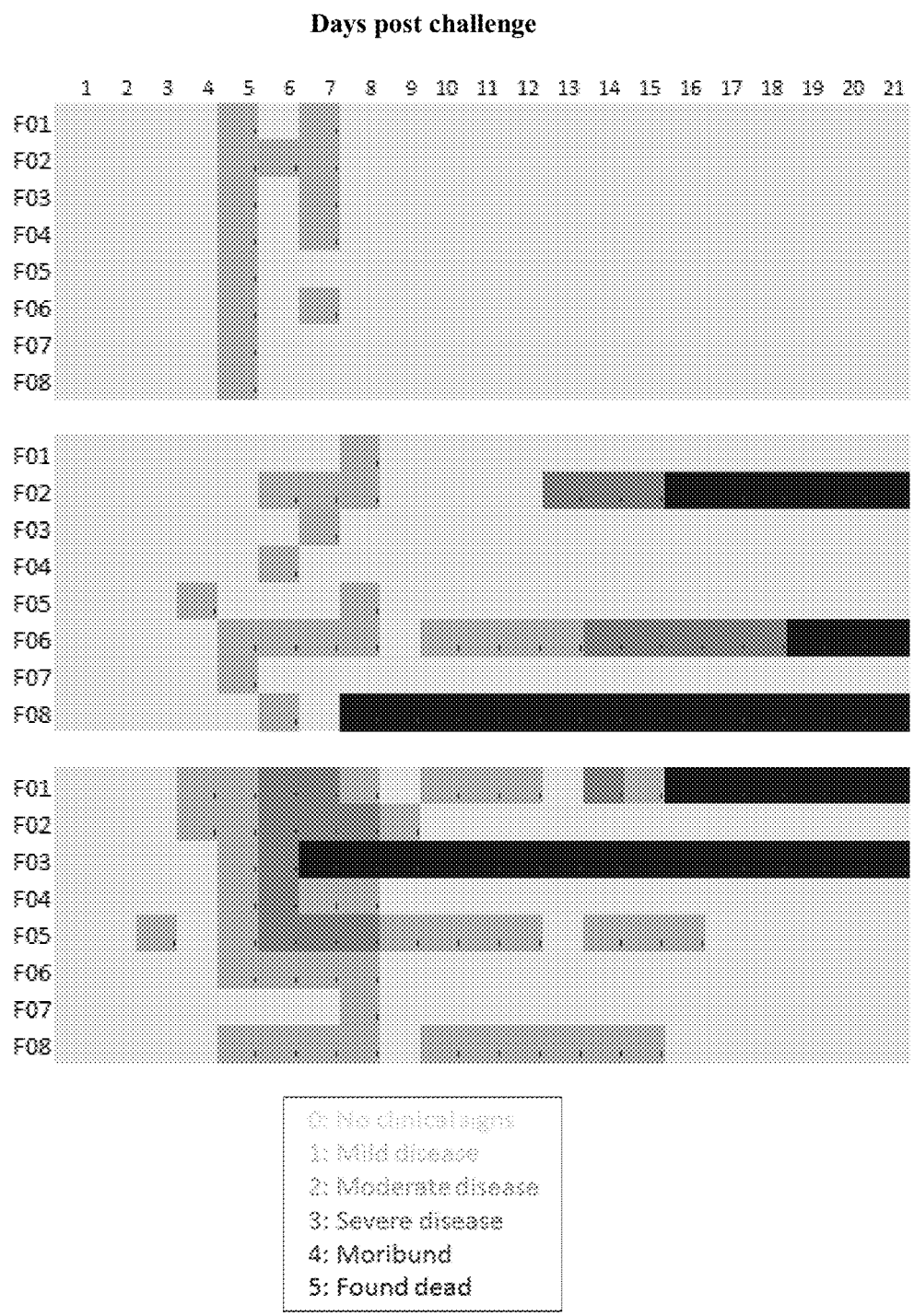

FIGS. 24A-B provide a graphical representation of the daily clinical scores recorded during the 21-day observation period after the F.t. challenge.

Individual animals assessed based on set metrics, and scored from 0 to 5 depending on severity of symptoms. A score of 0 means no clinical signs of infection were observed (green), whereas a score of 5 means the animal has succumbed to infection (red). As expected, the animals in groups 1-3 all died (except for animal #4 in group 2) (FIG. 24A), mirroring the survival plot. In group 4 (the full NLP formulation delivered by i.n.) (FIG. 24B), only 4 animals have scores higher than 0, and only for 1 observation. In contrast, the animals in group 6 (receiving all component delivered i.n., with no NLP) (FIG. 24B) had significantly more severe clinical scores, indicating that while only 1 animal succumbed to the infection, the majority has more severe manifestation of the disease. This underscores the enhanced protective effects of the formulations prepared with the NLP.

Example 19: Extraction and Purification of CPS of F. *Tularensis*

Bacteria are grown for approximately 48 h on chocolate agar medium plates at 37° C., collected and suspended in a solution of 6 mM Trizma base, 10 mM EDTA, and 2.0% SDS (w/v), pH 6.8 supplemented with 50 mg/ml proteinase K, and incubated for 1 hour at 65° C. and then overnight at 37° C. Precipitate CPS with one tenth the volume of 0.3 M sodium acetate (0.1 ml per 1 ml sample) followed by 3 volumes cold 100% ethanol, flash-cooling in a dry ice-ethanol bath, and an overnight incubation at −20° C. Pellet CPS by centrifugation (10 min at 12,000×g at 4° C.). Resuspend pellets in deionized water. Repeat precipitated two additional times. Suspend samples in 15 mL buffer (10 mM Tris pH 7.4 containing 10 mM $CaCl_2$)) and treat with 80 U micrococcal nuclease overnight at 37° C. Add an equal volume of 95% phenol, incubate at 65° C. for 30 min, the cool on ice. Centrifuge the sample at 2,000×g for 10 min at 4° C. Collect the aqueous layer, then remove residual phenol by adding one-tenth volume of 0.3 M sodium acetate, followed by precipitation three times with 3 volumes of absolute ethanol. Resuspend the precipitated sample with distilled water and Triton X-114 (final concentration of 5% (v/v)), vortex, and incubated overnight at 4° C. Equilibrate at 37° C. for two hours, then centrifuge at 2000×g at 37° C. for ten minutes. Remove the aqueous upper layer, dialyze extensively against distilled water at room temperature and lyophilize. For final purification, lyophilized capsule can be reconstituted in 6 mM Tris base, 10 mM EDTA and 2.0% SDS (w/v), pH 6.8 injected onto and placed over a 1×20 cm Sephacryl SH500 column at 37° C.

Purified CPS material can be characterized using a variety of techniques including gel electrophoresis, ProQ Emerald glycoprotein stain or monoclonal antibodies (e.g. mAb 11B7) for Western blotting, MALDI Mass Spectrometry (MS), gas-chromatography coupled with MS, and anion exchange chromatography as will be understood by a skilled person.

Example 20: BLAST Analysis of Exemplary *Francisella* Protein Antigens

A BLAST analysis of exemplary *Francisella* protein antigen listed in Table 2 was performed. FIG. 26 shows the search parameters and databases used for querying the protein sequences. In particular, the search was limited to Francisellacease and excluded sequences derived from unculturable/environmental samples.

The results are illustrated in FIGS. 27A to 43B. For each query sequence, a grayscale representation of a graphic summary of the BLASTP search results and representation of an alignment hit table generated from the BLASTP search, are provided. The alignment hit table shows the summary information for each target sequence found by the alignment search. Each row in the table represents a hit. For each hit sequence, the following information is included: Query ID, accession number of the hit sequence, percentage identity, alignment length, number of mismatched residues, gap open penalty, the start position in the query sequence, the end position in the query sequence, the start position in the hit sequence, the end position in the hit sequence, E-value, bit score, and percentage similarity (positivity).

Example 21—Peptide Design Rationale

For the initial screen, peptides were designed to be 15 amino acids in length and sequentially shifted in sequence by 5 residues. 15 amino acids is the approximate length estimated to be required to contain a CD4 or a CD8 epitope regardless where they start in the sequence.

The protein antigen IglC (SEQ ID NO: 2) was then divided according to the above criteria into 51 IgC protein overlapping peptides. These division can be computed with software such as Microsoft Excel using the MID function, which provides the specific number of characters from a text string (starting position and number of characters can be specified).

The resulting peptides are listed in Table 9 below.

TABLE 9 sequences of peptides 1-51 mapped from an exemplary protein antigen IglC

| Peptide No. | Peptide sequence | SEQ ID NO |
|---|---|---|
| 1 | MIMSEMITRQQVTSG | 30 |
| 2 | EMITRQQVTSGETIH | 31 |
| 3 | RQQVTSGETIHVRTD | 32 |
| 4 | TSGETIHVRTDPTAC | 33 |
| 5 | TIHVRTDPTACIGSH | 34 |

TABLE 9-continued sequences of peptides 1-51 mapped from an exemplary protein antigen Ig1C

| Peptide No. | Peptide sequence | SEQ ID NO |
|---|---|---|
| 6 | RTDPTACIGSHPNCR | 35 |
| 7 | TACIGSHPNCRLFID | 36 |
| 8 | GSHPNCRLFIDSLTI | 37 |
| 9 | NCRLFIDSLTIAGEK | 38 |
| 10 | FIDSLTIAGEKLDKN | 39 |
| 11 | LTIAGEKLDKNIVAI | 40 |
| 12 | GEKLDKNIVAIDGGE | 41 |
| 13 | DKNIVAIDGGEDVTK | 42 |
| 14 | VAIDGGEDVTKADSA | 43 |
| 15 | GGEDVTKADSATAAA | 44 |
| 16 | VTKADSATAAASVIR | 45 |
| 17 | DSATAAASVIRLSIT | 46 |
| 18 | AAASVIRLSITPGSI | 47 |
| 19 | VIRLSITPGSINPTI | 48 |
| 20 | SITPGSINPTISITL | 49 |
| 21 | GSINPTISITLGVLI | 50 |
| 22 | PTISITLGVLIKSNV | 51 |
| 23 | ITLGVLIKSNVRTKI | 52 |
| 24 | VLIKSNVRTKIEEKV | 53 |
| 25 | SNVRTKIEEKVSSIL | 54 |
| 26 | TKIEEKVSSILQASA | 55 |
| 27 | EKVSSILQASATDMK | 56 |
| 28 | SILQASATDMKIKLG | 57 |
| 29 | ASATDMKIKLGNSNK | 58 |
| 30 | DMKIKLGNSNKKQEY | 59 |
| 31 | KLGNSNKKQEYKTDE | 60 |
| 32 | SNKKQEYKTDEAWGI | 61 |
| 33 | QEYKTDEAWGIMIDL | 62 |
| 34 | TDEAWGIMIDLSNLE | 63 |
| 35 | WGIMIDLSNLELYPI | 64 |
| 36 | IDLSNLELYPISAKA | 65 |
| 37 | NLELYPISAKAFSIS | 66 |
| 38 | YPISAKAFSISIEPT | 67 |
| 39 | AKAFSISIEPTELMG | 68 |
| 40 | SISIEPTELMGVSKD | 69 |
| 41 | EPTELMGVSKDGMRY | 70 |
| 42 | LMGVSKDGMRYHIIS | 71 |

TABLE 9-continued sequences of peptides 1-51 mapped from an exemplary protein antigen Ig1C

| Peptide No. | Peptide sequence | SEQ ID NO |
|---|---|---|
| 43 | SKDGMRYHIISIDGL | 72 |
| 44 | MRYHIISIDGLTTSQ | 73 |
| 45 | IISIDGLTTSQGSLP | 74 |
| 46 | DGLTTSQGSLPVCCA | 75 |
| 47 | TSQGSLPVCCAASTD | 76 |
| 48 | SLPVCCAASTDKGVA | 77 |
| 49 | CCAASTDKGVAKIGY | 78 |
| 50 | STDKGVAKIGYIAAA | 79 |
| 51 | GVAKIGYIAAA | 80 |

A peptide library with the peptides of Table 9 was prepared by a commercial provider.

Example 22: Identification of IgC-Specific Immune Epitopes in Fischer 344 Rats

Elucidating derivatives that may be protective in an efficacy evaluation can include mapping immune epitopes for the *F. tularensis* antigen. This example describes an approach to identify immune epitopes for *F. tularensis* IglC in the Fischer 344 rat model. The outlined approach was conducted using a live-attenuated bacterial delivery platform that overexpresses IglC (Lm-IglC) but represents an example of a broader approach to identify epitopes and derivatives of protective *F. tularensis* antigens.

Figure 44:
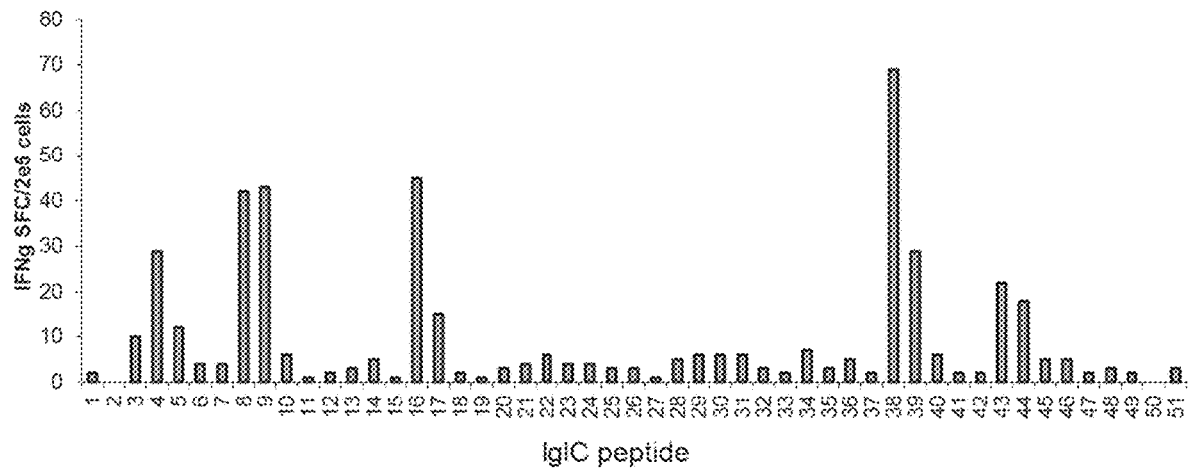
FIG. 44 illustrates in a plot the IglC-specific immune responses in Fischer 344 rat splenocytes. This figure represents the results from an ELISPOT assay to identify peptides within the IglC protein that stimulate IFNγ production by antigen-specific T cells from Fischer 344 rats immunized with a recombinant *Listeria monocytogenes* strain engineered to express the *Francisella tularensis* IglC protein (Lm-IglC). One Fischer 344 rat was vaccinated IM with $1 \times 10^8$ CFU of Lm-IglC and then boosted IV 4 weeks later with $1 \times 10^8$ CFU Lm-IglC. The splenocytes were harvested seven days after the boost and restimulated the next day with individual peptides that span the length the IglC protein shown on the X-axis. The number of IFNγ specific spot forming cells (SFC) per 200,000 lymphocytes are shown on the Y axis. Specific reactivity is indicated by a peak in the number of IFNγ secreting cells. The results show that there are potentially 5 epitopes that stimulate T cells in Fischer 344 rats.

Rats were immunized IM twice with $1\times10^8$ cfu of a live-attenuated bacterial delivery platform that overexpresses IglC (Lm-IglC) followed by one IV vaccination with $1\times10^8$ cfu Lm-IglC. Vaccinations were administered four weeks apart, and immune responses measured in spleens seven days after the last vaccination. Splenocytes were stimulated by individual 15aa peptides from an overlapping peptide library to IglC (MS56) and immune responses measured by IFN-γ ELISpot assay (FIG. 44). Several peptides (peptides #4, 8, 9, 16, 17, 38, 39, 43, and 44) in five different regions of the protein emerged as potentially containing IglC-specific epitopes (FIG. 44).

Figure 45:
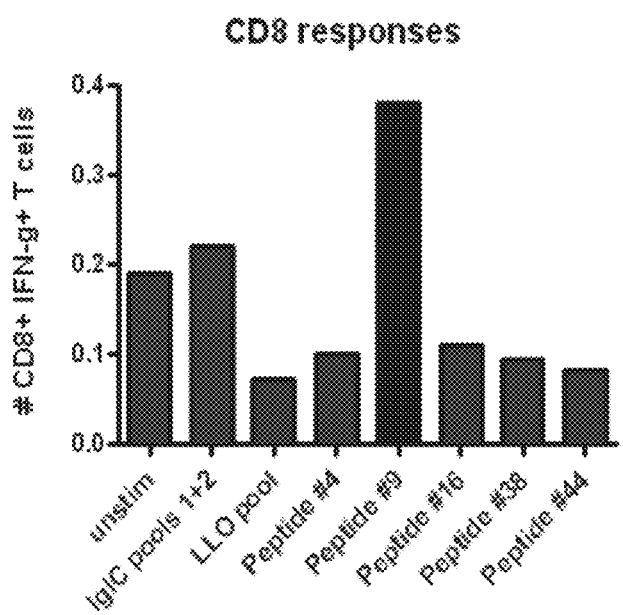
FIG. 45 illustrates in an exemplary embodiments flow cytometry analyses of T cells from Ig1C-immunized Fischer 344 rats to identify CD8 T cell epitopes. This figure shows that Ig1C peptide #9 is a CD8 T cell antigen in Fischer 344 rats. One Fischer 344 rat was vaccinated IV with $1 \times 10^8$ CFU Lm-IglC and then boosted 2 weeks later with $1 \times 10^7$ CFU IV Lm-IglC. Splenocytes were isolated six days after the boost and restimulated with pools of peptides from IglC (IglC pools 1+2) or listeriolysin O (LLO pool) or with individual IglC peptides #4, #9, #16, #38, and #44 as shown on the X-axis. The percent of CD8⁺ T cells expressing intracellular IFNγ is shown on the Y-axis. The results show that only IglC peptide 9 stimulated CD8 T cells to produce IFNγ, indicating that it is the only CD8 T cell epitope within the IglC protein.

To determine if these responses were due to either CD4+ or CD8+ epitopes, one Fischer 344 rat was vaccinated with $1\times10^8$ cfu Lm-IglC IV and boosted after two weeks with $1\times10^7$ cfu Lm-IglC IV. Six days after the boost vaccination, immune responses were measured in isolated splenocytes by intracellular cytokine straining (ICS) after stimulation with peptides from each region, #4, 9, 16, 38, and 44 or no peptide as a control (F-5) (FIG. 45). Peptide #9 was identified as stimulating a CD8-mediated response.

Figure 46:
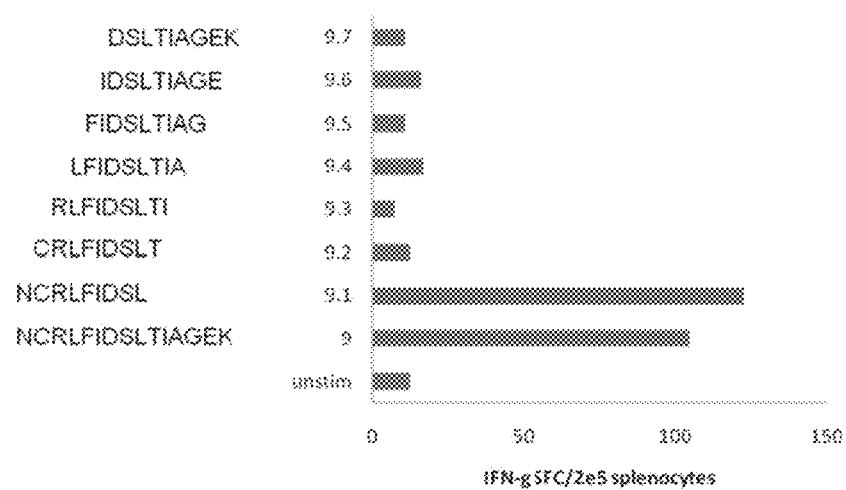
FIG. 46 illustrates in a plot the mapping IglC-specific CD8⁺ T cell epitope in Fischer 344 rats. This figure represents the results from an IFNγ ELISPOT assay to identify the specific 9 amino acid peptide within the 15 amino acid IglC peptide #9 that stimulated IFNγ production by CD8 T cells from immunized Fischer 344 rats. Fischer 344 rats were vaccinated IV with $1 \times 10^8$ CFU Lm-IglC and then boosted IV 6 weeks later with $1 \times 10^7$ CFU Lm-IglC. Six days after the boost, splenocytes were harvested and restimulated with overlapping 9 amino acids peptides that span the 15 amino acid IglC peptide #9 as shown on the Y-axis. The X-axis represents the IFN-γ response, enumerated as the number of IFN-γ specific spot-forming cells (SFC) per 200,000 lymphocytes. The results show that the sequence of the stimulatory peptide is NCRLFIDSL (SEQ ID NO: 30).

Fine-mapping of the peptide #9-specific response was performed using 9mer peptides that overlap the entire IglC peptide #9 (FIG. 46).

In particular, for the fine mapping of peptide #9, peptides were designed to be 9 amino acids in length, sequentially shifted in sequence by 1 residue. This allowed for the identification of the exact 9 AA peptide corresponding to the T-cell epitope.

The peptides listed in Table 10 were identified and synthesized.

TABLE 10

Sequences further mapped from peptide #9 in Table 10

| Peptide No. | Peptide Sequence | SEQ ID NO |
|---|---|---|
| 9 | NCRLFIDSLTIAGEK | 38 |
| 9.1 | NCRLFIDSL | 81 |
| 9.2 | CRLFIDSLT | 82 |
| 9.3 | RLFIDSLTI | 83 |
| 9.4 | LFIDSLTIA | 84 |
| 9.5 | FIDSLTIAG | 85 |
| 9.6 | IDSLTIAGE | 86 |
| 9.7 | DSLTIAGEK | 87 |

One Fischer 344 rat was vaccinated with $1 \times 10^8$ cfu Lm-IglC IV and boosted after six weeks with $1 \times 10^7$ cfu Lm-IglC IV. Six days after the boost vaccination, immune responses were measured in the spleen by ICS. Peptide 9.1 stimulated an immune response as great as the full-length peptide #9, while peptides 9.2 through 9.7 did not stimulate a response. Based on these data, peptide 9.1 (NCRLFIDSL (SEQ ID NO:81) was identified as an IglC-specific CD8+ T cell epitope in Fischer 344 rats (FIG. 46).

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified antigenic combinations for immunization against pathogenic Francisella bacteria and related nanolipoprotein particles, composition methods and systems. according to various embodiments and scope of the claims.

All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file IL-13256-CIP-Sequence-Listing_ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Okan, N. A. and D. L. Kasper, *The atypical lipopolysaccharide of Francisella*. Carbohydrate research, 2013. 378: p. 79-83.
2. Sun, P., et al., *New protein fold revealed by a 1.65 Å resolution crystal structure of Francisella tularensis pathogenicity island protein IglC*. Protein Sci, 2007. 16(11): p. 2560-3.
3. Huber, B., et al., *Description of Francisella hispaniensis sp. nov., isolated from human blood, reclassification of Francisella novicida* (Larson et al. 1955) Olsufiev et al. 1959 as *Francisella tularensis* subsp. *novicida* comb. nov.

and emended description of the genus *Francisella. Int J Syst Evol Microbiol*, 2010. 60(Pt 8): p. 1887-96.
4. Mikalsen, J. and D. J. Colquhoun, *Francisella asiatica sp. nov. isolated from farmed tilapia (Oreochromis sp.) and elevation of Francisella philomiragia subsp. noatunensis to species rank as Francisella noatunensis comb. nov., sp. nov. nt* J Syst Evol *Microbiol*, 2009.
5. Ottem, K. F., et al., *Elevation of Francisella philomiragia subsp. noatunensis* Mikalsen et al. (2007) *to Francisella noatunensis comb. nov.* [*syn. Francisella piscicida* Ottem et al. (2008) *syn. nov.*] *and characterization of Francisella noatunensis subsp. orientalis subsp. nov., two important fish pathogens*. J Appl Microbiol, 2009. 106(4): p. 1231-43.
6. Qu, P. H., et al., *Francisella guangzhouensis sp. nov., isolated from air-conditioning systems*. Int J Syst Evol Microbiol, 2013. 63(Pt 10): p. 3628-35.
7. Foley, J. E. and N. C. Nieto, *Tularemia*. Vet Microbiol, 2010. 140β-4): p. 332-8.
8. Davidson, E. and B. J. Doranz, *A high-throughput shotgun mutagenesis approach to mapping B-cell antibody epitopes*. Immunology, 2014. 143(1): p. 13-20.
9. Koren, E., et al., *Clinical validation of the "in silico" prediction of immunogenicity of a human recombinant therapeutic protein*. Clinical Immunology, 2007. 124(1): p. 26-32.
10. Lu, Z., et al., *Protective B-cell epitopes of Francisella tularensis O-polysaccharide in a mouse model of respiratory tularaemia*. Immunology, 2012. 136(3): p. 352-360.
11. Rynkiewicz, M. J., et al., *Structural analysis of a protective epitope of the Francisella tularensis O-polysaccharide*. Biochemistry, 2012. 51(28): p. 5684-5694.
12. Roche, M., et al., *Characterization of monoclonal antibodies to terminal and internal O-antigen epitopes of Francisella tularensis lipopolysaccharide*. Hybridoma (Larchmt), 2011. 30(1): p. 19-28.
13. Barker, J. H., et al., *Metabolic labeling to characterize the overall composition of Francisella lipid A and LPS grown in broth and in human phagocytes*. Innate Immun, 2014. 20(1): p. 88-103.
14. De Castro, C., et al., *Microbe-associated molecular patterns in innate immunity: Extraction and chemical analysis of gram-negative bacterial lipopolysaccharides*. Methods Enzymol, 2010. 480: p. 89-115.
15. Rezania, S., et al., *Extraction, Purification and Characterization of Lipopolysaccharide from Escherichia coli and Salmonella typhi*. Avicenna J Med Biotechnol, 2011. 3(1): p. 3-9.
16. Ridley, B. L., B. S. Jeyaretnam, and R. W. Carlson, *The type and yield of lipopolysaccharide from symbiotically deficient rhizobium lipopolysaccharide mutants vary depending on the extraction method*. Glycobiology, 2000. 10(10): p. 1013-23.
17. Apicella, M. A., et al., *Identification, characterization and immunogenicity of an O-antigen capsular polysaccharide of Francisella tularensis*. PLoS One, 2010. 5(7): p. e11060.
18. McCormick, A. A., et al., *Intranasal administration of a two-dose adjuvanted multi-antigen TMV-subunit conjugate vaccine fully protects mice against Francisella tularensis LVS challenge*. PLoS One, 2018. 13(4): p. e0194614.
19. Ashtekar, A. R., et al., *A mucosal subunit vaccine protects against lethal respiratory infection with Francisella tularensis LVS*. PLoS One, 2012. 7(11): p. e50460.
20. Post, D. M. B., et al., *Characterization of Inner and Outer Membrane Proteins from Francisella tularensis Strains LVS and Schu S4 and Identification of Potential Subunit Vaccine Candidates*. MBio, 2017. 8(5).
21. Altschul, S. F., et al., *Gapped BLAST and PSI-BLAST: a new generation of protein database search programs*. Nucleic Acids Res, 1997. 25(17): p. 3389-402.
22. Pearson, W. R., *Searching protein sequence libraries: comparison of the sensitivity and selectivity of the Smith-Waterman and FASTA algorithms*. Genomics, 1991. 11(3): p. 635-50.
23. Smith, T. F. and M. S. Waterman, *Identification of common molecular subsequences*. J Mol Biol, 1981. 147(1): p. 195-7.
24. Pearson, W. R. and D. J. Lipman, *Improved tools for biological sequence comparison*. Proc Natl Acad Sci USA, 1988. 85(8): p. 2444-8.
25. Johnson, L. S., S. R. Eddy, and E. Portugaly, *Hidden Markov model speed heuristic and iterative HMM search procedure*. BMC Bioinformatics, 2010. 11: p. 431.
26. Li Pira, G., et al., *High throughput T epitope mapping and vaccine development*. Journal of Biomedicine and Biotechnology, 2010. 2010: p. 1-12.
27. Nair, A. B. and S. Jacob, *A simple practice guide for dose conversion between animals and human*. J Basic Clin Pharm, 2016. 7(2): p. 27-31.
28. Watanabe, S., Y. Kumazawa, and J. Inoue, *Liposomal lipopolysaccharide initiates TRIF-dependent signaling pathway independent of CD14*. PLoS One, 2013. 8(4): p. e60078.
29. Hajjar, A. M., et al., *Lack of in vitro and in vivo recognition of Francisella tularensis subspecies lipopolysaccharide by Toll-like receptors*. Infect Immun, 2006. 74(12): p. 6730-8.
30. Schilling, B., et al., *Characterization of lipid A acylation patterns in Francisella tularensis, Francisella novicida, and Francisella philomiragia using multiple-stage mass spectrometry and matrix-assisted laser desorption/ionization on an intermediate vacuum source linear ion trap*. Anal Chem, 2007. 79(3): p. 1034-42.
31. Prior, J. L., et al., *Characterization of the O antigen gene cluster and structural analysis of the O antigen of Francisella tularensis subsp. tularensis*. J Med Microbiol, 2003. 52(Pt 10): p. 845-51.
32. Thomas, R. M., et al., *The immunologically distinct O antigens from Francisella tularensis subspecies tularensis and Francisella novicida are both virulence determinants and protective antigens*. Infect Immun, 2007. 75(1): p. 371-8.
33. Chalabaev, S., et al., *3-Deoxy-D-manno-octulosonic acid (Kdo) hydrolase identified in Francisella tularensis, Helicobacter pylori, and Legionella pneumophila*. Journal of Biological Chemistry, 2010. 285(45): p. 34330-34336.
34. Zhao, J. and C. R. Raetz, *A two-component Kdo hydrolase in the inner membrane of Francisella novicida*. Molecular microbiology, 2010. 78(4): p. 820-836.
35. Stead, C. M., et al., *Removal of the outer Kdo from Helicobacter pylori lipopolysaccharide and its impact on the bacterial surface*. Molecular microbiology, 2010. 78(4): p. 837-852.
36. Dreisbach, V. C., S. Cowley, and K. L. Elkins, *Purified lipopolysaccharide from Francisella tularensis live vaccine strain (LVS) induces protective immunity against LVS infection that requires B cells and gamma interferon*. Infect Immun, 2000. 68(4): p. 1988-96.

The invention claimed is:

1. An immunogenic nanolipoprotein particle comprising:
   one or more scaffold proteins;
   one or more membrane forming lipids;
   an antigenic *Francisella* polysaccharide component capable of triggering a humoral immune response in an individual, the *Francisella* polysaccharide component comprising, at least one antigenic polysaccharide from *Francisella* and/or a derivative thereof;
   a *Francisella* protein antigen component capable of triggering a cellular immune response in the individual, the *Francisella* protein antigen component comprising at least one protein antigen from *Francisella* and/or a derivative thereof, and
   an adjuvant,
wherein the one or more membrane forming lipids are arranged in a discoidal membrane lipid bilayer stabilized by the one or more scaffold protein,
and wherein the at least one antigenic polysaccharide from *Francisella* or the derivative thereof, the at least one protein antigen from *Francisella* and/or derivative thereof, and the adjuvant are attached to the discoidal membrane lipid bilayer.

2. The immunogenic nanolipoprotein particle of claim 1, further comprising:
   a functionalized membrane-forming lipid presenting an anchor compound substrate, wherein the at least one protein antigen from *Francisella* and/or derivative thereof and/or the at least one antigenic polysaccharide from *Francisella* and/or derivative thereof, is attached to an anchor compound and is further attached to the functionalized membrane-forming lipid through binding of the anchor compound with the anchor compound substrate.

3. The immunogenic nanolipoprotein particle of claim 1, wherein the immunogenic nanoparticle, the adjuvant, the antigenic *Francisella* polysaccharide component and the *Francisella* protein antigen component are at a ratio of 1:1:1:1 to 1:50:50:50.

4. The immunogenic nanolipoprotein particle of claim 1, wherein the immunogenic nanoparticle, the adjuvant, the antigenic *Francisella* polysaccharide component and the *Francisella* protein antigen component are at a ratio range of 1:2:2:2 to 1:10:10:10.

5. The immunogenic nanolipoprotein particle of claim 1, wherein the immunogenic nanoparticle, the adjuvant, the antigenic *Francisella* polysaccharide component and the *Francisella* protein antigen component are at a ratio of immunogenic nanoparticle:antigenic polysaccharide:protein:adjuvant of 1:2:2:2.

6. The immunogenic nanolipoprotein particle of claim 1, wherein the at least one antigenic polysaccharide from *Francisella* and/or a derivative thereof, comprises at least one of the antigenic polysaccharide from *Francisella* and/or a derivative having a general formula (XI):

$$\xi\!-\!M_1\!-\!L_1\!-\!M_2\!-\!L_2\!-\!M_3\!-\!L_3\!-\!M_4\!-\!L_4\!-\!\xi_n \quad (XI)$$

M1-M4 can each independently be selected from the group consisting of (Xa) to (Xw):

(Xa) α-D-Mannose or α-D-Man (Xb) β-D-Mannose or β-D-Man (Xc) α-D-Glucose or α-D-Glc (Xd) β-D-Glucose or β-D-Glc (Xe) α-D-glucosamine or α-D-GlcN (Xf) β-D-glucosamine or β-D-GlcN (Xg) α-D-N-Acetylglucosamine or α-D-GlcNAc

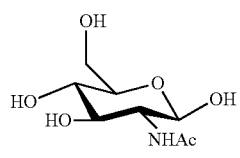

β-D-N-Acetylglucosamine or
β-D-GlcNAc

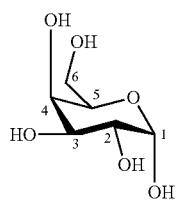

α-D-Galactose or α-D-Gal

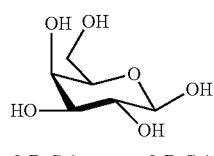

β-D-Galactose or β-D-Gal

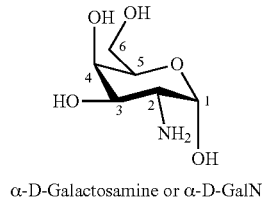

α-D-Galactosamine or α-D-GalN

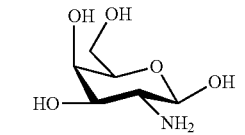

β-D-Galactosamine or β-D-GalN

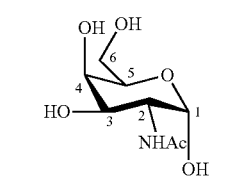

α-D-N-Acetylgalactosamine or
α-D-GalNAc

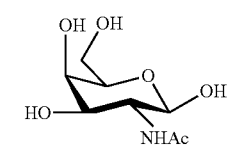

β-D-N-Acetylgalactosamine or
β-D-GalNAc (Xh)

(Xi)

(Xj)

(Xk)

(Xl)

(Xm)

(Xn)

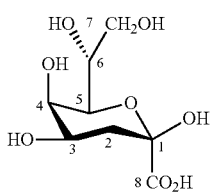

β-Kdo (β anomer of cyclized 3-Deoxy-
D-manno-oct-2-ulsonic acid)

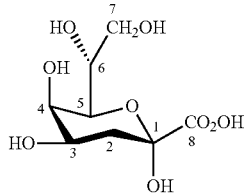

α-Kdo (α anomer of cyclized 3-Deoxy-
D-manno-oct-2-ulsonic acid)

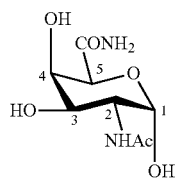

α-2-Acetamido-2-deoxy-D-
galacturonamide or α-D-GalNAcAN

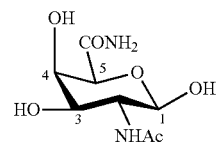

β-2-Acetamido-2-deoxy-D-
galacturonamide or β-D-GalNAcAN

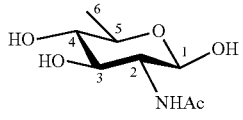

β-2-acetamido-2,6-dideoxy-D-
glucose or β-D-QuiNAc

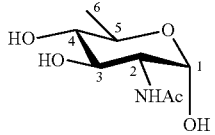

α-2-acetamido-2,6-dideoxy-D-
glucose or α-D-QuiNAc

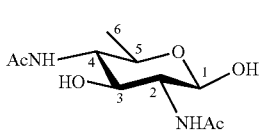

β-2,4-Diacetamido-2,4,6-trideoxy-D-
glucose or β-D-Qui2NAc4NAc (Xo)

(Xp)

(Xq)

(Xr)

(Xs)

(Xt)

(Xu)

(Xv)

α-2,N-Diacetamido-2,4,6-trideoxy-D-
glucose or α-D-Qui2NAc4NAc (Xw)

β-4-Formamido-4,6-dideoxy-D-glucose
or β-D-Qui4NFm in which L1-L4 can be selected independently from the group consisting of:

α (1→2), α (1→3), α (1→4), α (1→5), α (1→6), β (1→2), β (1→3), β (1→4), β (1→5), and β (1→6); and n is 1 to 1250.

7. The immunogenic nanolipoprotein particle of claim 1, wherein the at least one protein antigen from *Francisella* and/or a derivative thereof, comprises at least one protein antigen from *Francisella* and/or a derivative thereof having SEQ ID NOs: 2, 4, 6, 8, 10, 88, 14, 16, 18, 20, 22, and 24-29 and/or one or more protein antigens having at least 30% identity with the *Francisella* protein antigen having SEQ ID NOs: 2, 4, 6, 8, 10, 88, 14, 16, 18, 20, 22, and 24-29.

8. The immunogenic nanolipoprotein particle of claim 1, wherein the adjuvant comprises at least one adjuvant selected from at least one of immunostimulatory peptides, muramyl dipeptides, saponins, toxins, oligonucleotide CpG motifs, organic compounds, alpha-galactosyl ceramide, and lipotichoic acid, or hydrophilic adjuvants synthetically appended with a hydrophobic moiety, including microbial derivatives, plant derivatives, and immunostimulatory proteins, immunostimulatory carbohydrates and polysaccharides, and immunostimulatory nucleic acids.

9. An immunogenic composition comprising the immunogenic nanolipoprotein particle of claim 1 together with a suitable vehicle, the immunogenic nanolipoprotein particle in an amount effective to induce an immunogenic response against the *Francisella* bacterium in an individual.

10. A method of immunizing an individual against an infection of a *Francisella* bacterium, the method comprising administering to the subject an effective amount of the immunogenic nanolipoprotein particle of claim 1 or within a composition further comprising a suitable vehicle, the immunogenic nanolipoprotein in an amount effective to induce an immunogenic response against the *Francisella* bacterium in an individual.

11. The method of claim 10, wherein the administering is performed by intranasal inhalation.

12. The method of claim 10, wherein the administering is performed by intramuscular administration.

13. The immunogenic nanolipoprotein particle of claim 1, wherein the *Francisella* protein antigen component comprises a protein peptide selected from SEQ ID NO: 33, 37, 38, 45, 46, 67, 68, 72 and 73.

14. The immunogenic nanolipoprotein particle of claim 1, wherein the *Francisella* protein antigen component comprises a protein peptide selected from SEQ ID NO: 33, 38, 45, 67, and 73.

15. The immunogenic nanolipoprotein particle of claim 1, wherein the *Francisella* protein antigen component comprises a protein peptide having SEQ ID NO: 33.

16. The immunogenic nanolipoprotein particle of claim 1, wherein the *Francisella* protein antigen component comprises a protein peptide having SEQ ID NO: 81.

17. The immunogenic nanolipoprotein particle of claim 1, wherein the *Francisella* protein antigen component comprises DnaK, OmpA, SucB and/or LpnA.

18. The immunogenic nanolipoprotein particle of claim 1, wherein the antigenic polysaccharide component from the *Francisella* bacterium comprises a lipopolysaccharide molecule and/or a fragment thereof.

19. The immunogenic nanolipoprotein particle of claim 6, wherein the antigenic polysaccharide component from the *Francisella* bacterium comprises capsule polysaccharide (CPS) and/or a derivative of the capsule polysaccharide.

20. The immunogenic nanolipoprotein particle of claim 19, wherein n is 10-200.

21. The immunogenic nanolipoprotein particle of claim 19, wherein M1, M2, M3 and M4 are each independently selected from the group consisting of α-D-GalNAc (Xm), β-D-QuiNAc (Xs), and β-D-Qui4NFm (Xw).

22. The immunogenic nanolipoprotein particle of claim 19, wherein M1 and M2 are α-D-GalNAc (Xm).

23. The immunogenic nanolipoprotein particle of claim 19, wherein the M1-M4 can each independently be selected from the group consisting of β-D-Qui4NFm (Xw), α-D-GalNAcAN (Xq), α-D-GalNAcAN (Xq), and β-D-QuiNAc (Xs).

24. The immunogenic nanolipoprotein particle of claim 19, wherein L1, L2, L3 and L4 are each independently selected from the group consisting of α (1→4), α(1→3), β (1→2), and β (1→4).

25. The immunogenic nanolipoprotein particle of claim 19, the antigenic polysaccharide further comprises a lipid component.

26. The immunogenic nanolipoprotein particle of claim 25, wherein the lipid component has a general formula of Y1:

(Y1)

wherein
R10 to R13 are each independently represented by hydrogen H or Formula (Y11):

(Y11)

wherein R30 is hydrogen H, OH or represented by Formula (Y12):

$$H_3C-(CH_2)_{9-15}-CH_2-C(=O)-O-\xi \quad (Y12)$$

R20 and R21 is represented by Formula (Y10):

$$-\xi-P(=O)(OH)-O-M_{10} \quad (Y10)$$

wherein M10 is hydrogen H or a monosaccharide linked to the oxygen by the corresponding anomeric carbon, the monosaccharide is selected from the group consisting of Formulas (Xa) to (Xw), and wherein Z is a trisaccharide.

27. The immunogenic nanolipoprotein particle of claim 1, wherein the protein antigen component from the *Francisella* bacterium comprises IglC or a derivative thereof.

28. The immunogenic nanolipoprotein particle of claim 1, wherein the antigenic polysaccharide component from the *Francisella* bacterium is from *F. tularensis* LVS.

29. The immunogenic nanolipoprotein particle of claim 1, wherein the antigenic polysaccharide component from the *Francisella* bacterium is from *F. tularensis* subsp. *tularensis*.

30. The immunogenic nanolipoprotein particle of claim 1, wherein the adjuvant is an amphipathic or hydrophobic adjuvant.

31. The immunogenic nanolipoprotein particle of claim 1, wherein the adjuvant is a lipidic-anchored adjuvant.

32. The immunogenic nanolipoprotein particle of claim 1, wherein the adjuvant is selected from a saponin, an oligonucleotide CpG motifs, an immunostimulatory carbohydrate, an immunostimulatory polysaccharide, and immunostimulatory protein or peptide molecules.

33. The immunogenic composition of claim 9, wherein the composition comprises the antigenic polysaccharide component from the *Francisella* bacterium in an amount from about 0.1 to 100 μg, the protein antigen component from the *Francisella* bacterium in an amount from about 0.1 to 100 μg, and the adjuvant in an amount from about 0.001 to 200 μg.

34. The immunogenic composition of claim 9, wherein the composition comprises the antigenic polysaccharide component from the *Francisella* bacterium and the protein antigen component from the *Francisella* bacterium are at a ratio between 1:0.1 and 1:10 by mass.

35. The immunogenic composition of claim 34, wherein the antigenic polysaccharide component from the *Francisella* bacterium and the protein antigen component from the *Francisella* bacterium are at a ratio of 1:4 by mass.

36. The immunogenic composition of claim 9, wherein the composition comprises the adjuvant at a ratio of 1 to 50 adjuvant molecules per nanolipoprotein particle within the composition.

37. The immunogenic composition of claim 36, wherein the composition comprises from 2 to 10 adjuvant molecules per nanolipoprotein particle within the composition.

38. The immunogenic composition of claim 9, wherein the composition comprises the antigenic polysaccharide component from the *Francisella* bacterium, the protein antigen component from the *Francisella* bacterium and the adjuvant on a single nanolipoprotein particle, the composition comprising a same or different, nanolipoprotein particle.

39. The immunogenic composition of claim 9, wherein the composition further comprises the antigenic polysaccharide component from the *Francisella* bacterium, the protein antigen component from the *Francisella* bacterium and the adjuvant presented on a separate nanolipoprotein particle, the composition comprising a same or different, nanolipoprotein particle.

40. The immunogenic composition of claim 9, wherein the composition further comprises the antigenic polysaccharide component from the *Francisella* bacterium, the protein antigen component from the *Francisella* bacterium and the adjuvant further presented on an additional carrier selected from liposomes, polymeric micelles, microspheres, and nanoparticles.

41. The immunogenic composition of claim 9, wherein the composition further comprises the adjuvant to further increase the immunogenicity of the antigenic polysaccharide component from the *Francisella* bacterium and of the protein antigen component from the *Francisella* bacterium.

42. An immunogenic nanolipoprotein particle comprising:
   one or more scaffold proteins;
   one or more membrane forming lipids;
   an antigenic *Francisella* polysaccharide component capable of triggering a humoral immune response in an individual, the *Francisella* polysaccharide component comprising, at least one antigenic polysaccharide from *Francisella*;
   a *Francisella* protein antigen component capable of triggering a cellular immune response in the individual, the *Francisella* protein antigen component comprising at least one protein antigen from *Francisella*, and
   an adjuvant,
wherein the one or more membrane forming lipids are arranged in a discoidal membrane lipid bilayer stabilized by the one or more scaffold protein,
and wherein the at least one antigenic polysaccharide from *Francisella*, the at least one protein antigen from *Francisella*, and the adjuvant are attached to the discoidal membrane lipid bilayer.

\* \* \* \* \*